(12) United States Patent
Salcedo et al.

(10) Patent No.: US 7,348,003 B2
(45) Date of Patent: Mar. 25, 2008

(54) METHODS OF TREATING CANCER USING ANTIBODIES THAT IMMUNOSPECIFICALLY BIND TO TRAIL RECEPTORS

(75) Inventors: Theodora W. Salcedo, East Syracuse, NY (US); Steven M. Ruben, Brookeville, MD (US); Craig A. Rosen, Laytonsville, MD (US); Vivian R. Albert, Rockville, MD (US); Claire Dobson, Cambridge (GB); Tristan Vaughan, Cambridge (GB)

(73) Assignee: Human Genome Sciences, Inc., Rockville, MD (US)

( * ) Notice: Subject to any disclaimer, the term of this patent is extended or adjusted under 35 U.S.C. 154(b) by 23 days.

(21) Appl. No.: 10/986,047

(22) Filed: Nov. 12, 2004

(65) Prior Publication Data

US 2005/0129699 A1    Jun. 16, 2005

Related U.S. Application Data

(63) Continuation-in-part of application No. PCT/US03/25457, filed on Aug. 15, 2003, which is a continuation-in-part of application No. 10/139,785, filed on May 7, 2002, now Pat. No. 7,064,189.

(60) Provisional application No. 60/608,362, filed on Sep. 10, 2004, provisional application No. 60/425,730, filed on Nov. 13, 2002, provisional application No. 60/403,382, filed on Aug. 15, 2002, provisional application No. 60/468,050, filed on May 6, 2003, provisional application No. 60/293,473, filed on May 25, 2001, provisional application No. 60/294,981, filed on Jun. 4, 2001, provisional application No. 60/309,176, filed on Aug. 2, 2001, provisional application No. 60/323,807, filed on Sep. 21, 2001, provisional application No. 60/327,364, filed on Oct. 9, 2001, provisional application No. 60/331,044, filed on Nov. 7, 2001, provisional application No. 60/331,310, filed on Nov. 14, 2001, provisional application No. 60/341,237, filed on Dec. 20, 2001, provisional application No. 60/369,860, filed on Apr. 5, 2002.

(51) Int. Cl.
*A61K 39/395* (2006.01)
*G01N 33/53* (2006.01)
*C12P 21/04* (2006.01)
*C12P 21/08* (2006.01)
*C07K 16/00* (2006.01)
*C07H 21/04* (2006.01)

(52) U.S. Cl. .................. 424/133.1; 424/139.1; 424/142.1; 424/143.1; 424/155.1; 435/69.6; 435/70.21; 530/387.3; 530/387.9; 530/388.1; 530/388.15; 530/388.22; 530/388.8

(58) Field of Classification Search ............. 424/130.1, 424/133.1, 135.1, 142.1, 143.1, 155.1, 181.1; 435/69.6, 70.2
See application file for complete search history.

(56) References Cited

U.S. PATENT DOCUMENTS

| | | | |
|---|---|---|---|
| 4,002,531 | A | 1/1977 | Royer |
| 4,179,337 | A | 12/1979 | Davis et al. |
| 4,496,654 | A | 1/1985 | Katz et al. |
| 4,946,778 | A | 8/1990 | Ladner et al. |
| 5,349,053 | A | 9/1994 | Landolfi |
| 5,447,851 | A | 9/1995 | Beutler et al. |
| 5,478,925 | A | 12/1995 | Wallach et al. |
| 5,530,101 | A | 6/1996 | Queen et al. |
| 5,565,332 | A | 10/1996 | Hoogenboom et al. |
| 5,643,575 | A | 7/1997 | Martinez et al. |
| 5,763,223 | A | 6/1998 | Wiley et al. |
| 5,807,715 | A | 9/1998 | Morrison et al. |
| 6,072,047 | A | 6/2000 | Rauch et al. |
| 6,252,050 | B1 | 6/2001 | Ashkenazi et al. |
| 6,313,269 | B1 | 11/2001 | Deen et al. |
| 6,342,363 | B1 | 1/2002 | Ni et al. |
| 6,342,369 | B1 | 1/2002 | Ashkenazi |
| 6,433,147 | B1 | 8/2002 | Ni et al. |
| 6,461,823 | B1 | 10/2002 | Ni et al. |
| 6,569,642 | B1 | 5/2003 | Rauch et al. |
| 6,642,358 | B1 | 11/2003 | Rauch et al. |
| 6,743,625 | B2 | 6/2004 | Ni et al. |
| 6,872,568 | B1 | 3/2005 | Ni et al. |

(Continued)

FOREIGN PATENT DOCUMENTS

CA         2045869         12/1990

(Continued)

OTHER PUBLICATIONS

Lee et al. Journal of Biochemistry, 274(23): abstract, 1999.*
Defresne et al. Histochemistry, 101(5):abstract, 1994.*
Leroy et al. Journal of Lipid Research, 33(6):abstract , 1992.*

(Continued)

*Primary Examiner*—David J. Blanchard

(57) ABSTRACT

The present invention relates to antibodies and related molecules that immunospecifically bind to TRAIL receptor, TR4. Such antibodies have uses, for example, in the prevention and treatment of cancers and other proliferative disorders. The invention also relates to nucleic acid molecules encoding anti-TR4 antibodies, vectors and host cells containing these nucleic acids, and methods for producing the same. The present invention relates to methods and compositions for preventing, detecting, diagnosing, treating or ameliorating a disease or disorder, especially cancer and other hyperproliferative disorders, comprising administering to an animal, preferably a human, an effective amount of one or more antibodies or fragments or variants thereof, or related molecules, that immunospecifically bind to TRAIL receptor TR4.

43 Claims, 3 Drawing Sheets

U.S. PATENT DOCUMENTS

| | | | |
|---|---|---|---|
| 6,902,910 B2 | 6/2005 | Ni et al. |
| 6,943,020 B2 | 9/2005 | Ni et al. |
| 2001/0029030 A1 | 10/2001 | Alnemri |
| 2002/0004227 A1 | 1/2002 | Ashkenazi et al. |
| 2002/0004587 A1 | 1/2002 | Miller et al. |
| 2002/0048566 A1 | 4/2002 | El-Deiry et al. |
| 2002/0048785 A1 | 4/2002 | Holtzman |
| 2002/0072091 A1 | 6/2002 | Ni et al. |
| 2002/0098550 A1 | 7/2002 | Ni et al. |
| 2002/0115154 A1 | 8/2002 | Alnemri |
| 2002/0150985 A1 | 10/2002 | Adams et al. |
| 2002/0155109 A1 | 10/2002 | Lynch |
| 2002/0160446 A1 | 10/2002 | Holtzman |
| 2002/0169123 A1 | 11/2002 | El-Deiry et al. |
| 2003/0017161 A1 | 1/2003 | Ashkenazi et al. |
| 2003/0036168 A1 | 2/2003 | Ni et al. |
| 2003/0073187 A1 | 4/2003 | Ni et al. |
| 2003/0108516 A1 | 6/2003 | Ni et al. |
| 2003/0125540 A1 | 7/2003 | Holtzman |
| 2003/0133932 A1 | 7/2003 | Zhou et al. |
| 2003/0148455 A1 | 8/2003 | Adams et al. |
| 2003/0180296 A1 | 9/2003 | Salcedo et al. |
| 2003/0190685 A1 | 10/2003 | Salcedo et al. |
| 2003/0190687 A1 | 10/2003 | Zhou et al. |
| 2003/0198637 A1 | 10/2003 | Zhou et al. |
| 2003/0228309 A1 | 12/2003 | Salcedo et al. |
| 2004/0005314 A1 | 1/2004 | Escandon et al. |
| 2004/0009552 A1 | 1/2004 | Adams et al. |
| 2004/0101915 A1 | 5/2004 | Deveraux et al. |
| 2004/0120947 A1 | 6/2004 | Ashkenazi et al. |
| 2004/0126791 A1 | 7/2004 | Wajant et al. |
| 2004/0136950 A1 | 7/2004 | Ni et al. |
| 2004/0136951 A1 | 7/2004 | Ni et al. |
| 2004/0141952 A1 | 7/2004 | Ni et al. |
| 2004/0147725 A1 | 7/2004 | Chuntharapai et al. |
| 2004/0180049 A1 | 9/2004 | Ashkenazi et al. |
| 2004/0209290 A1 | 10/2004 | Cobleigh et al. |
| 2004/0214235 A1 | 10/2004 | Mori et al. |
| 2004/0228868 A1 | 11/2004 | Ashkenazi et al. |
| 2004/0235757 A1 | 11/2004 | Sabrina et al. |
| 2005/0079172 A1 | 4/2005 | Nasoff et al. |
| 2005/0112090 A9 | 5/2005 | Ni et al. |
| 2005/0129616 A1 | 6/2005 | Salcedo et al. |
| 2005/0129699 A1 | 6/2005 | Salcedo et al. |
| 2005/0214205 A1 | 9/2005 | Salcedo et al. |
| 2005/0214206 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0216960 A1 | 9/2005 | Winoto et al. |
| 2005/0222387 A1 | 10/2005 | Debatin et al. |
| 2005/0233958 A1 | 10/2005 | Ni et al. |
| 2005/0244417 A1 | 11/2005 | Ashkenazi et al. |
| 2005/0244857 A1 | 11/2005 | Ni et al. |
| 2005/0249729 A1 | 11/2005 | Mori et al. |
| 2005/0282230 A1 | 12/2005 | Ashkenazi et al. |
| 2006/0025576 A1 | 2/2006 | Miller et al. |
| 2006/0035334 A1 | 2/2006 | Adams et al. |
| 2006/0062786 A1 | 3/2006 | Salcedo et al. |
| 2006/0069246 A1 | 3/2006 | Holtzman |
| 2006/0073570 A1 | 4/2006 | Adams et al. |
| 2006/0084147 A1 | 4/2006 | Adams et al. |
| 2006/0088523 A1 | 4/2006 | Andya et al. |
| 2006/0115484 A1 | 6/2006 | Adams et al. |

FOREIGN PATENT DOCUMENTS

| | | |
|---|---|---|
| EP | 0 239 400 | 9/1987 |
| EP | 0 401 384 | 12/1990 |
| EP | 0 510 691 | 10/1992 |
| EP | 0 857 782 | 8/1998 |
| EP | 0 870 827 | 10/1998 |
| EP | 1 181 319 | 2/2002 |
| EP | 1 192 185 | 4/2002 |
| EP | 1 287 035 | 3/2003 |
| WO | WO 91/06570 | 5/1991 |
| WO | WO 91/09967 | 7/1991 |
| WO | WO 94/01548 | 1/1994 |
| WO | WO 95/06058 | 3/1995 |
| WO | WO 97/01633 | 1/1997 |
| WO | WO 98/30693 | 7/1998 |
| WO | WO 98/32856 | 7/1998 |
| WO | WO 98/35986 | 8/1998 |
| WO | WO 98/41629 | 9/1998 |
| WO | WO 98/46643 | 10/1998 |
| WO | WO 98/51793 | 11/1998 |
| WO | WO 99/00423 | 1/1999 |
| WO | WO 99/02653 | 1/1999 |
| WO | WO 99/09165 | 2/1999 |
| WO | WO 99/11791 | 3/1999 |
| WO | WO 99/12963 | 3/1999 |
| WO | WO 99/37684 | 7/1999 |
| WO | WO 99/64461 | 12/1999 |
| WO | WO 00/48619 | 8/2000 |
| WO | WO 00/66156 | 11/2000 |
| WO | WO 00/73349 | 12/2000 |
| WO | WO 00/75191 | 12/2000 |
| WO | WO 01/19861 | 3/2001 |
| WO | WO 01/77342 | 10/2001 |
| WO | WO 01/83560 | 11/2001 |
| WO | WO 02/02641 | 1/2002 |
| WO | WO 02/09755 | 2/2002 |
| WO | WO 02/16436 | 2/2002 |
| WO | WO 02/079377 | 10/2002 |
| WO | WO 02/085946 | 10/2002 |
| WO | WO 02/094880 | 11/2002 |
| WO | WO 02/097033 | 12/2002 |
| WO | WO 03/037913 | 5/2003 |
| WO | WO 03/038043 | 5/2003 |
| WO | WO 03/042367 | 5/2003 |
| WO | WO 03/054216 | 7/2003 |
| WO | WO 03/066661 | 8/2003 |
| WO | WO 03/086470 | 10/2003 |
| WO | WO 2004/016753 | 2/2004 |
| WO | WO 2004/050895 | 6/2004 |
| WO | WO 2004/052292 | 6/2004 |
| WO | WO 2004/085479 | 10/2004 |
| WO | WO 2005/016236 | 2/2005 |
| WO | WO 2005/025619 | 3/2005 |
| WO | WO 2005/056605 | 6/2005 |
| WO | WO 2005/094533 | 10/2005 |
| WO | WO 2005/100399 | 10/2005 |
| WO | WO 2006/009731 | 1/2006 |
| WO | WO 2006/017961 | 2/2006 |
| WO | WO 2006/029224 | 3/2006 |
| WO | WO 2006/029275 | 3/2006 |

OTHER PUBLICATIONS

Lederman et al. Molecular Immunology 28:1171-1181, 1991.*
Li et al. Proc. Natl. Acad. Sci. USA 77:3211-3214, 1980.*
Paul, W. E. Fundamental Immunology, 3rd Edition, pp. 292-295, 1993.*
Bendig M. M. Methods: A Companion to Methods in Enzymology, 8:83-93, 1995.*
Gura T. Science, 278:1041-1042, Nov. 7, 1997.*
Jain R. K. Scientific American, pp. 58-65, Jul. 1994.*
Allison, et al., "Transgenic expression of CD95 ligand on Islet β cells induces a granulocytic infiltration but does not confer immune privilege upon islet allografts," *Proc. Natl. Acad. Sci. USA*, 94:3943-3947 (Apr. 1997).

Allison, et al., "Mechanisms of β cell death in diabetes: a minor role for CD95," *Proc. Natl. Acad. Sci. USA*, 95:13818-13822 (Nov. 1998).

Barbas, et al., "In vitro evolution of a neutralizing human antibody to human immunodeficiency virus type 1 to enhance affinity and broaden strain cross-reactivity." *Proc. Natl. Acad. Sci.*, 91:3809-3813 (1994).

Beutler, B and Cerami, A, "Tumor Necrosis, Cachexia, Shock, and Inflammation: A Common Mediator," *Ann. Rev. Biochem.* 57:505-518, Annual Reviews Inc. (1988).

Bodmer, et al., "TRAMP, a novel apoptosis-mediating receptor with sequence homology to tumor necrosis factor receptor 1 and Fas(Apo-1/CD95)," *Immunity*, 6:79-88 (Jan. 1997).

Boldin, et al., "A novel protein that Interacts with the death domain of Fas/APO1 contains a sequence motif related to the death domain," *The Journal of Biological Chemistry*, 270(14):7795-7798 (Apr. 7, 1995).

Brojatsch, J et al., "CAR1, a TNRF-Related Protein, is a Cellular Receptor for Cytopathic Avian Leukosis-Sarcoma Viruses and Mediates Apoptosis," *Cell* 87:845-855, Cell Press (Nov. 1996).

Chapman, BS, "A region of the 75 kDa neurotrophin receptor homologous to the death domains of TNFR-1 and Fas," *FEBS Lett.* 374:216-220, Elsevier (1995).

Chaudhary et al., "Death receptor 5, a new member of the TNFR family, and DR4 Induce FADD-dependent apoptosis and activate the NF-kappa B pathway," *Immunity* 7(6):821-830 (1997).

Chicheportiche, et al., "TWEAK, a new secreted ligand in the tumor necrosis factor family that weakly induces apoptosis," *The Journal of Biological Chemistry*, 272(51):32401-32410 (Dec. 19, 1997).

Chinnaiyan, AM et al., "Signal Transduction by DR3, a Death Domain-Containing Receptor Related to TNFR-1 and CD95," *Science* 274(5289):990-992 (1996).

Chinnaiyan, et al., "FADD, a novel death domain-containing protein, interacts with the death domain Fas and Initiates apoptosis," *Cell*, 81:505-512 (May 19, 1995).

Chuntharapai, et al., "Isotype-dependent inhibition of tumor growth in vivo by monoclonal antibodies to death receptor 4", *Journal of Immunology*, vol. 166, No. 8, pp. 4891-4898, Apr. 2001.

Clerici, et al., "Type 1 and type 2 cytokines in HIV Infection—A possible role in apoptosis and disease progression," *Annals of Medicine*, 29(3):185-188 (1997).

Colman, "Effects of amino acid sequence changes on antibody-antigen interactions," *Research in Immunology*, 145:33-36 (1994).

Database, EMBL Nucleic Acid DB EBI, Hinxton UK. Sequence Accession No. AA100865, Oct. 30, 1996. Hillier et al. "The WashU-Merck EST Project".

Degli-Esposti, et al., "Cloning and characterization of TRAIL-R3, a novel member of the emerging TRAIL receptor family," *J. Exp. Med.*, 186(7):1165-1170 (Oct. 6, 1997).

Degli-Esposti, et al., "The novel receptor TRAIL-R4 Induces NF-κB and protects against TRAIL-mediated apoptosis, yet retains an Incomplete death domain," Immunity, 7:813-820 (Dec. 1997).

Dejosez, et al., "Sensitivity to TRAIL/APO-2L-mediated apoptosis in human renal cell carcinomas and its enhancement by topotecan", *Cell Death and Differentiation*, vol. 7, No. 11, pp. 1127-1136, Nov. 2000.

Delgado, C. et al, "Quantitative analysis of polyethylene glycol (PEG) in PIG-modified proteins/cytokines by aqueous two-phase systems," *J. Biochem. Biophys. Methods 29*:237-250 (1994).

Delgado, C., et al., "The Uses and Properties of PEG-Linked Proteins," *Crit. Rev. Ther. Drug Carrier Sys. 9*:249-304, CRC Press, Inc. (1992).

Deng, et al., "Selection of antibody single-chain variable fragments with improved carbohydrate binding by phage display," *J. Biol. Chem.*, 269:9533-9538 (1994).

Deng, et al., "Basis for selection of improved carbohydrate-binding single-chain antibodies from synthetic gene libraries," *Proc. Natl. Acad. Sci.*, 92:4992-4996 (1995).

Dillman, R., "Radiolabeled anti-CD20 1-8 monoclonal antibodies for the treatment of B-cell lymphoma", *Journal of Clinical Oncology*: Official Journal of the American Society of Clinical Oncology, vol. 20, No. 16, pp. 3545-3557, Aug. 2002.

Dillman, R.O., "Monoclonal Antibodies for Treating Cancer," *Ann. Internal. Med. 111*:592-603 (1989).

Dobson, et al., "Generation of human therapeutic anti-TRAIL-R1 agonistic antibodies by phage display", *Proceedings of the American Association for Cancer Research Annual Meeting*, vol. 43, p. 579, Mar. 2002.

Duan, et al., "RAIDD is a new 'death' adaptor molecule," *Nature*, 385:86-89 (Jan. 2, 1997).

Farrow, B. et al., "Activation of conventional PKC isoforms increases expression of the pro-apoptotic protein Bad and TRAIL receptors," *Int. J. Gastrointes. Cancer 32*(2-3):63-72 (2002).

Fiers, W., "Tumor necrosis factor. Characterization at the molecular, cellular, and in vivo level," *FEBS Lett.* 285:199-212, Elsevier Science B.V. (1991).

Frankfurt, et al., "Protection from apoptotic cell death by Interleukin-4 is increased by previously treated chronic lymphocytic leukemia patients," *Leukemia Research*, 21(1):9-16 (1997).

Fulda, et al., "Smac agonists sensitize for Apo2L/TRAIL- or anti-cancer drug-induced apoptosis and induce regression of malignant glioma in vivo", *Nature Medicine*, vol. 8, No. 8, pp. 808-815, Aug. 2002.

Georgakis, et al., "Activity of selective fully human agonistic antibodies to the TRAIL death receptors TRAIL-R1 and TRAIL-R2 in primary and cultured lymphoma cells: induction of apoptosis and enhancement of doxorubicin-and bortezomib-induced cell death", *British Journal of Haematology*, vol. 130, No. 4, pp. 501-510, Aug. 2005.

Gibson, S.B. et al., "Increased expression of death receptors 4 and 5 synergizes the apoptosis response to combined treatment with etoposide and TRAIL," *Mol. Cell Biol. 20*(1):205-212 (Jan. 2000).

Giovarelli, M. et al., "A 'stealth effect': adenocarcinoma cells engineered to express TRAIL elude tumor-specific and allogeneic T cell reactons,"*J. Immunol. 163*:4886-4893 (1999).

Gliniak, et al., "Enhanced therapeutic efficacy of TRAIL/Apo2O in combination with CPT-11 in the treatment of human tumor xenografts", *Proceedings of the the 91$^{st}$ Annual Meeting of the American Association for Cancer Research*, vol. 41, p. 70, Apr. 2000.

Gliniak, et al., "Tumor Necrosis Factor-Related Apoptosis-Inducing Ligand's Antitumor activity in vivo is Enhanced by the Chemotherapeutic Agent CPT-11", *Cancer Research, American Association for Cancer Research*, vol. 59, No. 24, pp. 6153-6158, Dec. 1999.

Goeddel, D.V., et al., "Tumor Necrosis Factors: Gene Structure and Biological Activities," Cold Spring Harb. Symp. Quant. Biol. 51 (Pt.1):597-609, Cold Spring Harbor Laboratory Press (1986).

Golstein, P., "Cell death: TRAIL and its receptors," Curr. Biol. 7:R750-R753, Current Biology Ltd. (Dec. 1997).

Gooch, et al., "Interleukin 4 inhibits growth and induces apoptosis in human breast cancer cells," Cancer Research, 58(18):4199-4208 (Sep. 15, 1998).

Goodman, J.W., "Immunogens & Antigens," In Basic & Clinical Immunology, Eds. Stites et al., Appleton & Lange: Norwalk, CT, pp. 50-57, 1988.

Grell, et al., "Induction of cell death by tumour necrosis factor (TNF) receptor 2, CD40 and CD30: a role for TNF-R1 activation by endogenous membrane-anchored TNF," The EMBO Journal, 1B(11):3034-3043 (1999).

Griffith, et al., "TRAIL: a molecule with multiple receptors and control mechanisms", *Current Opinion in Immunology*, vol. 10, No. 5, pp. 559-563, Oct. 1998.

Griffith, TS et al., "Functional analysis of TRAIL receptors using monoclonal antibodies," J. Immunol. 162:2597-2605 (1999).

Groves, et al., "Production of an ovine monoclonal antibody to testosterone by an interspecies fusion," Hybridoma, 6:71-76 (1987).

Gruss, H.J., and Dower, S.K., "Tumor Necrosis Factor Ligand Superfamily: Involvement in the Pathology of Malignant Lymphomas," Blood 85:3378-3404, The American Society of Hematology (1995).

Hardiman, et al., "Genetic structure and chromosomal mapping of MyD88," Genomics, 45:332-339 (1997).

Harrison, D.C. et al, "TR3 death receptor expression in the normal and Ischaemic brain," *Neuroscience 96*(1):147-160 (2000).

Hildeman, et al., "Activated T cell death in vivo mediated by proapoptotic Bcl-2 family member Bim," *Immunity*, 16:759-767 (Jun. 2002).

Hill, et al., "Prognostic significance of BCL-2 expression and bcl-2 major breakpoint region rearrangement in diffuse large cell non-Hodgkin's lymphoma: A British national lymphoma investigation study," *Blood*, 88(3):1046-1061 (1996).

Hofmann, et al., "The CARD domain: a new apoptotic signalling motif," *TIBS*, 22(5): 155-156 (May 1997).

Horigome, et al., "Tacrolimus-induced apoptosis and its prevention by interleukins in mitogen-activated human peripheral-blood mononuclear cells," *Immunopharmacoly*, 39(1):21-30 (Mar. 1998).

Hsu, et al., "TRADD-TRAF2 and TRADD-FADD interactions define two distinct TNF receptor 1 signal transduction pathways," *Cell*, 84:299-308 (Jan. 26, 1996).

Huang, et al., "Activation of Fas by FasL induces apoptosis by a mechanism that cannot be blocked by Bcl-2 or Bcl-$x_L$," *Proc. Natl. Acad. Sci. USA*, 96(26):14871-14876 (Dec. 21, 1999).

Huang, et al., "Bcl-2, Bcl-$x_L$ and adenovirus protein E1B19kD are functionally equivalent in their ability to inhibit cell death," *Oncogene*, 14;405-414, (1997).

Huston, JS, et al., "Protein Engineering of Single-Chain Fv Analogs and Fusion Proteins," *Met. Enzymol.* 203:46-88, Academic Press, Inc. (1991).

Ichikawa, et al., "Tumoricidal activity of a novel anti-human DR5 monoclonal antibody without hepatocyte cytotoxicity", *Nature Medicine*, vol. 7, No. 8, pp. 954-960, Aug. 2001.

Inoue, et al., "Histone Deacetylase Inhibitors Sensitize Human Colonic Adenocarcinoma Cell Lines to TNF-Related Apoptosis Inducing Ligand-Mediated Apoptosis", *International Journal of Molecular Medicine*, vol. 9, No. 5, pp. 521-525, May 2002.

Irmler, et al., "Direct physical interaction between the *Caenorhabditia elegans* 'death proteins' CED-3 and CED-4," *FEBS Letters*, 406:189-190 (1997).

Irmler, et al., "Inhibition of death receptor signals by cellular FLIP," *Nature*, 388:190-195 (Jul. 10, 1997).

Karin, et al., "Nf-κB at the crossroads of life and death," *Nature Immunology*, 3(3):221-227 (Mar. 2002).

Kelliher, et al. "The death domain kinase RIP mediates the TNF-Induced NF-κB signal," *Immunity*, 8:297-303 (Mar. 1998).

Lerner, R.A., "Antibodies of predetermined specificity in biology and medicine," *Adv. Immunol.* 36:1-44 (1984).

Lindner, et al., "Peripheral blood mononuclear cells induce programmed cell death in human endothelial cells and may prevent repair: Role of cytokines," *Blood*, 89(6):1931-1938 (1997).

Locksley, RM, et al., "The TNF and TNF Receptor Superfamilies: Integrating Mammalian Biology," *Cell 104*:487-501, Cell Press (Feb. 2001).

Lotem, et al., "Hematopoietic cytokines inhibit apoptosis induced by transforming growth factor-beta-1 and cancer chemotherapy compounds in myeloid leukemic cells," *Blood*, 80(7):1750-1757 (1992).

Lotem, et al., "Interferon-gamma inhibits apoptosis induced by wild-type p53 cytotoxic anti-cancer agents and viability factor deprivation in myeloid cells," *Leukemia (Basingstoke)*, 9(4):685-692 (1995).

MacFarlane, et al., "Identification and molecular cloning of two novel receptors for the cytotoxic ligand TRAIL," *The Journal of Biological Chemistry*, 272(41):25417-25420 (Oct. 10, 1997).

Mariani, S.M. et al, "Interleukin 1 beta-coverting enzyme related proteases/caspases are involved in TRAIL-induced apoptosis of myeloma and leukemia cells," *J. Cell Biol.* 137(1):221-229 (Apr. 1997).

Marsters, et al., "A novel receptor for Apo2L/TRAIL contains a truncated death domain," *Current Biology*, 7(12):1003-1006 (Oct. 6, 1997).

Mitsiades, et al., "TRAIL/Apo2L ligand selectively induces apoptosis and overcomes drug resistance in multiple myeloma: Therapeutic applications", *Blood*, vol. 98, No. 3, pp. 795-804, Aug. 2001.

Morpurgo, M., et al., "Covalent Modification of Mushroom Tyrosinase with Different Amphiphic Polymers for Pharmaceutical and Biocatalysis Applications," *Appl. Biochem. Biotechnol.* 56:59-72, Human Press Inc. (Jan. 1996).

Morrison, SL., et al., "Transfectomas Provide Novel Chimeric Antibodies," Science 229:1202-1207, *American Association for the Advancement of Science*(1985).

Muhlenbeck, F. et al., "The tumor necrosis factor-related apoptosis-inducing ligand receptors TRAIL-R1 and TRAIL-R2 have distinct cross-linking requirements for initiation of apoptosis and are non-redundant in JNK activation," *J. Biol. Chem. 275*(41):32208-32213 (Oct. 2000).

Muzio, et al., "FLICE, a novel FADD-homologous ICE/CED-3-like protease, is recruited to the CD95 (Fas/APO-1) death-inducing signaling complex," *Cell*, 85:817-827 (Jun. 14, 1996).

Muzio, et al., "IRAK (Pelle) family member IRAK-2 and MyD88 as proximal mediators of IL-1 signaling," *Science*, 278:1612-1615 (Nov. 28, 1997).

Nagata, S, "Apoptosis by Death Factor," *Cell 88*:355-365, Cell Press (Feb. 1997).

Naka, et al., "Effects of tumor necrosis factor-related apoptosis-inducing ligand alone and in combination with chemotherapeutic agents on patients' colon tumors growth in SCID mice", *Cancer Res.*, vol. 62, No. 20, pp. 5800-5806, Oct. 15, 2002.

NCBI Entrez, GenBank Accession No. W65310, Hiller, L. et al., National Center for Biotechnology Information (Oct. 1996).

NCBI Entrez, Genbank Report, Accession No. AA102383, from Hillier, L., et al. (Oct. 28, 1996).

NCBI Entrez, Genbank Report, Accession No. AA102745, from Hillier, L., et al. (Oct. 28, 1996).

NCBI Entrez, Genbank Report, Accession No. AA102746, from Hillier, L., et al. (Oct. 28, 1996).

NCBI Entrez, Genbank Report, Accession No. AA150849, from Hillier, L., et al. (Dec. 10, 1996).

NCBI Entrez, Genbank Report, Accession No. AA223122, from Hillier, L., et al. (Feb. 1997).

NCBI Entrez, Genbank Report, Accession No. AA232440, from Hillier, L., et al. (Feb. 1997).

NCBI Entrez, Genbank Report, Accession No. AA639619 from Strausberg, R. (1997).

NCBI Entrez, Genbank Report, Accession No. Z66083, from MacDonald, M., et al. (Oct. 1995).

NCBI Genbank Accession No. U90875, Pan, G. et al., (Apr. 1997).

Netwon, et al., "A dominant interfering mutant of FADD/MORT1 enhances deletion of autoreactive thymocytes and inhibits proliferation of mature T lymphcytes," *The EMBO Journal*, 17(3):706-718 (1998).

Newton, et al., "Effects of a dominant interfering mutant of FADD on signal transduction in activated T cells," *Current Biology*, 11(4):272-276 (Feb. 20, 2001).

Newton, et al., "FADD/MORT1 regulates the pre-TCR checkpoint and can function as a tumour suppressor," *The EMBO Journal*, 19(5):931-941 (2000).

Newton, et al., "Ionizing radiation and chemotherapeutic drugs induce apoptosis in lymphocytes in the absence of Fas or FADD/MORT1 signaling: Implications for cancer therapy," *J. Exp. Med.*, 191(1):195-200 (Jan. 3, 2000).

Nimmanapalli, et al., "Cotreatment with STI-571 enhances tumor necrosis factor alpha-related apoptosis-inducing ligand (TRAIL or apo-21)-induced apoptosis of Bcr-Abl-positive human acute leukemia cells", *Clinical Cancer Research: An Official Journal of the American Association for Cancer Research*, vol. 7, No. 2, pp. 350-357, Feb. 2001.

O'Connor, et al., "CD95 (Fas/APO-1) and p53 signal apoptosis independently in diverse cell types," *Cancer Research*, 60:1217-1220 (Mar. 1, 2000).

O'Connor, et al., "Fas, p53, and apoptosis," *Science*, 284:1431b (May 28, 1999).

Odaka, et al., "Immunosuppressant deoxyspergualin induces apoptolic cell death in dividing cells," *Immunology*, 95(3):370-376 (Nov. 1998).

Old, LJ, et al., "Tumor Necrosis Factor," *Scientific American*, pp. 59-77, Scientific American, Inc. (May 1988).

Ozawa, F. et al, "Effects and expression of TRAIL and its apoptosis-promoting receptors in human pancreatic cancer," Cancer Lett. 163(1):71-81 (2001).

Pan, et al., "TRUNDD, a new member of the TRAIL receptor family that antagonizes TRAIL signalling," FEBS Letters, 424:41-45 (1998).

Pan, G et al, "The Receptor for the Cytotoxic Ligand TRAIL," Science 276:111-113 (1997).

Pan, G et al., "An Antagonist Decoy Receptor and a Death Domain-Containing Receptor for TRAIL," Science 277:815-818 (1997).

PAUL, Fundamental Immunology, Raven Press, chapter 8, p. 242 (1993).

Pukac, et al., "HGS-ETR1, a fully human TRAIL-receptor 1 monoclonal antibody, induces cell death in multiple tumour types in vitro and in vivo", British Journal of Cancer, vol. 92, No. 8, pp. 1430-1441, Apr. 2005.

Rabizadeh, S et al., "Induction of Apoptosis by the Low-Affinity NGF Receptor," Science 261:345-348, American Association for the Advancement of Science (1993).

Reiger, et al., Glossary of Genetics and Cytogenetics, Classical and Molecular, 4th Ed., Springer-Verlay, Berlin (1976).

Rieger et al., "APO2 ligand: a novel lethal weapon against malignant glioma?" FEBS Letters 427(1): 124-128 (1998).

Roguska, MA, et al., "Humanization of murine monoclonal antibodies through variable domain resurfacing," Proc. Natl. Acad. Sci. USA 91:969-973 (1994).

Röhn, et al., "CCNU-dependent potentiation of TRAIL/Apo2L-induced apoptosis in human glioma cells is p53-independent but may involve enhanced cytochrome c release", Oncogene, vol. 20, No. 31, pp. 4128-4137, Jul. 2001.

Rudikoff, et al., "Single amino acid substitution altering antigen-binding specificity," Proc. Natl. Acad. Sci. USA, 79:1979 (1982).

Ruf et al., "Structure and Expression of the gene coding for the alpha-subunit of DNA-dependent RNA polymerase from the chloroplast genome of Zea mays," Nucleic Acids Res. 16(13):5741-5754 (1988).

Salcedo, et al., "TRM-1, a fully human TRAIL-R1 agonistic monoclonal antibody, displays in vitro and in vivo antitumor activity", Proceedings of the American Association for Cancer Research Annual Meeting, vol. 43, p. 856, Mar. 2002.

Schier et al., "Isolation of picomolar affinity anti-c-erbB-2 single-chain Fv by molecular evolution of the complementarity determining regions in the center of the antibody binding site," J. Mol. Biol., 263:551-567 (1996).

Schneider, et al., "TRAIL Receptors 1 (DR4) and 2 (DR5) signal FADD-dependent apoptosis and activate NF-□B," Immunity, 7:831-836 (Dec. 1997).

Screaton, et al., "LARD: A new lymphoid-specific death domain containing receptor regulated by alternative pre-mRNA splicing," Proc. Natl. Acad. Sci. USA, 94:4615-4619 (Apr. 1997).

Sheikh, SM, et al., "p53-dependent Regulation of the Death Receptor KILLER/DR5 Gene Expression in Response to Genotoxic Stress and Tumor Necrosis Factor α,"Cancer Res. 58:1593-1598, American Association for Cancer Research (Apr. 1998).

Sheridan JP et al., "Control of TRAIL-Induced apoptosis by a family of signaling and decoy receptors," Science 277:818-821 (1997).

Simonitsch, et al., "Autocrine self-elimination of cultured ovarian cancer cells by tumor necrosis factor alpha (TNF-alpha)," British Journal of Cancer, 78(7):862-870 (Oct. 1998).

Smith, et al., "CrmA expression in T lymphocytes of transgenic mice inhibits CD95 (Fas/APO-1)-transduced apoptosis, but does not cause lymphdenopathy or autoimmune disease," The EMBO Journal, 15(19):5167-5176 (1996).

Strader et al., "Structural basis of beta-adrenergic receptor function," FASEB 3:1825-1832 (1989).

Strasser. et a;/. "Bcl-2 and Fas/APO-1 regulate distinct pathways to lymphocyte apoptosis," The EMBO Journal, 14:6136-6147 (1995).

Stratagene Cloning Systems catalog, p. 304, 1994.

Tanaka, et al., "Expression and antitumor effects of TRAIL in human cholanglocarcinom", Hepatology, vol. 32, No. 3, pp. 523-527, Sep. 2000.

Tartaglia, et al., "A novel domain within the 55 kd TNF receptor signals cell death," Cell, 74(5):845-853 (1993).

Thome, et al., "Viral FLICE-inhibitory proteins (FLIPs) prevent apoptosis induced by death receptors," Nature, 386:517-521 (Apr. 3, 1997).

Trauth, et al., "Monoclonal antibody-mediated tumor regression by induction of apoptosis" Science, vol. 245, No. 4915, pp. 301-305, Jul. 21, 1989.

Uhlen, M., et al., "Fusion proteins in biotechnology and structural biology," Curr. Opin. Biotechnol. 3:363-369, Current Biology Ltd. (1992).

Uniprot Database Accession No. Q9UL86, May 1, 2000.

Van Geelen, et al., "Differential modulation of the TRAIL receptors and the CD95 receptor in colon carcinoma cell lines", Br. J. Cancer, vol. 89, No. 2, pp. 363-373, Jul. 21, 2003.

Vaughan, et al., "Human antibodies with sub-nanomolar affinities isolated from a large non-immunized phage display library", Nature Biotechnology, vol. 14, pp. 309-314, Mar. 1, 1996.

Villunger, et al., "Fas ligand, Bcl-2, granulocyte colony-stimulating factor, and p38 mitogen-activated protein kinase: regulators of distinct cell death and survival pathways in granulocytes," J. Exp. Med., 192(5):647-657 (Sep. 4, 2000).

Villunger, et al., "Fas ligand-induced c-Jun kinase activation in lymphoid cells requires extensive receptor aggregation but is independent of DAXX, and Fas-mediated cell death does not involve DAXX, RIP, or RAIDD," The Journal of Immunology, pp. 1337-1343 (2000).

Walczak, et al., "Tumoricidal activity of tumor necrosis factor-related apoptosis-inducing ligand in vivo", Nature Medicine, vol. 5, No. 2, pp. 157-163, Feb. 1999.

Walczak, H. et al., "TRAIL-R2: a novel apoptosis-mediating receptor for TRAIL," EMBO J. 16(17):5386-5397, Oxford University Press (1997).

Wallach, D., "TNF Ligand and TNF/NGF Receptor Familes," in Cytokine Reference. A compendium of cytokines and other mediators of host defense, Oppenheim, J.J., et al., eds., Academic Press, Inc., San Diego, CA, pp. 377-411 (Aug. 2000).

Wang, et al., "Requirement of p53 targets in chemosensitization of colonic carcinoma to death ligand therapy", Proc. Natl. Acad. Sci., vol. 100, No. 25, pp. 15095-15100, USA, Dec. 9, 2003.

Watanabe-Fukunaga, et al., "Lymphoproliferation disorder in mice explained by defects in Fas antigen that mediates apoptosis," Nature, 356:314-317 (Mar. 26, 1992).

Wiley, Sr., et al., "Identification and Characterization of a New Member of the TNF Family that Induces Apoptosis," Immunity 3:673-682, Cell Press (1995).

Wong, et al., "TRANCE is a novel ligand of the tumor necrosis factor receptor family that activates c-Jun N-terminal kinase in T cells," The Journal of Biological Chemistry, 272(40):25190-25194 (1997).

Wu, G.S. et al., "KILLER/DR5, a novel DNA-damage inducible death receptor gene, links the p53-tumor suppressor to caspase activation and apoptotic death," Adv. Exp. Med. Biol. 465:143-151 (2000).

Yoshida, et al., "Rapid B cell apoptosis induced by antigen receptor ligation does not require Fas (CD95/APO-1), the adaptor protein FADD/MORT-1 or CrmA-sensitive caspases but is defective in both MRL-+/+ and MRL-lpr/lpr mice," International Immunology, 12(4):517-526 (Jan. 4, 2000).

Zamai, L., et al., "Natural killer (NK) Cell-mediated Cytotoxicity: Differential Use of TRAIL and Fas Ligand by Immature and Mature Primary Human NK Cells," J. Exp. Med. 188:2375-2380, Rockefeller University Press (Dec. 1998).

Zou, et al., "Administration of interleukin 13 to simian immunodeficiency virus-infected macaques: Induction of intestinal epithelial atrophy," AIDS Research and Human Retroviruses, 14(9):775-783 (Jun. 10, 1998).

* cited by examiner

METHODS OF TREATING CANCER USING ANTIBODIES THAT IMMUNOSPECIFICALLY BIND TO TRAIL RECEPTORS

CROSS-REFERENCE TO RELATED APPLICATIONS

This application claims the benefit of priority under 35 U.S.C. § 119(e) based on U.S. Provisional Application Ser. No. 60/608,362 filed Sep. 10, 2004. This application is also a continuation-in-part and claims benefit of priority under 35 U.S.C. § 120 of International Application No. PCT/US03/25457, filed Aug. 15, 2003, which claims benefit under 35 U.S.C. § 119(e) based on U.S. Provisional Application Nos. 60/403,382, filed Aug. 15, 2002; 60/425,730, filed Nov. 13, 2002; and 60/468,050, filed May 6, 2003. This application is also a continuation-in-part and claims benefit of priority under 35 U.S.C. § 120 of Non-Provisional application Ser. No. 10/139,785, filed May 7, 2002, now U.S. Pat. No. 7,064,189, issued Jun. 20, 2006, which claims benefit under 35 U.S.C. § 119(e) based on U.S. Provisional Application Nos. 60/293,473, filed May 25, 2001; 60/294,981, filed Jun. 4, 2001; 60/309,176, filed Aug. 2, 2001; 60/323,807, filed Sep. 21, 2001; 60/327,364, filed Oct. 9, 2001; 60/331,044, filed Nov. 7, 2001; 60/331,310, filed Nov. 14, 2001; 60/341,237, filed Dec. 20, 2001; and 60/369,860, filed Apr. 5, 2002. Each of the above-identified priority applications is hereby incorporated by reference in its entirety.

FIELD OF THE INVENTION

The present invention relates to antibodies and related molecules that immunospecifically bind to TRAIL receptor, TR4. Such antibodies have uses, for example, in the prevention and treatment of cancers and other proliferative disorders. The invention also relates to nucleic acid molecules encoding anti-TR4 antibodies, vectors and host cells containing these nucleic acids, and methods for producing the same. The present invention relates to methods and compositions for preventing, detecting, diagnosing, treating or ameliorating a disease or disorder, especially cancer and other hyperproliferative disorders, comprising administering to an animal, preferably a human, an effective amount of one or more antibodies or fragments or variants thereof, or related molecules, that immunospecifically bind to TR4.

BACKGROUND OF THE INVENTION

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, at least eighteen members of the TNF ligand superfamily have been identified and at least nineteen members of the TNF-receptor superfamily have been characterized (See, e.g., Locksley et el., Cell (2001) 104:487-501).

Among the ligands there are included TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals, 22:291-295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al., Cell 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., Science 264:667-668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., Cell 74:845 (1993)).

Apoptosis, or programmed cell death, is a physiologic process essential to the normal development and homeostasis of multicellular organisms (H. Steller, Science 267, 1445-1449 (1995)). Derangements of apoptosis contribute to the pathogenesis of several human diseases including cancer, neurodegenerative disorders, and acquired immune deficiency syndrome (C. B. Thompson, Science 267, 1456-1462 (1995)). Recently, much attention has focused on the signal transduction and biological function of two cell surface death receptors, Fas/APO-1 and TNFR-1 (J. L. Cleveland, et al., Cell 81, 479-482 (1995); A. Fraser, et al., Cell 85, 781-784 (1996); S. Nagata, et al., Science 267, 1449-56 (1995)). Both are members of the TNF receptor family which also include TNFR-2, low affinity NGFR, CD40, and CD30, among others (C. A. Smith, et al., Science 248, 1019-23 (1990); M. Tewari, et al., in Modular Texts in Molecular and Cell Biology M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the *Drosophila* suicide gene, reaper (P. Golstein, et al., *Cell* 81, 185-6 (1995); K. White et al., *Science* 264, 677-83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan, et al., *Cell* 81, 505-12 (1995); M. P. Boldin, et al., *J. Biol Chem* 270, 7795-8 (1995); F. C. Kischkel, et al., *EMBO* 14, 5579-5588 (1995)), which in turn binds and presumably activates FLICE/MACH1, a member of the ICE/CED-3 family of pro-apoptotic proteases (M. Muzio et al., *Cell* 85, 817-827 (1996); M. P. Boldin, et al, *Cell* 85, 803-815 (1996)). While the central role of Fas/APO-1 is to trigger cell death, TNFR-1 can signal an array of diverse biological activities-many of which, stem from its ability to activate NF-kB (L. A. Tartaglia, et al., *Immunol Today* 13, 151-3 (1992)). Accordingly, TNFR-1 recruits the multivalent adapter molecule TRADD, which like FADD, also contains a death domain (H. Hsu, et al., *Cell* 81, 495-504 (1995); H. Hsu, et al., *Cell* 84, 299-308 (1996)). Through its associations with a number of signaling molecules including FADD, TRAF2, and RIP, TRADD can signal both apoptosis and NF-kB activation (H. Hsu, et al., *Cell* 84, 299-308 (1996); H. Hsu, et al., *Immunity* 4, 387-396 (1996)).

One TNF-related apoptosis inducing ligand has been reported by several groups and has been ascribed the name Apoptosis Inducing Molecule I (AIM-I) (Intenation Application No. WO 97/33899) and TNF-related apoptosis-inducing ligand or (TRAIL) (Wiley, S. R. et al., *Immunity* 3:673-682 (1995)). Pitti, R. M. et al., refer to the new molecule as Apo-2 ligand or ("Apo-2L"). For convenience, it will be referred to herein as TRAIL. The amino acid sequence of TRAIL is given in SEQ ID NO:66.

Unlike FAS ligand whose transcripts appear to be largely restricted to stimulated T-cells, significant levels of TRAIL are seen in many tissues, and it is constitutively transcribed by some cell lines. It has been shown that TRAIL acts independently from FAS ligand (Wiley, S. R., et al. (1995)), supra). Studies by Marsters, S. A. et al., have indicated that TRAIL activates apoptosis rapidly, within a time frame that is similar to death signalling by FAS/Apo-1L but much faster than TNF-induced apoptosis (*Current Biology*, 6:750-752 (1996)).

As many as five TRAIL receptors have been identified, including TR4 (also known as TRAIL receptor 1 (TRAIL-R1) and death receptor 4 (DR4), Pan et al., *Science* 276: 111-3 (1997), International Patent Application Nos. WO98/32856, WO00/67793, WO99/37684, WO2000/34355, WO99/02653, SEQ ID NO:1); TR7 (also referred to as TRAIL receptor 2 (TRAIL-R2), DR5, and KILLER, Pan et al., Science 277:815-8 (1997), Sheridan et al., Science 277:818-21 (1997), Chaudhury et al., Immunity 7:821-30 (1997), International Patent Application Nos. WO98/46643, WO99/09165, WO99/11791, WO98/41629, WO00/66156, and WO98/35986, SEQ ID NO:3); TR1 (also referred to as Osteoprotegrin (OPG) osteoclastogenesis inhibitory factor (OCIF), TNFRSF11B, and FTHMA-090 (International Patent Application Nos. WO98/12344, WO2000/54651, WO2001/04137, WO66/26217, WO98/07840, WO2000/21554, WO99/53942, and WO2001/03719, SEQ ID NO:5); TR5 (also referred to as TRAIL receptor 3 (TRAIL-R3), decoy receptor 1 (DcR1) and TRID) (Degli-Esposti et al., J. Exp. Med. 186:1165-70 (1997), International Patent Application Nos. WO98/30693, WO00/71150, WO99/00423, EP867509, WO98/58062, SEQ ID NO:2); and TR10 (also referred to as TRAIL Receptor 4 (TRAIL-R4), DcR2, and TRUNDD, Pan et al., FEBS Lett. 424:41-5 (1998), Degli-Eposti et al., Immunity 7:813-20 (1997), International Patent Application Nos. WO98/54202, WO00/73321, WO2000/08155, WO99/03992, WO 2000/34355 and WO9910484, SEQ ID NO:4). TR4 and TR7 contain death domains in their cytoplasmic tails and the triggering of these receptors results in apoptosis. On the other hand, TR1, TR5 and TR10 can inhibit apoptosis induced by the cytotoxic ligand TRAIL in part because of their absent or truncated cytoplasmic death domains, respectively. Each of the publications and patents cited above is hereby incorporated by reference in their entireties, particularly with respect to the nucleotide and amino acid sequences of the TRAIL receptors disclosed therein.

The effects of TNF family ligands and TNF family receptors are varied and influence numerous functions, both normal and abnormal, in the biological processes of the mammalian system. There is a clear need, therefore, for identification and characterization of compositions, such as antibodies, that influence the biological activity of TNF receptors, both normally and in disease states. In particular, there is a need to isolate and characterize antibodies that modulate the biological activities of TRAIL receptors.

SUMMARY OF THE INVENTION

The present invention encompasses antibodies (including molecules comprising, or alternatively consisting of, antibody fragments or variants thereof) that immunospecifically bind to a TR4 polypeptide or polypeptide fragment or variant of TR4. In particular, the invention encompasses antibodies (including molecules comprising, or alternatively consisting of, antibody fragments or variants thereof) that immunospecifically bind to a polypeptide or polypeptide fragment or variant of human TR4 such as that of SEQ ID NO:1. In some embodiments, an antibody of the invention that immunospecifically bind to a TR4 polypeptide, also bind TR7 (e.g., SEQ ID NO:3), but not other proteins, including (TR1, TR5, and TR10 (SEQ ID NOS:5, 2 and 4.)

The present invention relates to methods and compositions for preventing, treating or ameliorating a disease or disorder comprising administering to an animal, preferably a human, an effective amount of one or more antibodies or fragments or variants thereof, or related molecules, that immunospecifically bind to TR4 or a fragment or variant thereof. In specific embodiments, the present invention relates to methods and compositions for preventing, treating or ameliorating a disease or disorder associated with TR4 function or TR4 ligand function or aberrant TR4 or TR4 ligand expression, comprising administering to an animal, preferably a human, an effective amount of one or more antibodies or fragments or variants thereof, or related molecules, that immunospecifically bind to a TR4 or a fragment or variant thereof. In highly preferred embodiments, the present invention relates to antibody-based methods and compositions for preventing, treating or ameliorating cancers and other hyperproliferative disorders (e.g., leukemia, carcinoma, and lymphoma). Other diseases and disorders which can be treated, prevented or ameliorated with the antibodies of the invention include, but are not limited to, neurodegenerative disorders (e.g., Parkinson's disease, Alzheimer's disease, and Huntington's disease), immune disorders (e.g., lupus, rheumatoid arthritis, multiple sclerosis, myasthenia gravis, Hashimoto's disease, and immunodeficiency syndrome), inflammatory disorders (e.g., asthma, allergic disorders, and rheumatoid arthritis), infectious diseases (e.g., AIDS, herpes viral infections, and other viral infections) and proliferative disorders.

In highly preferred embodiments, antibodies of the present invention are used in methods and compositions for preventing, diagnosing, prognosing, treating or ameliorating the following types of cancer: breast cancer, lung cancer, (including non-small cell lung cancer), colon cancer, cancer of the urinary tract, bladder cancer, kidney cancer, pancreatic cancer, liver cancer, stomach cancer, prostate cancer, leukemia, Non-Hodgkin's lymphoma, esophageal cancer, brain cancer, leukemia, ovarian cancer, testicular cancer, melanoma, uterine cancer, cervical cancer, cancer of the larynx, rectal cancer, and cancers of the oral cavity. In specific embodiments, antibodies of the invention are administered in combination with chemotherapeutics such as paclitaxel (Taxol), irinotecan (Camptosar, CPT-11), irinotecan analogs, and gemcitabine (GEMZAR™)) or other therapeutic agents useful in the treatment of cancers.

The present invention also encompasses methods and compositions for detecting, diagnosing, or prognosing diseases or disorders comprising administering to an animal, preferably a human, an effective amount of one or more antibodies or fragments or variants thereof, or related molecules, that immunospecifically bind to TR4 or a fragment or variant thereof. In specific embodiments, the present invention also encompasses methods and compositions for detecting, diagnosing, or prognosing diseases or disorders associated with TR4 function or TR4 ligand function or aberrant TR4 or TR4 ligand expression, comprising administering to an animal, preferably a human, an effective amount of one or more antibodies or fragments or variants thereof, or related molecules, that immunospecifically bind to TR4 or a fragment or variant thereof. In highly preferred embodiments, the present invention relates to antibody-based methods and compositions for detecting, diagnosing, or prognosing cancers and other hyperproliferative disorders (e.g., leukemia, carcinoma, and lymphoma). Other diseases and disorders which can be detected, diagnosed or prognosed with the antibodies of the invention include, but are not limited to, neurodegenerative disorders (e.g., Parkinson's disease, Alzheimer's disease, and Huntington's disease), immune disorders (e.g., lupus, rheumatoid arthritis, multiple sclerosis, myasthenia gravis, Hashimoto's disease, and immunodeficiency syndrome), inflammatory disorders (e.g., asthma, allergic disorders, and rheumatoid arthritis), infectious diseases (e.g., AIDS, herpes virus infections, and other viral infections), and proliferative disorders.

Another embodiment of the present invention includes the use of the antibodies of the invention as a diagnostic tool to monitor the expression of TR4 expression on cells.

The present inventors have generated single chain Fv's (scFvs) that immunospecifically bind TR4 polypeptides (e.g., SEQ ID NOs:1). Thus, the invention encompasses these scFvs, listed in Table 1. In addition, the invention encomasses cell lines engineered to express antibodies corresponding to these scFvs which are deposited with the American Type Culture Collection ("ATCC") as of the dates listed in Table 1 and given the ATCC Deposit Numbers identified in Table 1 The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

Further, the present invention encompasses the polynucleotides encoding the scFvs, as well as the amino acid sequences encoding the scFvs. Molecules comprising, or alternatively consisting of, fragments or variants of these scFvs (e.g., VH domains, VH CDRs, VL domains, or VL CDRs having an amino acid sequence of any one of the scFvs referred to in Table 1), that immunospecifically bind to TR4 or fragments or variants thereof are also encompassed by the invention, as are nucleic acid molecules that encode these antibodies and/or molecules. In highly preferred embodiments, the present invention encompasses antibodies, or fragments or variants thereof, that bind to the extracellular regions/domains of TR4 or fragments and variants thereof.

The present invention also provides antibodies that bind TR4 polypeptides which are coupled to a detectable label, such as an enzyme, a fluorescent label, a luminescent label, or a bioluminescent label. The present invention also provides antibodies that bind TR4 polypeptides which are coupled to a therapeutic or cytotoxic agent. The present invention also provides antibodies that bind TR4 polypeptides which are coupled to a radioactive material.

The present invention also provides antibodies that bind TR4 polypeptides that act as either TR4 agonists or TR4 antagonists. In specific embodiments, the antibodies of the invention stimulate apoptosis of TR4 expressing cells. In other specific embodiments, the antibodies of the invention inhibit TRAIL binding to TR4. In other specific embodiments, the antibodies of the invention upregulate TR4 expression.

The present invention also provides antibodies that inhibit apoptosis of TR4 expressing cells. In other specific embodiments, the antibodies of the invention downregulate TR4 expression.

In further embodiments, the antibodies of the invention have a dissociation constant ($K_D$) of $10^{-7}$ M or less. In preferred embodiments, the antibodies of the invention have a dissociation constant ($K_D$) of $10^{-9}$ M or less.

The present invention further provides antibodies that stimulate apoptosis of TR4 expressing cells better than an equal concentration of TRAIL polypeptide stimulates apoptosis of TR4 expressing cells.

The present invention further provides antibodies that stimulate apoptosis of TR4 expressing cells equally well in the presence or absence of antibody cross-linking reagents; and/or stimulate apoptosis with equal or greater potency as an equal concentration of TRAIL in the absence of a cross-linking antibody or other cross-linking agent.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention also provides for antibodies that preferentially bind TR4 and/or TR7 relative to their ability to bind other proteins (including TR1, TR5 and TR10).

In certain embodiments, properties of the antibodies of the present invention, as detailed in the Examples below, make the antibodies better therapeutic agents than previously described TR4 binding antibodies.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs). The present invention further provides mixtures of antibodies, wherein the mixture corresponds to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The present invention also provides for fusion proteins comprising an antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

DETAILED DESCRIPTION OF THE INVENTION

Definitions

Figure 1:
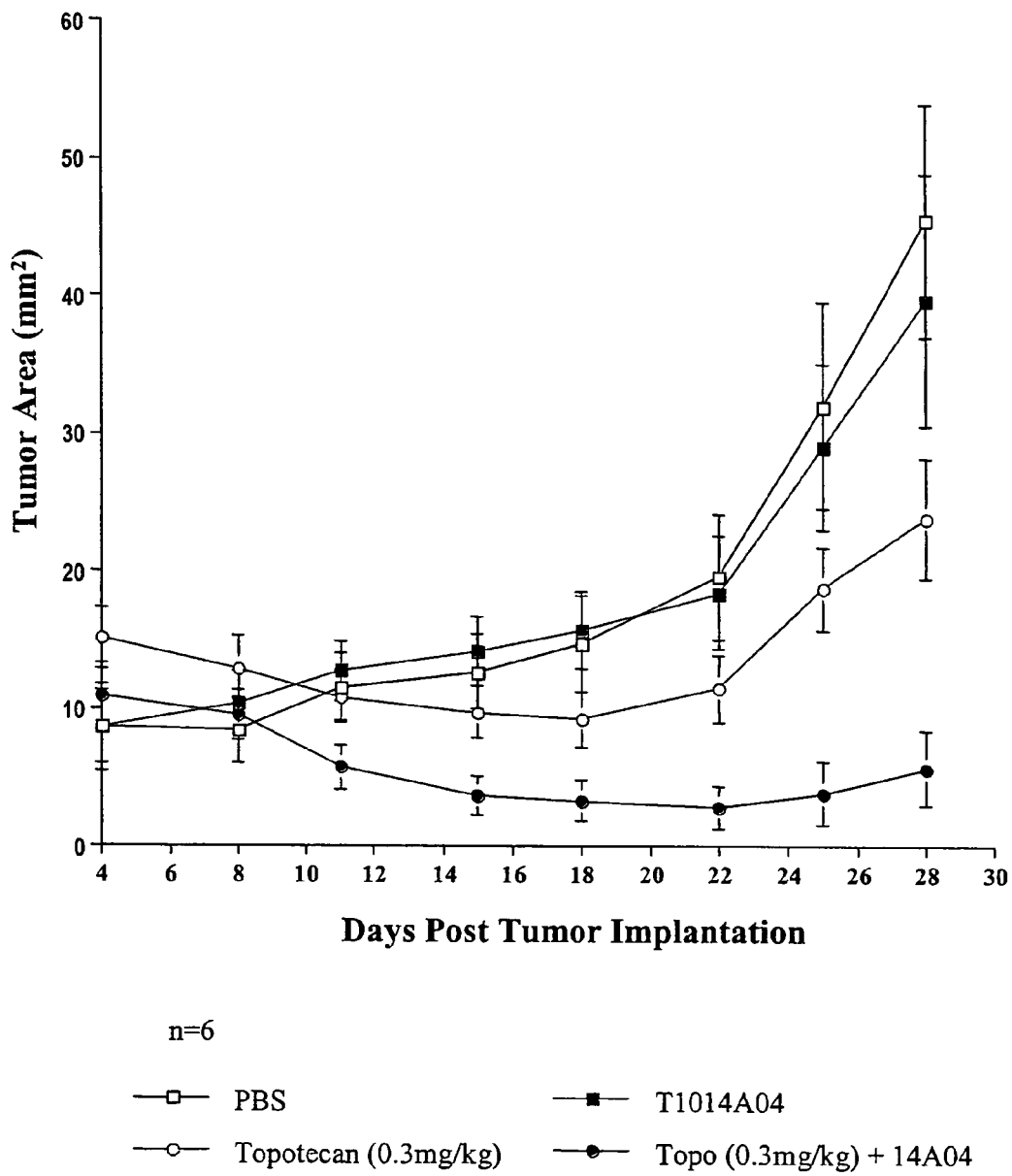
FIG. 1 shows the effect of T1014A04 treatment on SW480 tumor growth in Swiss nu/nu mice with or without Topotecan treatment at 0.3 mg/kg.

The term "antibody," as used herein, refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody. Antibodies that immunospecifically bind to TR4 may have cross-reactivity with other antigens, e.g., another TRAIL Receptor. Preferably, antibodies that immunospecifically bind to TR4 do not cross-react with other antigens (e.g., other TRAIL receptors or other members of the Tumor Necrosis Factor Receptor superfamily). Antibodies that immunospecifically bind to TR4 can be identified, for example, by immunoassays or other techniques known to those of skill in the art, e.g., the immunoassays described in the Examples below.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. Preferably, an antibody of the invention comprises, or alternatively consists of, a VH domain, VH CDR, VL domain, or VL CDR having an amino acid sequence of any one of those referred to in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')$_2$ fragments are tetravalent, whereas dimers of Fab fragments or scFv molecules are bivalent. Individual monomers withon an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., *Proceedings of the National Academy of Sciences* USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, *The Journal of Immunology* (2002) 25:396-404, which is hereby incorporated by reference in its entirety.

Alternatively, antibodies can be made to multimerize through recombinant DNA techniques. IgM and IgA naturally form antibody multimers through the interaction with the mature J chain polypeptide (e.g., SEQ ID NO:67). Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) *Clinical Immunology* 101:21-31. and Frigerio et al., (2000) *Plant Physiology* 123:1483-94., both of which are hereby incorporated by reference in their entireties.) IgA dimers are naturally secreted into the lumen of mucosa-lined organs. This secretion is mediated through interaction of the J chain with the polymeric IgA receptor (pIgR) on epithelial cells. If secretion of an IgA form of an antibody (or of an antibody engineered to to contain a J chain interaction domain) is not desired, it can be greatly reduced by expressing the antibody molecule in association with a mutant J chain that does not interact well with pIgR (e.g., SEQ ID NOS:68-70; Johansen et al., *The Journal of Immunology* (2001) 167:5185-5192 which is hereby incorporated by reference in its entirety). SEQ ID NO:68 is a mutant form of a human mature J chain with C134S mutation compared to the mature form of human J chain (SEQ ID NO:67). SEQ ID NO:69 is a mutant form of a human mature J chain with amino acids 113-137 deleted compared to the mature form of human J chain (SEQ ID NO:67). SEQ ID NO:70 shows a mutant form of human mature J chain with C109S and C134S mutation compared to the mature form of human J chain (SEQ ID NO:67). Expression of an antibody with one of these mutant J chains will reduce its ability to bind to the polymeric IgA receptor on epithelial cells, thereby reducing transport of the antibody across the epithelial cell and its resultant secretion into the lumen of mucosa lined organs. ScFv dimers can also be formed through recombinant techniques known in the art; an example of the construction of scFv dimers is given in Goel et al., (2000) *Cancer Research* 60:6964-6971 which is hereby incorporated by reference in its entirety. Antibody multimers may be purified using any suitable method known in the art, including, but not limited to, size exclusion chromatography.

Unless otherwise defined in the specification, specific binding or immunospecifc binding by an anti-TR4 antibody means that the anti-TR4 antibody binds TR4 but does not significantly bind to (i.e., cross react with) proteins other than TR4, such as other proteins in the same family of proteins). An antibody that binds TR4 protein and does not cross-react with other proteins is not necessarily an antibody that does not bind said other proteins in all conditions; rather, the TR4-specific antibody of the invention preferentially binds TR4 compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that TR4-specific antibodies bind to epitopes of TR4, an antibody that specifically binds TR4 may or may not bind fragments of TR4 and/or variants of TR4 (e.g., proteins that are at least 90% identical to TR4) depending on the presence or absence of the epitope bound by a given TR4-specific antibody in the TR4 fragment or variant. Likewise, TR4-specific antibodies of the invention may bind species orthologues of TR4 (including fragments thereof) depending on the presence or absence of the epitope recognized by the antibody in the orthologue. Additionally, TR4-specific antibodies of the invention may bind modified forms of TR4, for example, TR4 fusion proteins. In such a case when antibodies of the invention bind TR4 fusion proteins, the antibody must make binding contact with the TR4 moiety of the fusion protein in order for the binding to be specific. Antibodies that specifically bind to TR4 can be identified, for example, by immunoassays or other techniques known to those of skill in the art, e.g., the immunoassays described in the Examples below.

In some embodiments the present invention encompasses antibodies that immunospecifically or specifically bind both TR4 and TR7. Specific binding or immunospecifc binding by an antibody that immunospecifically binds TR4 and TR7 means that the antibody binds TR4 and TR7 but does not significantly bind to (i.e., cross react with) proteins other than TR4 or TR7, such as other proteins in the same family of proteins). An antibody that binds TR4 and TR7 proteins and does not cross-react with other proteins is not necessarily an antibody that does not bind said other proteins in all conditions; rather, the antibody that immunospcifically or specifically binds both TR4 and TR7 preferentially binds TR4 and TR7 compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that antibodies that bind TR4 and TR7 bind to epitopes common to TR4 and TR7, an antibody that specifically binds TR4 and TR7 may or may not bind fragments of TR4, TR7 and/or variants of TR4 or TR7 (e.g., proteins that are at least 90% identical to TR4 or TR7, respectively) depending on the presence or absence of the epitope bound by a given antibody in the TR4 or TR7 fragment or variant. Likewise, antibodies of the invention that immunospecifically bind TR4 and TR7 may bind species orthologues of TR4 and/or TR7 (including fragments thereof) depending on the presence or absence of the epitope recognized by the antibody in the orthologues. Additionally, antibodies of the invention that immunospecifically bind TR4 and TR7 may bind modified forms of TR4 or TR7, for example, TR4 or TR7 fusion proteins. In such a case when antibodies of the invention bind fusion proteins, the antibody must make binding contact with the TR4 or TR7 moiety of the fusion protein in order for the binding to be specific. Antibodies that specifically bind to TR4 or TR7 can be identified, for example, by immunoassays or other techniques known to those of skill in the art, e.g., the immunoassays described in the Examples below.

The term "variant" as used herein refers to a polypeptide that possesses a similar or identical function as a TR4 polypeptide, a fragment of a TR4 polypeptide, an anti-TR4 antibody or antibody fragment thereof, but does not necessarily comprise a similar or identical amino acid sequence of a TR4 polypeptide, a fragment of a TR4 polypeptide, an anti-TR4 antibody or antibody fragment thereof, or possess a similar or identical structure of a TR4 polypeptide, a fragment of a TR4 polypeptide, an anti-TR4 antibody or antibody fragment thereof, respectively. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of TR4 polypeptide (SEQ ID NO:1), a fragment of, an anti-TR4 antibody or antibody fragment thereof (including a VH domain, VHCDR, VL domain, or VLCDR having an amino acid sequence of any one or more scFvs referred to in Table 1) described herein; (b) a polypeptide encoded by a nucleotide sequence, the complementary sequence of which hybridizes under stringent conditions to a nucleotide sequence encoding TR4 (SEQ ID NO:1), a fragment of a TR4 polypeptide, an anti-TR4 antibody or antibody fragment thereof (including a VH domain, VHCDR, VL domain, or VLCDR having an amino acid sequence of any one of those referred to in Table 1), described herein, of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding a TR4 polypeptide, a fragment of a TR4 polypeptide, an anti-TR4 antibody or antibody fragment thereof (including a VH domain, VHCDR, VL domain, or VLCDR having an amino acid sequence of any one or more scFvs referred to in Table 1), described herein. A polypeptide with similar structure to a TR4 polypeptide, a fragment of a TR4 polypeptide, an anti-TR4 antibody or antibody fragment thereof, described herein refers to a polypeptide that has a similar secondary, tertiary or quaternary structure of a TR4 polypeptide, a fragment of a TR4 polypeptide, an anti-TR4 antibody, or antibody fragment thereof, described herein. The structure of a polypeptide can determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl. Acad. Sci.* USA 87:2264-2268(1990), modified as in Karlin and Altschul *Proc. Natl. Acad. Sci.* USA 90:5873-5877(1993). The BLASTn and BLASTx programs of Altschul, et al. *J. Mol. Biol.* 215:403-410(1990) have incorporated such an alogrithm. BLAST nucleotide searches can be performed with the BLASTn program (score=100, wordlength=12) to obtain nucleotide sequences homologous to a nucleic acid molecule of the invention. BLAST protein searches can be performed with the BLASTx program (score=50, wordlength=3) to obtain amino acid sequences homologous to a protein molecule of the invention. To obtain gapped alignments for comparison purposes, Gapped BLAST can be utilized as described in Altschul et al. *Nucleic Acids Res.* 25:3589-3402 (1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used. (See world wide web at ncbi.nlm.nih.gov).

Another example of a mathematical algorithm utilized for the comparison of sequences is the algorithm of Myers and Miller, CABIOS (1989). The ALIGN program (version 2.0) which is part of the GCG sequence alignment software package has incorporated such an alogrithm. Other algorithms for sequence analysis known in the art include ADVANCE and ADAM as described in Torellis and Robotti *Comput. Appl. Biosci.*, 10:3-5(1994); and FASTA described in Pearson and Lipman *Proc. Natl. Acad. Sci* 85:2444-8 (1988). Within FASTA, ktup is a control option that sets the sensitivity and speed of the search.

The term "derivative" as used herein, refers to a variant polypeptide of the invention that comprises, or alternatively consists of, an amino acid sequence of a TR4 polypeptide, a fragment of a TR4 polypeptide, or an antibody of the invention that immunospecifically binds to a TR4 polypeptide, which has been altered by the introduction of amino acid residue substitutions, deletions or additions. The term "derivative" as used herein also refers to a TR4 polypeptide, a fragment of a TR4 polypeptide, an antibody that immunospecifically binds to a TR4 polypeptide which has been modified, e.g., by the covalent attachment of any type of molecule to the polypeptide. For example, but not by way of limitation, a TR4 polypeptide, a fragment of a TR4 polypeptide, or an anti-TR4 antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a TR4 polypeptide, a fragment of a TR4 polypeptide, or an anti-TR4 antibody, may be modified by chemical modifications using techniques known to those of skill in the art, including, but not limited to, specific chemical cleavage, acetylation, formylation, metabolic synthesis of tunicamycin, etc. Further, a derivative of a TR4 polypeptide, a fragment of a TR4 polypeptide, or an anti-TR4 antibody, may contain one or more non-classical amino acids. A polypeptide derivative possesses a similar or identical function as a TR4 polypeptide, a fragment of a TR4 polypeptide, or an anti-TR4 antibody, described herein.

The term "epitopes" as used herein refers to portions of TR4 having antigenic or immunogenic activity in an animal, preferably a mammal. An epitope having immunogenic activity is a portion of TR4 that elicits an antibody response in an animal. An epitope having antigenic activity is a portion of TR4 to which an antibody immunospecifically binds as determined by any method known in the art, for example, by the immunoassays described herein. Antigenic epitopes need not necessarily be immunogenic.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues, of the amino acid sequence of TR4, or an anti-TR4 antibody (including molecules such as scFv's, that comprise, or alternatively consist of, antibody fragments or variants thereof).

The term "fusion protein" as used herein refers to a polypeptide that comprises, or alternatively consists of, an amino acid sequence of an anti-TR4 antibody of the invention and an amino acid sequence of a heterologous polypeptide (i.e., a polypeptide unrelated to an antibody or antibody domain).

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

Antibodies of the present invention are preferably provided in an isolated form, and preferably are substantially purified. By "isolated" is intended an antibody removed from its native environment. Thus, for eaxample, a polypeptide produced and/or contained within a recombinant host cell is considered isolated for purposes of the present invention.

By "isolated antibody" is intended an antibody removed from its native environment. Thus, an antibody produced and/or contained within a recombinant host cell is considered isolated for purposes of the present invention.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the heavy and the ligt chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547 1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int J Cancer Suppl* 7:51-52 (1992)).

Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Anti-TR4 Antibodies

Using phage display technology, the present inventors have identified single chain antibody molecules ("scFvs") that immunospecifically bind to TR4 (or fragments or variants thereof). Molecules comprising, or alternatively consisting of, fragments or variants of these scFvs (e.g., including VH domains, VH CDRS, VL domains, or VL CDRs having an amino acid sequence of any one of those referred to in Table 1), that immunospecifically bind to TR4 (or fragments or variants thereof) are also encompassed by the invention, as are nucleic acid molecules that encode these scFvs, and/or molecules.

In particular, the invention relates to scFvs comprising, or alternatively consisting of, an amino acid sequence selected from the group consisting of SEQ ID NOs: 42-53, preferably SEQ ID NOs:42 and 43 as referred to in Table 1 below. Molecules comprising, or alternatively consisting of, fragments or variants of these scFvs (e.g., including VH domains, VH CDRs, VL domains, or VL CDRs having an amino acid sequence of any one of those referred to in Table 1), that immunospecifically bind to TR4 are also encompassed by the invention, as are nucleic acid molecules that encode these scFvs, and/or molecules (e.g., SEQ ID NOs: 54-65).

ScFvs corresponding to SEQ ID NOS:42-53 were selected for their ability bind TR4 polypeptide.

The present invention provides antibodies (including molecules comprising, or alternatively consisting of, antibody In a preferred embodiment, an antibody of the invention is the antibody expressed by cell line NSO αTRAIL 1985 BU #81 P:15 Jun. 21, 2001 (See Table 1).

In a preferred embodiment, an antibody of the invention is the antibody expressed by cell line TRAIL (NSO) 14G03 #39 P:14 Jul. 2, 2001 (See Table 1).

In a preferred embodiment, an antibody of the invention is the antibody expressed by cell line NSO anti-TRAIL 14F08 #28 P:11 (See Table 1).

TABLE 1 scFvs that Immunospecifically bind to TRAIL Receptors

| scFv | scFv protein SEQ ID NO: | scFv DNA SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 | Cell Line Expressing antibody | ATCC Deposit Number | ATCC Deposit Date |
|---|---|---|---|---|---|---|---|---|---|---|---|---|---|
| T1014A04 | 42 | 54 | 1-118 | 26-35 | 50-66 | 99-107 | 135-245 | 157-170 | 186-192 | 225-234 | NSO αTRAIL 1985 BU #81 P: 15 Jun. 21, 2001 | PTA-3571 | Jul. 30, 2001 |
| T1014G03 | 43 | 55 | 1-118 | 26-35 | 50-66 | 99-107 | 135-245 | 157-170 | 186-192 | 225-234 | TRAIL (NSO) 14G03 #39 P: 14 Jul. 2, 2001 | PTA-3570 | Jul. 30, 2001 |
| T1014A02 | 44 | 56 | 1-116 | 26-35 | 50-65 | 98-105 | 134-244 | 156-168 | 184-190 | 223-233 | | | |
| T1014A12 | 45 | 57 | 1-118 | 26-35 | 50-66 | 99-107 | 135-245 | 157-170 | 186-192 | 225-234 | | | |
| T1014B01 | 46 | 58 | 1-118 | 26-35 | 50-66 | 99-107 | 135-245 | 157-170 | 186-192 | 225-234 | | | |
| T1014B11 | 47 | 59 | 1-118 | 26-35 | 50-66 | 99-107 | 135-245 | 157-170 | 186-192 | 225-234 | | | |
| T1014F08 | 48 | 60 | 1-118 | 26-35 | 50-66 | 99-107 | 135-245 | 157-170 | 186-192 | 225-234 | NSO anti-TRAIL 14F08 #28 P: 11 | PTA-3675 | Aug. 29, 2001 |
| T1014G04 | 49 | 61 | 1-118 | 26-35 | 50-66 | 99-107 | 135-245 | 157-170 | 186-192 | 225-234 | | | |
| T1015A02 | 50 | 62 | 1-123 | 26-37 | 52-67 | 100-112 | 140-250 | 162-174 | 190-196 | 229-239 | | | |
| T1015A07 | 51 | 63 | 1-118 | 26-35 | 50-66 | 99-107 | 135-245 | 157-170 | 186-192 | 225-234 | | | |
| T1015E01 | 52 | 64 | 1-118 | 26-35 | 50-66 | 99-107 | 135-245 | 157-170 | 186-192 | 225-234 | | | |
| T1006F07 | 53 | 65 | 1-125 | 26-35 | 50-66 | 99-114 | 142-249 | 164-174 | 190-196 | 229-238 | | | | fragments or variants thereof) that immunospecifically bind to a polypeptide or a polypeptide fragment of TR4. In particular, the invention provides antibodies corresponding to the scFvs referred to in Table 1. Such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule, as described in more detail in Example 5 below.

NS0 cell lines that express IgG1 antibodies that comprise the VH and VL domains of scFvs of the invention have been deposited with the American Type Culture Collection ("ATCC") on the dates listed in Table 1 and given the ATCC Deposit Numbers identified in Table 1. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. Accordingly, in one embodiment, the invention provides antibodies that comprise the VH and VL domains of scFvs of the invention.

The present invention encompasses antibodies (including molecules comprising, or alternatively consisting of, antibody fragments or variants thereof) that immunospecifically bind to a TR4 polypeptide or a fragment, variant, or fusion protein thereof. A TR4 polypeptide includes, but is not limited to, TR4 (SEQ ID NO:1) or the polypeptide encoded by the cDNA in clone HCUDS60 contained in ATCC Deposit 97853 deposited Jan. 21, 1997. In some embodiments, antibodies of the present invention may immunospecifically bind to both TR4 as described above and to TR7 (SEQ ID NO:3) or the polypeptide encoded by the cDNA in clone HLYBX88 contained in ATCC Deposit 97920 deposited Mar. 7, 1997. TRAIL receptors may be produced through recombinant expression of nucleic acids encoding the polypeptides of SEQ ID NOS:1-5, (TR4, TR5, TR7, TR10, and TR1; e.g., the cDNAs in the ATCC Deposit Numbers 97853, (TR4) 97798 (TR5, deposited Nov. 20, 1996), 97920 (TR7), or 209040 (TR10, deposited May 15, 1997).

In one embodiment, the antibodies of the invention preferentially bind TR4 (SEQ ID NO:1), or fragments, variants, or fusion proteins thereof (e.g., the extracellular region of TR4 fused to an Fc domain) relative to their ability to bind other proteins including TR1, TR5, TR7, or TR10 (SEQ ID NOS:5, 2, 3, and 4) or fragments, variants, or fusion proteins thereof. In other preferred embodiments, the antibodies of the invention preferentially bind to TR4 and TR7 (SEQ ID NOS:1 and 3), or fragments or variants thereof relative to their ability to bind other proteins including TR1, TR5 or TR10 (SEQ ID NOS:5, 2 and 4) or fragments, variants, or fusion proteins thereof. In other preferred embodiments, the antibodies of the invention bind TR1 TR4, TR5, TR7 and TR10 (SEQ ID NOS:5, 1, 2, 3, and 4). An antibody's ability to preferentially bind one antigen compared to another antigen may be determined using any method known in the art.

TR4 Polypeptides

In certain embodiments of the present invention, the antibodies of the present invention bind TR4 polypeptide, or fragments or variants thereof. The following section describes the TR4 polypeptides, fragments and variants that may be bound by the antibodies of the invention in more detail. The TR4 polypeptides, fragments and variants which may be bound by the antibodies of the invention are also described in International Publication Numbers, for example, WO98/32856 and WO00/67793 which are herein incorporated by reference in their entireties.

In certain embodiments, the antibodies of the present invention immunospecifically bind TR4 polypeptide. An antibody that immunospecifically binds TR4 may, in some embodiments, bind fragments, variants (including species orthologs of TR4), multimers or modified forms of TR4. For example, an antibody immunospecific for TR4 may bind the TR4 moiety of a fusion protein comprising all or a portion of TR4.

TR4 proteins may be found as monomers or multimers (i.e., dimers, trimers, tetramers, and higher multimers). Accordingly, the present invention relates to antibodies that bind TR4 proteins found as monomers or as part of multimers. In specific embodiments, antibodies of the invention bind TR4 monomers, dimers, trimers or tetramers. In additional embodiments, antibodies of the invention bind at least dimers, at least trimers, or at least tetramers containing one or more TR4 polypeptides.

Antibodies of the invention may bind TR4 homomers or heteromers. As used herein, the term homomer, refers to a multimer containing only TR4 proteins of the invention (including TR4 fragments, variants, and fusion proteins, as described herein). These homomers may contain TR4 proteins having identical or different polypeptide sequences. In a specific embodiment, a homomer of the invention is a multimer containing only TR4 proteins having an identical polypeptide sequence. In another specific embodiment, antibodies of the invention bind TR4 homomers containing TR4 proteins having different polypeptide sequences. In specific embodiments, antibodies of the invention bind a TR4 homodimer (e.g., containing TR4 proteins having identical or different polypeptide sequences). In additional embodiments, antibodies of the invention bind at least a homodimer, at least a homotrimer, or at least a homotetramer of TR4.

In specific embodiments antibodies of the presnt invention bind TR4 homotrimers (e.g., containing TR4 proteins having identical or different polypeptide sequences).

As used herein, the term heteromer refers to a multimer containing heterologous proteins (i.e., proteins containing polypeptide sequences that do not correspond to a polypeptide sequences encoded by the TR4 gene) in addition to the TR4 proteins of the invention. In a specific embodiment, antibodies of the invention bind a heterodimer, a heterotrimer, or a heterotetramer. In additional embodiments, the antibodies of the invention bind at least a homodimer, at least a homotrimer, or at least a homotetramer containing one or more TR4 polypeptides.

In specific embodiments antibodies of the presnt invention bind a TR4 heterotrimer (e.g., containing 1 or 2 TR4 proteins and 2 or 1, respectively, TR7 proteins).

Multimers bound by one or more antibodies of the invention may be the result of hydrophobic, hydrophilic, ionic and/or covalent associations and/or may be indirectly linked, by for example, liposome formation. Thus, in one embodiment, multimers bound by one or more antibodies of the invention, such as, for example, homodimers or homotrimers, are formed when TR4 proteins contact one another in solution. In another embodiment, heteromultimers bound by one or more antibodies of the invention, such as, for example, heterotrimers or heterotetramers, are formed when proteins of the invention contact antibodies to the TR4 polypeptides (including antibodies to the heterologous polypeptide sequence in a fusion protein) in solution. In other embodiments, multimers bound by one or more antibodies of the invention are formed by covalent associations with and/or between the TR4 proteins of the invention. Such covalent associations may involve one or more amino acid residues contained in the polypeptide sequence of the protein (e.g., the polypeptide sequence recited in SEQ ID NO:1 or the polypeptide encoded by the deposited cDNA clone of ATCC Deposit 97853). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR4 fusion protein. In one example, covalent associations are between the heterologous sequence contained in a fusion protein (see, e.g., U.S. Pat. No. 5,478,925). In a specific example, the covalent associations are between the heterologous sequence contained in a TR4-Fc fusion protein (as described herein). In another specific example, covalent associations of fusion proteins are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers that may be bound by one or more antibodies of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers that may be bound by one or more antibodies of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins that may be bound by one or more antibodies of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that may be bound by one or more antibodies of the invention (see, e.g., U.S. Pat. No. 5,478,925, which is herein incorporated by reference in its entirety).

Alternatively, multimers that may be bound by one or more antibodies of the invention may be generated using genetic engineering techniques known in the art. In one embodiment, proteins contained in multimers that may be bound by one or more antibodies of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that may be bound by one or more antibodies of the invention are generated by ligating a polynucleotide sequence encoding a TR4 polypeptide to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant TR4 polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more TR4 polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple TR4 polypeptides separated by peptide linkers may be produced using conventional recombinant DNA technology. In specific embodiments, antibodies of the invention bind proteins comprising multiple TR4 polypeptides separated by peptide linkers.

Another method for preparing multimer TR4 polypeptides involves use of TR4 polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR4 proteins are those described in PCT application WO 94/10308, hereby incorporated by reference. Recombinant fusion proteins comprising a soluble TR4 polypeptide fused to a peptide that dimerizes or trimerizes in solution are expressed in suitable host cells, and the resulting soluble multimeric TR4 is recovered from the culture supernatant using techniques known in the art. In specific embodiments, antibodies of the invention bind TR4-leucine zipper fusion protein monomers and/or TR4-leucine zipper fusion protein multimers.

Certain members of the TNF family of proteins believed to exist in trimeric form (Beutler and Huffel, *Science* 264:667, 1994; Banner et al., *Cell* 73:431, 1993). Thus, trimeric TR4 may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, now U.S. Pat. No. 5,716,805, hereby incorporated by reference. In specific embodiments, antibodies of the invention bind TR4-leucine zipper fusion protein trimers.

Other peptides derived from naturally occurring trimeric proteins may be employed in preparing trimeric TR4. In specific embodiments, antibodies of the invention bind TR4-fusion protein monomers and/or TR4 fusion protein trimers.

Antibodies of the invention that bind TR4 receptor polypeptides may bind them as isolated polypeptides or in their naturally occurring state. By "isolated polypeptide" is intended a polypeptide removed from its native environment. Thus, a polypeptide produced and/or contained within a recombinant host cell is considered isolated for purposes of the present invention. Also, intended as an "isolated polypeptide" are polypeptides that have been purified, partially or substantially, from a recombinant host cell. For example, a recombinantly produced version of the TR4 polypeptide is substantially purified by the one-step method described in Smith and Johnson, *Gene* 67:31-40 (1988). Thus, antibodies of the present invention may bind recombinantly produced TR4 receptor polypeptides. In a specific embodiment, antibodies of the present invention bind a TR4 receptor expressed on the surface of a cell, wherein said TR4 polypeptide is encoded by a polynucleotide encoding amino acids 1 to 468 of SEQ ID NO:1 operably associated with a regulatory sequence that controls expression of said polynucleotide.

Antibodies of the present invention may bind TR4 polypeptide fragments comprising or alternatively, consisting of, an amino acid sequence contained in SEQ ID NO:1, encoded by the cDNA contained in ATCC deposit Number 97853, or encoded by nucleic acids which hybridize (e.g., under stringent hybridization conditions) to the nucleotide sequence contained in ATCC deposit Number 97853, or the complementary strand thereto. Protein fragments may be "free-standing," or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 23, 24 to 43, 44 to 63, 64 to 83, 84 to 103, 104 to 123, 124 to 143, 144 to 163, 164 to 183, 184 to 203, 204 to 223, 224 to 238, 239 to 264, 265 to 284, 285 to 304, 305 to 324, 325 to 345, 346 to 366, 367 to 387, 388 to 418, 419 to 439, and/or 440 to 468 of SEQ ID NO:1. In this context "about" includes the particularly recited value, larger or smaller by several (5, 4, 3, 2, or 1) amino acids, at either extreme or at both extremes. Moreover, polypeptide fragments bound by the antibodies of the invention can be at least about 10, 20, 30, 40, 50, 60, 70, 80, 90, 100, 110, 120, 130, 140, 150, 175 or 200 amino acids in length. In this context "about" includes the particularly recited value, larger or smaller by several (5, 4, 3, 2, or 1) amino acids, at either extreme or at both extremes.

Preferably, antibodies of the present invention bind polypeptide fragments selected from the group: a polypeptide comprising or alternatively, consisting of, the TR4 receptor extracellular domain (predicted to constitute amino acid residues from about 24 to about 238 in SEQ ID NO:1);

a polypeptide comprising or alternatively, consisting of, both TR4 cysteine rich domains (both of which may be found in the protein fragment consisting of amino acid residues from about 131 to about 229 in SEQ ID NO:1); a polypeptide comprising or alternatively, consisting of, the TR4 cysteine rich domain consisting of amino acid residues from about 131 to about 183 in SEQ ID NO:1); a polypeptide comprising or alternatively, consisting of, the TR4 cysteine rich domain consisting of amino acid residues from about 184 to about 229 in SEQ ID NO:1); a polypeptide comprising or alternatively, consisting of, the TR4 receptor transmembrane domain (predicted to constitute amino acid residues from about 239 to about 264 in SEQ ID NO:1); a polypeptide comprising or alternatively, consisting of, fragment of the predicted mature TR4 polypeptide, wherein the fragment has a TR4 functional activity (e.g., antigenic activity or biological acitivity); a polypeptide comprising or alternatively, consisting of, the TR4 receptor intracellular domain (predicted to constitute amino acid residues from about 265 to about 468 in SEQ ID NO:1); a polypeptide comprising or alternatively, consisting of, the TR4 receptor extracellular and intracellular domains with all or part of the transmembrane domain deleted; a polypeptide comprising, or alternatively consisting of, the TR4 receptor death domain (predicted to constitute amino acid residues from about 379 to about 422 in SEQ ID NO:1); and a polypeptide comprising, or alternatively, consisting of, one, two, three, four or more, epitope bearing portions of the TR4 receptor protein. In additional embodiments, the polypeptide fragments of the invention comprise, or alternatively, consist of, any combination of 1, 2, 3, 4, 5, 6, 7, or all 8 of the above members. The amino acid residues constituting the TR4 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain. Polynucleotides encoding these polypeptides are also encompassed by the invention.

It is believed that one or both of the extracellular cysteine rich motifs of TR4 is important for interactions between TR4 and its ligands (e.g., TRAIL). Accordingly, in highly preferred embodiments, antibodies of the present invention bind TR4 polypeptide fragments comprising, or alternatively consisting of amino acid residues 131 to 183, and/or 184 to 229 of SEQ ID NO:1. In another highly preferred embodiment, antibodies of the present invention bind TR4 polypeptides comprising, or alternatively consisting of both of the extracellular cysteine rich motifs (amino acid residues 131 to 229 of SEQ ID NO:1.) In another preferred embodiment, antibodies of the present invention bind TR4 polypeptides comprising, or alternatively consisting the extracellular soluble domain of TR4 (amino acid residues 24-238 of SEQ ID NO:1.) In highly preferred embodiments, the antibodies of the invention that bind all or a portion of the extracellular soluble domain of TR4 (e.g., one or both cysteine rich domains) prevent TRAIL ligand from binding to TR4. In other highly preferred embodiments, the antibodies of the invention that bind all or a portion of the extracellular soluble domain of TR4 (e.g., one or both cysteine rich domains) agonize the TR4 receptor. In other highly preferred embodiments, the antibodies of the invention that bind all or a portion of the extracellular soluble domain of TR4 (e.g., one or both cysteine rich domains) induce cell death of the cell expressing the TR4 receptor.

Antibodies of the invention may also bind fragments comprising, or alternatively consisting of structural or functional attributes of TR4. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) TR4. Certain preferred regions are those set out in Table 2 and include, but are not limited to, regions of the aforementioned types identified by analysis of the amino acid sequence depicted in (SEQ ID NO:1), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; and Jameson-Wolf high antigenic index regions, as predicted using the default parameters of these computer programs.

The data representing the structural or functional attributes of TR4 set forth in Table 2, as described above, was generated using the various modules and algorithms of the DNA*STAR set on default parameters. Column I represents the results of a Garnier-Robson analysis of alpha helical regions; Column II represents the results of a Chou-Fasman analysis of alpha helical regions; Column III represents the results of a Garnier Robson analysis of beta sheet regions; Column IV represents the results of a Chou-Fasman analysis of beta sheet regions; Column V represents the results of a Garnier Robson analysis of turn regions; Column VI represents the results of a Chou-Fasman analysis of turn regions; Column VII represents the results of a Garnier Robson analysis of coil regions; Column VIII represents a Kyte-Doolittle hydrophilicity plot; Column; Column IX represents the results of an Eisenberg analysis of alpha amphipathic regions; Column X represents the results of an Eisenberg analysis of beta amphipathic regions; Column XI represents the results of a Karplus-Schultz analysis of flexible regions; Column XII represents the Jameson-Wolf antigenic index score; and Column XIII represents the Emini surface probability plot.

In a preferred embodiment, the data presented in columns VIII, XII, and XIII of Table 2 can be used to determine regions of TR4 which exhibit a high degree of potential for antigenicity. Regions of high antigenicity are determined from the data presented in columns VIII, XII, and/or XIII by choosing values which represent regions of the polypeptide which are likely to be exposed on the surface of the polypeptide in an environment in which antigen recognition may occur in the process of initiation of an immune response.

The above-mentioned preferred regions set out in Table 2 include, but are not limited to, regions of the aforementioned types identified by analysis of the amino acid sequence set out in SEQ ID NO:1. As set out in Table 2, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions. Among preferred polypeptide fragments bound by one or more antibodies of the invention are those that comprise regions of TR4 that combine several structural features, such as several (e.g., 1, 2, 3, or 4) of the same or different region features set out above and in Table 2.

TABLE 2

| Res | Position | I | II | III | IV | V | VI | VII | VIII | IX | X | XI | XII | XIII |
|---|---|---|---|---|---|---|---|---|---|---|---|---|---|---|
| Met | 1 | . | . | B | . | . | . | . | 0.12 | . | . | . | −0.10 | 0.90 |
| Ala | 2 | . | . | . | . | . | . | C | −0.08 | * | * | . | 0.25 | 1.08 |
| Pro | 3 | . | . | . | . | . | . | C | 0.42 | * | * | . | 0.10 | 0.86 |
| Pro | 4 | . | . | . | . | . | T | C | −0.04 | * | * | . | 1.05 | 1.69 |
| Pro | 5 | A | . | . | . | . | T | . | 0.31 | . | * | F | 1.00 | 1.24 |
| Ala | 6 | A | . | . | . | . | T | . | 0.10 | . | * | F | 1.00 | 1.10 |
| Arg | 7 | A | . | . | . | . | T | . | 0.34 | . | * | . | 0.10 | 0.58 |
| Val | 8 | . | . | B | B | . | . | . | −0.03 | . | * | . | −0.30 | 0.37 |
| His | 9 | . | . | B | B | . | . | . | −0.52 | . | * | . | −0.30 | 0.37 |
| Leu | 10 | . | . | B | B | . | . | . | −1.12 | . | * | . | −0.60 | 0.17 |
| Gly | 11 | . | . | B | B | . | . | . | −1.12 | . | * | . | −0.60 | 0.18 |
| Ala | 12 | . | . | B | B | . | . | . | −2.09 | . | * | . | −0.60 | 0.14 |
| Phe | 13 | . | . | B | B | . | . | . | −1.54 | . | * | . | −0.60 | 0.12 |
| Leu | 14 | . | . | B | B | . | . | . | −1.72 | . | . | . | −0.60 | 0.18 |
| Ala | 15 | . | . | B | B | . | . | . | −0.91 | . | . | . | −0.60 | 0.27 |
| Val | 16 | . | . | B | B | . | . | . | −0.78 | . | . | . | −0.60 | 0.51 |
| Thr | 17 | . | . | B | B | . | . | . | −0.53 | . | . | F | −0.45 | 0.95 |
| Pro | 18 | . | . | . | B | . | . | C | −0.13 | . | . | F | 0.05 | 0.93 |
| Asn | 19 | . | . | . | . | . | T | C | 0.09 | . | . | F | 0.60 | 1.69 |
| Pro | 20 | . | . | . | . | . | T | C | 0.09 | . | . | F | 0.60 | 1.18 |
| Gly | 21 | . | . | . | . | T | T | . | 0.64 | . | . | F | 0.65 | 0.77 |
| Ser | 22 | . | . | . | . | . | T | C | 0.61 | . | . | F | 0.45 | 0.64 |
| Ala | 23 | . | . | . | . | . | . | C | 0.51 | . | . | F | 0.25 | 0.41 |
| Ala | 24 | . | . | . | . | . | T | C | 0.51 | . | . | F | 0.45 | 0.60 |
| Ser | 25 | . | . | B | . | . | T | . | 0.13 | . | . | F | 0.85 | 0.78 |
| Gly | 26 | A | . | . | . | . | T | . | −0.11 | . | . | F | 0.85 | 0.78 |
| Thr | 27 | A | . | . | . | . | T | . | −0.40 | . | . | F | 0.85 | 0.78 |
| Glu | 28 | A | A | . | . | . | . | . | −0.40 | . | . | F | 0.45 | 0.58 |
| Ala | 29 | A | A | . | . | . | . | . | −0.12 | . | . | . | 0.30 | 0.60 |
| Ala | 30 | A | A | . | . | . | . | . | −0.03 | . | . | . | 0.30 | 0.60 |
| Ala | 31 | A | A | . | . | . | . | . | 0.01 | . | . | . | 0.30 | 0.53 |
| Ala | 32 | A | A | . | . | . | . | . | 0.37 | . | . | . | −0.30 | 0.71 |
| Thr | 33 | A | . | . | . | . | T | . | −0.49 | * | . | F | 1.00 | 1.40 |
| Pro | 34 | A | . | . | . | . | T | . | −0.19 | . | . | F | 1.00 | 1.03 |
| Ser | 35 | . | . | B | . | . | T | . | 0.06 | . | . | F | 0.40 | 1.07 |
| Lys | 36 | . | . | B | . | . | T | . | 0.34 | . | . | F | 0.25 | 0.73 |
| Val | 37 | . | . | B | B | . | . | . | 0.63 | . | . | F | −0.15 | 0.64 |
| Trp | 38 | . | . | B | B | . | . | . | 0.36 | . | . | F | −0.15 | 0.64 |
| Gly | 39 | . | . | B | B | . | . | . | 0.22 | * | * | F | −0.15 | 0.32 |
| Ser | 40 | . | . | . | . | . | . | C | 0.63 | * | * | F | −0.05 | 0.43 |
| Ser | 41 | . | . | . | . | . | T | C | −0.30 | * | * | F | 0.45 | 0.80 |
| Ala | 42 | . | . | . | . | . | T | C | 0.56 | * | * | F | 1.05 | 0.57 |
| Gly | 43 | . | . | . | . | . | T | C | 0.63 | * | * | F | 1.35 | 0.73 |
| Arg | 44 | . | . | B | . | . | T | . | 1.09 | * | * | F | 1.49 | 0.84 |
| Ile | 45 | . | . | B | . | . | . | . | 1.04 | * | * | F | 1.78 | 1.63 |
| Glu | 46 | . | . | B | . | . | . | . | 1.00 | * | * | F | 2.12 | 1.63 |
| Pro | 47 | . | . | B | . | . | . | . | 1.24 | * | * | F | 2.51 | 0.83 |
| Arg | 48 | . | . | . | . | T | T | . | 1.70 | * | * | F | 3.40 | 1.17 |
| Gly | 49 | . | . | . | . | T | T | . | 1.24 | * | * | F | 3.06 | 1.32 |
| Gly | 50 | . | . | . | . | T | T | . | 1.54 | * | * | F | 2.57 | 0.84 |
| Gly | 51 | . | . | . | . | . | T | C | 0.73 | * | * | F | 2.03 | 0.44 |
| Arg | 52 | . | . | . | . | . | T | C | 0.73 | * | * | F | 1.39 | 0.36 |
| Gly | 53 | . | . | B | . | . | T | . | 0.31 | * | * | F | 0.85 | 0.57 |
| Ala | 54 | . | . | B | . | . | T | . | 0.36 | . | * | F | 0.85 | 0.83 |
| Leu | 55 | . | . | B | . | . | . | . | 0.10 | . | * | F | 0.65 | 0.57 |
| Pro | 56 | . | . | B | . | . | . | . | 0.10 | . | * | F | −0.25 | 0.57 |
| Thr | 57 | . | . | B | . | . | . | . | −0.01 | . | * | F | −0.25 | 0.55 |
| Ser | 58 | . | . | B | . | . | T | . | 0.30 | . | . | F | 0.10 | 1.16 |
| Met | 59 | . | . | B | . | . | T | . | 0.54 | . | . | F | 0.40 | 1.02 |
| Gly | 60 | . | . | B | . | . | . | . | 1.14 | . | . | F | 0.25 | 0.70 |
| Gln | 61 | . | . | . | . | T | T | . | 1.06 | . | . | F | 0.65 | 0.81 |
| His | 62 | . | . | . | . | . | . | C | 0.78 | . | * | F | 0.40 | 1.10 |
| Gly | 63 | . | . | . | . | . | T | C | 1.19 | . | * | F | 0.60 | 1.12 |
| Pro | 64 | . | . | . | . | . | T | C | 1.20 | . | * | F | 1.20 | 1.27 |
| Ser | 65 | . | . | . | . | . | T | C | 1.66 | . | * | F | 1.05 | 0.94 |
| Ala | 66 | . | . | B | . | . | T | . | 1.07 | . | * | F | 1.30 | 1.86 |
| Arg | 67 | . | . | B | . | . | . | . | 0.76 | * | * | . | 1.29 | 1.22 |
| Ala | 68 | . | . | B | . | . | . | . | 1.21 | * | * | . | 1.48 | 0.90 |
| Arg | 69 | . | . | B | . | . | T | . | 0.83 | . | * | . | 2.17 | 1.74 |
| Ala | 70 | . | . | B | . | . | T | . | 0.92 | . | * | F | 2.51 | 0.90 |
| Gly | 71 | . | . | . | . | T | T | . | 1.17 | . | * | F | 3.40 | 1.37 |
| Arg | 72 | . | . | . | . | . | T | C | 0.84 | * | * | F | 2.71 | 0.69 |
| Ala | 73 | . | . | . | . | . | T | C | 1.54 | * | * | F | 2.48 | 1.06 |
| Pro | 74 | . | . | . | . | . | T | C | 1.22 | * | * | F | 2.70 | 2.10 |
| Gly | 75 | . | . | . | . | . | T | C | 1.22 | * | * | F | 2.62 | 1.66 |
| Pro | 76 | . | . | . | . | . | T | C | 1.68 | * | * | F | 2.24 | 1.66 |
| Arg | 77 | . | . | . | . | . | . | C | 1.57 | * | . | F | 2.60 | 2.10 |

TABLE 2-continued

| Res | Position | I | II | III | IV | V | VI | VII | VIII | IX | X | XI | XII | XIII |
|-----|----------|---|----|-----|----|---|-----|------|------|----|---|----|----|-----|
| Pro | 78 | . | A | B | . | . | . | . | 1.57 | * | . | F | 1.94 | 3.68 |
| Ala | 79 | . | A | B | . | . | . | . | 1.48 | * | . | F | 1.68 | 2.40 |
| Arg | 80 | . | A | B | . | . | . | . | 1.61 | * | * | F | 1.42 | 1.64 |
| Glu | 81 | . | A | B | . | . | . | . | 1.93 | * | * | F | 1.16 | 1.64 |
| Ala | 82 | A | A | . | . | . | . | . | 1.01 | * | * | F | 0.90 | 3.19 |
| Ser | 83 | A | . | . | . | . | . | T | 1.33 | * | * | F | 1.30 | 1.34 |
| Pro | 84 | A | . | . | . | . | . | T | 1.07 | * | * | F | 1.30 | 1.52 |
| Arg | 85 | A | . | . | . | . | . | T | 0.92 | * | * | F | 1.00 | 1.12 |
| Leu | 86 | A | . | . | . | . | . | T | 0.97 | . | * | . | 0.85 | 1.13 |
| Arg | 87 | A | . | . | B | . | . | . | 1.24 | . | * | . | 0.75 | 1.46 |
| Val | 88 | A | . | . | B | . | . | . | 0.84 | * | * | . | 0.75 | 1.08 |
| His | 89 | A | . | . | B | . | . | . | 1.10 | . | * | . | -0.15 | 1.13 |
| Lys | 90 | A | . | . | B | . | . | . | 0.29 | * | * | F | 0.90 | 1.16 |
| Thr | 91 | . | . | B | B | . | . | . | 0.24 | * | * | F | 0.00 | 1.35 |
| Phe | 92 | . | . | B | B | . | . | . | -0.72 | * | * | . | -0.30 | 0.74 |
| Lys | 93 | . | . | B | B | . | . | . | -0.72 | * | * | . | -0.30 | 0.27 |
| Phe | 94 | . | . | B | B | . | . | . | -1.03 | * | . | . | -0.60 | 0.14 |
| Val | 95 | . | . | B | B | . | . | . | -1.93 | * | . | . | -0.60 | 0.16 |
| Val | 96 | . | . | B | B | . | . | . | -2.43 | . | * | . | -0.60 | 0.06 |
| Val | 97 | . | . | B | B | . | . | . | -2.54 | . | * | . | -0.60 | 0.06 |
| Gly | 98 | . | . | B | B | . | . | . | -2.59 | . | * | . | -0.60 | 0.06 |
| Val | 99 | . | . | B | B | . | . | . | -2.74 | . | . | . | -0.60 | 0.15 |
| Leu | 100 | . | . | B | B | . | . | . | -2.74 | * | . | . | -0.60 | 0.15 |
| Leu | 101 | . | . | B | B | . | . | . | -2.10 | * | . | . | -0.60 | 0.11 |
| Gln | 102 | . | . | B | B | . | . | . | -1.54 | * | . | . | -0.60 | 0.23 |
| Val | 103 | . | . | B | B | . | . | . | -1.50 | . | . | . | -0.60 | 0.37 |
| Val | 104 | . | . | B | . | . | . | T | -1.23 | . | . | . | -0.20 | 0.61 |
| Pro | 105 | . | . | B | . | . | . | T | -1.01 | * | . | F | 0.25 | 0.35 |
| Ser | 106 | A | . | . | . | . | . | T | -0.51 | * | . | F | -0.05 | 0.48 |
| Ser | 107 | A | . | . | . | . | . | T | -1.40 | * | * | F | 0.25 | 0.94 |
| Ala | 108 | A | . | . | . | . | . | . | -0.50 | . | * | F | 0.05 | 0.43 |
| Ala | 109 | A | . | . | . | . | . | . | -0.46 | . | * | . | 0.50 | 0.63 |
| Thr | 110 | A | . | . | . | . | . | . | -0.28 | . | * | . | -0.10 | 0.39 |
| Ile | 111 | A | . | . | . | . | . | . | 0.02 | . | * | . | -0.10 | 0.53 |
| Lys | 112 | . | . | B | . | . | . | . | 0.32 | . | * | . | 0.50 | 0.87 |
| Leu | 113 | . | . | B | . | . | . | . | 0.61 | . | * | F | 1.05 | 1.04 |
| His | 114 | . | . | B | . | . | . | . | 0.31 | . | * | F | 1.30 | 1.99 |
| Asp | 115 | . | . | . | . | . | T | C | 0.28 | * | * | F | 1.80 | 0.70 |
| Gln | 116 | . | . | . | . | T | T | . | 0.86 | . | * | F | 1.65 | 0.84 |
| Ser | 117 | . | . | . | . | T | T | . | 0.81 | . | . | F | 2.50 | 0.89 |
| Ile | 118 | . | . | . | . | T | T | . | 1.62 | . | . | F | 2.25 | 0.92 |
| Gly | 119 | . | . | . | . | . | . | C | 1.37 | . | . | F | 1.00 | 0.92 |
| Thr | 120 | . | . | . | . | . | . | C | 1.37 | . | . | F | 0.45 | 0.72 |
| Gln | 121 | . | . | B | . | . | . | C | 1.33 | . | . | F | 0.65 | 1.79 |
| Gln | 122 | . | . | B | . | . | . | . | 1.33 | . | . | F | 0.20 | 2.46 |
| Trp | 123 | . | . | B | . | . | . | . | 2.01 | . | . | . | 0.05 | 2.28 |
| Glu | 124 | . | . | . | . | . | . | C | 1.54 | . | . | . | 0.25 | 2.04 |
| His | 125 | . | . | . | . | . | . | C | 1.51 | . | . | . | 0.10 | 0.97 |
| Ser | 126 | . | . | . | . | . | T | C | 1.51 | . | . | F | 0.45 | 0.91 |
| Pro | 127 | . | . | . | . | T | T | . | 0.70 | . | . | F | 1.55 | 0.91 |
| Leu | 128 | . | . | . | . | T | T | . | 0.32 | . | . | F | 0.65 | 0.55 |
| Gly | 129 | . | . | . | . | T | T | . | 0.11 | . | . | F | 0.65 | 0.22 |
| Glu | 130 | . | . | . | . | T | . | . | -0.07 | . | . | F | 0.45 | 0.22 |
| Leu | 131 | . | . | B | . | . | . | . | -0.11 | * | . | . | 0.18 | 0.42 |
| Cys | 132 | . | . | B | . | . | . | . | -0.20 | * | . | F | 1.21 | 0.42 |
| Pro | 133 | . | . | B | . | . | . | . | 0.58 | * | * | F | 1.69 | 0.32 |
| Pro | 134 | . | . | . | . | . | T | T | 1.03 | . | * | F | 1.47 | 0.53 |
| Gly | 135 | . | . | . | . | . | T | T | 0.73 | . | * | F | 2.80 | 1.94 |
| Ser | 136 | . | . | . | . | . | T | C | 1.54 | * | . | F | 2.32 | 1.68 |
| His | 137 | . | . | . | . | . | . | C | 2.32 | * | . | F | 2.48 | 1.88 |
| Arg | 138 | . | . | B | . | . | . | . | 2.32 | * | . | F | 2.34 | 3.72 |
| Ser | 139 | . | . | B | . | . | . | . | 2.19 | * | . | F | 2.40 | 4.29 |
| Glu | 140 | . | . | . | . | . | T | . | 1.94 | * | . | F | 2.86 | 3.12 |
| Arg | 141 | . | . | . | . | . | T | . | 1.58 | * | . | F | 3.40 | 1.61 |
| Pro | 142 | . | . | . | . | . | T | T | 1.61 | . | * | F | 2.91 | 0.64 |
| Gly | 143 | . | . | . | . | . | T | T | 1.61 | . | * | F | 2.57 | 0.60 |
| Ala | 144 | . | . | . | . | . | T | T | 1.24 | . | * | . | 2.08 | 0.60 |
| Cys | 145 | . | . | . | . | . | T | . | 0.93 | . | * | . | 1.41 | 0.21 |
| Asn | 146 | . | . | B | . | . | . | . | 0.82 | . | * | . | 0.84 | 0.30 |
| Arg | 147 | . | . | B | . | . | . | . | 0.69 | * | . | . | 1.01 | 0.52 |
| Cys | 148 | . | . | B | . | . | . | T | 0.18 | * | . | F | 1.83 | 0.96 |
| Thr | 149 | . | . | B | . | . | . | T | 0.42 | * | . | F | 1.70 | 0.44 |
| Glu | 150 | . | . | B | . | . | . | T | 0.84 | * | . | . | 1.53 | 0.22 |
| Gly | 151 | . | . | B | . | . | . | T | 0.53 | * | . | . | 0.76 | 0.65 |
| Val | 152 | . | . | B | B | . | . | . | 0.42 | . | * | F | 0.19 | 0.65 |
| Gly | 153 | . | . | B | B | . | . | . | 0.50 | . | . | . | -0.13 | 0.61 |
| Tyr | 154 | . | . | B | B | . | . | . | 0.51 | . | . | . | -0.60 | 0.62 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Thr | 155 | . | . | B | B | . | . | . | 0.51 | . | . | F | −0.30 | 1.12 |
| Asn | 156 | . | . | . | B | . | . | C | 0.86 | . | . | F | 0.20 | 1.81 |
| Ala | 157 | . | . | . | . | T | T | . | 0.90 | . | . | F | 0.80 | 1.86 |
| Ser | 158 | . | . | . | . | T | T | . | 0.54 | . | . | F | 0.80 | 1.06 |
| Asn | 159 | . | . | . | . | T | T | . | 0.20 | . | . | F | 0.35 | 0.57 |
| Asn | 160 | . | . | . | . | T | T | . | −0.16 | * | . | F | 0.35 | 0.57 |
| Leu | 161 | . | A | B | . | . | . | . | −0.97 | * | . | . | −0.60 | 0.23 |
| Phe | 162 | . | A | B | . | . | . | . | −0.59 | . | . | . | −0.60 | 0.12 |
| Ala | 163 | . | A | B | . | . | . | . | −0.96 | . | . | . | −0.60 | 0.11 |
| Cys | 164 | . | A | B | . | . | . | . | −1.27 | * | . | . | −0.60 | 0.07 |
| Leu | 165 | . | . | B | . | . | T | . | −1.86 | . | . | . | −0.20 | 0.12 |
| Pro | 166 | . | . | B | . | . | T | . | −1.71 | * | . | . | −0.20 | 0.12 |
| Cys | 167 | . | . | . | . | T | T | . | −0.97 | * | . | . | 0.20 | 0.12 |
| Thr | 168 | A | . | . | . | . | T | . | −0.68 | . | . | . | 0.10 | 0.30 |
| Ala | 169 | A | . | . | . | . | T | . | −0.01 | . | . | . | 0.50 | 0.26 |
| Cys | 170 | A | . | . | . | . | T | . | 0.80 | . | . | . | 0.70 | 0.80 |
| Lys | 171 | A | . | . | . | . | T | . | 1.01 | . | . | F | 1.15 | 0.96 |
| Ser | 172 | A | . | . | . | . | T | . | 1.68 | . | * | F | 1.30 | 1.65 |
| Asp | 173 | A | . | . | . | . | T | . | 2.10 | . | * | F | 1.30 | 5.33 |
| Glu | 174 | A | A | . | . | . | . | . | 2.39 | . | * | F | 0.90 | 5.22 |
| Glu | 175 | A | A | . | . | . | . | . | 2.84 | . | * | F | 1.24 | 5.22 |
| Glu | 176 | A | A | . | . | . | . | . | 2.13 | . | * | F | 1.58 | 4.83 |
| Arg | 177 | . | A | . | . | T | . | . | 2.12 | . | . | F | 2.32 | 1.50 |
| Ser | 178 | . | . | . | . | . | T | C | 1.81 | . | . | F | 2.86 | 1.25 |
| Pro | 179 | . | . | . | . | T | T | . | 1.50 | * | . | F | 3.40 | 1.04 |
| Cys | 180 | . | . | . | . | T | T | . | 1.61 | * | . | F | 2.61 | 0.77 |
| Thr | 181 | . | . | . | . | T | T | . | 1.61 | * | . | F | 2.67 | 1.12 |
| Thr | 182 | . | . | . | . | T | . | . | 1.19 | * | * | F | 2.38 | 1.16 |
| Thr | 183 | . | . | . | . | T | T | . | 0.90 | . | . | F | 2.49 | 3.13 |
| Arg | 184 | . | . | . | . | T | T | . | 0.44 | . | . | F | 2.40 | 2.19 |
| Asn | 185 | . | . | . | . | T | T | . | 1.11 | . | . | F | 2.50 | 0.81 |
| Thr | 186 | . | . | . | . | T | T | . | 0.76 | * | . | F | 2.25 | 0.98 |
| Ala | 187 | . | . | . | . | T | . | . | 1.11 | * | . | . | 1.65 | 0.27 |
| Cys | 188 | . | . | . | . | T | . | . | 1.21 | * | . | . | 1.40 | 0.33 |
| Gln | 189 | . | . | B | . | . | . | . | 0.76 | * | . | . | 0.75 | 0.36 |
| Cys | 190 | . | . | B | . | . | . | . | 0.44 | . | . | . | 0.50 | 0.35 |
| Lys | 191 | . | . | B | . | . | T | . | 0.06 | . | * | F | 0.85 | 0.94 |
| Pro | 192 | . | . | . | . | T | T | . | 0.76 | . | . | F | 0.65 | 0.47 |
| Gly | 193 | . | . | . | . | T | T | . | 1.42 | . | * | F | 1.74 | 1.72 |
| Thr | 194 | . | . | B | . | . | T | . | 1.42 | . | * | F | 1.68 | 1.38 |
| Phe | 195 | . | . | B | . | . | . | . | 2.09 | . | * | F | 1.82 | 1.49 |
| Arg | 196 | . | . | . | . | T | . | . | 1.74 | . | * | F | 2.56 | 2.42 |
| Asn | 197 | . | . | . | . | T | T | . | 1.37 | . | * | F | 3.40 | 2.25 |
| Asp | 198 | . | . | . | . | T | T | . | 1.71 | . | * | F | 3.06 | 2.63 |
| Asn | 199 | . | . | . | . | . | T | C | 1.42 | . | * | F | 2.52 | 2.32 |
| Ser | 200 | A | . | . | . | . | T | . | 1.46 | . | * | F | 1.98 | 1.43 |
| Ala | 201 | A | . | . | . | . | . | . | 1.46 | . | * | . | 1.14 | 0.46 |
| Glu | 202 | A | . | . | . | . | . | . | 1.50 | * | . | . | 0.80 | 0.56 |
| Met | 203 | A | . | . | . | . | . | . | 0.83 | * | . | . | 1.11 | 0.83 |
| Cys | 204 | A | . | . | . | . | T | . | 0.53 | * | . | . | 1.62 | 0.44 |
| Arg | 205 | . | . | . | . | T | T | . | 0.52 | * | . | . | 2.33 | 0.34 |
| Lys | 206 | . | . | . | . | T | T | . | 0.77 | * | . | F | 2.49 | 0.50 |
| Cys | 207 | . | . | . | . | T | T | . | 0.10 | * | . | F | 3.10 | 0.92 |
| Ser | 208 | . | . | . | . | T | . | . | 0.49 | * | * | F | 2.59 | 0.25 |
| Thr | 209 | . | . | . | . | T | . | . | 1.27 | * | * | F | 1.98 | 0.19 |
| Gly | 210 | . | . | . | . | T | . | . | 0.81 | * | . | F | 1.67 | 0.71 |
| Cys | 211 | . | . | B | . | . | T | . | 0.17 | * | * | F | 1.16 | 0.53 |
| Pro | 212 | . | . | . | . | T | T | . | −0.02 | * | * | F | 1.25 | 0.36 |
| Arg | 213 | . | . | . | . | T | T | . | 0.32 | * | * | F | 0.65 | 0.27 |
| Gly | 214 | . | . | B | . | . | T | . | −0.22 | * | * | . | 0.85 | 1.01 |
| Met | 215 | . | . | B | B | . | . | . | 0.17 | * | * | . | 0.30 | 0.48 |
| Val | 216 | . | . | B | B | . | . | . | 0.83 | * | * | . | 0.79 | 0.49 |
| Lys | 217 | . | . | B | B | . | . | . | 0.38 | * | * | . | 0.98 | 0.83 |
| Val | 218 | . | . | B | B | . | . | . | −0.04 | * | * | F | 1.32 | 0.45 |
| Lys | 219 | . | . | B | B | . | . | . | 0.09 | . | * | F | 1.51 | 0.88 |
| Asp | 220 | . | . | B | . | . | . | . | 0.40 | . | * | F | 1.90 | 0.68 |
| Cys | 221 | . | . | B | . | . | . | . | 0.96 | . | * | F | 0.81 | 0.96 |
| Thr | 222 | . | . | . | . | . | T | C | 0.91 | . | * | F | 1.62 | 0.65 |
| Pro | 223 | . | . | . | . | T | T | . | 0.88 | . | * | F | 1.63 | 0.65 |
| Trp | 224 | . | . | . | . | T | T | . | 0.83 | . | * | F | 0.54 | 0.84 |
| Ser | 225 | A | . | . | . | . | T | . | 0.17 | . | . | F | 1.00 | 1.01 |
| Asp | 226 | A | A | . | . | . | . | . | −0.02 | . | . | F | 0.45 | 0.35 |
| Ile | 227 | A | A | . | . | . | . | . | 0.26 | * | . | . | −0.30 | 0.25 |
| Glu | 228 | A | A | . | . | . | . | . | 0.51 | * | . | . | 0.30 | 0.25 |
| Cys | 229 | . | A | B | . | . | . | . | 0.80 | * | . | . | 0.60 | 0.30 |
| Val | 230 | A | A | . | . | . | . | . | 0.80 | * | * | . | 0.60 | 0.74 |
| His | 231 | A | A | . | . | . | . | . | 0.46 | * | * | . | 0.60 | 0.58 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Lys | 232 | A | A | . | . | . | . | . | 1.34 | * | . | F | 0.60 | 1.06 |
| Glu | 233 | . | A | . | . | . | T | . | 1.00 | * | . | F | 1.30 | 2.30 |
| Ser | 234 | . | . | . | . | . | T | T | 1.63 | * | . | F | 1.70 | 1.68 |
| Gly | 235 | . | . | . | . | . | T | T | 2.49 | * | . | F | 1.70 | 1.14 |
| Asn | 236 | . | . | . | . | . | T | T | 1.63 | * | . | F | 1.40 | 1.06 |
| Gly | 237 | . | . | . | . | . | T | C | 1.30 | * | . | F | 0.45 | 0.55 |
| His | 238 | . | . | . | . | B | . | C | 0.44 | . | . | . | −0.40 | 0.59 |
| Asn | 239 | . | . | . | . | B | . | C | −0.14 | . | . | . | −0.40 | 0.27 |
| Ile | 240 | . | . | . | B | B | . | . | −0.61 | . | . | . | −0.60 | 0.19 |
| Trp | 241 | . | . | . | B | B | . | . | −1.47 | . | . | . | −0.60 | 0.12 |
| Val | 242 | . | . | . | B | B | . | . | −1.98 | . | . | . | −0.60 | 0.05 |
| Ile | 243 | . | . | . | B | B | . | . | −2.26 | . | . | . | −0.60 | 0.06 |
| Leu | 244 | . | . | . | B | B | . | . | −3.07 | . | . | . | −0.60 | 0.08 |
| Val | 245 | . | . | . | B | B | . | . | −3.03 | . | . | . | −0.60 | 0.09 |
| Val | 246 | . | . | . | B | B | . | . | −3.60 | . | . | . | −0.60 | 0.09 |
| Thr | 247 | . | . | . | B | B | . | . | −2.96 | . | . | . | −0.60 | 0.08 |
| Leu | 248 | . | . | . | B | B | . | . | −2.88 | . | . | . | −0.60 | 0.17 |
| Val | 249 | . | . | . | B | B | . | . | −2.88 | . | * | . | −0.60 | 0.19 |
| Val | 250 | . | . | . | B | B | . | . | −2.83 | . | . | . | −0.60 | 0.11 |
| Pro | 251 | . | . | . | B | B | . | . | −2.83 | . | . | . | −0.60 | 0.11 |
| Leu | 252 | . | . | . | B | B | . | . | −3.11 | . | . | . | −0.60 | 0.11 |
| Leu | 253 | A | . | . | . | B | . | . | −3.16 | . | . | . | −0.60 | 0.15 |
| Leu | 254 | A | . | . | . | B | . | . | −3.11 | . | . | . | −0.60 | 0.07 |
| Val | 255 | A | . | . | . | B | . | . | −3.14 | . | . | . | −0.60 | 0.07 |
| Ala | 256 | A | . | . | . | B | . | . | −3.79 | . | . | . | −0.60 | 0.06 |
| Val | 257 | . | . | . | B | B | . | . | −3.64 | . | . | . | −0.60 | 0.05 |
| Leu | 258 | . | . | . | B | B | . | . | −3.50 | . | . | . | −0.60 | 0.04 |
| Ile | 259 | . | . | . | B | B | . | . | −3.36 | . | . | . | −0.60 | 0.02 |
| Val | 260 | . | . | . | B | B | . | . | −3.39 | . | . | . | −0.60 | 0.02 |
| Cys | 261 | . | . | . | B | B | . | . | −3.14 | . | . | . | −0.60 | 0.01 |
| Cys | 262 | . | . | . | B | B | . | . | −2.59 | . | . | . | −0.60 | 0.02 |
| Cys | 263 | . | . | . | B | B | . | . | −2.12 | . | . | . | −0.60 | 0.03 |
| Ile | 264 | . | . | . | B | B | . | . | −1.90 | . | . | . | −0.60 | 0.06 |
| Gly | 265 | . | . | . | . | . | T | T | . | −1.39 | . | . | F | 0.35 | 0.06 |
| Ser | 266 | . | . | . | . | . | T | T | . | −1.07 | . | . | F | 0.35 | 0.11 |
| Gly | 267 | . | . | . | . | . | T | T | . | −0.40 | . | . | F | 0.65 | 0.16 |
| Cys | 268 | . | . | . | . | . | T | T | . | 0.06 | . | . | F | 1.25 | 0.27 |
| Gly | 269 | . | . | . | . | . | T | . | . | 0.99 | . | * | F | 1.39 | 0.31 |
| Gly | 270 | . | . | . | . | . | T | . | . | 0.67 | . | . | F | 2.03 | 0.62 |
| Asp | 271 | . | . | . | . | . | T | C | . | 0.37 | . | . | F | 2.37 | 0.62 |
| Pro | 272 | . | . | . | . | . | T | T | . | 0.71 | * | * | F | 2.91 | 0.62 |
| Lys | 273 | . | . | . | . | . | T | T | . | 1.49 | * | * | F | 3.40 | 1.05 |
| Cys | 274 | . | . | . | B | . | . | T | . | 0.98 | * | * | . | 2.51 | 1.23 |
| Met | 275 | . | . | . | B | B | . | . | . | 0.66 | * | * | . | 1.62 | 0.59 |
| Asp | 276 | . | . | . | B | B | . | . | . | −0.04 | * | * | . | 1.28 | 0.16 |
| Arg | 277 | . | . | . | B | B | . | . | . | −0.12 | . | * | . | 0.04 | 0.26 |
| Val | 278 | . | . | . | B | B | . | . | . | −0.06 | . | * | . | −0.60 | 0.27 |
| Cys | 279 | . | . | . | B | B | . | . | . | −0.20 | . | . | . | 0.30 | 0.32 |
| Phe | 280 | . | . | . | B | B | . | . | . | 0.06 | . | * | . | −0.60 | 0.13 |
| Trp | 281 | . | . | . | B | B | . | . | . | −0.76 | . | . | . | −0.60 | 0.18 |
| Arg | 282 | . | . | . | B | B | . | . | . | −1.68 | . | . | . | −0.60 | 0.28 |
| Leu | 283 | . | . | . | B | B | . | . | . | −0.71 | . | . | . | −0.60 | 0.26 |
| Gly | 284 | . | . | . | . | B | T | . | . | −0.39 | . | * | . | −0.20 | 0.49 |
| Leu | 285 | . | . | . | . | B | . | C | . | 0.10 | . | * | . | 0.50 | 0.25 |
| Leu | 286 | . | . | . | . | B | . | C | . | 0.04 | . | * | . | 0.20 | 0.46 |
| Arg | 287 | . | . | . | . | B | . | C | . | −0.66 | . | . | F | 0.65 | 0.46 |
| Gly | 288 | . | . | . | . | . | T | C | . | 0.16 | . | . | F | 1.35 | 0.57 |
| Pro | 289 | . | . | . | . | . | T | C | . | 0.50 | . | * | F | 2.70 | 1.19 |
| Gly | 290 | . | . | . | . | . | T | C | . | 1.31 | * | * | F | 3.00 | 1.01 |
| Ala | 291 | . | A | . | . | . | . | T | . | 1.53 | . | * | F | 2.50 | 1.65 |
| Glu | 292 | . | A | . | . | . | . | . | . | 1.39 | . | . | F | 2.00 | 1.08 |
| Asp | 293 | . | A | . | . | . | . | . | . | 1.73 | . | . | F | 1.70 | 1.48 |
| Asn | 294 | . | A | . | . | . | . | T | . | 1.94 | . | * | . | 1.45 | 2.36 |
| Ala | 295 | . | A | . | . | . | . | T | . | 1.40 | . | . | . | 1.15 | 2.36 |
| His | 296 | . | A | . | . | . | . | T | . | 1.18 | * | . | . | 1.00 | 0.99 |
| Asn | 297 | . | A | . | . | . | . | T | . | 0.88 | . | . | . | 0.10 | 0.51 |
| Glu | 298 | . | A | . | . | . | . | . | . | 0.88 | * | . | . | −0.10 | 0.67 |
| Ile | 299 | . | A | . | . | . | . | . | . | 0.29 | * | * | . | −0.10 | 0.80 |
| Leu | 300 | . | A | . | . | . | . | . | . | 0.88 | * | . | . | −0.10 | 0.50 |
| Ser | 301 | . | A | . | . | . | . | . | . | 0.61 | * | . | F | 0.65 | 0.48 |
| Asn | 302 | . | A | . | . | . | . | T | . | −0.20 | * | . | F | 0.25 | 0.92 |
| Ala | 303 | . | A | . | . | . | . | T | . | −0.50 | * | . | F | 0.25 | 0.92 |
| Asp | 304 | . | A | . | . | . | . | T | . | 0.08 | * | . | F | 0.85 | 0.92 |
| Ser | 305 | . | . | . | . | . | T | C | . | 0.19 | * | . | F | 1.05 | 0.83 |
| Leu | 306 | . | . | . | . | B | . | C | . | −0.37 | * | . | F | 0.05 | 0.71 |
| Ser | 307 | . | . | . | B | B | . | . | . | −0.67 | * | . | F | −0.15 | 0.31 |
| Thr | 308 | . | . | . | B | B | . | . | . | −0.08 | * | . | . | −0.60 | 0.31 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Phe | 309 | . | . | B | B | . | . | . | −0.08 | * | . | . | −0.30 | 0.66 |
| Val | 310 | A | . | . | B | . | . | . | 0.22 | . | . | F | −0.15 | 0.85 |
| Ser | 311 | A | A | . | . | . | . | . | 0.43 | . | . | F | 0.00 | 1.03 |
| Glu | 312 | A | A | . | . | . | . | . | 0.73 | . | . | F | 0.00 | 1.17 |
| Gln | 313 | A | A | . | . | . | . | . | 0.74 | . | . | F | 0.90 | 2.73 |
| Gln | 314 | A | A | . | . | . | . | . | 1.44 | . | . | F | 0.90 | 2.73 |
| Met | 315 | A | A | . | . | . | . | . | 2.30 | . | . | F | 0.90 | 2.73 |
| Glu | 316 | A | A | . | . | . | . | . | 2.39 | . | . | F | 0.90 | 2.73 |
| Ser | 317 | A | A | . | . | . | . | . | 1.80 | . | * | F | 0.90 | 2.44 |
| Gln | 318 | A | A | . | . | . | . | . | 1.80 | . | * | F | 0.90 | 2.49 |
| Glu | 319 | A | A | . | . | . | . | . | 0.99 | . | * | F | 0.90 | 2.40 |
| Pro | 320 | A | A | . | . | . | . | . | 1.28 | . | * | F | 0.90 | 1.48 |
| Ala | 321 | A | A | . | . | . | . | . | 0.93 | . | . | F | 0.60 | 1.23 |
| Asp | 322 | A | A | . | B | . | . | . | 0.38 | . | . | F | 0.45 | 0.70 |
| Leu | 323 | A | A | . | B | . | . | . | 0.07 | . | . | F | −0.15 | 0.34 |
| Thr | 324 | . | A | B | B | . | . | . | −0.79 | . | . | F | −0.15 | 0.48 |
| Gly | 325 | . | A | B | B | . | . | . | −0.58 | . | . | . | −0.30 | 0.21 |
| Val | 326 | . | . | B | B | . | . | . | −0.29 | . | . | . | −0.60 | 0.45 |
| Thr | 327 | . | . | B | B | . | . | . | −0.50 | . | . | . | −0.60 | 0.42 |
| Val | 328 | . | . | B | B | . | . | . | −0.03 | . | * | F | −0.17 | 0.65 |
| Gln | 329 | . | . | B | B | . | . | . | 0.28 | . | * | F | 0.11 | 0.87 |
| Ser | 330 | . | . | . | . | . | T | C | 0.03 | . | * | F | 2.04 | 1.05 |
| Pro | 331 | . | . | . | . | . | T | C | 0.89 | . | * | F | 2.32 | 1.42 |
| Gly | 332 | . | . | . | . | T | T | . | 0.53 | . | * | F | 2.80 | 1.42 |
| Glu | 333 | A | . | . | . | . | T | . | 0.58 | . | * | F | 1.97 | 0.57 |
| Ala | 334 | . | . | B | . | . | . | . | −0.23 | . | * | . | 0.74 | 0.30 |
| Gln | 335 | . | . | B | . | . | . | . | −0.28 | . | . | . | 0.46 | 0.25 |
| Cys | 336 | . | . | B | . | . | . | . | −0.28 | . | . | . | 0.18 | 0.14 |
| Leu | 337 | . | . | B | . | . | . | . | −0.52 | . | * | . | −0.40 | 0.22 |
| Leu | 338 | . | . | B | . | . | . | . | −0.52 | . | * | . | −0.40 | 0.13 |
| Gly | 339 | . | A | . | . | . | . | C | −0.52 | . | * | F | 0.05 | 0.42 |
| Pro | 340 | A | A | . | . | . | . | . | −0.52 | . | * | F | −0.15 | 0.51 |
| Ala | 341 | A | A | . | . | . | . | . | −0.20 | . | * | F | 0.60 | 1.07 |
| Glu | 342 | A | A | . | . | . | . | . | 0.31 | . | * | F | 0.90 | 1.07 |
| Ala | 343 | A | A | . | . | . | . | . | 1.12 | * | * | F | 0.75 | 0.93 |
| Glu | 344 | A | A | . | . | . | . | . | 1.58 | . | * | F | 0.90 | 1.60 |
| Gly | 345 | A | A | . | . | . | . | . | 1.90 | . | * | F | 0.90 | 1.80 |
| Ser | 346 | A | . | . | . | . | T | . | 2.60 | . | * | F | 1.30 | 3.50 |
| Gln | 347 | A | . | . | . | . | T | . | 1.79 | . | * | F | 1.30 | 3.96 |
| Arg | 348 | A | . | . | . | . | T | . | 1.57 | . | * | F | 1.30 | 3.30 |
| Arg | 349 | . | . | B | . | . | T | . | 0.71 | . | * | F | 1.30 | 2.03 |
| Arg | 350 | . | . | B | B | . | . | . | 0.84 | . | * | F | 0.75 | 0.87 |
| Leu | 351 | . | . | B | B | . | . | . | 0.56 | . | * | . | 0.60 | 0.69 |
| Leu | 352 | . | . | B | B | . | . | . | 0.56 | . | * | . | 0.30 | 0.35 |
| Val | 353 | . | . | B | B | . | . | . | 0.10 | * | * | . | −0.30 | 0.29 |
| Pro | 354 | . | . | B | . | . | T | . | −0.60 | * | . | . | −0.20 | 0.35 |
| Ala | 355 | . | . | . | . | T | T | . | −0.71 | . | * | . | 0.50 | 0.43 |
| Asn | 356 | . | . | . | . | . | T | C | −0.11 | . | . | F | 1.65 | 0.96 |
| Gly | 357 | . | . | . | . | . | T | C | 0.39 | . | . | F | 1.95 | 0.96 |
| Ala | 358 | . | . | . | . | . | . | C | 1.24 | . | . | F | 2.20 | 1.37 |
| Asp | 359 | . | . | . | . | . | T | C | 1.14 | . | . | F | 3.00 | 1.48 |
| Pro | 360 | A | . | . | . | . | T | . | 0.92 | * | . | F | 2.50 | 2.16 |
| Thr | 361 | A | . | . | . | . | T | . | 0.32 | . | . | F | 1.90 | 1.76 |
| Glu | 362 | A | . | . | . | . | T | . | −0.14 | . | . | F | 1.60 | 1.04 |
| Thr | 363 | A | . | . | B | . | . | . | −0.26 | . | . | F | 0.15 | 0.56 |
| Leu | 364 | A | . | . | B | . | . | . | −0.96 | * | . | . | −0.60 | 0.33 |
| Met | 365 | A | . | . | B | . | . | . | −0.74 | * | . | . | −0.60 | 0.17 |
| Leu | 366 | A | . | . | B | . | . | . | −0.39 | * | . | . | −0.60 | 0.19 |
| Phe | 367 | A | . | . | B | . | . | . | −1.09 | * | . | . | −0.60 | 0.47 |
| Phe | 368 | A | . | . | B | . | . | . | −1.37 | * | . | . | −0.60 | 0.41 |
| Asp | 369 | A | . | . | B | . | . | . | −0.56 | * | . | . | −0.60 | 0.50 |
| Lys | 370 | A | A | . | . | . | . | . | −0.84 | * | . | . | −0.30 | 0.93 |
| Phe | 371 | A | A | . | B | . | . | . | −0.89 | * | . | . | −0.30 | 0.75 |
| Ala | 372 | A | A | . | B | . | . | . | −0.40 | * | . | . | −0.30 | 0.34 |
| Asn | 373 | . | A | B | B | . | . | . | −0.40 | * | . | . | −0.60 | 0.26 |
| Ile | 374 | . | A | B | B | . | . | . | −0.40 | * | . | . | −0.60 | 0.26 |
| Val | 375 | . | A | B | B | . | . | . | −0.74 | . | . | . | −0.60 | 0.43 |
| Pro | 376 | . | A | B | B | . | . | C | −0.33 | . | . | . | −0.10 | 0.36 |
| Phe | 377 | . | . | . | . | T | T | . | 0.26 | . | . | . | 0.20 | 0.54 |
| Asp | 378 | . | . | . | . | T | T | . | 0.26 | . | . | F | 0.80 | 1.21 |
| Ser | 379 | . | . | . | . | T | T | . | 0.33 | . | . | F | 1.40 | 1.35 |
| Trp | 380 | A | . | . | . | . | T | . | 0.59 | * | * | F | 0.40 | 1.29 |
| Asp | 381 | A | A | . | . | . | . | . | 0.91 | * | . | . | −0.15 | 0.76 |
| Gln | 382 | A | A | . | . | . | . | . | 1.61 | * | . | . | −0.15 | 1.11 |
| Leu | 383 | A | A | . | . | . | . | . | 0.80 | * | . | . | −0.15 | 1.84 |
| Met | 384 | A | A | . | . | . | . | . | 1.10 | * | . | . | 0.30 | 0.91 |
| Arg | 385 | A | A | . | . | . | . | . | 0.58 | * | . | . | 0.30 | 0.87 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Gln | 386 | A | A | . | . | . | . | . | 0.27 | * | . | . | −0.30 | 0.87 |
| Leu | 387 | A | A | . | . | . | . | . | 0.31 | * | . | . | 0.45 | 1.27 |
| Asp | 388 | A | A | . | . | . | . | . | 1.12 | * | . | . | 0.75 | 1.30 |
| Leu | 389 | A | A | . | . | . | . | . | 1.72 | * | . | F | 0.60 | 1.21 |
| Thr | 390 | A | . | . | . | . | T | . | 0.72 | * | . | F | 1.30 | 2.54 |
| Lys | 391 | A | . | . | . | . | T | . | 0.72 | . | * | F | 1.30 | 1.07 |
| Asn | 392 | A | . | . | . | . | T | . | 0.68 | * | * | F | 1.30 | 2.16 |
| Glu | 393 | A | . | . | . | . | T | . | −0.18 | * | . | F | 1.30 | 1.11 |
| Ile | 394 | . | . | B | B | . | . | . | 0.74 | * | . | F | 0.75 | 0.41 |
| Asp | 395 | . | . | B | B | . | . | . | 0.47 | * | * | . | 0.60 | 0.50 |
| Val | 396 | . | . | B | B | . | . | . | 0.08 | * | * | . | 0.60 | 0.29 |
| Val | 397 | . | . | B | B | . | . | . | −0.23 | . | . | . | 0.51 | 0.41 |
| Arg | 398 | . | . | B | . | . | T | . | −0.82 | * | . | . | 1.12 | 0.36 |
| Ala | 399 | . | . | B | . | . | T | . | −0.28 | * | . | . | 0.73 | 0.49 |
| Gly | 400 | . | . | . | . | T | T | . | −0.49 | * | . | F | 2.09 | 0.65 |
| Thr | 401 | . | . | . | . | . | T | C | 0.02 | * | * | F | 2.10 | 0.51 |
| Ala | 402 | . | . | . | . | . | . | C | 0.88 | * | * | F | 1.09 | 0.50 |
| Gly | 403 | . | . | . | . | . | T | C | 0.18 | * | * | F | 1.68 | 0.85 |
| Pro | 404 | . | . | . | . | . | T | C | −0.04 | . | . | F | 1.47 | 0.59 |
| Gly | 405 | . | . | . | . | . | T | C | 0.06 | . | . | F | 1.26 | 0.48 |
| Asp | 406 | A | . | . | . | . | T | . | −0.22 | . | . | F | 0.25 | 0.76 |
| Ala | 407 | A | A | . | . | . | . | . | −0.23 | . | . | . | −0.30 | 0.50 |
| Leu | 408 | A | A | . | . | . | . | . | −0.70 | . | . | . | −0.60 | 0.50 |
| Tyr | 409 | A | A | . | . | . | . | . | −1.09 | * | . | . | −0.60 | 0.25 |
| Ala | 410 | A | A | . | . | . | . | . | −0.70 | * | . | . | −0.60 | 0.24 |
| Met | 411 | A | A | . | . | . | . | . | −0.99 | * | . | . | −0.60 | 0.59 |
| Leu | 412 | A | A | . | . | . | . | . | −1.26 | * | . | . | −0.60 | 0.39 |
| Met | 413 | A | A | . | . | . | . | . | −0.44 | * | . | . | −0.60 | 0.29 |
| Lys | 414 | A | A | . | B | . | . | . | −0.16 | * | . | . | −0.60 | 0.47 |
| Trp | 415 | A | A | . | B | . | . | . | 0.12 | * | . | . | 0.15 | 1.14 |
| Val | 416 | A | A | . | B | . | . | . | 0.38 | * | * | . | 0.45 | 1.66 |
| Asn | 417 | A | . | . | . | . | T | . | 1.30 | * | . | F | 1.75 | 0.82 |
| Lys | 418 | A | . | . | . | . | T | . | 1.90 | * | . | F | 2.20 | 1.53 |
| Thr | 419 | . | . | . | . | . | T | C | 1.27 | * | . | F | 3.00 | 3.32 |
| Gly | 420 | . | . | . | . | . | T | C | 1.26 | * | . | F | 2.70 | 2.08 |
| Arg | 421 | . | . | . | . | T | . | . | 1.22 | * | . | F | 2.40 | 1.40 |
| Asn | 422 | . | . | . | . | . | T | C | 1.19 | * | . | F | 1.65 | 0.68 |
| Ala | 423 | . | . | B | . | . | T | . | 0.83 | . | . | . | 1.00 | 0.93 |
| Ser | 424 | . | . | B | . | . | T | . | 0.33 | . | . | . | 0.70 | 0.69 |
| Ile | 425 | . | . | B | . | . | T | . | −0.13 | . | * | . | −0.20 | 0.35 |
| His | 426 | . | . | B | . | . | . | . | −0.24 | . | * | . | −0.60 | 0.29 |
| Thr | 427 | . | A | B | . | . | . | . | −0.83 | * | * | . | −0.60 | 0.36 |
| Leu | 428 | A | A | . | . | . | . | . | −1.06 | * | * | . | −0.60 | 0.52 |
| Leu | 429 | A | A | . | . | . | . | . | −0.76 | * | * | . | −0.60 | 0.31 |
| Asp | 430 | A | A | . | . | . | . | . | 0.24 | * | * | . | −0.30 | 0.38 |
| Ala | 431 | A | A | . | . | . | . | . | −0.32 | * | * | . | 0.30 | 0.89 |
| Leu | 432 | A | A | . | . | . | . | . | −0.01 | * | * | . | 0.75 | 1.07 |
| Glu | 433 | A | A | . | . | . | . | . | 0.80 | * | * | . | 0.75 | 1.11 |
| Arg | 434 | A | A | . | . | . | . | . | 1.72 | * | * | F | 0.90 | 1.90 |
| Met | 435 | A | A | . | . | . | . | . | 1.69 | * | * | F | 0.90 | 4.52 |
| Glu | 436 | A | A | . | . | . | . | . | 1.69 | * | * | F | 0.90 | 3.55 |
| Glu | 437 | A | A | . | . | . | . | . | 2.54 | * | . | F | 0.90 | 1.83 |
| Arg | 438 | A | A | . | . | . | . | . | 2.54 | * | * | F | 0.90 | 3.70 |
| His | 439 | A | A | . | . | . | . | . | 2.48 | * | * | F | 0.90 | 3.70 |
| Ala | 440 | A | A | . | . | . | . | . | 2.19 | * | * | F | 0.90 | 4.28 |
| Lys | 441 | A | A | . | . | . | . | . | 2.19 | * | * | F | 0.90 | 1.53 |
| Glu | 442 | A | A | . | . | . | . | . | 2.19 | * | . | F | 0.90 | 1.95 |
| Lys | 443 | A | A | . | . | . | . | . | 1.27 | * | * | F | 0.90 | 3.22 |
| Ile | 444 | A | A | . | . | . | . | . | 0.49 | * | * | F | 0.90 | 1.33 |
| Gln | 445 | A | A | . | . | . | . | . | 0.22 | * | * | F | 0.75 | 0.63 |
| Asp | 446 | A | A | . | . | . | . | . | 0.18 | * | * | F | −0.15 | 0.23 |
| Leu | 447 | A | A | . | . | . | . | . | −0.12 | * | . | . | −0.30 | 0.56 |
| Leu | 448 | A | A | . | . | . | . | . | −0.51 | * | . | . | 0.55 | 0.43 |
| Val | 449 | A | A | . | . | . | . | . | 0.42 | * | . | F | 0.95 | 0.26 |
| Asp | 450 | A | . | . | . | . | T | . | −0.28 | * | . | F | 1.60 | 0.62 |
| Ser | 451 | . | . | . | . | T | T | . | −1.17 | * | . | F | 2.25 | 0.65 |
| Gly | 452 | . | . | . | . | T | T | . | −0.60 | * | . | F | 2.50 | 0.62 |
| Lys | 453 | . | . | . | B | . | T | . | −0.60 | . | . | F | 1.25 | 0.58 |
| Phe | 454 | . | A | B | . | . | . | . | 0.26 | . | . | . | 0.15 | 0.36 |
| Ile | 455 | . | A | B | . | . | . | . | 0.26 | . | . | . | 0.20 | 0.62 |
| Tyr | 456 | . | A | B | . | . | . | . | 0.21 | . | . | . | 0.55 | 0.52 |
| Leu | 457 | . | A | B | . | . | . | . | 0.24 | . | . | . | −0.03 | 0.59 |
| Glu | 458 | . | A | B | . | . | . | . | −0.14 | . | . | F | 0.54 | 1.22 |
| Asp | 459 | . | A | . | . | T | . | . | 0.26 | . | . | F | 1.66 | 0.77 |
| Gly | 460 | . | . | . | . | T | T | . | 0.56 | . | . | F | 2.78 | 1.26 |
| Thr | 461 | . | . | . | . | . | T | C | −0.06 | * | . | F | 2.70 | 0.73 |
| Gly | 462 | . | . | . | . | . | T | C | 0.46 | * | . | F | 2.13 | 0.33 |

TABLE 2-continued

| Res | Position | I | II | III | IV | V | VI | VII | VIII | IX | X | XI | XII | XIII |
|-----|----------|---|----|-----|----|---|-----|-----|------|----|----|----|-----|------|
| Ser | 463 | . | . | . | . | . | T | C | −0.36 | . | . | F | 1.26 | 0.44 |
| Ala | 464 | A | . | . | . | . | . | . | −0.36 | . | . | . | 0.14 | 0.25 |
| Val | 465 | . | . | B | . | . | . | . | −0.40 | . | . | . | 0.17 | 0.44 |
| Ser | 466 | . | . | B | . | . | . | . | −0.48 | . | . | . | −0.10 | 0.42 |
| Leu | 467 | . | . | B | . | . | . | . | −0.52 | . | . | . | −0.10 | 0.53 |
| Glu | 468 | A | . | . | . | . | . | . | −0.61 | . | . | . | 0.50 | 0.92 |

In another aspect, the invention provides an antibody that binds a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides are therefore useful to raise antibodies, including monoclonal antibodies, that bind to a TR4 polypeptide of the invention. See, for instance, Wilson et al., Cell 37:767-778 (1984) at 777. Antigenic epitope-bearing peptides and polypeptides preferably contain a sequence of at least seven, more preferably at least nine and most preferably between at least about 15 to about 30 amino acids contained within the amino acid sequence of SEQ ID NO:1.

Antibodies of the invention may bind one or more antigenic TR4 polypeptides or peptides including, but not limited to: a polypeptide comprising amino acid residues from about 35 to about 92 of SEQ ID NO:1; a polypeptide comprising amino acid residues from about 114 to about 160 of SEQ ID NO:1; a polypeptide comprising amino acid residues from about 169 to about 240 of SEQ ID NO:1; a polypeptide comprising amino acid residues from about 267 to about 298 of SEQ ID NO:1; a polypeptide comprising amino acid residues from about 330 to about 364 of SEQ ID NO:1; a polypeptide comprising amino acid residues from about 391 to about 404 of SEQ ID NO:1; and/or a polypeptide comprising amino acid residues from about 418 to about 465 of SEQ ID NO:1. In this context "about" includes the particularly recited range, larger or smaller by several (5, 4, 3, 2, or 1) amino acids, at either terminus or at both termini. As indicated above, the inventors have determined that the above polypeptide fragments are antigenic regions of the TR4 protein. Epitope-bearing TR4 peptides and polypeptides may be produced by any conventional means. Houghten, R. A., "General method for the rapid solid-phase synthesis of large numbers of peptides: specificity of antigen-antibody interaction at the level of individual amino acids," Proc. Natl. Acad. Sci. USA 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, TR4 polypeptides and the epitope-bearing fragments thereof described herein (e.g., corresponding to a portion of the extracellular domain such as, for example, amino acid residues 1 to 240 of SEQ ID NO:1 can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)). Fusion proteins that have a disulfide-linked dimeric structure due to the IgG part can also be more efficient in binding and neutralizing other molecules than the monomeric TR4 protein or protein fragment alone (Fountoulakis et al., J Biochem 270:3958-3964 (1995)). Thus, antibodies of the invention may bind fusion proteins that comprise all or a portion of a TR4 polypeptide such as TR4.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified TR4 polypeptides or TR4 polypeptide fragments or variants.

For instance, for many proteins, including the extracellular domain of a membrane associated protein or the mature form(s) of a secreted protein, it is known in the art that one or more amino acids may be deleted from the N-terminus or C-terminus without substantial loss of biological function, or loss of the ability to be bound by a specific antibody. For instance, Ron et al., J. Biol. Chem., 268:2984-2988 (1993) reported modified KGF proteins that had heparin binding activity even if 3, 8, or 27 amino-terminal amino acid residues were missing. In the present case, since TR4 is a member of the death domain containing receptor (DDCR) polypeptide family, deletions of N-terminal amino acids up to the cysteine residue at position 109 in SEQ ID NO:1 may retain some biological activity such as the ability to induce apoptosis. Polypeptides having further N-terminal deletions including the cysteine residue at position 109 (C-109) in SEQ ID NO:1 would not be expected to retain such biological activities because this residue is conserved among family members and may be required for forming a disulfide bridge to provide structural stability which is needed for ligand binding.

However, even if deletion of one or more amino acids from the N-terminus of a protein results in modification or loss of one or more biological functions of the protein, other functional activities (e.g., biological activities, ability to multimerize, ability to bind TR4 ligand (e.g., TRAIL)) may still be retained. For example, the ability of shortened TR4 polypeptides to induce and/or bind to antibodies which recognize the complete or mature forms of the TR4 polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TR4 polypeptide with a large number of deleted N-terminal amino acid residues may retain some biological or immunogenic activities. In fact, peptides composed of as few as six TR4 amino acid residues may often evoke an immune response.

Accordingly, the present invention further provides antibodies that bind polypeptides having one or more residues deleted from the amino terminus of the TR4 amino acid sequence of SEQ ID NO:1 up to the serine residue at position number 463 and polynucleotides encoding such polypeptides. In particular, the present invention provides antibodies that bind polypeptides comprising the amino acid sequence of residues $n^1$-468 of SEQ ID NO:1, where $n^1$ is an integer from 2 to 463 corresponding to the position of the amino acid residue in SEQ ID NO:1.

More in particular, the invention provides antibodies that bind polypeptides comprising, or alternatively consisting of, the amino acid sequence of residues of A-2 to E-468; P-3 to E-468; P-4 to E-468; P-5 to E-468; A-6 to E-468; R-7 to E-468; V-8 to E-468; H-9 to E-468; L-10 to E-468; G-11 to E-468; A-12 to E-468; F-13 to E-468; L-14 to E-468; A-15 to E-468; V-16 to E-468; T-17 to E-468; P-18 to E-468; N-19 to E-468; P-20 to E-468; G-21 to E-468; S-22 to E-468; A-23 to E-468; A-24 to E-468; S-25 to E-468; G-26 to E-468; T-27 to E-468; E-28 to E-468; A-29 to E-468; A-30 to E-468; A-31 to E-468; A-32 to E-468; T-33 to E-468; P-34 to E-468; S-35 to E-468; K-36 to E-468; V-37 to E-468; W-38 to E-468; G-39 to E-468; S-40 to E-468; S-41 to E-468; A-42 to E-468; G-43 to E-468; R-44 to E-468; I-45 to E-468; E-46 to E-468; P-47 to E-468; R-48 to E-468; G-49 to E-468; G-50 to E-468; G-51 to E-468; R-52 to E-468; G-53 to E-468; A-54 to E-468; L-55 to E-468; P-56 to E-468; T-57 to E-468; S-58 to E-468; M-59 to E-468; G-60 to E-468; Q-61 to E-468; H-62 to E-468; G-63 to E-468; P-64 to E-468; S-65 to E-468; A-66 to E-468; R-67 to E-468; A-68 to E-468; R-69 to E-468; A-70 to E-468; G-71 to E-468; R-72 to E-468; A-73 to E-468; P-74 to E-468; G-75 to E-468; P-76 to E-468; R-77 to E-468; P-78 to E-468; A-79 to E-468; R-80 to E-468; E-81 to E-468; A-82 to E-468; S-83 to E-468; P-84 to E-468; R-85 to E-468; L-86 to E-468; R-87 to E-468; V-88 to E-468; H-89 to E-468; K-90 to E-468; T-91 to E-468; F-92 to E-468; K-93 to E-468; F-94 to E-468; V-95 to E-468; V-96 to E-468; V-97 to E-468; G-98 to E-468; V-99 to E-468; L-100 to E-468; L-101 to E-468; Q-102 to E-468; V-103 to E-468; V-104 to E-468; P-105 to E-468; S-106 to E-468; S-107 to E-468; A-108 to E-468; A-109 to E-468; T-110 to E-468; I-111 to E-468; K-112 to E-468; L-113 to E-468; H-114 to E-468; D-115 to E-468; Q-116 to E-468; S-117 to E-468; I-118 to E-468; G-119 to E-468; T-120 to E-468; Q-121 to E-468; Q-122 to E-468; W-123 to E-468; E-124 to E-468; H-125 to E-468; S-126 to E-468; P-127 to E-468; L-128 to E-468; G-129 to E-468; E-130 to E-468; L-131 to E-468; C-132 to E-468; P-133 to E-468; P-134 to E-468; G-135 to E-468; S-136 to E-468; H-137 to E-468; R-138 to E-468; S-139 to E-468; E-140 to E-468; R-141 to E-468; P-142 to E-468; G-143 to E-468; A-144 to E-468; C-145 to E-468; N-146 to E-468; R-147 to E-468; C-148 to E-468; T-149 to E-468; E-150 to E-468; G-151 to E-468; V-152 to E-468; G-153 to E-468; Y-154 to E-468; T-155 to E-468; N-156 to E-468; A-157 to E-468; S-158 to E-468; N-159 to E-468; N-160 to E-468; L-161 to E-468; F-162 to E-468; A-163 to E-468; C-164 to E-468; L-165 to E-468; P-166 to E-468; C-167 to E-468; T-168 to E-468; A-169 to E-468; C-170 to E-468; K-171 to E-468; S-172 to E-468; D-173 to E-468; E-174 to E-468; E-175 to E-468; E-176 to E-468; R-177 to E-468; S-178 to E-468; P-179 to E-468; C-180 to E-468; T-181 to E-468; T-182 to E-468; T-183 to E-468; R-184 to E-468; N-185 to E-468; T-186 to E-468; A-187 to E-468; C-188 to E-468; Q-189 to E-468; C-190 to E-468; K-191 to E-468; P-192 to E-468; G-193 to E-468; T-194 to E-468; F-195 to E-468; R-196 to E-468; N-197 to E-468; D-198 to E-468; N-199 to E-468; S-200 to E-468; A-201 to E-468; E-202 to E-468; M-203 to E-468; C-204 to E-468; R-205 to E-468; K-206 to E-468; C-207 to E-468; S-208 to E-468; T-209 to E-468; G-210 to E-468; C-211 to E-468; P-212 to E-468; R-213 to E-468; G-214 to E-468; M-215 to E-468; V-216 to E-468; K-217 to E-468; V-218 to E-468; K-219 to E-468; D-220 to E-468; C-221 to E-468; T-222 to E-468; P-223 to E-468; W-224 to E-468; S-225 to E-468; D-226 to E-468; I-227 to E-468; E-228 to E-468; C-229 to E-468; V-230 to E-468; H-231 to E-468; K-232 to E-468; E-233 to E-468; S-234 to E-468; G-235 to E-468; N-236 to E-468; G-237 to E-468; H-238 to E-468; N-239 to E-468; I-240 to E-468; W-241 to E-468; V-242 to E-468; I-243 to E-468; L-244 to E-468; V-245 to E-468; V-246 to E-468; T-247 to E-468; L-248 to E-468; V-249 to E-468; V-250 to E-468; P-251 to E-468; L-252 to E-468; L-253 to E-468; L-254 to E-468; V-255 to E-468; A-256 to E-468; V-257 to E-468; L-258 to E-468; I-259 to E-468; V-260 to E-468; C-261 to E-468; C-262 to E-468; C-263 to E-468; I-264 to E-468; G-265 to E-468; S-266 to E-468; G-267 to E-468; C-268 to E-468; G-269 to E-468; G-270 to E-468; D-271 to E-468; P-272 to E-468; K-273 to E-468; C-274 to E-468; M-275 to E-468; D-276 to E-468; R-277 to E-468; V-278 to E-468; C-279 to E-468; F-280 to E-468; W-281 to E-468; R-282 to E-468; L-283 to E-468; G-284 to E-468; L-285 to E-468; L-286 to E-468; R-287 to E-468; G-288 to E-468; P-289 to E-468; G-290 to E-468; A-291 to E-468; E-292 to E-468; D-293 to E-468; N-294 to E-468; A-295 to E-468; H-296 to E-468; N-297 to E-468; E-298 to E-468; I-299 to E-468; L-300 to E-468; S-301 to E-468; N-302 to E-468; A-303 to E-468; D-304 to E-468; S-305 to E-468; L-306 to E-468; S-307 to E-468; T-308 to E-468; F-309 to E-468; V-310 to E-468; S-311 to E-468; E-312 to E-468; Q-313 to E-468; Q-314 to E-468; M-315 to E-468; E-316 to E-468; S-317 to E-468; Q-318 to E-468; E-319 to E-468; P-320 to E-468; A-321 to E-468; D-322 to E-468; L-323 to E-468; T-324 to E-468; G-325 to E-468; V-326 to E-468; T-327 to E-468; V-328 to E-468; Q-329 to E-468; S-330 to E-468; P-331 to E-468; G-332 to E-468; E-333 to E-468; A-334 to E-468; Q-335 to E-468; C-336 to E-468; L-337 to E-468; L-338 to E-468; G-339 to E-468; P-340 to E-468; A-341 to E-468; E-342 to E-468; A-343 to E-468; E-344 to E-468; G-345 to E-468; S-346 to E-468; Q-347 to E-468; R-348 to E-468; R-349 to E-468; R-350 to E-468; L-351 to E-468; L-352 to E-468; V-353 to E-468; P-354 to E-468; A-355 to E-468; N-356 to E-468; G-357 to E-468; A-358 to E-468; D-359 to E-468; P-360 to E-468; T-361 to E-468; E-362 to E-468; T-363 to E-468; L-364 to E-468; M-365 to E-468; L-366 to E-468; F-367 to E-468; F-368 to E-468; D-369 to E-468; K-370 to E-468; F-371 to E-468; A-372 to E-468; N-373 to E-468; I-374 to E-468; V-375 to E-468; P-376 to E-468; F-377 to E-468; D-378 to E-468; S-379 to E-468; W-380 to E-468; D-381 to E-468; Q-382 to E-468; L-383 to E-468; M-384 to E-468; R-385 to E-468; Q-386 to E-468; L-387 to E-468; D-388 to E-468; L-389 to E-468; T-390 to E-468; K-391 to E-468; N-392 to E-468; E-393 to E-468; I-394 to E-468; D-395 to E-468; V-396 to E-468; V-397 to E-468; R-398 to E-468; A-399 to E-468; G-400 to E-468; T-401 to E-468; A-402 to E-468; G-403 to E-468; P-404 to E-468; G-405 to E-468; D-406 to E-468; A-407 to E-468; L-408 to E-468; Y-409 to E-468; A-410 to E-468; M-411 to E-468; L-412 to E-468; M-413 to E-468; K-414 to E-468; W-415 to E-468; V-416 to E-468; N-417 to E-468; K-418 to E-468; T-419 to E-468; G-420 to E-468; R-421 to E-468; N-422 to E-468; A-423 to E-468; S-424 to E-468; I-425 to E-468; H-426 to E-468; T-427 to E-468; L-428 to E-468; L-429 to E-468; D-430 to E-468; A-431 to E-468; L-432 to E-468; E-433 to E-468; R-434 to E-468; M-435 to E-468; E-436 to E-468; E-437 to E-468; R-438 to E-468; H-439 to E-468; A-440 to E-468; K-441 to E-468; E-442 to E-468; K-443 to E-468; I-444 to E-468; Q-445 to E-468; D-446 to E-468; L-447 to E-468; L-448 to E-468; V-449 to E-468; D-450 to E-468; S-451 to E-468; G-452 to E-468; K-453 to E-468; F-454 to E-468; I-455 to E-468; Y-456 to E-468; L-457 to E-468; E-458 to E-468; D-459 to E-468; G-460 to E-468; T-461 to E-468; G-462 to E-468; and/or S-463 to E-468 of the TR4 sequence of SEQ ID NO:1.

In another embodiment, N-terminal deletions of the TR4 polypeptide can be described by the general formula n2 to 238 where n2 is a number from 2 to 238 corresponding to the amino acid sequence identified of SEQ ID NO:1. In specific embodiments, antibodies of the invention bind N terminal deletions of the TR4 comprising, or alternatively consisting of, the amino acid sequence of residues: A-2 to H-238; P-3 to H-238; P-4 to H-238; P-5 to H-238; A-6 to H-238; R-7 to H-238; V-8 to H-238; H-9 to H-238; L-10 to H-238; G-11 to H-238; A-12 to H-238; F-13 to H-238; L-14 to H-238; A-15 to H-238; V-16 to H-238; T-17 to H-238; P-18 to H-238; N-19 to H-238; P-20 to H-238; G-21 to H-238; S-22 to H-238; A-23 to H-238; A-24 to H-238; S-25 to H-238; G-26 to H-238; T-27 to H-238; E-28 to H-238; A-29 to H-238; A-30 to H-238; A-31 to H-238; A-32 to H-238; T-33 to H-238; P-34 to H-238; S-35 to H-238; K-36 to H-238; V-37 to H-238; W-38 to H-238; G-39 to H-238; S-40 to H-238; S-41 to H-238; A-42 to H-238; G-43 to H-238; R-44 to H-238; I-45 to H-238; E-46 to H-238; P-47 to H-238; R-48 to H-238; G-49 to H-238; G-50 to H-238; G-51 to H-238; R-52 to H-238; G-53 to H-238; A-54 to H-238; L-55 to H-238; P-56 to H-238; T-57 to H-238; S-58 to H-238; M-59 to H-238; G-60 to H-238; Q-61 to H-238; H-62 to H-238; G-63 to H-238; P-64 to H-238; S-65 to H-238; A-66 to H-238; R-67 to H-238; A-68 to H-238; R-69 to H-238; A-70 to H-238; G-71 to H-238; R-72 to H-238; A-73 to H-238; P-74 to H-238; G-75 to H-238; P-76 to H-238; R-77 to H-238; P-78 to H-238; A-79 to H-238; R-80 to H-238; E-81 to H-238; A-82 to H-238; S-83 to H-238; P-84 to H-238; R-85 to H-238; L-86 to H-238; R-87 to H-238; V-88 to H-238; H-89 to H-238; K-90 to H-238; T-91 to H-238; F-92 to H-238; K-93 to H-238; F-94 to H-238; V-95 to H-238; V-96 to H-238; V-97 to H-238; G-98 to H-238; V-99 to H-238; L-100 to H-238; L-101 to H-238; Q-102 to H-238; V-103 to H-238; V-104 to H-238; P-105 to H-238; S-106 to H-238; S-107 to H-238; A-108 to H-238; A-109 to H-238; T-110 to H-238; I-111 to H-238; K-112 to H-238; L-113 to H-238; H-114 to H-238; D-115 to H-238; Q-116 to H-238; S-117 to H-238; I-118 to H-238; G-119 to H-238; T-120 to H-238; Q-121 to H-238; Q-122 to H-238; W-123 to H-238; E-124 to H-238; H-125 to H-238; S-126 to H-238; P-127 to H-238; L-128 to H-238; G-129 to H-238; E-130 to H-238; L-131 to H-238; C-132 to H-238; P-133 to H-238; P-134 to H-238; G-135 to H-238; S-136 to H-238; H-137 to H-238; R-138 to H-238; S-139 to H-238; E-140 to H-238; R-141 to H-238; P-142 to H-238; G-143 to H-238; A-144 to H-238; C-145 to H-238; N-146 to H-238; R-147 to H-238; C-148 to H-238; T-149 to H-238; E-150 to H-238; G-151 to H-238; V-152 to H-238; G-153 to H-238; Y-154 to H-238; T-155 to H-238; N-156 to H-238; A-157 to H-238; S-158 to H-238; N-159 to H-238; N-160 to H-238; L-161 to H-238; F-162 to H-238; A-163 to H-238; C-164 to H-238; L-165 to H-238; P-166 to H-238; C-167 to H-238; T-168 to H-238; A-169 to H-238; C-170 to H-238; K-171 to H-238; S-172 to H-238; D-173 to H-238; E-174 to H-238; E-175 to H-238; E-176 to H-238; R-177 to H-238; S-178 to H-238; P-179 to H-238; C-180 to H-238; T-181 to H-238; T-182 to H-238; T-183 to H-238; R-184 to H-238; N-185 to H-238; T-186 to H-238; A-187 to H-238; C-188 to H-238; Q-189 to H-238; C-190 to H-238; K-191 to H-238; P-192 to H-238; G-193 to H-238; T-194 to H-238; F-195 to H-238; R-196 to H-238; N-197 to H-238; D-198 to H-238; N-199 to H-238; S-200 to H-238; A-201 to H-238; E-202 to H-238; M-203 to H-238; C-204 to H-238; R-205 to H-238; K-206 to H-238; C-207 to H-238; S-208 to H-238; T-209 to H-238; G-210 to H-238; C-211 to H-238; P-212 to H-238; R-213 to H-238; G-214 to H-238; M-215 to H-238; V-216 to H-238; K-217 to H-238; V-218 to H-238; K-219 to H-238; D-220 to H-238; C-221 to H-238; T-222 to H-238; P-223 to H-238; W-224 to H-238; S-225 to H-238; D-226 to H-238; I-227 to H-238; E-228 to H-238; C-229 to H-238; V-230 to H-238; H-231 to H-238; K-232 to H-238; and/or E-233 to H-238; of the TR4 extracellular domain sequence of SEQ ID NO:1.

As mentioned above, even if deletion of one or more amino acids from the C-terminus of a protein results in modification of loss of one or more biological functions of the protein, other functional activities (e.g., biological activities, ability to multimerize, ability to bind DR4 ligand (e.g., TRAIL)) may still be retained. For example the ability of the shortened TR4 polypeptide to induce and/or bind to antibodies which recognize the complete or mature forms of the TR4 polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TR4 polypeptide with a large number of deleted C-terminal amino acid residues may retain some biological or immunogenic activities. In fact, peptides composed of as few as six TR4 amino acid residues may often evoke an immune response.

Accordingly, the present invention further provides antibodies that bind polypeptides having one or more residues deleted from the carboxy terminus of the amino acid sequence of the TR4 polypeptide sequence of SEQ ID NO:1 up to the alanine residue at position number 30, and polynucleotides encoding such polypeptides. In particular, the present invention provides antibodies that bind polypeptides comprising the amino acid sequence of residues 24-m1 of SEQ ID NO:1, where m1 is an integer from 30 to 467 corresponding to the position of the amino acid residue in SEQ ID NO:1.

More in particular, the invention provides antibodies that bind polypeptides comprising, or alternatively consisting of, the amino acid sequence of residues A-24 to L-467; A-24 to S-466; A-24 to V-465; A-24 to A-464; A-24 to S-463; A-24 to G-462; A-24 to T-461; A-24 to G-460; A-24 to D-459; A-24 to E-458; A-24 to L-457; A-24 to Y-456; A-24 to I-455; A-24 to F-454; A-24 to K-453; A-24 to G-452; A-24 to S-451; A-24 to D-450; A-24 to V-449; A-24 to L-448; A-24 to L-447; A-24 to D-446; A-24 to Q-445; A-24 to 1-444; A-24 to K-443; A-24 to E-442; A-24 to K-441; A-24 to A-440; A-24 to H-439; A-24 to R-438; A-24 to E-437; A-24 to E-436; A-24 to M-435; A-24 to R-434; A-24 to E-433; A-24 to L-432; A-24 to A-431; A-24 to D-430; A-24 to L-429; A-24 to L-428; A-24 to T-427; A-24 to H-426; A-24 to I-425; A-24 to S-424; A-24 to A-423; A-24 to N-422; A-24 to R-421; A-24 to G-420; A-24 to T-419; A-24 to K-418; A-24 to N-417; A-24 to V-416; A-24 to W-415; A-24 to K-414; A-24 to M-413; A-24 to L-412; A-24 to M-411; A-24 to A-410; A-24 to Y-409; A-24 to L-408; A-24 to A-407; A-24 to D-406; A-24 to G-405; A-24 to P-404; A-24 to G-403; A-24 to A-402; A-24 to T-401; A-24 to G-400; A-24 to A-399; A-24 to R-398; A-24 to V-397; A-24 to V-396; A-24 to D-395; A-24 to I-394; A-24 to E-393; A-24 to N-392; A-24 to K-391; A-24 to T-390; A-24 to L-389; A-24 to D-388; A-24 to L-387; A-24 to Q-386; A-24 to R-385; A-24 to M-384; A-24 to L-383; A-24 to Q-382; A-24 to D-381; A-24 to W-380; A-24 to S-379; A-24 to D-378; A-24 to F-377; A-24 to P-376; A-24 to V-375; A-24 to I-374; A-24 to N-373; A-24 to A-372; A-24 to F-371; A-24 to K-370; A-24 to D-369; A-24 to F-368; A-24 to F-367; A-24 to L-366; A-24 to M-365; A-24 to L-364; A-24 to T-363; A-24 to E-362; A-24 to T-361; A-24 to P-360; A-24 to D-359; A-24 to A-358; A-24 to G-357; A-24 to N-356; A-24 to A-355; A-24 to P-354; A-24 to V-353; A-24 to L-352; A-24 to L-351; A-24 to R-350; A-24 to R-349; A-24 to R-348; A-24 to Q-347; A-24 to S-346; A-24 to G-345; A-24 to E-344; A-24 to A-343; A-24 to E-342; A-24 to A-341; A-24 to P-340; A-24 to G-339; A-24 to L-338; A-24 to L-337; A-24 to C-336; A-24 to Q-335; A-24 to A-334; A-24 to E-333; A-24 to G-332; A-24 to P-331; A-24 to S-330; A-24 to Q-329; A-24 to V-328; A-24 to T-327; A-24 to V-326; A-24 to G-325; A-24 to T-324; A-24 to L-323; A-24 to D-322; A-24 to A-321; A-24 to P-320; A-24 to E-319; A-24 to Q-318; A-24 to S-317; A-24 to E-316; A-24 to M-315; A-24 to Q-314; A-24 to Q-313; A-24 to E-312; A-24 to S-311; A-24 to V-310; A-24 to F-309; A-24 to T-308; A-24 to S-307; A-24 to L-306; A-24 to S-305; A-24 to D-304; A-24 to A-303; A-24 to N-302; A-24 to S-301; A-24 to L-300; A-24 to I-299; A-24 to E-298; A-24 to N-297; A-24 to H-296; A-24 to A-295; A-24 to N-294; A-24 to D-293; A-24 to E-292; A-24 to A-291; A-24 to G-290; A-24 to P-289; A-24 to G-288; A-24 to R-287; A-24 to L-286; A-24 to L-285; A-24 to G-284; A-24 to L-283; A-24 to R-282; A-24 to W-281; A-24 to F-280; A-24 to C-279; A-24 to V-278; A-24 to R-277; A-24 to D-276; A-24 to M-275; A-24 to C-274; A-24 to K-273; A-24 to P-272; A-24 to D-271; A-24 to G-270; A-24 to G-269; A-24 to C-268; A-24 to G-267; A-24 to S-266; A-24 to G-265; A-24 to I-264; A-24 to C-263; A-24 to C-262; A-24 to C-261; A-24 to V-260; A-24 to I-259; A-24 to L-258; A-24 to V-257; A-24 to A-256; A-24 to V-255; A-24 to L-254; A-24 to L-253; A-24 to L-252; A-24 to P-251; A-24 to V-250; A-24 to V-249; A-24 to L-248; A-24 to T-247; A-24 to V-246; A-24 to V-245; A-24 to L-244; A-24 to I-243; A-24 to V-242; A-24 to W-241; A-24 to I-240; A-24 to N-239; A-24 to H-238; A-24 to G-237; A-24 to N-236; A-24 to G-235; A-24 to S-234; A-24 to E-233; A-24 to K-232; A-24 to H-231; A-24 to V-230; A-24 to C-229; A-24 to E-228; A-24 to I-227; A-24 to D-226; A-24 to S-225; A-24 to W-224; A-24 to P-223; A-24 to T-222; A-24 to C-221; A-24 to D-220; A-24 to K-219; A-24 to V-218; A-24 to K-217; A-24 to V-216; A-24 to M-215; A-24 to G-214; A-24 to R-213; A-24 to P-212; A-24 to C-211; A-24 to G-210; A-24 to T-209; A-24 to S-208; A-24 to C-207; A-24 to K-206; A-24 to R-205; A-24 to C-204; A-24 to M-203; A-24 to E-202; A-24 to A-201; A-24 to S-200; A-24 to N-199; A-24 to D-198; A-24 to N-197; A-24 to R-196; A-24 to F-195; A-24 to T-194; A-24 to G-193; A-24 to P-192; A-24 to K-191; A-24 to C-190; A-24 to Q-189; A-24 to C-188; A-24 to A-187; A-24 to T-186; A-24 to N-185; A-24 to R-184; A-24 to T-183; A-24 to T-182; A-24 to T-181; A-24 to C-180; A-24 to P-179; A-24 to S-178; A-24 to R-177; A-24 to E-176; A-24 to E-175; A-24 to E-174; A-24 to D-173; A-24 to S-172; A-24 to K-171; A-24 to C-170; A-24 to A-169; A-24 to T-168; A-24 to C-167; A-24 to P-166; A-24 to L-165; A-24 to C-164; A-24 to A-163; A-24 to F-162; A-24 to L-161; A-24 to N-160; A-24 to N-159; A-24 to S-158; A-24 to A-157; A-24 to N-156; A-24 to T-155; A-24 to Y-154; A-24 to G-153; A-24 to V-152; A-24 to G-151; A-24 to E-150; A-24 to T-149; A-24 to C-148; A-24 to R-147; A-24 to N-146; A-24 to C-145; A-24 to A-144; A-24 to G-143; A-24 to P-142; A-24 to R-141; A-24 to E-140; A-24 to S-139; A-24 to R-138; A-24 to H-137; A-24 to S-136; A-24 to G-135; A-24 to P-134; A-24 to P-133; A-24 to C-132; A-24 to L-131; A-24 to E-130; A-24 to G-129; A-24 to L-128; A-24 to P-127; A-24 to S-126; A-24 to H-125; A-24 to E-124; A-24 to W-123; A-24 to Q-122; A-24 to Q-121; A-24 to T-120; A-24 to G-119; A-24 to I-118; A-24 to S-117; A-24 to Q-116; A-24 to D-115; A-24 to H-114; A-24 to L-113; A-24 to K-112; A-24 to I-111; A-24 to T-110; A-24 to A-109; A-24 to A-108; A-24 to S-107; A-24 to S-106; A-24 to P-105; A-24 to V-104; A-24 to V-103; A-24 to Q-102; A-24 to L-101; A-24 to L-100; A-24 to V-99; A-24 to G-98; A-24 to V-97; A-24 to V-96; A-24 to V-95; A-24 to F-94; A-24 to K-93; A-24 to F-92; A-24 to T-91; A-24 to K-90; A-24 to H-89; A-24 to V-88; A-24 to R-87; A-24 to L-86; A-24 to R-85; A-24 to P-84; A-24 to S-83; A-24 to A-82; A-24 to E-81; A-24 to R-80; A-24 to A-79; A-24 to P-78; A-24 to R-77; A-24 to P-76; A-24 to G-75; A-24 to P-74; A-24 to A-73; A-24 to R-72; A-24 to G-71; A-24 to A-70; A-24 to R-69; A-24 to A-68; A-24 to R-67; A-24 to A-66; A-24 to S-65; A-24 to P-64; A-24 to G-63; A-24 to H-62; A-24 to Q-61; A-24 to G-60; A-24 to M-59; A-24 to S-58; A-24 to T-57; A-24 to P-56; A-24 to L-55; A-24 to A-54; A-24 to G-53; A-24 to R-52; A-24 to G-51; A-24 to G-50; A-24 to G-49; A-24 to R-48; A-24 to P-47; A-24 to E-46; A-24 to I-45; A-24 to R-44; A-24 to G-43; A-24 to A-42; A-24 to S-41; A-24 to S-40; A-24 to G-39; A-24 to W-38; A-24 to V-37; A-24 to K-36; A-24 to S-35; A-24 to P-34; A-24 to T-33; A-24 to A-32; A-24 to A-31; and/or A-24 to A-30 of the TR4 sequence of SEQ ID NO:1.

In another embodiment, antibodies of the invention bind C-terminal deletions of the TR4 polypeptide that can be described by the general formula $24\text{-}m^2$ where $m^2$ is a number from 30 to 238 corresponding to the amino acid sequence identified of SEQ ID NO:1. In specific embodiments, the invention provides antibodies that bind TR4 polypeptides comprising, or alternatively consisting of, the amino acid sequence of residues: A-24 to G-237; A-24 to N-236; A-24 to G-235; A-24 to S-234; A-24 to E-233; A-24 to K-232; A-24 to H-231; A-24 to V-230; A-24 to C-229; A-24 to E-228; A-24 to I-227; A-24 to D-226; A-24 to S-225; A-24 to W-224; A-24 to P-223; A-24 to T-222; A-24 to C-221; A-24 to D-220; A-24 to K-219; A-24 to V-218; A-24 to K-217; A-24 to V-216; A-24 to M-215; A-24 to G-214; A-24 to R-213; A-24 to P-212; A-24 to C-211; A-24 to G-210; A-24 to T-209; A-24 to S-208; A-24 to C-207; A-24 to K-206; A-24 to R-205; A-24 to C-204; A-24 to M-203; A-24 to E-202; A-24 to A-201; A-24 to S-200; A-24 to N-199; A-24 to D-198; A-24 to N-197; A-24 to R-196; A-24 to F-195; A-24 to T-194; A-24 to G-193; A-24 to P-192; A-24 to K-191; A-24 to C-190; A-24 to Q-189; A-24 to C-188; A-24 to A-187; A-24 to T-186; A-24 to N-185; A-24 to R-184; A-24 to T-183; A-24 to T-182; A-24 to T-181; A-24 to C-180; A-24 to P-179; A-24 to S-178; A-24 to R-177; A-24 to E-176; A-24 to E-175; A-24 to E-174; A-24 to D-173; A-24 to S-172; A-24 to K-171; A-24 to C-170; A-24 to A-169; A-24 to T-168; A-24 to C-167; A-24 to P-166; A-24 to L-165; A-24 to C-164; A-24 to A-163; A-24 to F-162; A-24 to L-161; A-24 to N-160; A-24 to N-159; A-24 to S-158; A-24 to A-157; A-24 to N-156; A-24 to T-155; A-24 to Y-154; A-24 to G-153; A-24 to V-152; A-24 to G-151; A-24 to E-150; A-24 to T-149; A-24 to C-148; A-24 to R-147; A-24 to N-146; A-24 to C-145; A-24 to A-144; A-24 to G-143; A-24 to P-142; A-24 to R-141; A-24 to E-140; A-24 to S-139; A-24 to R-138; A-24 to H-137; A-24 to S-136; A-24 to G-135; A-24 to P-134; A-24 to P-133; A-24 to C-132; A-24 to L-131; A-24 to E-130; A-24 to G-129; A-24 to L-128; A-24 to P-127; A-24 to S-126; A-24 to H-125; A-24 to E-124; A-24 to W-123; A-24 to Q-122; A-24 to Q-121; A-24 to T-120; A-24 to G-119; A-24 to I-118; A-24 to S-117; A-24 to Q-116; A-24 to D-115; A-24 to H-114; A-24 to L-113; A-24 to K-112; A-24 to I-111; A-24 to T-110; A-24 to A-109; A-24 to A-108; A-24 to S-107; A-24 to S-106; A-24 to P-105; A-24 to V-104; A-24 to V-103; A-24 to Q-102; A-24 to L-101; A-24 to L-100; A-24 to V-99; A-24 to G-98; A-24 to V-97; A-24 to V-96; A-24 to V-95; A-24 to F-94; A-24 to K-93; A-24 to F-92; A-24 to T-91; A-24 to K-90; A-24 to H-89; A-24 to V-88; A-24 to R-87; A-24 to L-86; A-24 to R-85; A-24 to P-84; A-24 to S-83; A-24 to A-82; A-24 to E-81; A-24 to R-80; A-24 to A-79; A-24 to P-78; A-24 to R-77; A-24 to P-76; A-24 to G-75; A-24 to P-74; A-24 to A-73; A-24 to R-72; A-24 to G-71; A-24 to A-70; A-24 to R-69; A-24 to A-68; A-24 to R-67; A-24 to A-66; A-24 to S-65; A-24 to P-64; A-24 to G-63; A-24 to H-62; A-24 to Q-61; A-24 to G-60; A-24 to M-59; A-24 to S-58; A-24 to T-57; A-24 to P-56; A-24 to L-55; A-24 to A-54; A-24 to G-53; A-24 to R-52; A-24 to G-51; A-24 to G-50; A-24 to G-49; A-24 to R-48; A-24 to P-47; A-24 to E-46; A-24 to I-45; A-24 to R-44; A-24 to G-43; A-24 to A-42; A-24 to S-41; A-24 to S-40; A-24 to G-39; A-24 to W-38; A-24 to V-37; A-24 to K-36; A-24 to S-35; A-24 to P-34; A-24 to T-33; A-24 to A-32; A-24 to A-31; and/or A-24 to A-30; of the TR4 extracellular domain sequence of SEQ ID NO:1.

The present invention further provides antibodies that bind polypeptides having one or more residues from the carboxy terminus of the amino acid sequence of the TR4 polypeptide of SEQ ID NO:1, up to C-221 of SEQ ID NO:1. In particular, the present invention provides antibodies that bind polypeptides having the amino acid sequence of residues 1-$m^9$ of the amino acid sequence in SEQ ID NO:1, where $m^9$ is any integer in the range of 221-468 and residue C-221 is the position of the first residue from the C-terminus of the complete TR4 polypeptide (shown in SEQ ID NO:1) believed to be required for receptor binding activity of the TR4 protein.

The invention also provides antibodies that bind polypeptides having one or more amino acids deleted from both the amino and the carboxyl termini of a TR4 polypeptide, which may be described generally as having residues $n^1$-$m^1$ and/or $n^2$-$m^2$ of SEQ ID NO:1, where $n^1$, $n^2$, $m^1$, and $m^2$ are integers as described above.

Also included are antibodies that bind a polypeptide consisting of a portion of the complete TR4 amino acid sequence encoded by the cDNA clone contained in ATCC Deposit No. 97853, where this portion excludes from 1 to about 108 amino acids from the amino terminus of the complete amino acid sequence encoded by the cDNA clone contained in ATCC Deposit No. 97853, or from 1 to about 247 amino acids from the carboxy terminus, or any combination of the above amino terminal and carboxy terminal deletions, of the complete amino acid sequence encoded by the cDNA clone contained in ATCC Deposit No. 97853.

Preferably, antibodies of the present invention bind fragments of TR4 comprising a portion of the extracellular domain; i.e., within residues 24-238 of SEQ ID NO:1, since any portion therein is expected to be soluble.

It will be recognized in the art that some amino acid sequence of TR4 can be varied without significant effect of the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes antibodies that bind variations of the TR4 protein which show substantial TR4 protein activity or which include regions of TR4 such as the protein fragments discussed below. Such mutants include deletions, insertions, inversions, repeats, and type substitution. Guidance concerning which amino acid changes are likely to be phenotypically silent can be found in Bowie, J. U. et al., *Science* 247:1306-1310 (1990).

Thus, antibodies of the present invention may bind a fragment, derivative, or analog of the polypeptide of SEQ ID NO:1, or that encoded by the cDNA in ATCC deposit 97853. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR4 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the antibodies of the present invention may bind a TR4 receptor that contains one or more amino acid substitutions, deletions or additions, either from natural mutations or human manipulation.

As indicated, changes are preferably of a minor nature, such as conservative amino acid substitutions that do not significantly affect the folding or activity of the protein (see Table 3).

TABLE 3

| Conservative Amino Acid Substitutions. | |
|---|---|
| Aromatic | Phenylalanine<br>Tryptophan<br>Tyrosine |
| Hydrophobic | Leucine<br>Isoleucine<br>Valine |
| Polar | Glutamine<br>Asparagine |
| Basic | Arginine<br>Lysine<br>Histidine |
| Acidic | Aspartic Acid<br>Glutamic Acid |
| Small | Alanine<br>Serine<br>Threonine<br>Methionine<br>Glycine |

In specific embodiments, the number of substitutions, additions or deletions in the amino acid sequence of SEQ ID NO:1 and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

In specific embodiments, the antibodies of the invention bind TR4 polypeptides or fragments or variants thereof (especially a fragment comprising or alternatively consisting of, the extracellular soluble domain of TR4), that contains any one or more of the following conservative mutations in TR4: M1 replaced with A, G, I, L, S, T, or V; A2 replaced with G, I, L, S, T, M, or V; A6 replaced with G, I, L, S, T, M, or V; R7 replaced with H, or K; V8 replaced with A, G, I, L, S, T, or M; H9 replaced with K, or R; L10 replaced with A, G, I, S, T, M, or V; G11 replaced with A, I, L, S, T, M, or V; A12 replaced with G, I, L, S, T, M, or V; F13 replaced with W, or Y; L14 replaced with A, G, I, S, T, M, or V; A15 replaced with G, I, L, S, T, M, or V; V16 replaced with A, G, I, L, S, T, or M; T17 replaced with A, G, I, L, S, M, or V; N19 replaced with Q; G21 replaced with A, I, L, S, T, M, or V; S22 replaced with A, G, I, L, T, M, or V; A23 replaced with G, I, L, S, T, M, or V; A24 replaced with G, I, L, S, T, M, or V; S25 replaced with A, G, I, L, T, M, or V; G26 replaced with A, I, L, S, T, M, or V; T27 replaced with A, G, I, L, S, M, or V; E28 replaced with D; A29 replaced with G, I, L, S, T, M, or V; A30 replaced with G, I, L, S, T, M, or V; A31 replaced with G, I, L, S, T, M, or V; A32 replaced with G, I, L, S, T, M, or V; T33 replaced with A, G, I, L, S, M, or V; S35 replaced with A, G, I, L, T, M, or V; K36 replaced with H, or R; V37 replaced with A, G, I, L, S, T, or M; W38 replaced with F, or Y; G39 replaced with A, I, L, S, T, M, or V; S40 replaced with A, G, I, L, T, M, or V; S41 replaced with A, G, I, L, T, M, or V; A42 replaced with G, I, L, S, T, M, or V; G43 replaced with A, I, L, S, T, M, or V; R44 replaced with H, or K; I45 replaced with A, G, L, S, T, M, or V; E46 replaced with D; R48 replaced with H, or K; G49 replaced with A, I, L, S, T, M, or V; G50 replaced with A, I, L, S, T, M, or V; G51 replaced with A, I, L, S, T, M, or V; R52 replaced with H, or K; G53 replaced with A, I, L, S, T, M, or V; A54 replaced with G, I, L, S, T, M, or V; L55 replaced with A, G, I, S, T, M, or V; T57 replaced with A, G, I, L, S, M, or V; S58 replaced with A, G, I, L, T, M, or V; M59 replaced with A, G, I, L, S, T, or V; G60 replaced with A, I, L, S, T, M, or V; Q61 replaced with N; H62 replaced with K, or R; G63 replaced with A, I, L, S, T, M, or V; S65 replaced with A, G, I, L, T, M, or V; A66 replaced with G, I, L, S, T, M, or V; R67 replaced with H, or K; A68 replaced with G, I, L, S, T, M, or V; R69 replaced with H, or K; A70 replaced with G, I, L, S, T, M, or V; G71 replaced with A, I, L, S, T, M, or V; R72 replaced with H, or K; A73 replaced with G, I, L, S, T, M, or V; G75 replaced with A, I, L, S, T, M, or V; R77 replaced with H, or K; A79 replaced with G, I, L, S, T, M, or V; R80 replaced with H, or K; E81 replaced with D; A82 replaced with G, I, L, S, T, M, or V; S83 replaced with A, G, I, L, T, M, or V; R85 replaced with H, or K; L86 replaced with A, G, I, S, T, M, or V; R87 replaced with H, or K; V88 replaced with A, G, I, L, S, T, or M; H89 replaced with K, or R; K90 replaced with H, or R; T91 replaced with A, G, I, L, S, M, or V; F92 replaced with W, or Y; K93 replaced with H, or R; F94 replaced with W, or Y; V95 replaced with A, G, I, L, S, T, or M; V96 replaced with A, G, I, L, S, T, or M; V97 replaced with A, G, I, L, S, T, or M; G98 replaced with A, I, L, S, T, M, or V; V99 replaced with A, G, I, L, S, T, or M; L100 replaced with A, G, I, S, T, M, or V; L101 replaced with A, G, I, S, T, M, or V; Q102 replaced with N; V103 replaced with A, G, I, L, S, T, or M; V104 replaced with A, G, I, L, S, T, or M; S106 replaced with A, G, I, L, T, M, or V; S107 replaced with A, G, I, L, T, M, or V; A108 replaced with G, I, L, S, T, M, or V; A109 replaced with G, I, L, S, T, M, or V; T110 replaced with A, G, I, L, S, M, or V; I111 replaced with A, G, L, S, T, M, or V; K112 replaced with H, or R; L113 replaced with A, G, I, S, T, M, or V; H114 replaced with K, or R; D115 replaced with E; Q116 replaced with N; S117 replaced with A, G, I, L, T, M, or V; I118 replaced with A, G, L, S, T, M, or V; G119 replaced with A, I, L, S, T, M, or V; T120 replaced with A, G, I, L, S, M, or V; Q121 replaced with N; Q122 replaced with N; W123 replaced with F, or Y; E124 replaced with D; H125 replaced with K, or R; S126 replaced with A, G, I, L, T, M, or V; L128 replaced with A, G, I, S, T, M, or V; G129 replaced with A, I, L, S, T, M, or V; E130 replaced with D; L131 replaced with A, G, I, S, T, M, or V; G135 replaced with A, I, L, S, T, M, or V; S136 replaced with A, G, I, L, T, M, or V; H137 replaced with K, or R; R138 replaced with H, or K; S139 replaced with A, G, I, L, T, M, or V; E140 replaced with D; R141 replaced with H, or K; G143 replaced with A, I, L, S, T, M, or V; A144 replaced with G, I, L, S, T, M, or V; N146 replaced with Q; R147 replaced with H, or K; T149 replaced with A, G, I, L, S, M, or V; E150 replaced with D; G151 replaced with A, I, L, S, T, M, or V; V152 replaced with A, G, I, L, S, T, or M; G153 replaced with A, I, L, S, T, M, or V; Y154 replaced with F, or W; T155 replaced with A, G, I, L, S, M, or V; N156 replaced with Q; A157 replaced with G, I, L, S, T, M, or V; S158 replaced with A, G, I, L, T, M, or V; N159 replaced with Q; N160 replaced with Q; L161 replaced with A, G, I, S, T, M, or V; F162 replaced with W, or Y; A163 replaced with G, I, L, S, T, M, or V; L165 replaced with A, G, I, S, T, M, or V; T168 replaced with A, G, I, L, S, M, or V; A169 replaced with G, I, L, S, T, M, or V; K171 replaced with H, or R; S172 replaced with A, G, I, L, T, M, or V; D173 replaced with E; E174 replaced with D; E175 replaced with D; E176 replaced with D; R177 replaced with H, or K; S178 replaced with A, G, I, L, T, M, or V; T181 replaced with A, G, I, L, S, M, or V; T182 replaced with A, G, I, L, S, M, or V; T183 replaced with A, G, I, L, S, M, or V; R184 replaced with H, or K; N185 replaced with Q; T186 replaced with A, G, I, L, S, M, or V; A187 replaced with G, I, L, S, T, M, or V; Q189 replaced with N; K191 replaced with H, or R; G193 replaced with A, I, L, S, T, M, or V; T194 replaced with A, G, I, L, S, M, or V; F195 replaced with W, or Y; R196 replaced with H, or K; N197 replaced with Q; D198 replaced with E; N199 replaced with Q; S200 replaced with A, G, I, L, T, M, or V; A201 replaced with G, I, L, S, T, M, or V; E202 replaced with D; M203 replaced with A, G, I, L, S, T, or V; R205 replaced with H, or K; K206 replaced with H, or R; S208 replaced with A, G, I, L, T, M, or V; T209 replaced with A, G, I, L, S, M, or V; G210 replaced with A, I, L, S, T, M, or V; R213 replaced with H, or K; G214 replaced with A, I, L, S, T, M, or V; M215 replaced with A, G, I, L, S, T, or V; V216 replaced with A, G, I, L, S, T, or M; K217 replaced with H, or R; V218 replaced with A, G, I, L, S, T, or M; K219 replaced with H, or R; D220 replaced with E; T222 replaced with A, G, I, L, S, M, or V; W224 replaced with F, or Y; S225 replaced with A, G, I, L, T, M, or V; D226 replaced with E; I227 replaced with A, G, L, S, T, M, or V; E228 replaced with D; V230 replaced with A, G, I, L, S, T, or M; H231 replaced with K, or R; K232 replaced with H, or R; E233 replaced with D; S234 replaced with A, G, I, L, T, M, or V; G235 replaced with A, I, L, S, T, M, or V; N236 replaced with Q; G237 replaced with A, I, L, S, T, M, or V; H238 replaced with K, or R; N239 replaced with Q; I240 replaced with A, G, L, S, T, M, or V; W241 replaced with F, or Y; V242 replaced with A, G, I, L, S, T, or M; I243 replaced with A, G, L, S, T, M, or V; L244 replaced with A, G, I, S, T, M, or V; V245 replaced with A, G, I, L, S, T, or M; V246 replaced with A, G, I, L, S, T, or M; T247 replaced with A, G, I, L, S, M, or V; L248 replaced with A, G, I, S, T, M, or V; V249 replaced with A, G, I, L, S, T, or M; V250 replaced with A, G, I, L, S, T, or M; L252 replaced with A, G, I, S, T, M, or V; L253 replaced with A, G, I, S, T, M, or V; L254 replaced with A, G, I, S, T, M, or V; V255 replaced with A, G, I, L, S, T, or M; A256 replaced with G. I, L, S, T, M, or V; V257 replaced with A, G, I, L, S, T, or M; L258 replaced with A, G, I, S, T, M, or V; I259 replaced with A, G, L, S, T, M, or V; V260 replaced with A, G, I, L, S, T, or M; I264 replaced with A, G, L, S, T, M, or V; G265 replaced with A, I, L, S, T, M, or V; S266 replaced with A, G, I, L, T, M, or V; G267 replaced with A, I, L, S, T, M, or V; G269 replaced with A, I, L, S, T, M, or V; G270 replaced with A, I, L, S, T, M, or V; D271 replaced with E; K273 replaced with H, or R; M275 replaced with A, G, I, L, S, T, or V; D276 replaced with E; R277 replaced with H, or K; V278 replaced with A, G, I, L, S, T, or M; F280 replaced with W, or Y; W281 replaced with F, or Y; R282 replaced with H, or K; L283 replaced with A, G, I, S, T, M, or V; G284 replaced with A, I, L, S, T, M, or V; L285 replaced with A, G, I, S, T, M, or V; L286 replaced with A, G, I, S, T, M, or V; R287 replaced with H, or K; G288 replaced with A, I, L, S, T, M, or V; G290 replaced with A, I, L, S, T, M, or V; A291 replaced with G, I, L, S, T, M, or V; E292 replaced with D; D293 replaced with E; N294 replaced with Q; A295 replaced with G, I, L, S, T, M, or V; H296 replaced with K, or R; N297 replaced with Q; E298 replaced with D; I299 replaced with A, G, L, S, T, M, or V; L300 replaced with A, G, I, S, T, M, or V; S301 replaced with A, G, I, L, T, M, or V; N302 replaced with Q; A303 replaced with G, I, L, S, T, M, or V; D304 replaced with E; S305 replaced with A, G, I, L, T, M, or V; L306 replaced with A, G, I, S, T, M, or V; S307 replaced with A, G, I, L, T, M, or V; T308 replaced with A, G, I, L, S, M, or V; F309 replaced with W, or Y; V310 replaced with A, G, I, L, S, T, or M; S311 replaced with A, G, I, L, T, M, or V; E312 replaced with D; Q313 replaced with N; Q314 replaced with N; M315 replaced with A, G, I, L, S, T, or V; E316 replaced with D; S317 replaced with A, G, I, L, T, M, or V; Q318 replaced with N; E319 replaced with D; A321 replaced with G, I, L, S, T, M, or V; D322 replaced with E; L323 replaced with A, G, I, S, T, M, or V; T324 replaced with A, G, I, L, S, M, or V; G325 replaced with A, I, L, S, T, M, or V; V326 replaced with A, G, I, L, S, T, or M; T327 replaced with A, G, I, L, S, M, or V; V328 replaced with A, G, I, L, S, T, or M, Q329 replaced with N; S330 replaced with A, G, I, L, T, M, or V; G332 replaced with A, I, L, S, T, M, or V; E333 replaced with D; A334 replaced with G, I, L, S, T, M, or V; Q335 replaced with N; L337 replaced with A, G, I, S, T, M, or V; L338 replaced with A, G, I, S, T, M, or V; G339 replaced with A, I, L, S, T, M, or V; A341 replaced with G, I, L, S, T, M, or V; E342 replaced with D; A343 replaced with G, I, L, S, T, M, or V; E344 replaced with D; G345 replaced with A, I, L, S, T, M, or V; S346 replaced with A, G, I, L, T, M, or V; Q347 replaced with N; R348 replaced with H, or K; R349 replaced with H, or K; R350 replaced with H, or K; L351 replaced with A, G, I, S, T, M, or V; L352 replaced with A, G, I, S, T, M, or V; V353 replaced with A, G, I, L, S, T, or M; A355 replaced with G, I, L, S, T, M, or V; N356 replaced with Q; G357 replaced with A, I, L, S, T, M, or V; A358 replaced with G, I, L, S, T, M, or V; D359 replaced with E; T361 replaced with A, G, I, L, S, M, or V; E362 replaced with D; T363 replaced with A, G, I, L, S, M, or V; L364 replaced with A, G, I, S, T, M, or V; M365 replaced with A, G, I, L, S, T, or V; L366 replaced with A, G, I, S, T, M, or V; F367 replaced with W, or Y; F368 replaced with W, or Y; D369 replaced with E; K370 replaced with H, or R; F371 replaced with W, or Y; A372 replaced with G, I, L, S, T, M, or V; N373 replaced with Q; I374 replaced with A, G, L, S, T, M, or V; V375 replaced with A, G, I, L, S, T, or M; F377 replaced with W, or Y; D378 replaced with E; S379 replaced with A, G, I, L, T, M, or V; W380 replaced with F, or Y; D381 replaced with E; Q382 replaced with N; L383 replaced with A, G, I, S, T, M, or V; M384 replaced with A, G, I, L, S, T, or V; R385 replaced with H, or K; Q386 replaced with N; L387 replaced with A, G, I, S, T, M, or V; D388 replaced with E; L389 replaced with A, G, I, S, T, M, or V; T390 replaced with A, G, I, L, S, M, or V; K391 replaced with H, or R; N392 replaced with Q; E393 replaced with D; I394 replaced with A, G, L, S, T, M, or V; D395 replaced with E; V396 replaced with A, G, I, L, S, T, or M; V397 replaced with A, G, I, L, S, T, or M; R398 replaced with H, or K; A399 replaced with G, I, L, S, T, M, or V; G400 replaced with A, I, L, S, T, M, or V; T401 replaced with A, G, I, L, S, M, or V; A402 replaced with G, I, L, S, T, M, or V; G403 replaced with A, I, L, S, T, M, or V; G405 replaced with A, I, L, S, T, M, or V; D406 replaced with E; A407 replaced with G, I, L, S, T, M, or V; L408 replaced with A, G, I, S, T, M, or V; Y409 replaced with F, or W; A410 replaced with G, I, L, S, T, M, or V; M411 replaced with A, G, I, L, S, T, or V; L412 replaced with A, G, I, S, T, M, or V; M413 replaced with A, G, I, L, S, T, or V; K414 replaced with H, or R; W415 replaced with F, or Y; V416 replaced with A, G, I, L, S, T, or M; N417 replaced with Q; K418 replaced with H, or R; T419 replaced with A, G, I, L, S, M, or V; G420 replaced with A, I, L, S, T, M, or V; R421 replaced with H, or K; N422 replaced with Q; A423 replaced with G, I, L, S, T, M, or V; S424 replaced with A, G, I, L, T, M, or V; I425 replaced with A, G, L, S, T, M, or V; H426 replaced with K, or R; T427 replaced with A, G, I, L, S, M, or V; L428 replaced with A, G, I, S, T, M, or V; L429 replaced with A, G, I, S, T, M, or V; D430 replaced with E; A431 replaced with G, I, L, S, T, M, or V; L432 replaced with A, G, I, S, T, M, or V; E433 replaced with D; R434 replaced with H, or K; M435 replaced with A, G, I, L, S, T, or V; E436 replaced with D; E437 replaced with D; R438 replaced with H, or K; H439 replaced with K, or R; A440 replaced with G, I, L, S, T, M, or V; K441 replaced with H, or R; E442 replaced with D; K443 replaced with H, or R; I444 replaced with A, G, L, S, T, M, or V; Q445 replaced with N; D446 replaced with E; L447 replaced with A, G, I, S, T, M, or V; L448 replaced with A, G, I, S, T, M, or V; V449 replaced with A, G, I, L, S, T, or M; D450 replaced with E; S451 replaced with A, G, I, L, T, M, or V; G452 replaced with A, I, L, S, T, M, or V; K453 replaced with H, or R; F454 replaced with W, or Y; I455 replaced with A, G, L, S, T, M, or V; Y456 replaced with F, or W; L457 replaced with A, G, I, S, T, M, or V; E458 replaced with D; D459 replaced with E; G460 replaced with A, I, L, S, T, M, or V; T461 replaced with A, G, I, L, S, M, or V; G462 replaced with A, I, L, S, T, M, or V; S463 replaced with A, G, I, L, T, M, or V; A464 replaced with G, I, L, S, T, M, or V; V465 replaced with A, G, I, L, S, T, or M; S466 replaced with A, G, I, L, T, M, or V; L467 replaced with A, G, I, S, T, M, or V; and/or E-468 replaced with D of SEQ ID NO:1.

In specific embodiments, the antibodies of the invention bind TR4 polypeptides or fragments or variants thereof (especially a fragment comprising or alternatively consisting of, the extracellular soluble domain of TR4), that contains any one or more of the following non-conservative mutations in TR4: M1 replaced with D, E, H, K, R, N, Q, F, W, Y, P, or C; A2 replaced with D, E, H, K, R, N, Q, F, W, Y, P, or C; P3 replaced with D, E, H, K, R, A, G, I, L, S, T, M, V, N, Q, F, W, Y, or C; P4replaced with D, E, H, K, R, A, G, I, L, S, T, M, V, N, Q, F, W, Y, or C; P5 replaced with D, E, H, K, R, A, G, I, L, S, T, M, V, N, Q, F, W, Y, or C; A6 replaced with D, E, H, K, R, N, Q, F, W, Y, P, or C; R7 replaced with D, E, A, G, I, L, S, T, M, V, N, Q, F, W, Y, P, or C; V8 replaced with D, E, H, K, R, N, Q, F, W, Y, P, or C; H9 replaced with D, E, A, G, I, L, S, T, M, V, N, Q, F, W, Y, P, or C; L10 replaced with D, E, H, K, R, N, Q, F, W, Y, P, or C; G11 replaced with D, E, H, K, R, N, Q, F, W, Y, P, or C; A12 replaced with D, E, H, K, R, N, Q, F, W, Y, P, or C; F13 replaced with D, E, H, K, R, N, Q, A, G, I, L, S, T, M, V, P, or C; L14 replaced with D, E, H, K, R, N, Q, F, W, Y, P, or C; A15 replaced with D, E, H, K, R, N, Q, F, W, Y, P, or C; V16 replaced with D, E, H, K, R, N, Q, F, W, Y, P, or C; T17 replaced with D, E, H, K, R, N, Q, F, W, Y, P, or C; P18 replaced with D, E, H, K, R, A, G, I, L, S, T, M, V, N, Q, F, W, Y, or C; N19 replaced with D, E, H, K, R, A, G, I, L, S, T, M, V, F, W, Y, P, or C; P20 replaced with D, E, H, K, R, A, G, I, L, S, T, M, V, N, Q, F, W, Y, or C; G21 replaced with D, E, H, K, R, N, Q, F, W, Y, P, or C; S22 replaced with D, E, H, K, R, N, Q, F, W, Y, P, or C; A23 replaced with D, E, H, K, R, N, Q, F, W, Y, P, or C; A24 replaced with D, E, H, K, R, N, Q, F, W, Y, P, or C; S25 replaced with D, E, H, K, R, N, Q, F, W, Y, P, or C; G26 replaced with D, E, H, K, R, N, Q, F, W, Y, P, or C; T27 replaced with D, E, H, K, R, N, Q, F, W, Y, P, or C; E28 replaced with H, K, R, A, G, I, L, S, T, M, V, N, Q, F, W, Y, P, or C; A29 replaced with D, E, H, K, R, N, Q, F, W, Y, P, or C; A30 replaced with D, E, H, K, R, N, Q, F, W, Y, P, or C; A31 replaced with D, E, H, K, R, N, Q, F, W, Y, P, or C; A32 replaced with D, E, H, K, R, N, Q, F, W, Y, P, or C; T33 replaced with D, E, H, K, R, N, Q, F, W, Y, P, or C; P34 replaced with D, E, H, K, R, A, G, I, L, S, T, M, V, N, Q, F, W, Y, or C; S35 replaced with D, E, H, K, R, N, Q, F, W, Y, P, or C; K36 replaced with D, E, A, G, I, L, S, T, M, V, N, Q, F, W, Y, P, or C; V37 replaced with D, E, H, K, R, N, Q, F, W, Y, P, or C; W38 replaced with D, E, H, K, R, N, Q, A, G, I, L, S, T, M, V, P, or C; G39 replaced with D, E, H, K, R, N, Q, F, W, Y, P, or C; S40 replaced with D, E, H, K, R, N, Q, F, W, Y, P, or C; S41 replaced with D, E, H, K, R, N, Q, F, W, Y, P, or C; A42 replaced with D, E, H, K, R, N, Q, F, W, Y, P, or C; G43 replaced with D, E, H, K, R, N, Q, F, W, Y, P, or C; R44 replaced with D, E, A, G, I, L, S, T, M, V, N, Q, F, W, Y, P, or C; I45 replaced with D, E, H, K, R, N, Q, F, W, Y, P, or C; E46 replaced with H, K, R, A, G, I, L, S, T, M, V, N, Q, F, W, Y, P, or C; P47 replaced with D, E, H, K, R, A, G, I, L, S, T, M, V, N, Q, F, W, Y, or C; R48 replaced with D, E, A, G, I, L, S, T, M, V, N, Q, F, W, Y, P, or C; G49 replaced with D, E, H, K, R, N, Q, F, W, Y, P, or C; G50 replaced with D, E, H, K, R, N, Q, F, W, Y, P, or C; G51 replaced with D, E, H, K, R, N, Q, F, W, Y, P, or C; R52 replaced with D, E, A, G, I, L, S, T, M, V, N, Q, F, W, Y, P, or C; G53 replaced with D, E, H, K, R, N, Q, F, W, Y, P, or C; A54 replaced with D, E, H, K, R, N, Q, F, W, Y, P, or C; L55 replaced with D, E, H, K, R, N, Q, F, W, Y, P, or C; P56 replaced with D, E, H, K, R, A, G, I, L, S, T, M, V, N, Q, F, W, Y, or C; T57 replaced with D, E, H, K, R, N, Q, F, W, Y, P, or C; S58 replaced with D, E, H, K, R, N, Q, F, W, Y, P, or C; M59 replaced with D, E, H, K, R, N, Q, F, W, Y, P, or C; G60 replaced with D, E, H, K, R, N, Q, F, W, Y, P, or C; Q61 replaced with D, E, H, K, R, A, G, I, L, S, T, M, V, F, W, Y, P, or C; H62 replaced with D, E, A, G, I, L, S, T, M, V, N, Q, F, W, Y, P, or C; G63 replaced with D, E, H, K, R, N, Q, F, W, Y, P, or C; P64 replaced with D, E, H, K, R, A, G, I, L, S, T, M, V, N, Q, F, W, Y, or C; S65 replaced with D, E, H, K, R, N, Q, F, W, Y, P, or C; A66 replaced with D, E, H, K, R, N, Q, F, W, Y, P, or C; R67 replaced with D, E, A, G, I, L, S, T, M, V, N, Q, F, W, Y, P, or C; A68 replaced with D, E, H, K, R, N, Q, F, W, Y, P, or C; R69 replaced with D, E, A, G, I, L, S, T, M, V, N, Q, F, W, Y, P, or C; A70 replaced with D, E, H, K, R, N, Q, F, W, Y, P, or C; G71 replaced with D, E, H, K, R, N, Q, F, W, Y, P, or C; R72 replaced with D, E, A, G, I, L, S, T, M, V, N, Q, F, W, Y, P, or C; A73 replaced with D, E, H, K, R, N, Q, F, W, Y, P, or C; P74 replaced with D, E, H, K, R, A, G, I, L, S, T, M, V, N, Q, F, W, Y, or C; G75 replaced with D, E, H, K, R, N, Q, F, W, Y, P, or C; P76 replaced with D, E, H, K, R, A, G, I, L, S, T, M, V, N, Q, F, W, Y, or C; R77 replaced with D, E, A, G, I, L, S, T, M, V, N, Q, F, W, Y, P, or C; P78 replaced with D, E, H, K, R, A, G, I, L, S, T, M, V, N, Q, F, W, Y, or C; A79 replaced with D, E, H, K, R, N, Q, F, W, Y, P, or C; R80 replaced with D, E, A, G, I, L, S, T, M, V, N, Q, F, W, Y, P, or C; E81 replaced with H, K, R, A, G, I, L, S, T, M, V, N, Q, F, W, Y, P, or C; A82replaced with D, E, H, K, R, N, Q, F, W, Y, P, or C; S83 replaced with D, E, H, K, R, N, Q, F, W, Y, P, or C; P84 replaced with D, E, H, K, R, A, G, I, L, S, T, M, V, N, Q, F, W, Y, or C; R85 replaced with D, E, A, G, I, L, S, T, M, V, N, Q, F, W, Y, P, or C; L86 replaced with D, E, H, K, R, N, Q, F, W, Y, P, or C; R87 replaced with D, E, A, G, I, L, S, T, M, V, N, Q, F, W, Y, P, or C; V88 replaced with D, E, H, K, R, N, Q, F, W, Y, P, or C; H89 replaced with D, E, A, G, I, L, S, T, M, V, N, Q, F, W, Y, P, or C; K90 replaced with D, E, A, G, I, L, S, T, M, V, N, Q, F, W, Y, P, or C; T91 replaced with D, E, H, K, R, N, Q, F, W, Y, P, or C; F92 replaced with D, E, H, K, R, N, Q, A, G, I, L, S, T, M, V, P, or C; K93 replaced with D, E, A, G, I, L, S, T, M, V, N, Q, F, W, Y, P, or C; F94 replaced with D, E, H, K, R, N, Q, A, G, I, L, S, T, M, V, P, or C; V95 replaced with D, E, H, K, R, N, Q, F, W, Y, P, or C; V96 replaced with D, E, H, K, R, N, Q, F, W, Y, P, or C; V97 replaced with D, E, H, K, R, N, Q, F, W, Y, P, or C; G98 replaced with D, E, H, K, R, N, Q, F, W, Y, P, or C; V99 replaced with D, E, H, K, R, N, Q, F, W, Y, P, or C; L100 replaced with D, E, H, K, R, N, Q, F, W, Y, P, or C; L101 replaced with D, E, H, K, R, N, Q, F, W, Y, P, or C; Q102 replaced with D, E, H, K, R, A, G, I, L, S, T, M, V, F, W, Y, P, or C; V103 replaced with D, E, H, K, R, N, Q, F, W, Y, P, or C; V104 replaced with D, E, H, K, R, N, Q, F, W, Y, P, or C; P105 replaced with D, E, H, K, R, A, G, I, L, S, T, M, V, N, Q, F, W, Y, or C; S106 replaced with D, E, H, K, R, N, Q, F, W, Y, P, or C; S107 replaced with D, E, H, K, R, N, Q, F, W, Y, P, or C; A108 replaced with D, E, H, K, R, N, Q, F, W, Y, P, or C; A109 replaced with D, E, H, K, R, N, Q, F, W, Y, P, or C; T110 replaced with D, E, H, K, R, N, Q, F, W, Y, P, or C; I111 replaced with D, E, H, K, R, N, Q, F, W, Y, P, or C; K112 replaced with D, E, A, G, I, L, S, T, M, V, N, Q, F, W, Y, P, or C; L113 replaced with D, E, H, K, R, N, Q, F, W, Y, P, or C; H114 replaced with D, E, A, G, I, L, S, T, M, V, N, Q, F, W, Y, P, or C; D115 replaced with H, K, R, A, G, I, L, S, T, M, V, N, Q, F, W, Y, P, or C; Q116 replaced with D, E, H, K, R, A, G, I, L, S, T, M, V, F, W, Y, P, or C; S117 replaced with D, E, H, K, R, N, Q, F, W, Y, P, or C; I118 replaced with D, E, H, K, R, N, Q, F, W, Y, P, or C; G119 replaced with D, E, H, K, R, N, Q, F, W, Y, P, or C; T120 replaced with D, E, H, K, R, N, Q, F, W, Y, P, or C; Q121 replaced with D, E, H, K, R, A, G, I, L, S, T, M, V, F, W, Y, P, or C; Q122 replaced with D, E, H, K, R, A, G, I, L, S, T, M, V, F, W, Y, P, or C; W1123 replaced with D, E, H, K, R, N, Q, A, G, I, L, S, T, M, V, P, or C; E124 replaced with H, K, R, A, G, I, L, S, T, M, V, N, Q, F, W, Y, P, or C; H125 replaced with D, E, A, G, I, L, S, T, M, V, N, Q, F, W, Y, P, or C; S126 replaced with D, E, H, K, R, N, Q, F, W, Y, P, or C; P127 replaced with D, E, H, K, R, A, G, I, L, S, T, M, V, N, Q, F, W, Y, or C; L128 replaced with D, E, H, K, R, N, Q, F, W, Y, P, or C; G129 replaced with D, E, H, K, R, N, Q, F, W, Y, P, or C; E130 replaced with H, K, R, A, G, I, L, S, T, M, V, N, Q, W, Y, P, or C; L131 replaced with D, E, H, K, R, N, Q, F, W, Y, P, or C; C132 replaced with D, E, H, K, R, A, G, I, L, S, T, M, V, N, Q, F, W, Y, or P; P133 replaced with D, E, H, K, R, A, G, I, L, S, T, M, V, N, Q, F, W, Y, or C; P134 replaced with D, E, H, K, R, A, G, I, L, S, T, M, V, N, Q, F, W, Y, or C; G135 replaced with D, E, H, K, R, N, Q, F, W, Y, P, or C; S136 replaced with D, E, H, K, R, N, Q, F, W, Y, P, or C; H137 replaced with D, E, A, G, I, L, S, T, M, V, N, Q, F, W, Y, P, or C; R138 replaced with D, E, A, G, I, L, S, T, M, V, N, Q, F, W, Y, P, or C; S139 replaced with D, E, H, K, R, N, Q, F, W, Y, P, or C; E140 replaced with H, K, R, A, G, I, L, S, T, M, V, N, Q, F, W, Y, P, or C; R141 replaced with D, E, A, G, I, L, S, T, M, V, N, Q, F, W, Y, P, or C; P142 replaced with D, E, H, K, R, A, G, I, L, S, T, M, V, N, Q, F, W, Y, or C; G143 replaced with D, E, H, K, R, N, Q, F, W, Y, P, or C; A144 replaced with D, E, H, K, R, N, Q, F, W, Y, P, or C; C145 replaced with D, E, H, K, R, A, G, I, L, S, T, M, V, N, Q, F, W, Y, or P; N146 replaced with D, E, H, K, R, A, G, I, L, S, T, M, V, F, W, Y, P, or C; R147 replaced with D, E, A, G, I, L, S, T, M, V, N, Q, F, W, Y, P, or C; C148 replaced with D, E, H, K, R, A, G, I, L, S, T, M, V, N, Q, F, W, Y, or P; T149 replaced with D, E, H, K, R, N, Q, F, W, Y, P, or C; E150 replaced with H, K, R, A, G, I, L, S, T, M, V, N, Q, F, W, Y, P, or C; G151 replaced with D, E, H, K, R, N, Q, F, W, Y, P, or C; V152 replaced with D, E, H, K, R, N, Q, F, W, Y, P, or C; G153 replaced with D, E, H, K, R, N, Q, F, W, Y, P, or C; Y154 replaced with D, E, H, K, R, N, Q, A, G, I, L, S, T, M, V, P, or C; T155 replaced with D, E, H, K, R, N, Q, F, W, Y, P, or C; N156 replaced with D, E, H, K, R, A, G, I, L, S, T, M, V, F, W, Y, P, or C; A157 replaced with D, E, H, K, R, N, Q, F, W, Y, P, or C; S158 replaced with D, E, H, K, R, N, Q, F, W, Y, P, or C; N159 replaced with D, E, H, K, R, A, G, I, L, S, T, M, V, F, W, Y, P, or C; N160 replaced with D, E, H, K, R, A, G, I, L, S, T, M, V, F, W, Y, P, or C; L161 replaced with D, E, H, K, R, N, Q, F, W, Y, P, or C; F162 replaced with D, E, H, K, R, N, Q, A, G, I, L, S, T, M, V, P, or C; A163 replaced with D, E, H, K, R, N, Q, F, W, Y, P, or C; C164 replaced with D, E, H, K, R, A, G, I, L, S, T, M, V, N, Q, F, W, Y, or P; L165 replaced with D, E, H, K, R, N, Q, F, W, Y, P, or C; P166 replaced with D, E, H, K, R, A, G, I, L, S, T, M, V, N, Q, F, W, Y, or C; C167 replaced with D, E, H, K, R, A, G, I, L, S, T, M, V, N, Q, F, W, Y, or P; T168 replaced with D, E, H, K, R, N, Q, F, W, Y, P, or C; A169 replaced with D, E, H, K, R, N, Q, F, W, Y, P, or C; C170 replaced with D, E, H, K, R, A, G, I, L, S, T, M, V, N, Q, F, W, Y, or P; K171 replaced with D, E, A, G, I, L, S, T, M, V, N, Q, F, W, Y, P, or C; S172 replaced with D, E, H, K, R, N, Q, F, W, Y, P, or C; D173 replaced with H, K, R, A, G, I, L, S, T, M, V, N, Q, F, W, Y, P, or C; E174 replaced with H, K, R, A, G, I, L, S, T, M, V, N, Q, F, W, Y, P, or C; E175 replaced with H, K, R, A, G, I, L, S, T, M, V, N, Q, F, W, Y, P, or C; E176 replaced with H, K, R, A, G, I, L, S, T, M, V, N, Q, F, W, Y, P, or C; R177 replaced with D, E, A, G, I, L, S, T, M, V, N, Q, F, W, Y, P, or C; S178 replaced with D, E, H, K, R, N, Q, F, W, Y, P, or C; P179 replaced with D, E, H, K, R, A, G, I, L, S, T, M, V, N, Q, F, W, Y, or C; C180 replaced with D, E, H, K, R, A, G, I, L, S, T, M, V, N, Q, F, W, Y, or P; T181 replaced with D, E, H, K, R, N, Q, F, W, Y, P, or C; T182 replaced with D, E, H, K, R, N, Q, F, W, Y, P, or C; T183 replaced with D, E, H, K, R, N, Q, F, W, Y, P, or C; R184 replaced with D, E, A, G, I, L, S, T, M, V, N, Q, F, W, Y, P, or C; N185 replaced with D, E, H, K, R, A, G, I, L, S, T, M, V, F, W, Y, P, or C; T186 replaced with D, E, H, K, R, N, Q, F, W, Y, P, or C; A187 replaced with D, E, H, K, R, N, Q, F, W, Y, P, or C; C188 replaced with D, E, H, K, R, A, G, I, L, S, T, M, V, N, Q, F, W, Y, or P; Q189 replaced with D, E, H, K, R, A, G, I, L, S, T, M, V, F, W, Y, P, or C; C190 replaced with D, E, H, K, R, A, G, I, L, S, T, M, V, N, Q, F, W, Y, or P; K191 replaced with D, E, A, G, I, L, S, T, M, V, N, Q, F, W, Y, P, or C; P192 replaced with D, E, H, K, R, A, G, I, L, S, T, M, V, N, Q, F, W, Y, or C; G193 replaced with D, E, H, K, R, N, Q, F, W, Y, P, or C; T194 replaced with D, E, H, K, R, N, Q, F, W, Y, P, or C; F195 replaced with D, E, H, K, R, N, Q, A, G, I, L, S, T, M, V, P, or C; R196 replaced with D, E, A, G, I, L, S, T, M, V, N, Q, F, W, Y, P, or C; N197 replaced with D, E, H, K, R, A, G, I, L, S, T, M, V, F, W, Y, P, or C; D198 replaced with H, K, R, A, G, I, L, S, T, M, V, N, Q, F, W, Y, P, or C; N199 replaced with D, E, H, K, R, A, G, I, L, S, T, M, V, F, W, Y, P, or C; S200 replaced with D, E, H, K, R, N, Q, F, W, Y, P, or C; A201 replaced with D, E, H, K, R, N, Q, F, W, Y, P, or C; E202 replaced with H, K, R, A, G, I, L, S, T, M, V, N, Q, F, W, Y, P, or C; M203 replaced with D, E, H, K, R, N, Q, F, W, Y, P, or C; C204 replaced with D, E, H, K, R, A, G, I, L, S, T, M, V, N, Q, F, W, Y, or P; R205 replaced with D, E, A, G, I, L, S, T, M, V, N, Q, F, W, Y, P, or C; K206 replaced with D, E, A, G, I, L, S, T, M, V, N, Q, F, W, Y, P, or C; C207 replaced with D, E, H, K, R, A, G, I, L, S, T, M, V, N, Q, F, W, Y, or P; S208 replaced with D, E, H, K, R, N, Q, F, W, Y, P, or C; T209 replaced with D, E, H, K, R, N, Q, F, W, Y, P, or C; G210 replaced with D, E, H, K, R, N, Q, F, W, Y, P, or C; C211 replaced with D, E, H, K, R, A, G, I, L, S, T, M, V, N, Q, F, W, Y, or P; P212 replaced with D, E, H, K, R, A, G, I, L, S, T, M, V, N, Q, F, W, Y, or C; R213 replaced with D, E, A, G, I, L, S, T, M, V, N, Q, F, W, Y, P, or C; G214 replaced with D, E, H, K, R, N, Q, F, W, Y, P, or C; M215 replaced with D, E, H, K, R, N, Q, F, W, Y, P, or C; V216 replaced with D, E, H, K, R, N, Q, F, W, Y, P, or C; K217 replaced with D, E, A, G, I, L, S, T, M, V, N, Q, F, W, Y, P, or C; V218 replaced with D, E, H, K, R, N, Q, F, W, Y, P, or C; K219 replaced with D, E, A, G, I, L, S, T, M, V, N, Q, F, W, Y, P, or C; D220 replaced with H, K, R, A, G, I, L, S, T, M, V, N, Q, F, W, Y, P, or C; C221 replaced with D, E, H, K, R, A, G, I, L, S, T, M, V, N, Q, F, W, Y, or P; T222 replaced with D, E, H, K, R, N, Q, F, W, Y, P, or C; P223 replaced with D, E, H, K, R, A, G, I, L, S, T, M, V, N, Q, F, W, Y, or C; W224 replaced with D, E, H, K, R, N, Q, A, G, I, L, S, T, M, V, P, or C; S225 replaced with D, E, H, K, R, N, Q, F, W, Y, P, or C; D226 replaced with H, K, R, A, G, I, L, S, T, M, V, N, Q, F, W, Y, P, or C; I227 replaced with D, E, H, K, R, N, Q, F, W, Y, P, or C; E228 replaced with H, K, R, A, G, I, L, S, T, M, V, N, Q, F, W, Y, P, or C; C229 replaced with D, E, H, K, R, A, G, I, L, S, T, M, V, N, Q, F, W, Y, or P; V230 replaced with D, E, H, K, R, N, Q, F, W, Y, P, or C; H231 replaced with D, E, A, G, I, L, S, T, M, V, N, Q, F, W, Y, P, or C; K232 replaced with D, E, A, G, I, L, S, T, M, V, N, Q, F, W, Y, P, or C; E233 replaced with H, K, R, A, G, I, L, S, T, M, V, N, Q, F, W, Y, P, or C; S234 replaced with D, E, H, K, R, N, Q, F, W, Y, P, or C; G235 replaced with D, E, H, K, R, N, Q, F, W, Y, P, or C; N236 replaced with D, E, H, K, R, A, G, I, L, S, T, M, V, F, W, Y, P, or C; G237 replaced with D, E, H, K, R, N, Q, F, W, Y, P, or C; H238 replaced with D, E, A, G, I, L, S, T, M, V, N, Q, F, W, Y, P, or C; N239 replaced with D, E, H, K, R, A, G, I, L, S, T, M, V, F, W, Y, P, or C; I240 replaced with D, E, H, K, R, N, Q, F, W, Y, P, or C; W241 replaced with D, E, H, K, R, N, Q, A, G, I, L, S, T, M, V, P, or C; V242 replaced with D, E, H, K, R, N, Q, F, W, Y, P, or C; I243 replaced with D, E, H, K, R, N, Q, F, W, Y, P, or C; L244 replaced with D, E, H, K, R, N, Q, F, W, Y, P, or C; V245 replaced with D, E, H, K, R, N, Q, F, W, Y, P, or C; V246 replaced with D, E, H, K, R, N, Q, F, W, Y, P, or C; T247 replaced with D, E, H, K, R, N, Q, F, W, Y, P, or C; L248 replaced with D, E, H, K, R, N, Q, F, W, Y, P, or C; V249 replaced with D, E, H, K, R, N, Q, F, W, Y, P, or C; V250 replaced with D, E, H, K, R, N, Q, F, W, Y, P, or C; P251 replaced with D, E, H, K, R, A, G, I, L, S, T, M, V, N, Q, F, W, Y, or C; L252 replaced with D, E, H, K, R, N, Q, F, W, Y, P, or C; L253 replaced with D, E, H, K, R, N, Q, F, W, Y, P, or C; L254 replaced with D, E, H, K, R, N, Q, F, W, Y, P, or C; V255 replaced with D, E, H, K, R, N, Q, F, W, Y, P, or C; A256 replaced with D, E, H, K, R, N, Q, F, W, Y, P, or C; V257 replaced with D, E, H, K, R, N, Q, F, W, Y, P, or C; L258 replaced with D, E, H, K, R, N, Q, F, W, Y, P, or C; I259 replaced with D, E, H, K, R, N, Q, F, W, Y, P, or C; V260 replaced with D, E, H, K, R, N, Q, F, W, Y, P, or C; C261 replaced with D, E, H, K, R, A, G, I, L, S, T, M, V, N, Q, F, W, Y, or P; C262 replaced with D, E, H, K, R, A, G, I, L, S, T, M, V, N, Q, F, W, Y, or P; C263 replaced with D, E, H, K, R, A, G, I, L, S, T, M, V, N, Q, F, W, Y, or P; I264 replaced with D, E, H, K, R, N, Q, F, W, Y, P, or C; G265 replaced with D, E, H, K, R, N, Q, F, W, Y, P, or C; S266 replaced with D, E, H, K, R, N, Q, F, W, Y, P, or C; G267 replaced with D, E, H, K, R, N, Q, F, W, Y, P, or C; C268 replaced with D, E, H, K, R, A, G, I, L, S, T, M, V, N, Q, F, W, Y, or P; G269 replaced with D, E, H, K, R, N, Q, F, W, Y, P, or C; G270 replaced with D, E, H, K, R, N, Q, F, W, Y, P, or C; D271 replaced with H, K, R, A, G, I, L, S, T, M, V, N, Q, F, W, Y, P, or C; P272 replaced with D, E, H, K, R, A, G, I, L, S, T, M, V, N, Q, F, W, Y, or C; K273 replaced with D, E, A, G, I, L, S, T, M, V, N, Q, F, W, Y, P, or C; C274 replaced with D, E, H, K, R, A, G, I, L, S, T, M, V, N, Q, F, W, Y, or P; M275 replaced with D, E, H, K, R, N, Q, F, W, Y, P, or C; D276 replaced with H, K, R, A, G, I, L, S, T, M, V, N, Q, F, W, Y, P, or C; R277 replaced with D, E, A, G, I, L, S, T, M, V, N, Q, F, W, Y, P, or C; V278 replaced with D, E, H, K, R, N, Q, F, W, Y, P, or C; C279 replaced with D, E, H, K, R, A, G, I, L, S, T, M, V, N, Q, F, W, Y, or P; F280 replaced with D, E, H, K, R, N, Q, A, G, I, L, S, T, M, V, P, or C; W281 replaced with D, E, H, K, R, N, Q, A, G, I, L, S, T, M, V, P, or C; R282 replaced with D, E, A, G, I, L, S, T, M, V, N, Q, F, W, Y, P, or C; L283 replaced with D, E, H, K, R, N, Q, F, W, Y, P, or C; G284 replaced with D, E, H, K, R, N, Q, F, W, Y, P, or C; L285 replaced with D, E, H, K, R, N, Q, F, W, Y, P, or C; L286 replaced with D, E, H, K, R, N, Q, F, W, Y, P, or C; R287 replaced with D, E, A, G, I, L, S, T, M, V, N, Q, F, W, Y, P, or C; G288 replaced with D, E, H, K, R, N, Q, F, W, Y, P, or C; P289 replaced with D, E, H, K, R, A, G, I, L, S, T, M, V, N, Q, F, W, Y, or C; G290 replaced with D, E, H, K, R, N, Q, F, W, Y, P, or C; A291 replaced with D, E, H, K, R, N, Q, F, W, Y, P, or C; E292 replaced with H, K, R, A, G, I, L, S, T, M, V, N, Q, F, W, Y, P, or C; D293 replaced with H, K, R, A, G, I, L, S, T, M, V, N, Q, F, W, Y, P, or C; N294 replaced with D, E, H, K, R, A, G, I, L, S, T, M, V, F, W, Y, P, or C; A295 replaced with D, E, H, K, R, N, Q, F, W, Y, P, or C; H296 replaced with D, E, A, G, I, L, S, T, M, V, N, Q, F, W, Y, P, or C; N297 replaced with D, E, H, K, R, A, G, I, L, S, T, M, V, F, W, Y, P, or C; E298 replaced with H, K, R, A, G, I, L, S, T, M, V, N, Q, F, W, Y, P, or C; I299 replaced with D, E, H, K, R, N, Q, F, W, Y, P, or C; L300 replaced with D, E, H, K, R, N, Q, F, W, Y, P, or C; S301 replaced with D, E, H, K, R, N, Q, F, W, Y, P, or C; N302 replaced with D, E, H, K, R, A, G, I, L, S, T, M, V, F, W, Y, P, or C; A303 replaced with D, E, H, K, R, N, Q, F, W, Y, P, or C; D304 replaced with H, K, R, A, G, I, L, S, T, M, V, N, Q, F, W, Y, P, or C; S305 replaced with D, E, H, K, R, N, Q, F, W, Y, P, or C; L306 replaced with D, E, H, K, R, N, Q, F, W, Y, P, or C; S307 replaced with D, E, H, K, R, N, Q, F, W, Y, P, or C; T308 replaced with D, E, H, K, R, N, Q, F, W, Y, P, or C; F309 replaced with D, E, H, K, R, N, Q, A, G, I, L, S, T, M, V, P, or C; V310 replaced with D, E, H, K, R, N, Q, F, W, Y, P, or C; S311 replaced with D, E, H, K, R, N, Q, F, W, Y, P, or C; E312 replaced with H, K, R, A, G, I, L, S, T, M, V, N, Q, F, W, Y, P, or C; Q313 replaced with D, E, H, K, R, A, G, I, L, S, T, M, V, F, W, Y, P, or C; Q314 replaced with D, E, H, K, R, A, G, I, L, S, T, M, V, F, W, Y, P, or C; M315 replaced with D, E, H, K, R, N, Q, F, W, Y, P, or C; E316 replaced with H, K, R, A, G, I, L, S, T, M, V, N, Q, F, W, Y, P, or C; S317 replaced with D, E, H, K, R, N, Q, F, W, Y, P, or C; Q318 replaced with D, E, H, K, R, A, G, I, L, S, T, M, V, F, W, Y, P, or C; E319 replaced with H, K, R, A, G, I, L, S, T, M, V, N, Q, F, W, Y, P, or C; P320 replaced with D, E, H, K, R, A, G, I, L, S, T, M, V, N, Q, F, W, Y, or C; A321 replaced with D, E, H, K, R, N, Q, F, W, Y, P, or C; D322 replaced with H, K, R, A, G, I, L, S, T, M, V, N, Q, F, W, Y, P, or C; L323 replaced with D, E, H, K, R, N, Q, F, W, Y, P, or C; T324 replaced with D, E, H, K, R, N, Q, F, W, Y, P, or C; G325 replaced with D, E, H, K, R, N, Q, F, W, Y, P, or C; V326 replaced with D, E, H, K, R, N, Q, F, W, Y, P, or C; T327replaced with D, E, H, K, R, N, Q, F, W, Y, P, or C; V328 replaced with D, E, H, K, R, N, Q, F, W, Y, P, or C; Q329 replaced with D, E, H, K, R, A, G, I, L, S, T, M, V, F, W, Y, P, or C; S330 replaced with D, E, H, K, R, N, Q, F, W, Y, P, or C; P331 replaced with D, E, H, K, R, A, G, I, L, S, T, M, V, N, Q, F, W, Y, or C; G332 replaced with D, E, H, K, R, N, Q, F, W, Y, P, or C; E333 replaced with H, K, R, A, G, I, L, S, T, M, V, N, Q, F, W, Y, P, or C; A334 replaced with D, E, H, K, R, N, Q, F, W, Y, P, or C; Q335 replaced with D, E, H, K, R, A, G, I, L, S, T, M, V, F, W, Y, P, or C; C336 replaced with D, E, H, K, R, A, G, I, L, S, T, M, V, N, Q, F, W, Y, or P; L337 replaced with D, E, H, K, R, N, Q, F, W, Y, P, or C; L338 replaced with D, E, H, K, R, N, Q, F, W, Y, P, or C; G339 replaced with D, E, H, K, R, N, Q, F, W, Y, P, or C; P340 replaced with D, E, H, K, R, A, G, I, L, S, T, M, V, N, Q, F, W, Y, or C; A341 replaced with D, E, H, K, R, N, Q, F, W, Y, P, or C; E342 replaced with H, K, R, A, G, I, L, S, T, M, V, N, Q, F, W, Y, P, or C; A343 replaced with D, E, H, K, R, N, Q, F, W, Y, P, or C; E344 replaced with H, K, R, A, G, I, L, S, T, M, V, N, Q, F, W, Y, P, or C; G345 replaced with D, E, H, K, R, N, Q, F, W, Y, P, or C; S346 replaced with D, E, H, K, R, N, Q, F, W, Y, P, or C; Q347 replaced with D, E, H, K, R, A, G, I, L, S, T, M, V, F, W, Y, P, or C; R348 replaced with D, E, A, G, I, L, S, T, M, V, N, Q, F, W, Y, P, or C; R349 replaced with D, E, A, G, I, L, S, T, M, V, N, Q, F, W, Y, P, or C; R350 replaced with D, E, A, G, I, L, S, T, M, V, N, Q, F, W, Y, P, or C; L351 replaced with D, E, H, K, R, N, Q, F, W, Y, P, or C; L352 replaced with D, E, H, K, R, N, Q, F, W, Y, P, or C; V353 replaced with D, E, H, K, R, N, Q, F, W, Y, P, or C; P354 replaced with D, E, H, K, R, A, G, I, L, S, T, M, V, N, Q, F, W, Y, or C; A355 replaced with D, E, H, K, R, N, Q, F, W, Y, P, or C; N356 replaced with D, E, H, K, R, A, G, I, L, S, T, M, V, F, W, Y, P, or C; G357 replaced with D, E, H, K, R, N, Q, F, W, Y, P, or C; A358 replaced with D, E, H, K, R, N, Q, F, W, Y, P, or C; D359 replaced with H, K, R, A, G, I, L, S, T, M, V, N, Q, F, W, Y, P, or C; P360 replaced with D, E, H, K, R, A, G, I, L, S, T, M, V, N, Q, F, W, Y, or C; T361 replaced with D, E, H, K, R, N, Q, F, W, Y, P, or C; E362 replaced with H, K, R, A, G, I, L, S, T, M, V, N, Q, F, W, Y, P, or C; T363 replaced with D, E, H, K, R, N, Q, F, W, Y, P, or C; L364 replaced with D, E, H, K, R, N, Q, F, W, Y, P, or C; M365 replaced with D, E, H, K, R, N, Q, F, W, Y, P, or C; L366 replaced with D, E, H, K, R, N, Q, F, W, Y, P, or C; F367 replaced with D, E, H, K, R, N, Q, A, G, I, L, S, T, M, V, P, or C; F368 replaced with D, E, H, K, R, N, Q, A, G, I, L, S, T, M, V, P, or C; D369 replaced with H, K, R, A, G, I, L, S, T, M, V, N, Q, F, W, Y, P, or C; K370 replaced with D, E, A, G, I, L, S, T, M, V, N, Q, F, W, Y, P, or C; F371 replaced with D, E, H, K, R, N, Q, A, G, I, L, S, T, M, V, P, or C; A372 replaced with D, E, H, K, R, N, Q, F, W, Y, P, or C; N373 replaced with D, E, H, K, R, A, G, I, L, S, T, M, V, F, W, Y, P, or C; I374 replaced with D, E, H, K, R, N, Q, F, W, Y, P, or C; V375 replaced with D, E, H, K, R, N, Q, F, W, Y, P, or C; P376 replaced with D, E, H, K, R, A, G, I, L, S, T, M, V, N, Q, F, W, Y, or C; F377 replaced with D, E, H, K, R, N, Q, A, G, I, L, S, T, M, V, P, or C; D378 replaced with H, K, R, A, G, I, L, S, T, M, V, N, Q, F, W, Y, P, or C; S379 replaced with D, E, H, K, R, N, Q, F, W, Y, P, or C; W380 replaced with D, E, H, K, R, N, Q, A, G, I, L, S, T, M, V, P, or C; D381 replaced with H, K, R, A, G, I, L, S, T, M, V, N, Q, F, W, Y, P, or C; Q382 replaced with D, E, H, K, R, A, G, I, L, S, T, M, V, F, W, Y, P, or C; L383 replaced with D, E, H, K, R, N, Q, F, W, Y, P, or C; M384 replaced with D, E, H, K, R, N, Q, F, W, Y, P, or C; R385 replaced with D, E, A, G, I, L, S, T, M, V, N, Q, F, W, Y, P, or C; Q386 replaced with D, E, H, K, R, A, G, I, L, S, T, M, V, F, W, Y, P, or C; L387 replaced with D, E, H, K, R, N, Q, F, W, Y, P, or C; D388 replaced with H, K, R, A, G, I, L, S, T, M, V, N, Q, F, W, Y, P, or C; L389 replaced with D, E, H, K, R, N, Q, F, W, Y, P, or C; T390 replaced with D, E, H, K, R, N, Q, F, W, Y, P, or C; K391 replaced with D, E, A, G, I, L, S, T, M, V, N, Q, F, W, Y, P, or C; N392 replaced with D, E, H, K, R, A, G, I, L, S, T, M, V, F, W, Y, P, or C; E393 replaced with H, K, R, A, G, I, L, S, T, M, V, N, Q, F, W, Y, P, or C; I394 replaced with D, E, H, K, R, N, Q, F, W, Y, P, or C; D395 replaced with H, K, R, A, G, I, L, S, T, M, V, N, Q, F, W, Y, P, or C; V396 replaced with D, E, H, K, R, N, Q, F, W, Y, P, or C; V397 replaced with D, E, H, K, R, N, Q, F, W, Y, P, or C; R398 replaced with D, E, A, G, I, L, S, T, M, V, N, Q, F, W, Y, P, or C; A399 replaced with D, E, H, K, R, N, Q, F, W, Y, P, or C; G400 replaced with D, E, H, K, R, N, Q, F, W, Y, P, or C; T401 replaced with D, E, H, K, R, N, Q, F, W, Y, P, or C; A402 replaced with D, E, H, K, R, N, Q, F, W, Y, P, or C; G403 replaced with D, E, H, K, R, N, Q, F, W, Y, P, or C; P404 replaced with D, E, H, K, R, A, G, I, L, S, T, M, V, N, Q, F, W, Y, or C; G405 replaced with D, E, H, K, R, N, Q, F, W, Y, P, or C; D406 replaced with H, K, R, A, G, I, L, S, T, M, V, N, Q, F, W, Y, P, or C; A407 replaced with D, E, H, K, R, N, Q, F, W, Y, P, or C; L408 replaced with D, E, H, K, R, N, Q, F, W, Y, P, or C; Y409 replaced with D, E, H, K, R, N, Q, A, G, I, L, S, T, M, V, P, or C; A410 replaced with D, E, H, K, R, N, Q, F, W, Y, P, or C; M411 replaced with D, E, H, K, R, N, Q, F, W, Y, P, or C; L412 replaced with D, E, H, K, R, N, Q, F, W, Y, P, or C; M413 replaced with D, E, H, K, R, N, Q, F, W, Y, P, or C; K414 replaced with D, E, A, G, I, L, S, T, M, V, N, Q, F, W, Y, P, or C; W415 replaced with D, E, H, K, R, N, Q, A, G, I, L, S, T, M, V, P, or C; V416 replaced with D, E, H, K, R, N, Q, F, W, Y, P, or C; N417 replaced with D, E, H, K, R, A, G, I, L, S, T, M, V, F, W, Y, P, or C; K418 replaced with D, E, A, G, I, L, S, T, M, V, N, Q, F, W, Y, P, or C; T419 replaced with D, E, H, K, R, N, Q, F, W, Y, P, or C; G420 replaced with D, E, H, K, R, N, Q, F, W, Y, P, or C; R421 replaced with D, E, A, G, I, L, S, T, M, V, N, Q, F, W, Y, P, or C; N422 replaced with D, E, H, K, R, A, G, I, L, S, T, M, V, F, W, Y, P, or C; A423 replaced with D, E, H, K, R, N, Q, F, W, Y, P, or C; S424 replaced with D, E, H, K, R, N, Q, F, W, Y, P, or C; I425 replaced with D, E, H, K, R, N, Q, F, W, Y, P, or C; H426 replaced with D, E, A, G, I, L, S, T, M, V, N, Q, F, W, Y, P, or C; T427 replaced with D, E, H, K, R, N, Q, F, W, Y, P, or C; L428 replaced with D, E, H, K, R, N, Q, F, W, Y, P, or C; L429 replaced with D, E, H, K, R, N, Q, F, W, Y, P, or C; D430 replaced with H, K, R, A, G, I, L, S, T, M, V, N, Q, F, W, Y, P, or C; A431 replaced with D, E, H, K, R, N, Q, F, W, Y, P, or C; L432 replaced with D, E, H, K, R, N, Q, F, W, Y, P, or C; E433 replaced with H, K, R, A, G, I, L, S, T, M, V, N, Q, F, W, Y, P, or C; R434 replaced with D, E, A, G, I, L, S, T, M, V, N, Q, F, W, Y, P, or C; M435 replaced with D, E, H, K, R, N, Q, F, W, Y, P, or C; E436 replaced with H, K, R, A, G, I, L, S, T, M, V, N, Q, F, W, Y, P, or C; E437 replaced with H, K, R, A, G, I, L, S, T, M, V, N, Q, F, W, Y, P, or C; R438 replaced with D, E, A, G, I, L, S, T, M, V, N, Q, F, W, Y, P, or C; H439 replaced with D, E, A, G, I, L, S, T, M, V, N, Q, F, W, Y, P, or C; A440 replaced with D, E, H, K, R, N, Q, F, W, Y, P, or C; K441 replaced with D, E, A, G, I, L, S, T, M, V, N, Q, F, W, Y, P, or C; E442 replaced with H, K, R, A, G, I, L, S, T, M, V, N, Q, F, W, Y, P, or C; K443 replaced with D, E, A, G, I, L, S, T, M, V, N, Q, F, W, Y, P, or C; I444 replaced with D, E, H, K, R, N, Q, F, W, Y, P, or C; Q445 replaced with D, E, H, K, R, A, G, I, L, S, T, M, V, F, W, Y, P, or C; D446 replaced with H, K, R, A, G, I, L, S, T, M, V, N, Q, F, W, Y, P, or C; L447 replaced with D, E, H, K, R, N, Q, F, W, Y, P, or C; L448 replaced with D, E, H, K, R, N, Q, F, W, Y, P, or C; V449 replaced with D, E, H, K, R, N, Q, F, W, Y, P, or C; D450 replaced with H, K, R, A, G, I, L, S, T, M, V, N, Q, F, W, Y, P, or C; S451 replaced with D, E, H, K, R, N, Q, F, W, Y, P, or C; G452 replaced with D, E, H, K, R, N, Q, F, W, Y, P, or C; K453 replaced with D, E, A, G, I, L, S, T, M, V, N, Q, F, W, Y, P, or C; F454 replaced with D, E, H, K, R, N, Q, A, G, I, L, S, T, M, V, P, or C; I455 replaced with D, E, H, K, R, N, Q, F, W, Y, P, or C; Y456 replaced with D, E, H, K, R, N, Q, A, G, I, L, S, T, M, V, P, or C; L457 replaced with D, E, H, K, R, N, Q, F, W, Y, P, or C; E458 replaced with H, K, R, A, G, I, L, S, T, M, V, N, Q, F, W, Y, P, or C; D459 replaced with H, K, R, A, G, I, L, S, T, M, V, N, Q, F, W, Y, P, or C; G460 replaced with D, E, H, K, R, N, Q, F, W, Y, P, or C; T461 replaced with D, E, H, K, R, N, Q, F, W, Y, P, or C; G462 replaced with D, E, H, K, R, N, Q, F, W, Y, P, or C; S463 replaced with D, E, H, K, R, N, Q, F, W, Y, P, or C; A464 replaced with D, E, H, K, R, N, Q, F, W, Y, P, or C; V465 replaced with D, E, H, K, P, N, Q, F, W, Y, P, or C; S466 replaced with D, E, H, K, R, N, Q, F, W, Y, P, or C; L467 replaced with D, E, H, K, R, N, Q, F, W, Y, P, or C; and/or E-468 replaced with H, K, R, A, G, I, L, S, T, M, V, N, Q, F, W, Y, P, or C of SEQ ID NO:1.

Amino acids in the TR4 protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of TR4 that are essential for TR4 function. In other preferred embodiments, antibodies of the present invention bind regions of TR4 that are essential for TR4 function and inhibit or abolish TR4 function. In other preferred embodiments, antibodies of the present invention bind regions of TR4 that are essential for TR4 function and enhance TR4 function.

Additionally, protein engineering may be employed to improve or alter the characteristics of TR4 polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified TR4 polypeptides.

Non-naturally occurring variants of TR4 may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., Gene 34:315 (1985)), restriction selection mutagenesis (see e.g., Wells et al., *Philos. Trans. R. Soc. London Ser A* 317:415 (1986)).

Thus, the invention also encompasses antibodies that bind TR4 derivatives and analogs that have one or more amino acid residues deleted, added, or substituted to generate TR4 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the TR4 polypeptides and/or an amino acid deletion at the second position of any one or more such recognition sequences will prevent glycosylation of the TR4 at the modified tripeptide sequence (see, e.g., Miyajimo et al., EMBO J. 5(6):1193-1197). Additionally, one or more of the amino acid residues of TR4 polypeptides (e.g., arginine and lysine residues) may be deleted or substituted with another residue to eliminate undesired processing by proteases such as, for example, furins or kexins.

The antibodies of the present invention also include antibodies that bind a polypeptide comprising, or alternatively, consisting of the polypeptide encoded by the deposited cDNA (the deposit having ATCC Accession Number 97853) including the leader; a polypeptide comprising, or alternatively, consisting of the mature polypeptide encoded by the deposited the cDNA minus the leader (i.e., the mature protein); a polypeptide comprising, or alternatively, consisting of the polypeptide of SEQ ID NO:1 including the leader; a polypeptide comprising, or alternatively, consisting of the polypeptide of SEQ ID NO:1 minus the amino terminal methionine; a polypeptide comprising, or alternatively, consisting of the polypeptide of SEQ ID NO:1 minus the leader; a polypeptide comprising, or alternatively, consisting of the TR4 extracellular domain; a polypeptide comprising, or alternatively, consisting of the TR4 cysteine rich domain; a polypeptide comprising, or alternatively, consisting of the TR4 transmembrane domain; a polypeptide comprising, or alternatively, consisting of the TR4 intracellular domain; a polypeptide comprising, or alternatively, consisting of the TR4 death domain; a polypeptide comprising, or alternatively, consisting of soluble polypeptides comprising all or part of the extracellular and intracelluar domains but lacking the transmembrane domain; as well as polypeptides which are at least 80% identical, more preferably at least 90% or 95% identical, still more preferably at least 96%, 97%, 98% or 99% identical to the polypeptides described above (e.g., the polypeptide encoded by the deposited cDNA clone (the deposit having ATCC Accession Number 97853), the polypeptide of SEQ ID NO:1, and portions of such polypeptides with at least 30 amino acids and more preferably at least 50 amino acids.

By a polypeptide having an amino acid sequence at least, for example, 95% "identical" to a reference amino acid sequence of a TR4 polypeptide is intended that the amino acid sequence of the polypeptide is identical to the reference sequence except that the polypeptide sequence may include up to five amino acid alterations per each 100 amino acids of the reference amino acid of the TR4 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:1 or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to antibodies that bind proteins containing polypeptides at least 90%, 95%, 96%, 97%, 98% or 99% identical to the TR4 polypeptide sequence set forth herein as $n^1$-$m^1$, and/or $n^2$-$m^2$. In preferred embodiments, the application is directed to antibodies that bind proteins containing polypeptides at least 90%, 95%, 96%, 97%, 98% or 99% identical to polypeptides having the amino acid sequence of the specific TR4 N- and C-terminal deletions recited herein.

In certain preferred embodiments, antibodies of the invention bind TR4 fusion proteins as described above wherein the TR4 portion of the fusion protein are those described as $n^1$-$m^1$, and/or $n^2$-$m^2$ herein.

TR7

In certain embodiments of the present invention, the antibodies of the present invention bind TR7 polypeptide, or fragments or variants thereof. The following section describes the TR7 polypeptides, fragments and variants that may be bound by the antibodies of the invention in more detail. The TR7 polypeptides, fragments and variants which may be bound by the antibodies of the invention are also described in, for example, International Publication Numbers WO98/41629, WO00/66156, and WO98/35986 which are herein incorporated by reference in their entireties.

In certain embodiments, the antibodies of the present invention immunospecifically bind TR7 polypeptide. An antibody that immunospecifically binds TR7 may, in some embodiments, bind fragments, variants (including species orthologs of TR7), multimers or modified forms of TR7. For example, an antibody immunospecific for TR7 may bind the TR7 moiety of a fusion protein comprising all or a portion of TR7.

TR7 proteins may be found as monomers or multimers (i.e., dimers, trimers, tetramers, and higher multimers). Accordingly, the present invention relates to antibodies that bind TR7 proteins found as monomers or as part of multimers. In specific embodiments, the TR7 polypeptides are monomers, dimers, trimers or tetramers. In additional embodiments, the multimers of the invention are at least dimers, at least trimers, or at least tetramers.

Antibodies of the invention may bind TR7 homomers or heteromers. As used herein, the term homomer, refers to a multimer containing only TR7 proteins of the invention (including TR7 fragments, variants, and fusion proteins, as described herein). These homomers may contain TR7 proteins having identical or different polypeptide sequences. In a specific embodiment, a homomer of the invention is a multimer containing only TR7 proteins having an identical polypeptide sequence. In another specific embodiment, antibodies of the invention bind TR7 homomers containing TR7 proteins having different polypeptide sequences. In specific embodiments, antibodies of the invention bind a TR7 homodimer (e.g., containing TR7 proteins having identical or different polypeptide sequences) or a homotrimer (e.g., containing TR7 proteins having identical or different polypeptide sequences). In additional embodiments, antibodies of the invention bind at least a homodimer, at least a homotrimer, or at least a homotetramer of TR7.

As used herein, the term heteromer refers to a multimer containing heterologous proteins (i.e., proteins containing polypeptide sequences that do not correspond to a polypeptide sequences encoded by the TR7 gene) in addition to the TR7 proteins of the invention. In a specific embodiment, antibodies of the invention bind a heterodimer, a heterotrimer, or a heterotetramer. In additional embodiments, the antibodies of the invention bind at least a homodimer, at least a homotrimer, or at least a homotetramer containing one or more TR7 polypeptides.

Multimers bound by one or more antibodies of the invention may be the result of hydrophobic, hydrophilic, ionic and/or covalent associations and/or may be indirectly linked, by for example, liposome formation. Thus, in one embodiment, multimers bound by one or more antibodies of the invention, such as, for example, homodimers or homotrimers, are formed when TR7 proteins contact one another in solution. In another embodiment, heteromultimers bound by one or more antibodies of the invention, such as, for example, heterotrimers or heterotetramers, are formed when TR7 proteins contact antibodies to the TR7 polypeptides (including antibodies to the heterologous polypeptide sequence in a fusion protein) in solution. In other embodiments, multimers bound by one or more antibodies of the invention are formed by covalent associations with and/or between the TR7 proteins of the invention. Such covalent associations may involve one or more amino acid residues contained in the polypeptide sequence of the protein (e.g., the polypeptide sequence recited in SEQ ID NO:3 or the polypeptide encoded by the deposited cDNA clone of ATCC Deposit 97920). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR7 fusion protein. In one example, covalent associations are between the heterologous sequence contained in a fusion protein (see, e.g., U.S. Pat. No. 5,478,925). In a specific example, the covalent associations are between the heterologous sequence contained in a TR7-Fc fusion protein (as described herein). In another specific example, covalent associations of fusion proteins are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers that may be bound by one or more antibodies of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers that may be bound by one or more antibodies of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins that may be bound by one or more antibodies of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that may be bound by one or more antibodies of the invention (see, e.g., U.S. Pat. No. 5,478,925, which is herein incorporated by reference in its entirety).

Alternatively, multimers that may be bound by one or more antibodies of the invention may be generated using genetic engineering techniques known in the art. In one embodiment, proteins contained in multimers that may be bound by one or more antibodies of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that may be bound by one or more antibodies of the invention are generated by ligating a polynucleotide sequence encoding a TR7 polypeptide to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant TR7 polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more TR7 polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple TR7 polypeptides separated by peptide linkers may be produced using conventional recombinant DNA technology. In specific embodiments, antibodies of the invention bind proteins comprising multiple TR7 polypeptides separated by peptide linkers.

Another method for preparing multimer TR7 polypeptides involves use of TR7 polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR7 proteins are those described in PCT application WO 94/10308, hereby incorporated by reference. Recombinant fusion proteins comprising a soluble TR7 polypeptide fused to a peptide that dimerizes or trimerizes in solution are expressed in suitable host cells, and the resulting soluble multimeric TR7 is recovered from the culture supernatant using techniques known in the art. In specific embodiments, antibodies of the invention bind TR7-leucine zipper fusion protein monomers and/or TR7-leucine zipper fusion protein multimers.

Certain members of the TNF family of proteins are believed to exist in trimeric form (Beutler and Huffel, *Science* 264:667, 1994; Banner et al., *Cell* 73:431, 1993). Thus, trimeric TR7 may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, now U.S. Pat. No. 5,716,805, hereby incorporated by reference. In specific embodiments, antibodies of the invention bind TR7-leucine zipper fusion protein trimers.

Other peptides derived from naturally occurring trimeric proteins may be employed in preparing trimeric TR7. In specific embodiments, antibodies of the invention bind TR7-fusion protein monomers and/or TR7 fusion protein trimers.

Antibodies that bind TR7 receptor polypeptides may bind them as isolated polypeptides or in their naturally occurring state. By "isolated polypeptide" is intended a polypeptide removed from its native environment. Thus, a polypeptide produced and/or contained within a recombinant host cell is considered isolated for purposes of the present invention. Also, intended as an "isolated polypeptide" are polypeptides that have been purified, partially or substantially, from a recombinant host cell. For example, a recombinantly produced version of the TR7 polypeptide is substantially purified by the one-step method described in Smith and Johnson, *Gene* 67:31-40 (1988). Thus, antibodies of the present invention may bind recombinantly produced TR7 receptor polypeptides. In a specific embodiment, antibodies of the present invention bind a TR7 receptor expressed on the surface of a cell comprising a polynucleotide encoding amino acids 1 to 411 of SEQ ID NO:3 operably associated with a regulatory sequence that controls gene expression.

Antibodies of the present invention may bind TR7 polypeptides or polypeptide fragments including polypeptides comprising or alternatively, consisting of, an amino acid sequence contained in SEQ ID NO:3, encoded by the cDNA contained in ATCC deposit Number 97920, or encoded by nucleic acids which hybridize (e.g., under stringent hybridization conditions) to the nucleotide sequence contained in the ATCC deposit Number 97920, or the complementary strand thereto. Protein fragments may be "free-standing," or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 51, 52 to 78, 79 to 91, 92 to 111, 112 to 134, 135 to 151, 152 to 178, 179 to 180, 181 to 208, 209 to 218, 219 to 231, 232 to 251, 252 to 271, 272 to 291, 292 to 311, 312 to 323, 324 to 361, 362 to 391, 392 to 411 of SEQ ID NO:3. In this context "about" includes the particularly recited ranges, larger or smaller by several (5, 4, 3, 2, or 1) amino acids, at either extreme or at both extremes. Moreover, polypeptide fragments can be at least about 10, 20, 30, 40, 50, 60, 70, 80, 90, 100, 110, 120, 130, 140, or 150 amino acids in length. In this context "about" includes the particularly recited value, larger or smaller by several (5, 4, 3, 2, or 1) amino acids, at either extreme or at both extremes.

Preferred polypeptide fragments of the present invention include a member selected from the group: a polypeptide comprising or alternatively, consisting of, the TR7 receptor extracellular domain (predicted to constitute amino acid residues from about 52 to about 184 in SEQ ID NO:3); a polypeptide comprising or alternatively, consisting of, both TR7 cysteine rich domains (both of which may be found in the protein fragment consisting of amino acid residues from about 84 to about 179 in SEQ ID NO:3); a polypeptide comprising or alternatively, consisting of, the TR7 cysteine rich domain consisting of amino acid residues from about 84 to about 131 in SEQ ID NO:3); a polypeptide comprising or alternatively, consisting of, the TR7 cysteine rich domain consisting of amino acid residues from about 132 to about 179 in SEQ ID NO:3); a polypeptide comprising or alternatively, consisting of, the TR7 receptor transmembrane domain (predicted to constitute amino acid residues from about 185 to about 208 in SEQ ID NO:3); a polypeptide comprising or alternatively, consisting of, fragment of the predicted mature TR7 polypeptide, wherein the fragment has a TR7 functional activity (e.g., antigenic activity or biological acitivity); a polypeptide comprising or alternatively, consisting of, the TR7 receptor intracellular domain (predicted to constitute amino acid residues from about 209 to about 411 in SEQ ID NO:3); a polypeptide comprising or alternatively, consisting of, the TR7 receptor extracellular and intracellular domains with all or part of the transmembrane domain deleted; a polypeptide comprising, or alternatively consisting of, the TR7 receptor death domain (predicted to constitute amino acid residues from about 324 to about 391 in SEQ ID NO:3); and a polypeptide comprising, or alternatively, consisting of, one, two, three, four or more, epitope bearing portions of the TR7 receptor protein. In additional embodiments, the polypeptide fragments of the invention comprise, or alternatively, consist of, any combination of 1, 2, 3, 4, 5, 6, 7, or all 8 of the above members. As above, with the leader sequence, the amino acid residues constituting the TR7 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain. Polypeptides encoded by these nucleic acid molecules are also encompassed by the invention.

As discussed above, it is believed that one or both of the extracellular cysteine rich motifs of TR7 is important for interactions between TR7 and its ligands (e.g., TRAIL). Accordingly, in highly preferred embodiments, antibodies of the present invention bind TR7 polypeptide fragments comprising, or alternatively consisting of, amino acid residues 84 to 131, and/or 132 to 179 of SEQ ID NO:3. In another highly preferred embodiment, antibodies of the present invention bind TR7 polypeptides comprising, or alternatively consisting of, both of the extracellular cysteine rich motifs (amino acid residues 84 to 179 of SEQ ID NO:3.) In another preferred embodiment, antibodies of the present invention bind TR7 polypeptides comprising, or alternatively consisting the extracellular soluble domain of TR7 (amino acid residues 52 to 184 of SEQ ID NO:2.) In other highly preferred embodiments, the antibodies of the invention that bind all or a portion of the extracellular soluble domain of TR7 (e.g., one or both cysteine rich domains) agonize the TR7 receptor.

In other highly preferred embodiments, the antibodies of the invention that bind all or a portion of the extracellular soluble domain of TR7 (e.g., one or both cysteine rich domains) induce cell death of the cell expressing the TR7 receptor.

Antibodies of the invention may also bind fragments comprising, or alternatively, consisting of structural or functional attributes of TR7. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophillic regions, hydrophobic regions, alpha amphipathic regions, beta amphipathic regions, surface forming regions, and high antigenic index regions (i.e., regions of polypeptides consisting of amino acid residues having an antigenic index of or equal to greater than 1.5, as identified using the default parameters of the Jameson-Wolf program) of TR7. Certain preferred regions are those disclosed in Table 4 and include, but are not limited to, regions of the aforementioned types identified by analysis of the amino acid sequence of SEQ ID NO:3, such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions and Hopp-Woods predicted hydrophobic regions; Eisenberg alpha and beta amphipathic regions; Emini surface-forming regions; and Jameson-Wolf high antigenic index regions, as predicted using the default parameters of these computer programs.

The data representing the structural or functional attributes of TR7 set forth in Table 4, as described above, was generated using the various modules and algorithms of the DNA*STAR set on default parameters. Column I represents the results of a Garnier-Robson analysis of alpha helical regions; Column II represents the results of a Chou-Fasman analysis of alpha helical regions; Column III represents the results of a Garnier Robson analysis of beta sheet regions; Column IV represents the results of a Chou-Fasman analysis of beta sheet regions; Column V represents the results of a Garnier Robson analysis of turn regions; Column VI represents the results of a Chou-Fasman analysis of turn regions; Column VII represents the results of a Garnier Robson analysis of coil regions; Column VIII represents a Kyte-Doolittle hydrophilicity plot; Column IX represents a Hopp-Woods hydrophobicity plot; Column X represents the results of an Eisenberg analysis of alpha amphipathic regions; Column XI represents the results of an Eisenberg analysis of beta amphipathic regions; Column XII represents the results of a Karplus-Schultz analysis of flexible regions; Column XIII represents the Jameson-Wolf antigenic index score; and Column XIV represents the Emini surface probability plot.

In a preferred embodiment, the data presented in columns VIII, IX, XIII, and XIV of Table 4 can be used to determine regions of TR7 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response. The columns in Table 4 present the result of different analysees of the TR7 protein sequence.

The above-mentioned preferred regions set out in Table 4 include, but are not limited to, regions of the aforementioned types identified by analysis of the amino acid sequence set out in SEQ ID NO:3. As set out in Table 4, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions. Preferably, antibodies of the present invention bind TR7 polypeptides or TR7 polypeptide fragments and variants comprising regions of TR7 that combine several structural features, such as several (e.g., 1, 2, 3, or 4) of the same or different region features set out above and in Table 4.

TABLE 4

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 1.11 | −0.70 | . | * | . | 1.29 | 2.18 |
| Glu | 2 | A | . | . | . | . | . | . | 1.50 | −0.70 | . | * | . | 1.63 | 1.69 |
| Gln | 3 | A | . | . | . | . | T | . | 1.89 | −0.73 | . | * | . | 2.17 | 2.28 |
| Arg | 4 | . | . | . | . | T | T | . | 1.69 | −0.76 | . | * | . | 2.91 | 3.71 |
| Gly | 5 | . | . | . | . | T | T | . | 1.87 | −0.87 | . | * | F | 3.40 | 2.17 |
| Gln | 6 | . | . | . | . | T | T | . | 1.88 | −0.44 | . | * | F | 2.76 | 1.93 |
| Asn | 7 | . | . | . | . | . | . | C | 1.29 | −0.34 | . | * | F | 1.87 | 1.00 |
| Ala | 8 | . | . | . | . | . | . | C | 0.99 | 0.16 | . | . | F | 1.08 | 1.02 |
| Pro | 9 | . | . | . | . | . | . | C | 0.53 | 0.11 | . | * | . | 0.44 | 0.79 |
| Ala | 10 | A | . | . | . | . | . | . | 0.29 | 0.14 | . | * | . | −0.10 | 0.48 |
| Ala | 11 | A | . | . | . | . | T | . | 0.40 | 0.24 | . | . | . | 0.10 | 0.48 |
| Ser | 12 | A | . | . | . | . | T | . | 0.44 | −0.26 | . | * | F | 0.85 | 0.61 |
| Gly | 13 | A | . | . | . | . | T | . | 1.14 | −0.69 | . | * | F | 1.30 | 1.22 |
| Ala | 14 | A | . | . | . | . | T | . | 1.32 | −1.19 | . | * | F | 1.30 | 2.36 |
| Arg | 15 | A | . | . | . | T | . | . | 1.57 | −1.19 | . | * | F | 1.50 | 2.39 |
| Lys | 16 | . | . | . | . | T | . | . | 1.94 | −1.14 | . | . | F | 1.50 | 2.39 |
| Arg | 17 | . | . | . | . | T | . | . | 1.90 | −1.14 | . | * | F | 1.80 | 3.66 |
| His | 18 | . | . | . | . | . | . | C | 2.03 | −1.21 | * | * | F | 1.90 | 1.85 |
| Gly | 19 | . | . | . | . | . | T | C | 2.73 | −0.79 | * | * | F | 2.40 | 1.43 |
| Pro | 20 | . | . | . | . | . | T | C | 2.62 | −0.79 | * | * | F | 2.70 | 1.43 |
| Gly | 21 | . | . | . | . | . | T | C | 1.99 | −0.79 | * | . | F | 3.00 | 1.82 |
| Pro | 22 | . | . | . | . | . | T | C | 1.99 | −0.79 | . | * | F | 2.70 | 1.86 |
| Arg | 23 | . | A | . | . | . | . | C | 1.68 | −1.21 | * | . | F | 2.30 | 2.35 |
| Glu | 24 | . | A | B | . | . | . | . | 1.43 | −1.21 | * | . | F | 2.10 | 2.35 |
| Ala | 25 | . | A | . | . | T | . | . | 1.76 | −1.14 | * | . | F | 2.50 | 1.54 |
| Arg | 26 | . | A | . | . | T | . | . | 1.89 | −1.57 | * | . | F | 2.50 | 1.54 |
| Gly | 27 | . | . | . | . | T | . | . | 1.76 | −1.14 | * | . | F | 3.00 | 1.37 |

TABLE 4-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 28 | . | . | . | . | . | T | . | C | 1.43 | −0.71 | * | * | F | 2.70 | 1.35 |
| Arg | 29 | . | . | . | . | . | . | T | C | 1.54 | −0.79 | * | * | F | 2.66 | 1.06 |
| Pro | 30 | . | . | . | . | . | . | T | C | 1.28 | −0.79 | * | * | F | 2.62 | 2.10 |
| Gly | 31 | . | . | . | . | . | . | T | C | 0.96 | −0.57 | * | * | F | 2.58 | 1.54 |
| Pro | 32 | . | . | . | . | . | . | T | C | 1.34 | −0.64 | * | * | F | 2.54 | 1.22 |
| Arg | 33 | . | . | . | . | . | . | . | C | 1.62 | −0.64 | * | * | F | 2.60 | 1.58 |
| Val | 34 | . | . | . | . | . | . | . | C | 0.70 | −0.59 | * | * | F | 2.34 | 2.30 |
| Pro | 35 | . | . | B | . | . | . | . | . | 0.06 | −0.33 | * | * | F | 1.58 | 1.23 |
| Lys | 36 | . | . | B | B | . | . | . | . | −0.41 | −0.11 | * | . | F | 0.97 | 0.46 |
| Thr | 37 | . | . | B | B | . | . | . | . | −1.06 | 0.57 | * | * | F | −0.19 | 0.52 |
| Leu | 38 | . | . | B | B | . | . | . | . | −2.02 | 0.57 | * | * | . | −0.60 | 0.25 |
| Val | 39 | . | . | B | B | . | . | . | . | −1.76 | 0.79 | . | . | . | −0.60 | 0.09 |
| Leu | 40 | A | . | . | B | . | . | . | . | −2.13 | 1.29 | . | . | . | −0.60 | 0.06 |
| Val | 41 | A | . | . | B | . | . | . | . | −3.03 | 1.30 | . | . | . | −0.60 | 0.08 |
| Val | 42 | A | . | . | B | . | . | . | . | −3.53 | 1.26 | . | . | . | −0.60 | 0.08 |
| Ala | 43 | A | . | . | B | . | . | . | . | −3.53 | 1.30 | . | . | . | −0.60 | 0.08 |
| Ala | 44 | A | . | . | B | . | . | . | . | −3.49 | 1.30 | . | . | . | −0.60 | 0.09 |
| Val | 45 | A | . | . | B | . | . | . | . | −3.53 | 1.34 | . | . | . | −0.60 | 0.10 |
| Leu | 46 | A | . | . | B | . | . | . | . | −2.98 | 1.34 | . | . | . | −0.60 | 0.07 |
| Leu | 47 | A | . | . | B | . | . | . | . | −2.71 | 1.23 | . | . | . | −0.60 | 0.09 |
| Leu | 48 | A | . | . | B | . | . | . | . | −2.12 | 1.23 | . | . | . | −0.60 | 0.13 |
| Val | 49 | A | . | . | B | . | . | . | . | −1.83 | 0.59 | . | . | . | −0.60 | 0.27 |
| Ser | 50 | A | . | . | B | . | . | . | . | −1.57 | 0.29 | . | * | . | −0.30 | 0.44 |
| Ala | 51 | A | A | . | . | . | . | . | . | −1.57 | 0.10 | . | . | . | −0.30 | 0.54 |
| Glu | 52 | A | A | . | . | . | . | . | . | −1.64 | 0.10 | . | . | . | −0.30 | 0.60 |
| Ser | 53 | A | A | . | B | . | . | . | . | −1.14 | 0.14 | . | . | . | −0.30 | 0.31 |
| Ala | 54 | A | A | . | B | . | . | . | . | −0.29 | 0.24 | . | . | . | −0.30 | 0.45 |
| Leu | 55 | A | A | . | B | . | . | . | . | 0.01 | 0.14 | . | . | . | −0.30 | 0.45 |
| Ile | 56 | A | A | . | B | . | . | . | . | 0.60 | 0.54 | . | . | . | −0.60 | 0.58 |
| Thr | 57 | A | A | . | B | . | . | . | . | −0.21 | 0.16 | . | . | F | −0.15 | 0.96 |
| Gln | 58 | A | A | . | B | . | . | . | . | −0.50 | 0.34 | . | . | F | −0.15 | 0.96 |
| Gln | 59 | A | A | . | B | . | . | . | . | −0.12 | 0.16 | . | . | F | 0.00 | 1.38 |
| Asp | 60 | . | A | . | B | T | . | . | . | 0.69 | −0.10 | . | . | F | 1.00 | 1.48 |
| Leu | 61 | . | A | . | . | . | . | . | C | 1.58 | −0.19 | . | * | F | 0.80 | 1.48 |
| Ala | 62 | . | A | . | . | . | . | . | C | 2.00 | −0.19 | . | * | F | 0.80 | 1.48 |
| Pro | 63 | . | A | . | . | . | . | . | C | 1.41 | −0.59 | . | * | F | 1.10 | 1.73 |
| Gln | 64 | . | A | . | . | T | . | . | . | 0.82 | −0.09 | . | * | F | 1.00 | 2.13 |
| Gln | 65 | A | A | . | . | . | . | . | . | 0.61 | −0.27 | . | * | F | 0.60 | 2.13 |
| Arg | 66 | A | A | . | . | . | . | . | . | 1.42 | −0.34 | . | * | F | 0.60 | 2.13 |
| Ala | 67 | A | A | . | . | . | . | . | . | 2.01 | −0.37 | . | * | F | 0.94 | 2.13 |
| Ala | 68 | A | A | . | . | . | . | . | . | 2.27 | −0.37 | * | * | F | 1.28 | 2.13 |
| Pro | 69 | A | A | . | . | . | . | . | . | 2.38 | −0.77 | * | * | F | 1.92 | 2.17 |
| Gln | 70 | . | A | . | . | T | . | . | . | 2.08 | −0.77 | * | . | F | 2.66 | 4.21 |
| Gln | 71 | . | . | . | . | T | T | . | . | 1.67 | −0.89 | * | * | F | 3.40 | 5.58 |
| Lys | 72 | . | . | . | . | T | T | . | . | 2.04 | −1.00 | . | . | F | 3.06 | 4.84 |
| Arg | 73 | . | . | . | . | T | T | . | . | 2.33 | −1.00 | . | . | F | 2.97 | 4.32 |
| Ser | 74 | . | . | . | . | T | T | . | C | 2.54 | −1.01 | . | . | F | 2.68 | 3.34 |
| Ser | 75 | . | . | . | . | T | T | . | C | 2.20 | −1.41 | . | . | F | 2.59 | 2.89 |
| Pro | 76 | . | . | . | . | T | T | . | . | 1.39 | −0.99 | . | . | F | 2.70 | 1.46 |
| Ser | 77 | . | . | . | . | T | T | . | . | 0.68 | −0.30 | . | . | F | 2.50 | 0.90 |
| Glu | 78 | . | . | . | . | T | T | . | . | 0.36 | −0.11 | . | * | F | 2.25 | 0.36 |
| Gly | 79 | . | . | . | . | T | . | . | . | 0.44 | −0.07 | . | . | F | 1.80 | 0.36 |
| Leu | 80 | . | . | . | . | T | . | . | . | 0.40 | −0.07 | . | . | F | 1.55 | 0.42 |
| Cys | 81 | . | . | . | . | . | . | . | C | 0.58 | −0.03 | . | . | . | 0.95 | 0.24 |
| Pro | 82 | . | . | . | . | . | T | . | C | 0.84 | 0.47 | * | . | F | 0.15 | 0.33 |
| Pro | 83 | . | . | . | . | . | T | T | . | −0.04 | 0.54 | * | . | F | 0.35 | 0.54 |
| Gly | 84 | . | . | . | . | . | T | T | . | 0.00 | 0.54 | * | . | . | 0.20 | 0.70 |
| His | 85 | . | . | . | . | . | T | . | C | 0.81 | 0.36 | * | . | . | 0.30 | 0.61 |
| His | 86 | . | . | . | . | . | . | . | C | 1.48 | −0.07 | * | . | . | 0.70 | 0.68 |
| Ile | 87 | . | . | . | . | . | . | . | C | 1.34 | −0.50 | * | * | . | 1.19 | 1.15 |
| Ser | 88 | . | . | . | . | . | . | . | C | 1.67 | −0.50 | * | * | F | 1.53 | 0.84 |
| Glu | 89 | . | . | . | . | . | T | . | . | 2.01 | −1.00 | * | * | F | 2.52 | 1.21 |
| Asp | 90 | . | . | . | . | . | T | . | . | 1.38 | −1.50 | * | * | F | 2.86 | 2.88 |
| Gly | 91 | . | . | . | . | . | T | . | . | 0.52 | −1.61 | * | * | F | 3.40 | 1.15 |
| Arg | 92 | . | . | . | . | . | T | T | . | 1.11 | −1.31 | * | * | F | 2.91 | 0.47 |
| Asp | 93 | . | . | . | . | . | T | T | . | 0.74 | −0.93 | . | * | F | 2.57 | 0.37 |
| Cys | 94 | . | . | . | . | . | T | T | . | 0.79 | −0.36 | . | * | . | 1.78 | 0.20 |
| Ile | 95 | . | . | . | . | . | T | . | . | 0.54 | −0.79 | . | * | . | 1.54 | 0.21 |
| Ser | 96 | . | . | . | . | . | T | . | . | 0.54 | −0.03 | . | * | . | 1.18 | 0.19 |
| Cys | 97 | . | . | . | . | . | T | T | . | 0.43 | 0.40 | . | * | . | 0.76 | 0.36 |
| Lys | 98 | . | . | . | . | . | T | T | . | 0.43 | 0.23 | . | . | . | 1.34 | 0.88 |
| Tyr | 99 | . | . | . | . | . | T | . | . | 0.86 | −0.46 | . | * | F | 2.52 | 1.10 |
| Gly | 100 | . | . | . | . | . | T | T | . | 1.44 | −0.09 | . | . | F | 2.80 | 3.22 |
| Gln | 101 | . | . | . | . | . | T | T | . | 1.43 | −0.27 | * | . | F | 2.52 | 2.16 |
| Asp | 102 | . | . | . | . | . | T | T | . | 2.07 | 0.21 | * | * | F | 1.64 | 1.99 |
| Tyr | 103 | . | . | . | . | . | T | T | . | 1.73 | −0.04 | * | * | F | 1.96 | 2.73 |
| Ser | 104 | . | . | . | . | . | T | T | . | 1.98 | 0.44 | * | . | F | 0.78 | 1.66 |

TABLE 4-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 105 | . | . | . | . | T | . | . | 2.32 | 0.44 | * | . | F | 0.30 | 1.60 |
| His | 106 | . | . | . | . | T | . | . | 1.51 | 0.44 | * | . | . | 0.15 | 1.70 |
| Trp | 107 | . | . | . | . | T | T | . | 0.70 | 0.37 | * | . | . | 0.65 | 1.05 |
| Asn | 108 | . | . | . | . | T | T | . | 0.24 | 0.67 | . | . | . | 0.20 | 0.60 |
| Asp | 109 | . | . | . | . | T | T | . | −0.12 | 0.97 | * | . | . | 0.20 | 0.38 |
| Leu | 110 | A | . | . | . | . | T | . | −0.62 | 1.04 | * | * | . | −0.20 | 0.19 |
| Leu | 111 | . | . | . | B | T | . | . | −0.48 | 0.81 | * | * | . | −0.20 | 0.10 |
| Phe | 112 | . | . | . | B | T | . | . | −0.86 | 0.41 | * | * | . | −0.20 | 0.12 |
| Cys | 113 | . | . | . | B | T | . | . | −1.17 | 0.99 | * | * | . | −0.20 | 0.08 |
| Leu | 114 | . | . | . | B | T | . | . | −1.06 | 0.79 | * | * | . | −0.20 | 0.13 |
| Arg | 115 | . | . | . | B | T | . | . | −0.91 | 0.10 | . | * | . | 0.10 | 0.30 |
| Cys | 116 | . | . | . | B | T | . | . | −0.10 | −0.11 | . | . | . | 0.70 | 0.30 |
| Thr | 117 | . | . | . | B | T | . | . | 0.30 | −0.69 | . | * | . | 1.00 | 0.61 |
| Arg | 118 | . | . | . | B | T | . | . | 0.62 | −0.99 | . | . | F | 1.49 | 0.42 |
| Cys | 119 | . | . | . | . | T | T | . | 1.43 | −0.56 | * | . | F | 2.23 | 0.77 |
| Asp | 120 | . | . | . | . | T | T | . | 0.47 | −1.13 | * | . | F | 2.57 | 0.92 |
| Ser | 121 | . | . | . | . | T | T | . | 1.13 | −0.97 | . | * | F | 2.91 | 0.35 |
| Gly | 122 | . | . | . | . | T | T | . | 0.63 | −0.97 | . | * | F | 3.40 | 1.13 |
| Glu | 123 | . | A | . | . | T | . | . | 0.22 | −0.86 | . | * | F | 2.51 | 0.56 |
| Val | 124 | A | A | . | . | . | . | . | 0.68 | −0.47 | . | * | F | 1.47 | 0.56 |
| Glu | 125 | . | A | . | . | T | . | . | 0.01 | −0.43 | . | * | . | 1.38 | 0.87 |
| Leu | 126 | . | A | . | . | T | . | . | 0.00 | −0.29 | . | * | . | 1.04 | 0.27 |
| Ser | 127 | . | . | . | . | T | T | C | 0.03 | 0.20 | * | . | F | 0.45 | 0.52 |
| Pro | 128 | . | . | . | . | T | T | . | −0.28 | 0.04 | . | . | F | 0.93 | 0.44 |
| Cys | 129 | . | . | . | . | T | T | . | 0.69 | 0.53 | . | . | F | 0.91 | 0.77 |
| Thr | 130 | . | . | . | . | T | T | . | 0.69 | −0.16 | . | * | F | 2.24 | 1.12 |
| Thr | 131 | . | . | . | . | T | . | . | 1.19 | −0.14 | . | * | F | 2.32 | 1.16 |
| Thr | 132 | . | . | . | . | T | T | . | 0.63 | −0.09 | . | * | F | 2.80 | 3.13 |
| Arg | 133 | . | . | . | . | T | T | . | 0.18 | −0.01 | . | . | F | 2.52 | 1.61 |
| Asn | 134 | . | . | . | . | T | T | . | 0.84 | 0.07 | . | . | F | 1.49 | 0.60 |
| Thr | 135 | . | . | . | . | T | T | . | 0.49 | −0.01 | . | . | F | 1.81 | 0.72 |
| Val | 136 | . | . | . | . | T | . | C | 0.80 | 0.07 | * | . | . | 0.58 | 0.20 |
| Cys | 137 | . | A | . | . | T | . | . | 1.11 | 0.07 | * | . | . | 0.10 | 0.21 |
| Gln | 138 | . | A | B | . | . | . | . | 0.66 | −0.33 | * | . | . | 0.30 | 0.25 |
| Cys | 139 | . | A | . | . | T | . | . | 0.34 | −0.39 | . | . | . | 0.70 | 0.34 |
| Glu | 140 | A | A | . | . | . | . | . | −0.04 | −0.54 | * | * | F | 0.75 | 0.91 |
| Glu | 141 | A | A | . | . | . | . | . | 0.92 | −0.33 | * | * | F | 0.45 | 0.46 |
| Gly | 142 | . | A | . | . | T | . | . | 1.59 | −0.73 | . | * | F | 1.30 | 1.67 |
| Thr | 143 | A | A | . | . | . | . | . | 1.59 | −1.30 | . | * | F | 0.90 | 1.67 |
| Phe | 144 | A | A | . | . | . | . | . | 2.26 | −1.30 | . | * | F | 0.90 | 1.67 |
| Arg | 145 | A | A | . | . | . | . | . | 1.96 | −1.30 | . | * | F | 0.90 | 2.81 |
| Glu | 146 | A | A | . | . | . | . | . | 1.74 | −1.34 | . | * | F | 0.90 | 2.61 |
| Glu | 147 | A | A | . | . | . | . | . | 2.09 | −1.40 | . | * | F | 0.90 | 4.66 |
| Asp | 148 | A | A | . | . | . | . | . | 1.80 | −2.19 | . | * | F | 0.90 | 4.12 |
| Ser | 149 | A | . | . | . | . | T | . | 1.83 | −1.57 | . | * | F | 1.30 | 2.35 |
| Pro | 150 | A | . | . | . | . | T | . | 1.83 | −1.00 | . | . | F | 1.15 | 0.73 |
| Glu | 151 | A | . | . | . | . | T | . | 1.88 | −1.00 | * | . | F | 1.15 | 0.85 |
| Met | 152 | A | . | . | . | . | T | . | 1.21 | −1.00 | * | * | . | 1.49 | 1.28 |
| Cys | 153 | A | . | . | . | . | T | . | 1.32 | −0.81 | * | * | . | 1.68 | 0.44 |
| Arg | 154 | A | . | . | . | . | T | . | 1.31 | −1.24 | * | . | . | 2.02 | 0.50 |
| Lys | 155 | . | . | . | . | T | T | . | 1.18 | −0.76 | * | * | F | 2.91 | 0.73 |
| Cys | 156 | . | . | . | . | T | T | . | 0.51 | −0.94 | * | . | F | 3.40 | 1.35 |
| Arg | 157 | . | . | . | . | T | . | . | 0.90 | −0.94 | * | . | F | 2.71 | 0.37 |
| Thr | 158 | . | . | . | . | T | . | . | 1.68 | −0.51 | * | . | F | 2.37 | 0.28 |
| Gly | 159 | . | . | . | . | T | . | . | 1.22 | −0.51 | * | . | F | 2.43 | 1.04 |
| Cys | 160 | . | . | . | . | . | T | C | 0.58 | −0.66 | . | * | F | 2.19 | 0.53 |
| Pro | 161 | . | . | . | . | T | T | . | 0.39 | −0.04 | . | * | F | 2.00 | 0.36 |
| Arg | 162 | . | . | . | . | T | T | . | 0.32 | 0.11 | . | * | F | 1.65 | 0.27 |
| Gly | 163 | . | . | . | . | T | T | . | −0.22 | −0.31 | * | * | . | 2.50 | 1.01 |
| Met | 164 | . | . | B | B | . | . | . | −0.22 | −0.24 | * | * | . | 1.30 | 0.48 |
| Val | 165 | . | . | B | B | . | . | . | 0.44 | −0.24 | * | * | . | 1.30 | 0.24 |
| Lys | 166 | . | . | B | B | . | . | . | −0.01 | −0.24 | * | * | . | 1.30 | 0.41 |
| Val | 167 | . | . | B | . | . | T | . | −0.43 | −0.10 | * | * | F | 1.85 | 0.22 |
| Gly | 168 | . | . | . | . | . | T | . | −0.30 | −0.23 | . | . | F | 2.25 | 0.44 |
| Asp | 169 | . | . | . | . | T | T | . | 0.01 | −0.44 | . | . | F | 2.50 | 0.34 |
| Cys | 170 | . | . | . | . | T | T | . | 0.57 | 0.47 | . | * | F | 1.35 | 0.48 |
| Thr | 171 | . | . | . | . | . | T | C | 0.52 | 0.21 | . | * | F | 1.20 | 0.65 |
| Pro | 172 | . | . | . | . | T | T | . | 0.49 | −0.21 | . | * | F | 1.75 | 0.65 |
| Trp | 173 | . | . | . | . | T | T | . | 0.83 | 0.47 | . | * | F | 0.60 | 0.84 |
| Ser | 174 | A | . | . | . | . | T | . | 0.17 | −0.10 | . | * | F | 1.00 | 1.01 |
| Asp | 175 | A | A | . | . | . | . | . | −0.02 | −0.01 | . | . | F | 0.45 | 0.35 |
| Ile | 176 | A | A | . | . | . | . | . | 0.26 | 0.20 | * | * | . | −0.30 | 0.25 |
| Glu | 177 | A | A | . | . | . | . | . | 0.51 | −0.21 | * | . | . | 0.30 | 0.25 |
| Cys | 178 | A | A | . | . | . | . | . | 0.80 | −0.60 | * | . | . | 0.60 | 0.30 |
| Val | 179 | A | A | . | . | . | . | . | 0.80 | −0.60 | * | * | . | 0.60 | 0.74 |
| His | 180 | A | A | . | . | . | . | . | 0.46 | −0.90 | . | * | . | 0.60 | 0.58 |
| Lys | 181 | A | A | . | . | . | . | . | 0.46 | −0.47 | * | . | F | 0.60 | 1.06 |

TABLE 4-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 182 | A | . | . | . | . | T | . | −0.43 | −0.36 | * | . | F | 1.00 | 1.00 |
| Ser | 183 | A | . | . | . | . | . | . | −0.66 | −0.31 | . | . | F | 0.85 | 0.52 |
| Gly | 184 | A | . | . | . | T | T | . | −0.14 | −0.13 | . | . | F | 1.25 | 0.18 |
| Ile | 185 | A | . | . | . | . | T | . | −0.97 | 0.30 | . | . | . | 0.10 | 0.10 |
| Ile | 186 | . | . | B | B | . | . | . | −1.32 | 0.94 | . | * | . | −0.60 | 0.06 |
| Ile | 187 | . | . | B | B | . | . | . | −2.18 | 1.04 | . | . | . | −0.60 | 0.08 |
| Gly | 188 | . | . | B | B | . | . | . | −2.47 | 1.26 | . | * | . | −0.60 | 0.09 |
| Val | 189 | . | . | B | B | . | . | . | −2.71 | 1.07 | . | . | . | −0.60 | 0.13 |
| Thr | 190 | A | . | . | B | . | . | . | −2.68 | 0.89 | . | * | . | −0.60 | 0.18 |
| Val | 191 | A | . | . | B | . | . | . | −2.64 | 0.84 | . | . | . | −0.60 | 0.14 |
| Ala | 192 | A | . | . | B | . | . | . | −2.57 | 1.06 | . | * | . | −0.60 | 0.14 |
| Ala | 193 | A | . | . | B | . | . | . | −3.11 | 1.10 | . | . | . | −0.60 | 0.08 |
| Val | 194 | A | . | . | B | . | . | . | −3.11 | 1.30 | . | . | . | −0.60 | 0.07 |
| Val | 195 | A | . | . | B | . | . | . | −3.39 | 1.30 | . | . | . | −0.60 | 0.05 |
| Leu | 196 | A | . | . | B | . | . | . | −3.39 | 1.30 | . | . | . | −0.60 | 0.05 |
| Ile | 197 | A | . | . | B | . | . | . | −3.50 | 1.44 | . | . | . | −0.60 | 0.05 |
| Val | 198 | A | . | . | B | . | . | . | −3.77 | 1.59 | . | . | . | −0.60 | 0.06 |
| Ala | 199 | A | . | . | B | . | . | . | −3.58 | 1.59 | . | . | . | −0.60 | 0.06 |
| Val | 200 | A | . | . | B | . | . | . | −2.68 | 1.47 | . | . | . | −0.60 | 0.04 |
| Phe | 201 | A | . | . | B | . | . | . | −2.17 | 0.79 | . | . | . | −0.60 | 0.12 |
| Val | 202 | A | . | . | B | . | . | . | −2.09 | 0.53 | . | . | . | −0.60 | 0.16 |
| Cys | 203 | A | . | . | . | . | T | . | −2.04 | 0.71 | . | . | . | −0.20 | 0.17 |
| Lys | 204 | A | . | . | . | . | T | . | −1.74 | 0.76 | . | . | . | −0.20 | 0.17 |
| Ser | 205 | A | . | . | . | . | T | . | −0.84 | 0.89 | . | . | . | −0.20 | 0.24 |
| Leu | 206 | A | . | . | . | . | T | . | −0.10 | 0.24 | . | . | . | 0.10 | 0.88 |
| Leu | 207 | A | A | . | . | . | . | . | −0.10 | −0.33 | . | . | . | 0.30 | 0.88 |
| Trp | 208 | A | A | . | . | . | . | . | −0.24 | 0.31 | . | . | . | −0.30 | 0.49 |
| Lys | 209 | A | A | . | . | . | . | . | −0.50 | 0.61 | . | . | . | −0.60 | 0.49 |
| Lys | 210 | A | A | . | . | . | . | . | −0.44 | 0.36 | * | . | . | −0.30 | 0.91 |
| Val | 211 | A | A | . | . | . | . | . | −0.44 | 0.43 | * | * | . | −0.45 | 1.36 |
| Leu | 212 | . | A | B | . | . | . | . | 0.41 | 0.20 | * | * | . | −0.30 | 0.56 |
| Pro | 213 | . | A | B | . | . | . | . | 0.36 | 0.20 | * | . | . | −0.30 | 0.56 |
| Tyr | 214 | . | . | . | B | T | . | . | −0.58 | 0.63 | * | . | . | −0.20 | 0.75 |
| Leu | 215 | . | . | . | B | T | . | . | −1.29 | 0.67 | * | * | . | −0.20 | 0.64 |
| Lys | 216 | . | . | . | B | T | . | . | −0.73 | 0.56 | * | . | . | −0.20 | 0.22 |
| Gly | 217 | . | . | B | B | . | . | . | −0.27 | 0.51 | * | . | . | −0.60 | 0.19 |
| Ile | 218 | . | . | B | B | . | . | . | −0.40 | 0.19 | * | . | . | −0.30 | 0.23 |
| Cys | 219 | . | . | B | . | . | T | . | −0.50 | −0.07 | * | . | . | 0.70 | 0.11 |
| Ser | 220 | . | . | . | . | T | T | . | −0.03 | 0.36 | * | * | F | 0.65 | 0.11 |
| Gly | 221 | . | . | . | . | T | T | . | −0.08 | 0.36 | . | . | F | 0.65 | 0.16 |
| Gly | 222 | . | . | . | . | T | T | . | 0.06 | −0.33 | . | . | F | 1.25 | 0.49 |
| Gly | 223 | . | . | . | . | . | . | C | 0.94 | −0.47 | . | . | F | 0.85 | 0.57 |
| Gly | 224 | . | . | . | . | . | . | C | 1.72 | −0.86 | * | . | F | 1.15 | 0.99 |
| Asp | 225 | . | . | . | . | . | T | C | 1.17 | −1.29 | . | * | F | 1.50 | 1.97 |
| Pro | 226 | . | . | . | . | . | T | C | 1.51 | −1.07 | * | . | F | 1.84 | 1.47 |
| Glu | 227 | . | . | B | . | . | T | . | 1.97 | −1.50 | * | . | F | 1.98 | 2.49 |
| Arg | 228 | . | . | B | . | . | T | . | 2.01 | −1.93 | * | . | F | 2.32 | 2.92 |
| Val | 229 | . | . | . | . | T | . | . | 2.06 | −1.54 | * | . | F | 2.86 | 2.53 |
| Asp | 230 | . | . | . | . | T | T | . | 2.06 | −1.59 | * | . | F | 3.40 | 1.96 |
| Arg | 231 | . | . | . | . | T | T | . | 2.38 | −1.19 | * | * | F | 3.06 | 1.73 |
| Ser | 232 | . | . | . | . | T | T | . | 2.17 | −1.19 | * | . | F | 2.72 | 4.57 |
| Ser | 233 | . | . | . | . | T | T | . | 1.71 | −1.40 | * | * | F | 2.72 | 4.23 |
| Gln | 234 | . | . | . | . | . | . | C | 1.98 | −0.97 | * | * | F | 2.32 | 2.14 |
| Arg | 235 | . | . | . | . | . | T | C | 1.98 | −0.47 | * | * | F | 2.22 | 1.61 |
| Pro | 236 | . | . | . | . | . | T | C | 1.87 | −0.86 | * | * | F | 2.86 | 2.08 |
| Gly | 237 | . | . | . | . | . | T | . | 2.17 | −1.24 | . | * | F | 3.40 | 2.01 |
| Ala | 238 | . | . | . | . | . | T | C | 1.61 | −1.24 | . | * | F | 2.86 | 1.65 |
| Glu | 239 | A | . | . | . | . | . | . | 0.80 | −0.60 | . | * | F | 1.97 | 0.79 |
| Asp | 240 | A | . | . | . | . | . | . | 0.69 | −0.34 | . | * | F | 1.33 | 0.66 |
| Asn | 241 | A | . | . | . | . | . | . | 0.90 | −0.37 | * | . | . | 0.99 | 1.05 |
| Val | 242 | A | . | . | . | . | . | . | 0.36 | −0.87 | * | . | . | 0.95 | 1.05 |
| Leu | 243 | A | . | . | . | . | . | . | 0.09 | −0.19 | * | . | . | 0.50 | 0.44 |
| Asn | 244 | A | . | . | B | . | . | . | −0.21 | 0.46 | * | . | . | −0.60 | 0.20 |
| Glu | 245 | A | . | . | B | . | . | . | −1.10 | 0.44 | * | . | . | −0.60 | 0.37 |
| Ile | 246 | A | . | . | B | . | . | . | −1.91 | 0.49 | * | . | . | −0.60 | 0.31 |
| Val | 247 | A | . | . | B | . | . | . | −1.06 | 0.49 | * | . | . | −0.60 | 0.16 |
| Ser | 248 | . | . | B | B | . | . | . | −0.46 | 0.49 | * | . | . | −0.60 | 0.16 |
| Ile | 249 | . | . | B | B | . | . | . | −0.77 | 0.91 | * | . | . | −0.60 | 0.35 |
| Leu | 250 | . | . | . | B | . | . | C | −0.77 | 0.71 | . | . | . | −0.40 | 0.69 |
| Gln | 251 | . | . | . | . | . | T | C | −0.73 | 0.47 | . | . | F | 0.15 | 0.89 |
| Pro | 252 | . | . | . | . | . | T | C | −0.09 | 0.73 | . | . | F | 0.15 | 0.94 |
| Thr | 253 | . | . | . | . | . | T | C | 0.21 | 0.47 | . | . | F | 0.30 | 1.76 |
| Gln | 254 | . | . | . | . | . | T | C | 1.10 | −0.21 | . | . | F | 1.20 | 1.76 |
| Val | 255 | . | A | . | . | . | . | C | 1.91 | −0.21 | . | . | F | 0.80 | 1.97 |
| Pro | 256 | . | A | . | . | . | . | C | 1.31 | −0.64 | . | . | F | 1.10 | 2.37 |
| Glu | 257 | A | A | . | . | . | . | . | 1.52 | −0.51 | . | * | F | 0.90 | 1.35 |
| Gln | 258 | A | A | . | . | . | . | . | 0.98 | −0.91 | . | * | F | 0.90 | 3.16 |

TABLE 4-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 259 | A | A | . | . | . | . | . | 0.98 | −0.91 | . | * | F | 0.90 | 1.51 |
| Met | 260 | A | A | . | . | . | . | . | 1.83 | −0.94 | . | * | F | 0.90 | 1.51 |
| Glu | 261 | A | A | . | . | . | . | . | 1.83 | −0.94 | . | * | . | 0.75 | 1.51 |
| Val | 262 | A | A | . | . | . | . | . | 1.24 | −0.91 | . | * | F | 0.90 | 1.35 |
| Gln | 263 | A | A | . | . | . | . | . | 1.24 | −0.41 | . | * | F | 0.60 | 1.38 |
| Glu | 264 | A | A | . | . | . | . | . | 1.03 | −1.03 | . | * | F | 0.90 | 1.38 |
| Pro | 265 | A | A | . | . | . | . | . | 1.32 | −0.60 | . | * | F | 1.18 | 2.88 |
| Ala | 266 | A | A | . | . | . | . | . | 0.98 | −0.76 | . | * | F | 1.46 | 2.40 |
| Glu | 267 | A | . | . | . | . | T | . | 0.98 | −0.73 | . | * | F | 2.14 | 1.37 |
| Pro | 268 | A | . | . | . | . | . | . | 0.98 | −0.09 | . | . | F | 1.97 | 0.66 |
| Thr | 269 | . | . | . | . | T | T | . | 0.38 | −0.11 | . | . | F | 2.80 | 1.05 |
| Gly | 270 | A | . | . | . | . | T | . | −0.22 | 0.00 | . | . | F | 1.37 | 0.60 |
| Val | 271 | A | . | . | . | . | . | . | 0.07 | 0.69 | . | . | . | 0.44 | 0.32 |
| Asn | 272 | . | . | B | . | . | . | . | −0.14 | 0.64 | . | . | . | 0.16 | 0.30 |
| Met | 273 | . | . | B | . | . | . | . | −0.28 | 0.59 | . | . | . | 0.18 | 0.46 |
| Leu | 274 | . | . | . | . | . | . | C | 0.03 | 0.59 | . | . | . | 0.40 | 0.62 |
| Ser | 275 | . | . | . | . | . | T | C | 0.08 | −0.06 | . | . | F | 1.95 | 0.66 |
| Pro | 276 | . | . | . | . | . | T | C | 0.93 | −0.07 | . | . | F | 2.25 | 0.90 |
| Gly | 277 | . | . | . | . | . | T | C | 0.90 | −0.69 | . | . | F | 3.00 | 1.89 |
| Glu | 278 | A | . | . | . | . | T | . | 0.69 | −0.87 | . | . | F | 2.50 | 1.92 |
| Ser | 279 | A | A | . | . | . | . | . | 0.69 | −0.57 | . | . | F | 1.80 | 1.02 |
| Glu | 280 | A | A | . | . | . | . | . | 0.99 | −0.31 | . | . | F | 1.05 | 0.85 |
| His | 281 | A | A | . | . | . | . | . | 0.99 | −0.74 | . | . | F | 1.05 | 0.85 |
| Leu | 282 | A | A | . | . | . | . | . | 0.74 | −0.31 | . | . | . | 0.30 | 0.98 |
| Leu | 283 | A | A | . | . | . | . | . | 0.74 | −0.20 | . | . | . | 0.30 | 0.57 |
| Glu | 284 | A | A | . | . | . | . | . | 0.46 | −0.20 | . | . | F | 0.45 | 0.73 |
| Pro | 285 | A | A | . | . | . | . | . | 0.46 | −0.20 | . | . | F | 0.45 | 0.89 |
| Ala | 286 | A | A | . | . | . | . | . | 0.60 | −0.89 | . | . | F | 0.90 | 1.88 |
| Glu | 287 | A | A | . | . | . | . | . | 1.11 | −1.57 | . | . | F | 0.90 | 2.13 |
| Ala | 288 | A | A | . | . | . | . | . | 1.92 | −1.19 | . | . | F | 0.90 | 1.84 |
| Glu | 289 | A | A | . | . | . | . | . | 2.03 | −1.21 | . | * | . | 0.90 | 3.16 |
| Arg | 290 | A | A | . | . | . | . | . | 2.36 | −1.71 | . | * | F | 0.90 | 3.57 |
| Ser | 291 | A | . | . | . | . | T | . | 3.06 | −1.71 | . | * | F | 1.30 | 6.92 |
| Gln | 292 | A | . | . | . | . | T | . | 2.24 | −2.21 | . | * | F | 1.30 | 7.83 |
| Arg | 293 | A | . | . | . | . | T | . | 2.02 | −1.53 | . | * | F | 1.30 | 3.30 |
| Arg | 294 | A | . | . | . | . | T | . | 1.17 | −0.84 | . | . | F | 1.30 | 2.03 |
| Arg | 295 | . | . | . | B | T | . | . | 0.84 | −0.59 | . | * | F | 1.15 | 0.87 |
| Leu | 296 | . | . | B | B | . | . | . | 0.56 | −0.56 | . | * | . | 0.60 | 0.69 |
| Leu | 297 | . | . | B | B | . | . | . | 0.56 | −0.06 | . | * | . | 0.30 | 0.35 |
| Val | 298 | . | . | . | B | . | . | C | 0.44 | 0.34 | * | * | . | 0.20 | 0.29 |
| Pro | 299 | . | . | . | . | . | T | C | −0.01 | 0.34 | * | . | . | 0.90 | 0.61 |
| Ala | 300 | . | . | . | . | . | T | C | −0.12 | 0.09 | * | * | F | 1.35 | 0.73 |
| Asn | 301 | . | . | . | . | . | T | C | 0.48 | −0.60 | . | * | F | 2.70 | 1.65 |
| Glu | 302 | . | . | . | . | . | T | C | 0.98 | −0.81 | . | . | F | 3.00 | 1.65 |
| Gly | 303 | . | . | . | . | . | . | C | 1.83 | −0.76 | . | . | F | 2.50 | 2.35 |
| Asp | 304 | . | . | . | . | . | T | C | 1.73 | −1.26 | . | . | F | 2.40 | 2.54 |
| Pro | 305 | . | . | . | . | . | T | C | 1.51 | −1.17 | . | * | F | 2.10 | 2.11 |
| Thr | 306 | A | . | . | . | . | T | . | 1.62 | −0.49 | . | * | F | 1.30 | 1.76 |
| Glu | 307 | A | . | . | . | . | T | . | 1.62 | −0.91 | * | * | F | 1.30 | 2.07 |
| Thr | 308 | A | . | . | B | . | . | . | 1.30 | −0.51 | * | * | F | 0.90 | 2.31 |
| Leu | 309 | A | . | . | B | . | . | . | 0.60 | −0.37 | * | * | F | 0.45 | 0.86 |
| Arg | 310 | A | . | . | B | . | . | . | 0.81 | −0.07 | * | * | . | 0.30 | 0.43 |
| Gln | 311 | A | . | . | B | . | . | . | 1.12 | −0.07 | * | * | . | 0.30 | 0.50 |
| Cys | 312 | A | . | . | . | . | T | . | 0.42 | −0.56 | * | * | . | 1.15 | 1.01 |
| Phe | 313 | A | . | . | . | . | T | . | 0.14 | −0.46 | * | * | . | 0.70 | 0.45 |
| Asp | 314 | . | . | . | . | T | T | . | 0.96 | 0.04 | * | * | . | 0.50 | 0.26 |
| Asp | 315 | A | . | . | . | . | T | . | 0.03 | −0.36 | * | * | . | 0.70 | 0.81 |
| Phe | 316 | A | A | . | . | . | . | . | −0.82 | −0.24 | * | . | . | 0.30 | 0.77 |
| Ala | 317 | A | A | . | . | . | . | . | −0.37 | −0.39 | * | . | . | 0.30 | 0.34 |
| Asp | 318 | A | A | . | . | . | . | . | −0.37 | 0.04 | * | * | . | −0.30 | 0.32 |
| Leu | 319 | A | A | . | . | . | . | . | −0.37 | 0.83 | . | . | . | −0.60 | 0.32 |
| Val | 320 | . | A | . | . | . | . | C | −0.67 | 0.04 | . | . | . | −0.10 | 0.52 |
| Pro | 321 | . | A | . | . | . | . | C | −0.26 | −0.07 | . | . | . | 0.50 | 0.42 |
| Phe | 322 | . | . | . | . | T | T | . | 0.33 | 0.84 | . | . | . | 0.20 | 0.54 |
| Asp | 323 | A | . | . | . | . | T | . | 0.12 | 0.16 | . | . | . | 0.25 | 1.25 |
| Ser | 324 | A | . | . | . | . | T | . | 0.12 | −0.06 | . | . | F | 1.00 | 1.25 |
| Trp | 325 | A | . | . | . | . | T | . | 0.38 | 0.20 | * | * | F | 0.40 | 1.19 |
| Glu | 326 | A | A | . | . | . | . | . | 0.70 | 0.03 | * | . | F | −0.15 | 0.71 |
| Pro | 327 | A | A | . | . | . | . | . | 1.44 | 0.03 | * | . | . | −0.15 | 1.03 |
| Leu | 328 | A | A | . | . | . | . | . | 0.63 | −0.36 | * | . | . | 0.45 | 1.96 |
| Met | 329 | A | A | . | . | . | . | . | 0.59 | −0.59 | * | . | . | 0.60 | 0.93 |
| Arg | 330 | A | A | . | . | . | . | . | 0.07 | −0.16 | * | . | . | 0.30 | 0.60 |
| Lys | 331 | A | A | . | . | . | . | . | −0.53 | 0.10 | * | . | . | −0.30 | 0.60 |
| Leu | 332 | A | A | . | . | . | . | . | −0.32 | 0.03 | * | . | . | −0.30 | 0.60 |
| Gly | 333 | A | A | . | . | . | . | . | 0.49 | −0.59 | * | . | . | 0.60 | 0.51 |
| Leu | 334 | A | A | . | . | . | . | . | 1.09 | −0.19 | * | . | . | 0.30 | 0.41 |
| Met | 335 | A | A | . | . | . | . | . | 0.09 | −0.19 | * | * | . | 0.30 | 0.86 |

TABLE 4-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 336 | A | A | . | . | . | . | . | 0.09 | −0.19 | . | * | F | 0.45 | 0.61 |
| Asn | 337 | A | A | . | . | . | . | . | 0.04 | −0.61 | * | * | F | 0.90 | 1.48 |
| Glu | 338 | A | A | . | . | . | . | . | −0.20 | −0.66 | * | * | F | 0.90 | 1.11 |
| Ile | 339 | A | A | . | . | . | . | . | 0.66 | −0.77 | * | * | F | 0.75 | 0.67 |
| Lys | 340 | A | A | . | . | . | . | . | 0.67 | −0.77 | . | * | F | 0.75 | 0.83 |
| Val | 341 | A | A | . | . | . | . | . | 0.67 | −0.67 | . | * | . | 0.60 | 0.49 |
| Ala | 342 | A | A | . | . | . | . | . | 0.08 | −0.67 | . | . | . | 0.75 | 1.20 |
| Lys | 343 | A | A | . | . | . | . | . | −0.51 | −0.86 | . | * | . | 0.60 | 0.61 |
| Ala | 344 | A | A | . | . | . | . | . | 0.03 | −0.36 | . | * | . | 0.30 | 0.83 |
| Glu | 345 | A | A | . | . | . | . | . | −0.04 | −0.57 | * | . | . | 0.60 | 0.81 |
| Ala | 346 | A | A | . | . | . | . | . | 0.92 | −0.57 | * | . | . | 0.60 | 0.55 |
| Ala | 347 | A | A | . | . | . | . | . | 1.51 | −0.57 | . | * | . | 0.75 | 1.07 |
| Gly | 348 | A | . | . | . | . | . | . | 1.16 | −1.07 | . | * | . | 0.95 | 1.03 |
| His | 349 | A | . | . | . | . | T | . | 0.93 | −0.59 | . | . | . | 1.15 | 1.47 |
| Arg | 350 | A | . | . | . | . | T | . | 0.69 | −0.40 | . | . | F | 1.00 | 1.20 |
| Asp | 351 | A | . | . | . | . | T | . | 0.97 | −0.14 | . | . | F | 1.00 | 1.90 |
| Thr | 352 | A | . | . | . | . | T | . | 0.96 | −0.09 | . | . | F | 1.00 | 2.02 |
| Leu | 353 | A | . | . | B | . | . | . | 0.49 | 0.03 | . | . | . | −0.15 | 1.02 |
| Tyr | 354 | A | . | . | B | . | . | . | −0.37 | 0.71 | . | * | . | −0.60 | 0.50 |
| Thr | 355 | A | . | . | B | . | . | . | −0.43 | 1.40 | . | * | . | −0.60 | 0.24 |
| Met | 356 | A | . | . | B | . | . | . | −0.72 | 0.91 | * | . | . | −0.60 | 0.59 |
| Leu | 357 | A | . | . | B | . | . | . | −1.27 | 1.14 | * | . | . | −0.60 | 0.40 |
| Ile | 358 | A | . | . | B | . | . | . | −0.46 | 1.03 | * | * | . | −0.60 | 0.20 |
| Lys | 359 | A | . | . | B | . | . | . | −0.17 | 0.94 | * | * | . | −0.60 | 0.33 |
| Trp | 360 | A | . | . | B | . | . | . | −0.17 | 0.33 | * | * | . | 0.00 | 0.81 |
| Val | 361 | A | . | . | B | . | . | . | 0.09 | 0.13 | * | * | . | 0.45 | 1.66 |
| Asn | 362 | . | . | . | . | . | T | C | 1.01 | −0.13 | * | . | F | 1.95 | 0.82 |
| Lys | 363 | . | . | . | . | . | T | C | 1.90 | −0.13 | * | * | F | 2.40 | 1.53 |
| Thr | 364 | . | . | . | . | . | T | C | 1.27 | −1.04 | * | . | F | 3.00 | 3.44 |
| Gly | 365 | . | . | . | . | . | T | C | 1.26 | −1.19 | * | . | F | 2.70 | 2.16 |
| Arg | 366 | . | A | . | . | T | . | . | 1.26 | −1.20 | * | . | F | 2.20 | 1.45 |
| Asp | 367 | . | A | . | . | . | . | C | 1.22 | −0.56 | * | . | F | 1.55 | 0.75 |
| Ala | 368 | A | A | . | . | . | . | . | 0.87 | −0.54 | . | . | F | 1.20 | 1.03 |
| Ser | 369 | A | A | . | . | . | . | . | 0.37 | −0.49 | . | . | . | 0.30 | 0.76 |
| Val | 370 | A | A | . | . | . | . | . | −0.10 | 0.20 | * | . | . | −0.30 | 0.37 |
| His | 371 | A | A | . | . | . | . | . | −0.21 | 0.89 | . | * | . | −0.60 | 0.30 |
| Thr | 372 | A | A | . | . | . | . | . | −0.80 | 0.39 | * | * | . | −0.30 | 0.38 |
| Leu | 373 | A | A | . | . | . | . | . | −1.02 | 0.50 | * | * | . | −0.60 | 0.52 |
| Leu | 374 | A | A | . | . | . | . | . | −0.72 | 0.54 | * | . | . | −0.60 | 0.31 |
| Asp | 375 | A | A | . | . | . | . | . | −0.18 | 0.04 | * | . | . | −0.30 | 0.38 |
| Ala | 376 | A | A | . | . | . | . | . | −0.96 | 0.04 | * | . | . | −0.30 | 0.66 |
| Leu | 377 | A | A | . | . | . | . | . | −0.99 | 0.04 | * | . | . | −0.30 | 0.66 |
| Glu | 378 | A | A | . | . | . | . | . | −0.18 | −0.21 | * | . | . | 0.30 | 0.39 |
| Thr | 379 | A | A | . | . | . | . | . | 0.74 | −0.21 | * | * | F | 0.45 | 0.67 |
| Leu | 380 | A | A | . | . | . | . | . | −0.07 | −0.71 | * | . | F | 0.90 | 1.59 |
| Gly | 381 | A | A | . | . | . | . | . | −0.07 | −0.71 | * | . | F | 0.75 | 0.76 |
| Glu | 382 | A | A | . | . | . | . | . | 0.79 | −0.21 | * | . | F | 0.45 | 0.53 |
| Arg | 383 | A | A | . | . | . | . | . | 0.79 | −0.70 | * | . | F | 0.90 | 1.28 |
| Leu | 384 | A | A | . | . | . | . | . | 1.14 | −0.99 | * | * | F | 0.90 | 2.24 |
| Ala | 385 | A | A | . | . | . | . | . | 1.07 | −1.41 | * | * | F | 0.90 | 2.59 |
| Lys | 386 | A | A | . | . | . | . | . | 1.41 | −0.73 | * | . | F | 0.75 | 0.93 |
| Gln | 387 | A | A | . | . | . | . | . | 1.41 | −0.73 | * | * | F | 0.90 | 1.95 |
| Lys | 388 | A | A | . | . | . | . | . | 1.27 | −1.41 | * | * | F | 0.90 | 3.22 |
| Ile | 389 | A | A | . | . | . | . | . | 1.27 | −1.41 | . | * | F | 0.90 | 2.19 |
| Glu | 390 | A | A | . | . | . | . | . | 1.04 | −0.73 | * | * | F | 0.90 | 1.04 |
| Asp | 391 | A | A | . | . | . | . | . | 0.70 | −0.44 | . | * | F | 0.45 | 0.43 |
| His | 392 | A | A | . | . | . | . | . | 0.40 | −0.06 | * | * | . | 0.30 | 0.82 |
| Leu | 393 | A | A | . | . | . | . | . | 0.01 | −0.36 | * | * | . | 0.30 | 0.64 |
| Leu | 394 | A | A | . | . | . | . | . | 0.94 | 0.07 | * | * | F | −0.15 | 0.38 |
| Ser | 395 | A | . | . | . | . | T | . | 0.24 | 0.07 | * | * | F | 0.25 | 0.55 |
| Ser | 396 | A | . | . | . | . | T | . | −0.36 | 0.36 | * | * | F | 0.25 | 0.58 |
| Gly | 397 | . | . | . | . | T | T | . | −0.57 | 0.29 | . | . | F | 0.65 | 0.70 |
| Lys | 398 | A | . | . | . | . | T | . | −0.57 | 0.36 | . | . | F | 0.25 | 0.82 |
| Phe | 399 | A | A | . | . | . | . | . | 0.24 | 0.66 | . | . | . | −0.60 | 0.50 |
| Met | 400 | . | A | B | . | . | . | . | 0.20 | 0.27 | . | * | . | −0.30 | 0.88 |
| Tyr | 401 | . | A | B | . | . | . | . | 0.50 | 0.27 | . | * | . | −0.30 | 0.44 |
| Leu | 402 | A | A | . | . | . | . | . | 0.26 | 0.67 | . | * | . | −0.60 | 0.81 |
| Glu | 403 | A | A | . | . | . | . | . | 0.21 | 0.39 | . | * | . | −0.30 | 0.82 |
| Gly | 404 | A | . | . | . | . | . | . | 0.61 | −0.23 | . | * | F | 0.65 | 0.88 |
| Asn | 405 | A | . | . | . | . | T | . | 0.62 | −0.60 | . | * | F | 1.30 | 1.43 |
| Ala | 406 | A | . | . | . | . | T | . | 0.27 | −0.79 | . | * | F | 1.15 | 0.83 |
| Asp | 407 | A | . | . | . | . | T | . | 0.78 | −0.17 | . | * | F | 0.85 | 0.83 |
| Ser | 408 | A | . | . | . | . | T | . | 0.39 | −0.21 | . | * | F | 0.85 | 0.69 |
| Ala | 409 | A | . | . | . | . | . | . | 0.34 | −0.19 | . | * | . | 0.50 | 0.88 |
| Met | 410 | A | . | . | . | . | . | . | −0.04 | −0.26 | . | . | . | 0.50 | 0.67 |
| Ser | 411 | A | . | . | . | . | . | . | 0.16 | 0.17 | . | . | . | −0.10 | 0.64 |

In another aspect, the invention provides an antibody that binds a peptide or polypeptide comprising, or alternatively, consisting of, one, two, three, four, five or more, epitope-bearing portions of a TR7. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci.* USA 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219: 660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides are therefore useful to raise antibodies, including monoclonal antibodies, that bind to a TR7 polypeptide. See, for instance, Wilson et al., *Cell* 37:767-778 (1984) at 777. Antigenic epitope-bearing peptides and polypeptides preferably contain a sequence of at least seven, more preferably at least nine and most preferably between at least about 15 to about 30 amino acids contained within the amino acid sequence of SEQ ID NO:3.

Antibodies of the invention may bind one or more antigenic TR7 polypeptides or peptides including, but not limited to: a polypeptide comprising, or alternatively consisting of, amino acid residues from about 62 to about 110 of SEQ ID NO:3, about 119 to about 164 of SEQ ID NO:3, about 224 to about 271 of SEQ ID NO:3, about 275 to about 370 of SEQ ID NO:3, about 69 to about 80 of SEQ ID NO:3, about 88 to about 95 of SEQ ID NO:3, about 99 to about 103 of SEQ ID NO:3, about 119 to about 123 of SEQ ID NO:3, about 130 to about 135 of SEQ ID NO:3, about 152 to about 163 of SEQ ID NO:3, about 226 to about 238 of SEQ ID NO:3, about 275 to about 279 of SEQ ID NO:3, about 301 to about 305 of SEQ ID NO:3, and/or about 362 to about 367 of SEQ ID NO:3. In this context "about" includes the particularly recited ranges, larger or smaller by several (5, 4, 3, 2, or 1) nucleotides, at either terminus or at both termini. As indicated above, the inventors have determined that the above polypeptide fragments are antigenic regions of the TR7 receptor protein.

Epitope-bearing TR7 peptides and polypeptides may be produced by any conventional means. R. A. Houghten, "General Method for the Rapid Solid-Phase Synthesis of Large Numbers of Peptides: Specificity of Antigen-Antibody Interaction at the Level of Individual Amino Acids," *Proc. Natl. Acad. Sci.* USA 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, TR7 receptor polypeptides and the epitope-bearing fragments thereof described herein (e.g., corresponding to a portion of the extracellular domain, such as, for example, amino acid residues 52 to 184 of SEQ ID NO:3 can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric TR7 protein or protein fragment alone (Fountoulakis et al., *J. Biochem.* 270:3958-3964 (1995)). TR7 fusion proteins may be used as an immunogen to elicit anti-TR7 antibodies. Thus, antibodies of the invention may bind fusion proteins that comprise all or a portion of a TR4 polypeptide such as TR7.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified TR7 polypeptides or TR7 polypeptide fragments or variants.

For instance, for many proteins, including the extracellular domain of a membrane associated protein or the mature form(s) of a secreted protein, it is known in the art that one or more amino acids may be deleted from the N-terminus or C-terminus without substantial loss of biological function or loss of the ability to be bound by a specific antibody. However, even if deletion of one or more amino acids from the N-terminus or C-terminus of a protein results in modification or loss of one or more biological functions of the protein, other TR7 functional activities may still be retained. For example, in many instances, the ability of the shortened protein to induce and/or bind to antibodies which recognize TR7 (preferably antibodies that bind specifically to TR7) will retained irrespective of the size or location of the deletion. In fact, polypeptides composed of as few as six TR7 amino acid residues may often evoke an immune response. Whether a particular polypeptide lacking N-terminal and/or C-terminal residues of a complete protein retains such immunologic activities can readily be determined by routine methods described herein and otherwise known in the art.

As mentioned above, even if deletion of one or more amino acids from the N-terminus of a protein results in modification or loss of one or more biological functions of the protein, other functional activities (e.g., biological activities, ability to multimerize, ability to bind TR7 ligand) may still be retained. For example, the ability of shortened TR7 polypeptides to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TR7 polypeptide with a large number of deleted N-terminal amino acid residues may retain some biological or immunogenic activities.

Accordingly, the present invention further provides antibodies that bind polypeptides having one or more residues deleted from the amino terminus of the TR7 amino acid sequence shown in SEQ ID NO:3 up to the alanine residue at position number 406 and polynucleotides encoding such polypeptides. In particular, the present invention provides antibodies that bind polypeptides comprising the amino acid sequence of residues $n^5$-411 of SEQ ID NO:3 where $n^5$ is an integer from 2 to 406 corresponding to the position of the amino acid residue in SEQ ID NO:3.

More in particular, the invention provides antibodies that bind polypeptides comprising, or alternatively consisting of, the amino acid sequence of residues: E-2 to S-411; Q-3 to S-411; R-4 to S-411; G-5 to S411; Q-6 to S-411; N-7 to S-411; A-8 to S-411; P-9 to S411; A-1 to S-411; A-11 to S-411; S-12 to S-411; G-13 to S-411; A-14 to S-411; R-15 to S-411; K-16 to S-411; R-17 to S-411; H-18 to S-411; G-19 to S-411; P-20 to S-411; G-21 to S-411; P-22 to S-411; R-23 to S-411; E-24 to S-411; A-25 to S-411; R-26 to S-411; G-27 to S-411; A-28 to S-411; R-29 to S411; P-30 to S-411; G-31 to S-411; P-32 to S-411; R-33 to S411; V-34 to S-411; P-35 to S-411; K-36 to S-411; T-37 to S411; L-38 to S411; V-39 to S-411; L-40 to S-411; V-41 to S-411; V-42 to S-411; A-43 to S-411; A-44 to S-411; V-45 to S-411; L-46 to S-411; L-47 to S-411; L-48 to S-411; V-49 to S-411; S-50 to S-411; A-51 to S-411; E-52 to S-411; S-53 to S411; A-54 to S-411; L-55 to S-411; I-56 to S-411; T-57 to S-411; Q-58 to S-411; Q-59 to S-411; D-60 to S-411; L-61 to S-411; A-62 to S-411; P-63 to S-411; Q-64 to S-411; Q-65 to S-411; R-66 to S-411; A-67 to S411; A-68 to S-411; P-69 to S411; Q-70 to S-411; Q-71 to S-411; K-72 to S-411; R-73 to S411; S-74 to S-411; S-75 to S-411; P-76 to S-411; S-77 to S-411; E-78 to S-411; G-79 to S-411; L-80 to S-411; C-81 to S-411; P-82 to S-411; P-83 to S411; G-84 to S-411; H-85 to S-411; H-86 to S-411; I-87 to S-411; S-88 to S411; E-89 to S-411; D-90 to S411; G-91 to S-411; R-92 to S-411; D-93 to S-411; C-94 to S-411; I-95 to S-411; S-96 to S-411; C-97 to S-411; K-98 to S-411; Y-99 to S-411; G-100 to S411; Q-101 to S-411; D-102 to S-411; Y-103 to S-411; S-104 to S411; T-105 to S-411; H-106 to S-411; W-107 to S-411; N-108 to S-411; D-109 to S-411; L-110 to S-411; L-111 to S-411; F-112 to S-411; C-113 to S-411; L-114 to S-411; R-115 to S-411; C-116 to S-411; T-117 to S-411; R-118 to S-411; C-119 to S-411; D-120 to S-411; S-121 to S411; G-122 to S411; E-123 to S-411; V-124 to S411; E-125 to S411; L-126 to S-411; S-127 to S411; P-128 to S411; C-129 to S-411; T-130 to S-411; T-131 to S-411; T-132 to S-411; R-133 to S-411; N-134 to S-411; T-135 to S-411; V-136 to S-411; C-137 to S-411; Q-138 to S-411; C-139 to S-411; E-140 to S-411; E-141 to S411; G-142 to S411; T-143 to S411; F-144 to S-411; R-145 to S-411; E-146 to S-411; E-147 to S-411; D-148 to S-411; S-149 to S-411; P-150 to S-411; E-151 to S-411; M-152 to S-411; C-153 to S-411; R-154 to S-411; K-155 to S-411; C-156 to S411; R-157 to S-411; T-158 to S-411; G-159 to S411; C-160 to S-411; P-161 to S-411; R-162 to S411; G-163 to S411; M-164 to S-411; V-165 to S411; K-166 to S-411; V-167 to S411; G-168 to S-411; D-169 to S-411; C-170 to S411; T-171 to S411; P-172 to S-411; W-173 to S411; S-174 to S-411; D-175 to S-411; I-176 to S-411; E-177 to S-411; C-178 to S-411; V-179 to S-411; H-180 to S-411; K-181 to S-411; E-182 to S-411; S-183 to S-411; G-184 to S-411; I-185 to S-411; I-186 to S-411; I-187 to S-411; G-188 to S-411; V-189 to S-411; T-190 to S-411; V-191 to S411; A-192 to S-411; A-193 to S-411; V-194 to S-411; V-195 to S-411; L-196 to S-411; I-197 to S-411; V-198 to S-411; A-199 to S-411; V-200 to S-411; F-201 to S-411; V-202 to S411; C-203 to S411; K-204 to S-411; S-205 to S-411; L-206 to S-411; L-207 to S-411; W-208 to S-411; K-209 to S-411; K-210 to S-411; V-211 to S-411; L-212 to S-411; P-213 to S-411; Y-214 to S-411; L-215 to S-411; K-216 to S-411; G-217 to S-411; I-218 to S-411; C-219 to S-411; S-220 to S-411; G-221 to S-411; G-222 to S-411; G-223 to S-411; G-224 to S-411; D-225 to S-411; P-226 to S-411; E-227 to S-411; R-228 to S-411; V-229 to S-411; D-230 to S-411; R-231 to S-411; S-232 to S-411; S-233 to S-411; Q-234 to S-411; R-235 to S-411; P-236 to S411; G-237 to S-411; A-238 to S-411; E-239 to S-411; D-240 to S-411; N-241 to S-411; V-242 to S-411; L-243 to S-411; N-244 to S411; E-245 to S411; I-246 to S-411; V-247 to S-411; S-248 to S-411; I-249 to S-411; L-250 to S-411; Q-251 to S411; P-252 to S-411; T-253 to S-411; Q-254 to S411; V-255 to S-411; P-256 to S-411; E-257 to S-411; Q-258 to S-411; E-259 to S-411; M-260 to S-411; E-261 to S-411; V-262 to S-411; Q-263 to S-411; E-264 to S-411; P-265 to S-411; A-266 to S411; E-267 to S-411; P-268 to S-411; T-269 to S-411; G-270 to S-411; V-271 to S-411; N-272 to S-411; M-273 to S-411; L-274 to S-411; S-275 to S-411; P-276 to S411; G-277 to S-411; E-278 to S411; S-279 to S-411; E-280 to S-411; H-281 to S-411; L-282 to S-411; L-283 to S411; E-284 to S-411; P-285 to S-411; A-286 to S-411; E-287 to S-411; A-288 to S-411; E-289 to S-411; R-290 to S-411; S-291 to S-411; Q-292 to S-411; R-293 to S411; R-294 to S-411; R-295 to S-411; L-296 to S-411; L-297 to S411; V-298 to S-411; P-299 to S-411; A-300 to S-411; N-301 to S411; E-302 to S-411; G-303 to S-411; D-304 to S411; P-305 to S-411; T-306 to S-411; E-307 to S-411; T-308 to S-411; L-309 to S-411; R-310 to S-411; Q-311 to S-411; C-312 to S-411; F-313 to S411; D-314 to S-411; D-315 to S-411; F-316 to S411; A-317 to S-411; D-318 to S-411; L-319 to S-411; V-320 to S411; P-321 to S411; F-322 to S411; D-323 to S-411; S-324 to S-411; W-325 to S-411; E-326 to S-411; P-327 to S-411; L-328 to S-411; M-329 to S-411; R-330 to S-411; K-331 to S-411; L-332 to S411; G-333 to S-411; L-334 to S411; M-335 to S-411; D-336 to S-411; N-337 to S-411; E-338 to S411; I-339 to S-411; K-340 to S-411; V-341 to S411; A-342 to S-411; K-343 to S-411; A-344 to S-411; E-345 to S411; A-346 to S411; A-347 to S-411; G-348 to S411; H-349 to S411; R-350 to S-411; D-351 to S-411; T-352 to S411; L-353 to S-411; Y-354 to S-411; T-355 to S-411; M-356 to S-411; L-357 to S-411; I-358 to S-411; K-359 to S-411; W-360 to S-411; V-361 to S-411; N-362 to S-411; K-363 to S-411; T-364 to S-411; G-365 to S-411; R-366 to S-411; D-367 to S-411; A-368 to S-411; S-369 to S-411; V-370 to S-411; H-371 to S411; T-372 to S-411; L-373 to S-411; L-374 to S-411; D-375 to S-411; A-376 to S-411; L-377 to S-411; E-378 to S-411; T-379 to S-411; L-380 to S-411; G-381 to S-411; E-382 to S-411; R-383 to S-411; L-384 to S-411; A-385 to S-411; K-386 to S-411; Q-387 to S-411; K-388 to S411; I-389 to S-411; E-390 to S-411; D-391 to S-411; H-392 to S-411; L-393 to S-411; L-394 to S-411; S-395 to S-411; S-396 to S-411; G-397 to S-411; K-398 to S-411; F-399 to S-411; M-400 to S-411; Y-401 to S-411; L-402 to S-411; E-403 to S-411; G-404 to S-411; N-405 to S-411; and/or A-406 to S-411 of the TR7 sequence shown in SEQ ID NO:3.

In another embodiment, N-terminal deletions of the TR7 polypeptide can be described by the general formula $n^6$ to 184 where $n^6$ is a number from 1 to 179 corresponding to the amino acid sequence identified in SEQ ID NO:3. In specific embodiments, antibodies of the invention bind N terminal deletions of the TR7 comprising, or alternatively consisting of, the amino acid sequence of residues: E-2 to G-184; Q-3 to G-184; R-4 to G-184; G-5 to G-184; Q-6 to G-184; N-7 to G-184; A-8 to G-184; P-9 to G-184; A-10 to G-184; A-11 to G-184; S-12 to G-184; G-13 to G-184; A-14 to G-184; R-15 to G-184; K-16 to G-184; R-17 to G-184; H-18 to G-184; G-19 to G-184; P-20 to G-184; G-21 to G-184; P-22 to G-184; R-23 to G-184; E-24 to G-184; A-25 to G-184; R-26 to G-184; G-27 to G-184; A-28 to G-184; R-29 to G-184; P-30 to G-184; G-31 to G-184; P-32 to G-184; R-33 to G-184; V-34 to G-184; P-35 to G-184; K-36 to G-184; T-37 to G-184; L-38 to G-184; V-39 to G-184; L-40 to G-184; V-41 to G-184; V-42 to G-184; A43 to G-184; A-44 to G-184; V-45 to G-184; L-46 to G-184; L-47 to G-184; L-48 to G-184; V-49 to G-184; S-50 to G-184; A-51 to G-184; E-52 to G-184; S-53 to G-184; A-54 to G-184; L-55 to G-184; I-56 to G-184; T-57 to G-184; Q-58 to G-184; Q-59 to G-184; D-60 to G-184; L-61 to G-184; A-62 to G-184; P-63 to G-184; Q-64 to G-184; Q-65 to G-184; R-66 to G-184; A-67 to G-184; A-68 to G-184; P-69 to G-184; Q-70 to G-184; Q-71 to G-184; K-72 to G-184; R-73 to G-184; S-74 to G-184; S-75 to G-184; P-76 to G-184; S-77 to G-184; E-78 to G-184; G-79 to G-184; L-80 to G-184; C-81 to G-184; P-82 to G-184; P-83 to G-184; G-84 to G-184; H-85 to G-184; H-86 to G-184; I-87 to G-184; S-88 to G-184; E-89 to G-184; D-90 to G-184; G-91 to G-184; R-92 to G-184; D-93 to G-184; C-94 to G-184; I-95 to G-184; S-96 to G-184; C-97 to G-184; K-98 to G-184; Y-99 to G-184; G-100 to G-184; Q-101 to G-184; D-102 to G-184; Y-103 to G-184; S-104 to G-184; T-105 to G-184; H-106 to G-184; W-107 to G-184; N-108 to G-184; D-109 to G-184; L-110 to G-184; L-111 to G-184; F-112 to G-184; C-113 to G-184; L-114 to G-184; R-115 to G-184; C-116 to G-184; T-117 to G-184; R-118 to G-184; C-119 to G-184; D-120 to G-184; S-121 to G-184; G-122 to G-184; E-123 to G-184; V-124 to G-184; E-125 to G-184; L-126 to G-184; S-127 to G-184; P-128 to G-184; C-129 to G-184; T-130 to G-184; T-131 to G-184; T-132 to G-184; R-133 to G-184; N-134 to G-184; T-135 to G-184; V-136 to G-184; C-137 to G-184; Q-138 to G-184; C-139 to G-184; E-140 to G-184 ; E-141 to G-184; G-142 to G-184; T-143 to G-184; F-144 to G-184; R-145 to G-184; E-146 to G-184; E-147 to G-184; D-148 to G-184; S-149 to G-184; P-150 to G-184; E-151 to G-184; M-152 to G-184; C-153 to G-184; R-154 to G-184; K-155 to G-184; C-156 to G-184; R-157 to G-184; T-158 to G-184; G-159 to G-184; C-160 to G-184; P-161 to G-184 ; R-162 to G-184; G-163 to G-184; M-164 to G-184; V-165 to G-184; K-166 to G-184; V-167 to G-184; G-168 to G-184; D-169 to G-184; C-170 to G-184; T-171 to G-184; P-172 to G-184; W-173 to G-184; S-174 to G-184; D-175 to G-184; I-176 to G-184; E-177 to G-184; C-178 to G-184; and/or V-179 to G-184; of the TR7 extracellular domain sequence shown in SEQ ID NO:3.

Also as mentioned above, even if deletion of one or more amino acids from the C-terminus of a protein results in modification of loss of one or more biological functions of the protein, other functional activities (e.g., biological activities, ability to multimerize, ability to bind TR7 ligand (e.g., TRAIL)) may still be retained. For example, the ability of the shortened TR7 polypeptide to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TR7 polypeptide with a large number of deleted C-terminal amino acid residues may retain some biological or immunogenic activities. In fact, peptides composed of as few as six TR7 amino acid residues may often evoke an immune response.

Accordingly, the present invention further provides antibodies that bind polypeptides having one or more residues deleted from the carboxy terminus of the amino acid sequence of the TR7 polypeptide shown in SEQ ID NO:3 up to the glutamic acid residue at position number 52. In particular, the present invention provides antibodies that bind polypeptides comprising the amino acid sequence of residues: 52-$m^5$ of SEQ ID NO:3, where $m^5$ is an integer from 57 to 410 corresponding to the position of the amino acid residue in SEQ ID NO:3.

More in particular, the invention provides antibodies that bind polypeptides comprising, or alternatively consisting of, the amino acid sequence of residues: E-52 to M-410; E-52 to A-409; E-52 to S-408; E-52 to D-407; E-52 to A-406; E-52 to N-405; E-52 to G-404; E-52 to E-403; E-52 to L-402; E-52 to Y-401; E-52 to M-400; E-52 to F-399; E-52 to K-398; E-52 to G-397; E-52 to S-396; E-52 to S-395; E-52 to L-394; E-52 to L-393; E-52 to H-392; E-52 to D-391; E-52 to E-390; E-52 to I-389; E-52 to K-388; E-52 to Q-387; E-52 to K-386; E-52 to A-385; E-52 to L-384; E-52 to R-383; E-52 to E-382; E-52 to S-381; E-52 to L-380; E-52 to T-379; E-52 to E-378; E-52 to L-377; E-52 to A-376; E-52 to D-375; E-52 to L-374; E-52 to L-373; E-52 to T-372; E-52 to H-371; E-52 to V-370; E-52 to S-369; E-52 to A-368; E-52 to D-367; E-52 to R-366; E-52 to G-365; E-52 to T-364; E-52 to K-363; E-52 to N-362; E-52 to V-361; E-52 to W-360; E-52 to K-359; E-52 to I-358; E-52 to L-357; E-52 to M-356; E-52 to T-355; E-52 to Y-354; E-52 to L-353; E-52 to T-352; E-52 to D-351; E-52 to R-350; E-52 to H-349; E-52 to G-348; E-52 to A-347; E-52 to A-346; E-52 to E-345; E-52 to A-344; E-52 to K-343; E-52 to A-342; E-52 to V-341; E-52 to K-340; E-52 to I-339; E-52 to E-338; E-52 to N-337; E-52 to D-336; E-52 to M-335; E-52 to L-334; E-52 to G-333; E-52 to L-332; E-52 to K-331; E-52 to R-330; E-52 to M-329; E-52 to L-328; E-52 to P-327; E-52 to E-326; E-52 to W-325; E-52 to S-324; E-52 to D-323; E-52 to F-322; E-52 to P-321; E-52 to V-320; E-52 to L-319; E-52 to D-318; E-52 to A-317; E-52 to F-316; E-52 to D-315; E-52 to D-314; E-52 to F-313; E-52 to C-312; E-52 to Q-311; E-52 to R-310; E-52 to L-309; E-52 to T-308; E-52 to E-307; E-52 to T-306; E-52 to P-305; E-52 to D-304; E-52 to G-303; E-52 to E-302; E-52 to N-301; E-52 to A-300; E-52 to P-299; E-52 to V-298; E-52 to L-297; E-52 to L-296; E-52 to R-295; E-52 to R-294; E-52 to R-293; E-52 to Q-292; E-52 to S-291; E-52 to R-290; E-52 to E-289; E-52 to A-288; E-52 to E-287; E-52 to A-286; E-52 to P-285; E-52 to E-284; E-52 to L-283; E-52 to L-282; E-52 to H-281; E-52 to E-280; E-52 to S-279; E-52 to E-278; E-52 to G-277; E-52 to P-276; E-52 to S-275; E-52 to L-274; E-52 to M-273; E-52 to N-272; E-52 to V-271; E-52 to G-270; E-52 to T-269; E-52 to P-268; E-52 to E-267; E-52 to A-266; E-52 to P-265; E-52 to E-264; E-52 to Q-263; E-52 to V-262; E-52 to E-261; E-52 to M-260; E-52 to E-259; E-52 to Q-258; E-52 to E-257; E-52 to P-256; E-52 to V-255; E-52 to Q-254; E-52 to T-253; E-52 to P-252; E-52 to Q-251; E-52 to L-250; E-52 to I-249; E-52 to S-248; E-52 to V-247; E-52 to I-246; E-52 to E-245; E-52 to N-244; E-52 to L-243; E-52 to V-242; E-52 to N-241; E-52 to D-240; E-52 to E-239; E-52 to A-238; E-52 to G-237; E-52 to P-236; E-52 to R-235; E-52 to Q-234; E-52 to S-233; E-52 to S-232; E-52 to R-231; E-52 to D-230; E-52 to V-229; E-52 to R-228; E-52 to E-227; E-52 to P-226; E-52 to D-225; E-52 to G-224; E-52 to G-223; E-52 to G-222; E-52 to G-221; E-52 to S-220;

E-52 to C-219; E-52 to I-218; E-52 to G-217; E-52 to K-216; E-52 to L-215; E-52 to Y-214; E-52 to P-213; E-52 to L-212; E-52 to V-211; E-52 to K-210; E-52 to K-209; E-52 to W-208; E-52 to L-207; E-52 to L-206; E-52 to S-205; E-52 to K-204; E-52 to C-203; E-52 to V-202; E-52 to F-201; E-52 to V-200; E-52 to A-199; E-52 to V-198; E-52 to I-197; E-52 to L-196; E-52 to V-195; E-52 to V-194; E-52 to A-193; E-52 to A-192; E-52 to V-191; E-52 to T-190; E-52 to V-189; E-52 to G-188; E-52 to I-187; E-52 to I-186; E-52 to I-185; E-52 to G-184; E-52 to S-183; E-52 to E-182; E-52 to K-181; E-52 to H-180; E-52 to V-179; E-52 to C-178; E-52 to E-177; E-52 to I-176; E-52 to D-175; E-52 to S-174; E-52 to W-173; E-52 to P-172; E-52 to T-171; E-52 to C-170; E-52 to D-169; E-52 to G-168; E-52 to V-167; E-52 to K-166; E-52 to V-165; E-52 to M-164; E-52 to G-163; E-52 to R-162; E-52 to P-161; E-52 to C-160; E-52 to G-159; E-52 to T-158; E-52 to R-157; E-52 to C-156; E-52 to K-155; E-52 to R-154; E-52 to C-153; E-52 to M-152; E-52 to E-151; E-52 to P-150; E-52 to S-149; E-52 to D-148; E-52 to E-147; E-52 to E-146; E-52 to R-145; E-52 to F-144; E-52 to T-143; E-52 to G-142; E-52 to E-141; E-52 to E-140; E-52 to C-139; E-52 to Q-138; E-52 to C-137; E-52 to V-136; E-52 to T-135; E-52 to N-134; E-52 to R-133; E-52 to T-132; E-52 to T-131; E-52 to T-130; E-52 to C-129; E-52 to P-128; E-52 to S-127; E-52 to L-126; E-52 to E-125; E-52 to V-124; E-52 to E-123; E-52 to G-122; E-52 to S-121; E-52 to D-120; E-52 to C-119; E-52 to R-118; E-52 to T-117; E-52 to C-116; E-52 to R-115; E-52 to L-114; E-52 to C-113; E-52 to F-112; E-52 to L-11; E 52 to L-110; E-52 to D-109; E-52 to N-108; E-52 to W-107; E-52 to H-106; E-52 to T-105; E-52 to S-104; E-52 to Y-103; E-52 to D-102; E-52 to Q-101; E-52 to G-100; E-52 to Y-99; E-52 to K-98; E-52 to C-97; E-52 to S-96; E-52 to I-95; E-52 to C-94; E-52 to D-93; E-52 to R-92; E-52 to G-91; E-52 to D-90; E-52 to E-89; E-52 to S-88; E-52 to I-87; E-52 to H-86; E-52 to H-85; E-52 to G-84; E-52 to P-83; E-52 to P-82; E-52 to C-81; E-52 to L-80; E-52 to G-79; E-52 to E-78; E-52 to S-77; E-52 to P-76; E-52 to S-75; E-52 to S-74; E-52 to R-73; E-52 to K-72; E-52 to Q-71; E-52 to Q-70; E-52 to P-69; E-52 to A-68; E-52 to A-67; E-52 to R-66; E-52 to Q-65; E-52 to Q-64; E-52 to P-63; E-52 to A-62; E-52 to L-61; E-52 to D-60; E-52 to Q-59; E-52 to Q-58; and/or E-52 to T-57; of the TR7 sequence shown in SEQ ID NO:3.

In another embodiment, antibodies of the invention bind C-terminal deletions of the TR7 polypeptide that can be described by the general formula 52-$m^6$ where $m^6$ is a number from 57 to 183 corresponding to the amino acid sequence identified in SEQ ID NO:3. In specific embodiments, antibodies of the invention bind C terminal deletions of the TR7 polypeptide comprising, or alternatively, consisting of, amino acid residues: E-52 to S-183; E-52 to E-182; E-52 to K-181; E-52 to H-180; E-52 to V-179; E-52 to C-178; E-52 to E-177; E-52 to I-176; E-52 to D-175; E-52 to S-174; E-52 to W-173; E-52 to P-172; E-52 to T-171; E-52 to C-170; E-52 to D-169; E-52 to G-168; E-52 to V-167; E-52 to K-166; E-52 to V-165; E-52 to M-164; E-52 to G-163; E-52 to R-162; E-52 to P-161; E-52 to C-160; E-52 to G-159; E-52 to T-158; E-52 to R-157; E-52 to C-156; E-52 to K-155; E-52 to R-154; E-52 to C-153; E-52 to M-152; E-52 to E-151; E-52 to P-150; E-52 to S-149; E-52 to D-148; E-52 to E-147; E-52 to E-146; E-52 to R-145; E-52 to F-144; E-52 to T-143; E-52 to G-142; E-52 to E-141; E-52 to E-140; E-52 to C-139; E-52 to Q-138; E-52 to C-137; E-52 to V-136; E-52 to T-135; E-52 to N-134; E-52 to R-133; E-52 to T-132; E-52 to T-131; E-52 to T-130; E-52 to C-129; E-52 to P-128; E-52 to S-127; E-52 to L-126; E-52 to E-125; E-52 to V-124; E-52 to E-123; E-52 to G-122; E-52 to S-121; E-52 to D-120; E-52 to C-19; E-52 to R-118; E-52 to T-117; E-52 to C-116; E-52 to R-115; E-52 to L-114; E-52 to C-113; E-52 to F-112; E-52 to L-111; E-52 to L-110; E-52 to D-109; E-52 to N-108; E-52 to W-107; E-52 to H-106; E-52 to T-105; E-52 to S-104; E-52 to Y-103; E-52 to D-102; E-52 to Q-101; E-52 to G-100; E-52 to Y-99; E-52 to K-98; E-52 to C-97; E-52 to S-96; E-52 to I-95; E-52 to C-94; E-52 to D-93; E-52 to R-92; E-52 to G-91; E-52 to D-90; E-52 to E-89; E-52 to S-88; E-52 to I-87; E-52 to H-86; E-52 to H-85; E-52 to G-84; E-52 to P-83; E-52 to P-82; E-52 to C-81; E-52 to L-80; E-52 to G-79; E-52 to E-78; E-52 to S-77; E-52 to P-76; E-52 to S-75; E-52 to S-74; E-52 to R-73; E-52 to K-72; E-52 to Q-71; E-52 to Q-70; E-52 to P-69; E-52 to A-68; E-52 to A-67; E-52 to R-66; E-52 to Q-65; E-52 to Q-64; E-52 to P-63; E-52 to A-62; E-52 to L-61; E-52 to D-60; E-52 to Q-59; E-52 to Q-58; and/or E-52 to T-57; of the TR7 extracellular domain sequence shown in SEQ ID NO:3.

The invention also provides antibodies that bind polypeptides having one or more amino acids deleted from both the amino and the carboxyl termini of a TR7 polypeptide, which may be described generally as having residues $n^5$-$m^5$ and/or $n^6$-$m^6$ of SEQ ID NO:3, where $n^5$, $n^6$, $m^5$, and $m^6$ are integers as described above.

Also included are antibodies that bind a polypeptide consisting of a portion of the complete TR7 amino acid sequence encoded by the cDNA clone contained in ATCC Deposit No. 97920, where this portion excludes from 1 to about 78 amino acids from the amino terminus of the complete amino acid sequence encoded by the cDNA clone contained in ATCC Deposit No. 97920, or from 1 to about 233 amino acids from the carboxy terminus, or any combination of the above amino terminal and carboxy terminal deletions, of the complete amino acid sequence encoded by the cDNA clone contained in ATCC Deposit No. 97920.

Preferably, antibodies of the present invention bind the N- and C-terminal deletion mutants comprising only a portion of the extracellular domain; i.e., within residues 52-184 of SEQ ID NO:3, since any portion therein is expected to be soluble.

It will be recognized in the art that some amino acid sequence of TR7 can be varied without significant effect of the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes antibodies that bind variations of the TR7 protein which show substantial TR7 protein activity or which include regions of TR7, such as the protein portions discussed below. Such mutants include deletions, insertions, inversions, repeats, and type substitutions. Guidance concerning which amino acid changes are likely to be phenotypically silent can be found in Bowie, J. U. et al., Science 247:1306-1310 (1990).

Thus, antibodies of the present invention may bind a fragment, derivative, or analog of the polypeptide of SEQ ID NO:3, or that encoded by the cDNA in ATCC deposit 97920. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acids and with neutral or negatively charged amino acids. The latter results in proteins with reduced positive charge to improve the characteristics of the TR7 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the antibodies of the present invention may bind a TR7 receptor that contains one or more amino acid substitutions, deletions or additions, either from natural mutations or human manipulation.

As indicated, changes are preferably of a minor nature, such as conservative amino acid substitutions that do not significantly affect the folding or activity of the protein (see Table 3 above).

In specific embodiments, the number of substitutions, additions or deletions in the amino acid sequence of SEQ ID NO:3 and/or any of the polypeptide fragments described herein (e.g., the extracellular domain) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

In specific embodiments, the antibodies of the invention bind TR7 polypeptides or fragments or variants thereof (especially a fragment comprising or alternatively consisting of, the extracellular soluble domain of TR7), that contains any one or more of the following conservative mutations in TR7: M1 replaced with A, G, I, L, S, T, or V; E2 replaced with D; Q3 replaced with N; R4 replaced with H, or K; G5 replaced with A, I, L, S, T, M, or V; Q6 replaced with N; N7 replaced with Q; A8 replaced with G, I, L, S, T, M, or V; A10 replaced with G, I, L, S, T, M, or V; A11 replaced with G, I, L, S, T, M, or V; S12 replaced with A, G, I, L, T, M, or V; G13 replaced with A, I, L, S, T, M, or V; A14 replaced with G, I, L, S, T, M, or V; R 5 replaced with H, or K; K16 replaced with H, or R; R17 replaced with H, or K; H18 replaced with K, or R; G19 replaced with A, I, L, S, T, M, or V; G21 replaced with A, I, L, S, T, M, or V; R23 replaced with H, or K; E24 replaced with D; A25 replaced with G, I, L, S, T, M, or V; R26 replaced with H, or K; G27 replaced with A, I, L, S, T, M, or V; A28 replaced with G, I, L, S, T, M, or V; R29 replaced with H, or K; G31 replaced with A, I, L, S, T, M, or V; R33 replaced with H, or K; V34 replaced with A, G, I, L, S, T, or M; K36 replaced with H, or R; T37 replaced with A, G, I, L, S, M, or V; L38 replaced with A, G, I, S, T, M, or V; V39 replaced with A, G, I, L, S, T, or M; L40 replaced with A, G, I, S, T, M, or V; V41 replaced with A, G, I, L, S, T, or M; V42 replaced with A, G, I, L, S, T, or M; A43 replaced with G, I, L, S, T, M, or V; A44 replaced with G, I, L, S, T, M, or V; V45 replaced with A, G, I, L, S, T, or M; L46 replaced with A, G, I, S, T, M, or V; L47 replaced with A, G, I, S, T, M, or V; L48 replaced with A, G, I, S, T, M, or V; V49 replaced with A, G, I, L, S, T, or M; S50 replaced with A, G, I, L, T, M, or V; A51 replaced with G, I, L, S, T, M, or V; E52 replaced with D; S53 replaced with A, G, I, L, T, M, or V; A54 replaced with G, I, L, S, T, M, or V; L55 replaced with A, G, I, S, T, M, or V; I56 replaced with A, G, L, S, T, M, or V; T57 replaced with A, G, I, L, S, M, or V; Q58 replaced with N; Q59 replaced with N; D60 replaced with E; L61 replaced with A, G, I, S, T, M, or V; A62 replaced with G, I, L, S, T, M, or V; Q64 replaced with N; Q65 replaced with N; R66 replaced with H, or K; A67 replaced with G, I, L, S, T, M, or V; A68 replaced with G, I, L, S, T, M, or V; Q70 replaced with N; Q71 replaced with N; K72 replaced with H, or R; R73 replaced with H, or K; S74 replaced with A, G, I, L, T, M, or V; S75 replaced with A, G, I, L, T, M, or V; S77 replaced with A, G, I, L, T, M, or V; E78 replaced with D; G79 replaced with A, I, L, S, T, M, or V; L80 replaced with A, G, I, S, T, M, or V; G84 replaced with A, I, L, S, T, M, or V; H85 replaced with K, or R; H86 replaced with K, or R; I87 replaced with A, G, L, S, T, M, or V; S88 replaced with A, G, I, L, T, M, or V; E89 replaced with D; D90 replaced with E; G91 replaced with A, I, L, S, T, M, or V; R92 replaced with H, or K; D93 replaced with E; I95 replaced with A, G, L, S, T, M, or V; S96 replaced with A, G, I, L, T, M, or V; K98 replaced with H, or R; Y99 replaced with F, or W; G100 replaced with A, I, L, S, T, M, or V; Q101 replaced with N; D102 replaced with E; Y103 replaced with F, or W; S104 replaced with A, G, I, L, T, M, or V; T105 replaced with A, G, I, L, S, M, or V; H106 replaced with K, or R; W107 replaced with F, or Y; N108 replaced with Q; D109 replaced with E; L110 replaced with A, G, I, S, T, M, or V; L111 replaced with A, G, I, S, T, M, or V; F112 replaced with W, or Y; L114 replaced with A, G, I, S, T, M, or V; R115 replaced with H, or K; T117 replaced with A, G, I, L, S, M, or V; R118 replaced with H, or K; D120 replaced with E; S121 replaced with A, G, I, L, T, M, or V; G122 replaced with A, I, L, S, T, M, or V; E123 replaced with D; V124 replaced with A, G, I, L, S, T, or M; E125 replaced with D; L126 replaced with A, G, I, S, T, M, or V; S127 replaced with A, G, I, L, T, M, or V; T130 replaced with A, G, I, L, S, M, or V; T131 replaced with A, G, I, L, S, M, or V; T132 replaced with A, G, I, L, S, M, or V; R133 replaced with H, or K; N134 replaced with Q; T135 replaced with A, G, I, L, S, M, or V; V136 replaced with A, G, I, L, S, T, or M; Q138 replaced with N; E140 replaced with D; E141 replaced with D; G142 replaced with A, I, L, S, T, M, or V; T143 replaced with A, G, I, L, S, M, or V; F144 replaced with W, or Y; R145 replaced with H, or K; E146 replaced with D; E147 replaced with D; D148 replaced with E; S149 replaced with A, G, I, L, T, M, or V; E151 replaced with D; M152 replaced with A, G, I, L, S, T, or V; R154 replaced with H, or K; K155 replaced with H, or R; R157 replaced with H, or K; T158 replaced with A, G, I, L, S, M, or V; G159 replaced with A, I, L, S, T, M, or V; R162 replaced with H, or K; G163 replaced with A, I, L, S, T, M, or V; M164 replaced with A, G, I, L, S, T, or V; V165 replaced with A, G, I, L, S, T, or M; K166 replaced with H, or R; V167 replaced with A, G, I, L, S, T, or M; G168 replaced with A, I, L, S, T, M, or V; D169 replaced with E; T171 replaced with A, G, I, L, S, M, or V; W173 replaced with F, or Y; S174 replaced with A, G, I, L, T, M, or V; D175 replaced with E; I176 replaced with A, G, L, S, T, M, or V; E177 replaced with D; V179 replaced with A, G, I, L, S, T, or M; H180 replaced with K, or R; K181 replaced with H, or R; E182 replaced with D; S183 replaced with A, G, I, L, T, M, or V; G184 replaced with A, I, L, S, T, M, or V; I185 replaced with A, G, L, S, T, M, or V; I186 replaced with A, G, L, S, T, M, or V; I187 replaced with A, G, L, S, T, M, or V; G188 replaced with A, I, L, S, T, M, or V; V189 replaced with A, G, I, L, S, T, or M; T190 replaced with A, G, I, L, S, M, or V; V191 replaced with A, G, I, L, S, T, or M; A192 replaced with G, I, L, S, T, M, or V; A193 replaced with G, I, L, S, T, M, or V; V194 replaced with A, G, I, L, S, T, or M; V195 replaced with A, G, I, L, S, T, or M; L196 replaced with A, G, I, S, T, M, or V; I197 replaced with A, G, L, S, T, M, or V; V198 replaced with A, G, I, L, S, T, or M; A199 replaced with G, I, L, S, T, M, or V; V200 replaced with A, G, I, L, S, T, or M; F201 replaced with W, or Y; V202 replaced with A, G, I, L, S, T, or M; K204 replaced with H, or R; S205 replaced with A, G, I, L, T, M, or V; L206 replaced with A, G, I, S, T, M, or V; L207 replaced with A, G, I, S, T, M, or V; W208 replaced with F, or Y; K209 replaced with H, or R; K210 replaced with H, or R; V211 replaced with A, G, I, L, S, T, or M; L212 replaced with A, G, I, S, T, M, or V; Y214 replaced with F, or W; L215 replaced with A, G, I, S, T, M, or V; K216 replaced with H, or R; G217 replaced with A, I, L, S, T, M, or V; I218 replaced with A, G, L, S, T, M, or V; S220 replaced with A, G, I, L, T, M, or V; G221 replaced with A, I, L, S, T, M, or V; G222 replaced with A, I, L, S, T, M, or V; G223 replaced with A, I, L, S, T, M, or V; G224 replaced with A, I, L, S, T, M, or V; D225 replaced with E; E227 replaced with D; R228 replaced with H, or K; V229 replaced with A, G, I, L, S, T, or M; D230 replaced with E; R231 replaced with H, or K; S232 replaced with A, G, I, L, T, M, or V; S233 replaced with A, G, I, L, T, M, or V; Q234 replaced with N; R235 replaced with H, or K; G237 replaced with A, I, L, S, T, M, or V; A238 replaced with G, I, L, S, T, M, or V; E239 replaced with D; D240 replaced with E; N241 replaced with Q; V242 replaced with A, G, I, L, S, T, or M; L243 replaced with A, G, I, S, T, M, or V; N244 replaced with Q; E245 replaced with D; I246 replaced with A, G, L, S, T, M, or V; V247 replaced with A, G, I, L, S, T, or M; S248 replaced with A, G, I, L, T, M, or V; I249 replaced with A, G, L, S, T, M, or V; L250 replaced with A, G, I, S, T, M, or V; Q251 replaced with N; T253 replaced with A, G, I, L, S, M, or V; Q254 replaced with N; V255 replaced with A, G, I, L, S, T, or M; E257 replaced with D; Q258 replaced with N; E259 replaced with D; M260 replaced with A, G, I, L, S, T, or V; E261 replaced with D; V262 replaced with A, G, I, L, S, T, or M; Q263 replaced with N; E264 replaced with D; A266 replaced with G, I, L, S, T, M, or V; E267 replaced with D; T269 replaced with A, G, I, L, S, M, or V; G270 replaced with A, I, L, S, T, M, or V; V271 replaced with A, G, I, L, S, T, or M; N272 replaced with Q; M273 replaced with A, G, I, L, S, T, or V; L274 replaced with A, G, I, S, T, M, or V; S275 replaced with A, G, I, L, T, M, or V; G277 replaced with A, I, L, S, T, M, or V; E278 replaced with D; S279 replaced with A, G, I, L, T, M, or V; E280 replaced with D; H281 replaced with K, or R; L282 replaced with A, G, I, S, T, M, or V; L283 replaced with A, G, I, S, T, M, or V; E284 replaced with D; A286 replaced with G, I, L, S, T, M, or V; E287 replaced with D; A288 replaced with G, I, L, S, T, M, or V; E289 replaced with D; R290 replaced with H, or K; S291 replaced with A, G, I, L, T, M, or V; Q292 replaced with N; R293 replaced with H, or K; R294 replaced with H, or K; R295 replaced with H, or K; L296 replaced with A, G, I, S, T, M, or V; L297 replaced with A, G, I, S, T, M, or V; V298 replaced with A, G, I, L, S, T, or M; A300 replaced with G, I, L, S, T, M, or V; N301 replaced with Q; E302 replaced with D; G303 replaced with A, I, L, S, T, M, or V; D304 replaced with E; T306 replaced with A, G, I, L, S, M, or V; E307 replaced with D; T308 replaced with A, G, I, L, S, M, or V; L309 replaced with A, G, I, S, T, M, or V; R310 replaced with H, or K; Q311 replaced with N; F313 replaced with W, or Y; D314 replaced with E; D315 replaced with E; F316 replaced with W, or Y; A317 replaced with G, I, L, S, T, M, or V; D318 replaced with E; L319 replaced with A, G, I, S, T, M, or V; V320 replaced with A, G, I, L, S, T, or M; F322 replaced with W, or Y; D323 replaced with E; S324 replaced with A, G, I, L, T, M, or V; W325 replaced with F, or Y; E326 replaced with D; L328 replaced with A, G, I, S, T, M, or V; M329 replaced with A, G, I, L, S, T, or V; R330 replaced with H, or K; K331 replaced with H, or R; L332 replaced with A, G, I, S, T, M, or V; G333 replaced with A, I, L, S, T, M, or V; L334 replaced with A, G, I, S, T, M, or V; M335 replaced with A, G, I, L, S, T, or V; D336 replaced with E; N337 replaced with Q; E338 replaced with D; I339 replaced with A, G, L, S, T, M, or V; K340 replaced with H, or R; V341 replaced with A, G, I, L, S, T, or M; A342 replaced with G, I, L, S, T, M, or V; K343 replaced with H, or R; A344 replaced with G, I, L, S, T, M, or V; E345 replaced with D; A346 replaced with G, I, L, S, T, M, or V; A347 replaced with G, I, L, S, T, M, or V; G348 replaced with A, I, L, S, T, M, or V; H349 replaced with K, or R; R350 replaced with H, or K; D351 replaced with E; T352 replaced with A, G, I, L, S, M, or V; L353 replaced with A, G, I, S, T, M, or V; Y354 replaced with F, or W; T355 replaced with A, G, I, L, S, M, or V; M356 replaced with A, G, I, L, S, T, or V; L357 replaced with A, G, I, S, T, M, or V; I358 replaced with A, G, L, S, T, M, or V; K359 replaced with H, or R; W360 replaced with F, or Y; V361 replaced with A, G, I, L, S, T, or M; N362 replaced with Q; K363 replaced with H, or R; T364 replaced with A, G, I, L, S, M, or V; G365 replaced with A, I, L, S, T, M, or V; R366 replaced with H, or K; D367 replaced with E; A368 replaced with G, I, L, S, T, M, or V; S369 replaced with A, G, I, L, T, M, or V; V370 replaced with A, G, I, L, S, T, or M; H371 replaced with K, or R; T372 replaced with A, G, I, L, S, M, or V; L373 replaced with A, G, I, S, T, M, or V; L374 replaced with A, G, I, S, T, M, or V; D375 replaced with E; A376 replaced with G, I, L, S, T, M, or V; L377 replaced with A, G, I, S, T, M, or V; E378 replaced with D; T379 replaced with A, G, I, L, S, M, or V; L380 replaced with A, G, I, S, T, M, or V; G381 replaced with A, I, L, S, T, M, or V; E382 replaced with D; R383 replaced with H, or K; L384 replaced with A, G, I, S, T, M, or V; A385 replaced with G, I, L, S, T, M, or V; K386 replaced with H, or R; Q387 replaced with N; K388 replaced with H, or R; I389 replaced with A, G, L, S, T, M, or V; E390 replaced with D; D391 replaced with E; H392 replaced with K, or R; L393 replaced with A, G, I, S, T, M, or V; L394 replaced with A, G, I, S, T, M, or V; S395 replaced with A, G, I, L, T, M, or V; S396 replaced with A, G, I, L, T, M, or V; G397 replaced with A, I, L, S, T, M, or V; K398 replaced with H, or R; F399 replaced with W, or Y; M400 replaced with A, G, I, L, S, T, or V; Y401 replaced with F, or W; L402 replaced with A, G, I, S, T, M, or V; E403 replaced with D; G404 replaced with A, I, L, S, T, M, or V; N$_4$O$_5$ replaced with Q; A406 replaced with G, I, L, S, T, M, or V; D407 replaced with E; S408 replaced with A, G, I, L, T, M, or V; A409 replaced with G, I, L, S, T, M, or V; M410 replaced with A, G, I, L, S, T, or V; and/or S411 replaced with A, G, I, L, T, M, or V of SEQ ID NO:3.

In specific embodiments, the antibodies of the invention bind TR7 polypeptides or fragments or variants thereof (especially a fragment comprising or alternatively consisting of, the extracellular soluble domain of TR7), that contains any one or more of the following non-conservative mutations in TR7: M1 replaced with D, E, H, K, R, N, Q, F, W, Y, P, or C; E2 replaced with H, K, R, A, G, I, L, S, T, M, V, N, Q, F, W, Y, P, or C; Q3 replaced with D, E, H, K, R, A, G, I, L, S, T, M, V, F, W, Y, P, or C; R4 replaced with D, E, A, G, I, L, S, T, M, V, N, Q, F, W, Y, P, or C; G5 replaced with D, E, H, K, R, N, Q, F, W, Y, P, or C; Q6 replaced with D, E, H, K, R, A, G, I, L, S, T, M, V, F, W, Y, P, or C; N7 replaced with D, E, H, K, R, A, G, I, L, S, T, M, V, F, W, Y, P, or C; A8 replaced with D, E, H, K, R, N, Q, F, W, Y, P, or C; P9 replaced with D, E, H, K, R, A, G, I, L, S, T, M, V, N, Q, F, W, Y, or C; A10 replaced with D, E, H, K, R, N, Q, F, W, Y, P, or C; A11 replaced with D, E, H, K, R, N, Q, F, W, Y, P, or C; S12 replaced with D, E, H, K, R, N, Q, F, W, Y, P, or C; G13 replaced with D, E, H, K, R, N, Q, F, W, Y, P, or C; A14 replaced with D, E, H, K, R, N, Q, F, W, Y, P, or C; R15 replaced with D, E, A, G, I, L, S, T, M, V, N, Q, F, W, Y, P, or C; K16 replaced with D, E, A, G, I, L, S, T, M, V, N, Q, F, W, Y, P, or C; R17 replaced with D, E, A, G, I, L, S, T, M, V, N, Q, F, W, Y, P, or C; H18 replaced with D, E, A, G, I, L, S, T, M, V, N, Q, F, W, Y, P, or C; G19 replaced with D, E, H, K, R, N, Q, F, W, Y, P, or C; P20 replaced with D, E, H, K, R, A, G, I, L, S, T, M, V, N, Q, F, W, Y, or C; G21 replaced with D, E, H, K, R, N, Q, F, W, Y, P, or C; P22 replaced with D, E, H, K, R, A, G, I, L, S, T, M, V, N, Q, F, W, Y, or C; R23 replaced with D, E, A, G, I, L, S, T, M, V, N, Q, F, W, Y, P, or C; E24 replaced with H, K, R, A, G, I, L, S, T, M, V, N, Q, F, W, Y, P, or C; A25 replaced with D, E, H, K, R, N, Q, F, W, Y, P, or C; R26 replaced with D, E, A, G, I, L, S, T, M, V, N, Q, F, W, Y, P, or C; G27 replaced with D, E, H, K, R, N, Q, F, W, Y, P, or C; A28 replaced with D, E, H, K, R, N, Q, F, W, Y, P, or C; R29 replaced with D, E, A, G, I, L, S, T, M, V, N, Q, F, W, Y, P, or C; P30 replaced with D, E, H, K, R, A, G, I, L, S, T, M, V, N, Q, F, W, Y, or C; G31 replaced with D, E, H, K, R, N, Q, F, W, Y, P, or C; P32 replaced with D, E, H, K, R, A, G, I, L, S, T, M, V, N, Q, F, W, Y, or C; R33 replaced with D, E, A, G, I, L, S, T, M, V, N, Q, F, W, Y, P, or C; V34 replaced with D, E, H, K, R, N, Q, F, W, Y, P, or C; P35 replaced with D, E, H, K, R, A, G, I, L, S, T, M, V, N, Q, F, W, Y, or C; K36 replaced with D, E, A, G, I, L, S, T, M, V, N, Q, F, W, Y, P, or C; T37 replaced with D, E, H, K, R, N, Q, F, W, Y, P, or C; L38 replaced with D, E, H, K, R, N, Q, F, W, Y, P, or C; V39 replaced with D, E, H, K, R, N, Q, F, W, Y, P, or C; L40 replaced with D, E, H, K, R, N, Q, F, W, Y, P, or C; V41 replaced with D, E, H, K, R, N, Q, F, W, Y, P, or C; V42 replaced with D, E, H, K, R, N, Q, F, W, Y, P, or C; A43 replaced with D, E, H, K, R, N, Q, F, W, Y, P, or C; A44 replaced with D, E, H, K, R, N, Q, F, W, Y, P, or C; V45 replaced with D, E, H, K, R, N, Q, F, W, Y, P, or C; L46 replaced with D, E, H, K, R, N, Q, F, W, Y, P, or C; L47 replaced with D, E, H, K, R, N, Q, F, W, Y, P, or C; L48 replaced with D, E, H, K, R, N, Q, F, W, Y, P, or C; V49 replaced with D, E, H, K, R, N, Q, F, W, Y, P, or C; S50 replaced with D, E, H, K, R, N, Q, F, W, Y, P, or C; A51 replaced with D, E, H, K, R, N, Q, F, W, Y, P, or C; E52 replaced with H, K, R, A, G, I, L, S, T, M, V, N, Q, F, W, Y, P, or C; S53 replaced with D, E, H, K, R, N, Q, F, W, Y, P, or C; A54 replaced with D, E, H, K, R, N, Q, F, W, Y, P, or C; L55 replaced with D, E, H, K, R, N, Q, F, W, Y, P, or C; I56 replaced with D, E, H, K, R, N, Q, F, W, Y, P, or C; T57 replaced with D, E, H, K, R, N, Q, F, W, Y, P, or C; Q58 replaced with D, E, H, K, R, A, G, I, L, S, T, M, V, F, W, Y, P, or C; Q59 replaced with D, E, H, K, R A, G, I, L, S, T, M, V, F, W, Y, P, or C; D60 replaced with H, K, R, A, G, I, L, S, T, M, V, N, Q, F, W, Y, P, or C; L61 replaced with D, E, H, K, R, N, Q, F, W, Y, P, or C; A62 replaced with D, E, H, K, R, N, Q, F, W, Y, P, or C; P63 replaced with D, E, H, K, R, A, G, I, L, S, T, M, V, N, Q, F, W, Y, or C; Q64 replaced with D, E, H, K, R, A, G, I, L, S, T, M, V, F, W, Y, P, or C; Q65 replaced with D, E, H, K, R, A, G, I, L, S, T, M, V, F, W, Y, P, or C; R66 replaced with D, E, A, G, I, L, S, T, M, V, N, Q, F, W, Y, P, or C; A67 replaced with D, E, H, K, R, N, Q, F, W, Y, P, or C; A68 replaced with D, E, H, K, R, N, Q, F, W, Y, P, or C; P69 replaced with D, E, H, K, R, A, G, I, L, S, T, M, V, N, Q, F, W, Y, or C; Q70 replaced with D, E, H, K, R, A, G, I, L, S, T, M, V, F, W, Y, P, or C; Q71 replaced with D, E, H, K, R, A, G, I, L, S, T, M, V, F, W, Y, P, or C; K72replaced with D, E, A, G, I, L, S, T, M, V, N, Q, F, W, Y, P, or C; R73 replaced with D, E, A, G, I, L, S, T, M, V, N, Q, F, W, Y, P, or C; S74 replaced with D, E, H, K, R, N, Q, F, W, Y, P, or C; S75 replaced with D, E, H, K, R, N, Q, F, W, Y, P, or C; P76 replaced with D, E, H, K, R, A, G, I, L, S, T, M, V, N, Q, F, W, Y, or C; S77 replaced with D, E, H, K, R, N, Q, F, W, Y, P, or C; E78 replaced with H, K, R, A, G, I, L, S, T, M, V, N, Q, F, W, Y, P, or C; G79 replaced with D, E, H, K, R, N, Q, F, W, Y, P, or C; L80 replaced with D, E, H, K, R, N, Q, F, W, Y, P, or C; C81 replaced with D, E, H, K, R, A, G, I, L, S, T, M, V, N, Q, F, W, Y, or P; P82 replaced with D, E, H, K, R, A, G, I, L, S, T, M, V, N, Q, F, W, Y, or C; P83 replaced with D, E, H, K, R, A, G, I, L, S, T, M, V, N, Q, F, W, Y, or C; G84 replaced with D, E, H, K, R, N, Q, F, W, Y, P, or C; H85 replaced with D, E, A, G, I, L, S, T, M, V, N, Q, F, W, Y, P, or C; H86 replaced with D, E, A, G, I, L, S, T, M, V, N, Q, F, W, Y, P, or C; I87 replaced with D, E, H, K, R, N, Q, F, W, Y, P, or C; S88 replaced with D, E, H, K, R, N, Q, F, W, Y, P, or C; E89 replaced with H, K, R, A, G, I, L, S, T, M, V, N, Q, F, W, Y, P, or C; D90 replaced with H, K, R, A, G, I, L, S, T, M, V, N, Q, F, W, Y, P, or C; G91 replaced with D, E, H, K, R, N, Q, F, W, Y, P, or C; R92 replaced with D, E, A, G, I, L, S, T, M, V, N, Q, F, W, Y, P, or C; D93 replaced with H, K, R, A, G, I, L, S, T, M, V, N, Q, F, W, Y, P, or C; C94 replaced with D, E, H, K, R, A, G, I, L, S, T, M, V, N, Q, F, W, Y, or P; I95 replaced with D, E, H, K, R, N, Q, F, W, Y, P, or C; S96 replaced with D, E, H, K, R, N, Q, F, W, Y, P, or C; C97 replaced with D, E, H, K, R, A, G, I, L, S, T, M, V, N, Q, F, W, Y, or P; K98 replaced with D, E, A, G, I, L, S, T, M, V, N, Q, F, W, Y, P, or C; Y99 replaced with D, E, H, K, R, N, Q, A, G, I, L, S, T, M, V, P, or C; G100 replaced with D, E, H, K, R, N, Q, F, W, Y, P, or C; Q101 replaced with D, E, H, K, R, A, G, I, L, S, T, M, V, F, W, Y, P, or C; D102 replaced with H, K, R, A, G, I, L, S, T, M, V, N, Q, F, W, Y, P, or C; Y103 replaced with D, E, H, K, R, N, Q, A, G, I, L, S, T, M, V, P, or C; S104 replaced with D, E, H, K, R, N, Q, F, W, Y, P, or C; T105 replaced with D, E, H, K, R, N, Q, F, W, Y, P, or C; H106 replaced with D, E, A, G, I, L, S, T, M, V, N, Q, F, W, Y, P, or C; W107 replaced with D, E, H, K, R, N, Q, A, G, I, L, S, T, M, V, P, or C; N108 replaced with D, E, H, K, R, A, G, I, L, S, T, M, V, F, W, Y, P, or C; D109 replaced with H, K, R, A, G, I, L, S, T, M, V, N, Q, F, W, Y, P, or C; L110 replaced with D, E, H, K, R, N, Q, F, W, Y, P, or C; L I replaced with D, E, H, K, R, N, Q, F, W, Y, P, or C; F112 replaced with D, E, H, K, R, N, Q, A, G, I, L, S, T, M, V, P, or C; C113 replaced with D, E, H, K, R, A, G, I, L, S, T, M, V, N, Q, F, W, Y, or P; L114 replaced with D, E, H, K, R, N, Q, F, W, Y, P, or C; R115 replaced with D, E, A, G, I, L, S, T, M, V, N, Q, F, W, Y, P, or C; C116 replaced with D, E, H, K, R, A, G, I, L, S, T, M, V, N, Q, F, W, Y, or P; T117 replaced with D, E, H, K, R, N, Q, F, W, Y, P, or C; R118 replaced with D, E, A, G, I, L, S, T, M, V, N, Q, F, W, Y, P, or C; C119 replaced with D, E, H, K, R, A, G, I, L, S, T, M, V, N, Q, F, W, Y, or P; D120 replaced with H, K, R, A, G, I, L, S, T, M, V, N, Q, F, W, Y, P, or C;

S121 replaced with D, E, H, K, R, N, Q, F, W, Y, P, or C; G122 replaced with D, E, H, K, R, N, Q, F, W, Y, P, or C; E123 replaced with H, K, R, A, G, I, L, S, T, M, V, N, Q, F, W, Y, P, or C; V124 replaced with D, E, H, K, R, N, Q, F, W, Y, P, or C; E125 replaced with H, K, R, A, G, I, L, S, T, M, V, N, Q, F, W, Y, P, or C; L126 replaced with D, E, H, K, R, N, Q, F, W, Y, P, or C; S127 replaced with D, E, H, K, R, N, Q, F, W, Y, P, or C; P128 replaced with D, E, H, K, R, A, G, I, L, S, T, M, V, N, Q, F, W, Y, or C; C129 replaced with D, E, H, K, R, A, G, I, L, S, T, M, V, N, Q, F, W, Y, or P; T130 replaced with D, E, H, K, R, N, Q, F, W, Y, P, or C; T131 replaced with D, E, H, K, R, N, Q, F, W, Y, P, or C; T132 replaced with D, E, H, K, R, N, Q, F, W, Y, P, or C; R133 replaced with D, E, A, G, I, L, S, T, M, V, N, Q, F, W, Y, P, or C; N134 replaced with D, E, H, K, R, A, G, I, L, S, T, M, V, F, W, Y, P, or C; T135 replaced with D, E, H, K, R, N, Q, F, W, Y, P, or C; V136 replaced with D, E, H, K, R, N, Q, F, W, Y, P, or C; C137 replaced with D, E, H, K, R, A, G, I, L, S, T, M, V, N, Q, F, W, Y, or P; Q138 replaced with D, E, H, K, R, A, G, I, L, S, T, M, V, F, W, Y, P, or C; C139 replaced with D, E, H, K, R, A, G, I, L, S, T, M, V, N, Q, F, W, Y, or P; E140 replaced with H, K, R, A, G, I, L, S, T, M, V, N, Q, F, W, Y, P, or C; E141 replaced with H, K, R, A, G, I, L, S, T, M, V, N, Q, F, W, Y, P, or C; G142 replaced with D, E, H, K, R, N, Q, F, W, Y, P, or C; T143 replaced with D, E, H, K, R, N, Q, F, W, Y, P, or C; F144 replaced with D, E, H, K, R, N, Q, A, G, I, L, S, T, M, V, P, or C; R145 replaced with D, E, A, G, I, L, S, T, M, V, N, Q, F, W, Y, P, or C; E146 replaced with H, K, R, A, G, I, L, S, T, M, V, N, Q, F, W, Y, P, or C; E147 replaced with H, K, R, A, G, I, L, S, T, M, V, N, Q, F, W, Y, P, or C; D148 replaced with H, K, R, A, G, I, L, S, T, M, V, N, Q, F, W, Y, P, or C; S149 replaced with D, E, H, K, R, N, Q, F, W, Y, P, or C; P150 replaced with D, E, H, K, R, A, G, I, L, S, T, M, V, N, Q, F, W, Y, or C; E151 replaced with H, K, R, A, G, I, L, S, T, M, V, N, Q, F, W, Y, P, or C; M152 replaced with D, E, H, K, R, N, Q, F, W, Y, P, or C; C153 replaced with D, E, H, K, R, A, G, I, L, S, T, M, V, N, Q, F, W, Y, or P; R154 replaced with D, E, A, G, I, L, S, T, M, V, N, Q, F, W, Y, P, or C; K155 replaced with D, E, A, G, I, L, S, T, M, V, N, Q, F, W, Y, P, or C; C156 replaced with D, E, H, K, R, A, G, I, L, S, T, M, V, N, Q, F, W, Y, or P; R157 replaced with D, E, A, G, I, L, S, T, M, V, N, Q, F, W, Y, P, or C; T158 replaced with D, E, H, K, R, N, Q, F, W, Y, P, or C; G159 replaced with D, E, H, K, R, N, Q, F, W, Y, P, or C; C160 replaced with D, E, H, K, R, A, G, I, L, S, T, M, V, N, Q, F, W, Y, or P; P161 replaced with D, E, H, K, R, A, G, I, L, S, T, M, V, N, Q, F, W, Y, or C; R162 replaced with D, E, A, G, I, L, S, T, M, V, N, Q, F, W, Y, P, or C; G163 replaced with D, E, H, K, R, N, Q, F, W, Y, P, or C; M164 replaced with D, E, H, K, R, N, Q, F, W, Y, P, or C; V165 replaced with D, E, H, K, R, N, Q, F, W, Y, P, or C; K166 replaced with D, E, A, G, I, L, S, T, M, V, N, Q, F, W, Y, P, or C; V167 replaced with D, E, H, K, R, N, Q, F, W, Y, P, or C; G168 replaced with D, E, H, K, R, N, Q, F, W, Y, P, or C; D169 replaced with H, K, R, A, G, I, L, S, T, M, V, N, Q, F, W, Y, P, or C; C170replaced with D, E, H, K, R, A, G, I, L, S, T, M, V, N, Q, F, W, Y, or P; T171 replaced with D, E, H, K, R, N, Q, F, W, Y, P, or C; P172 replaced with D, E, H, K, R, A, G, I, L, S, T, M, V, N, Q, F, W, Y, or C; W173 replaced with D, E, H, K, R, N, Q, A, G, I, L, S, T, M, V, P, or C; S174 replaced with D, E, H, K, R, N, Q, F, W, Y, P, or C; D175 replaced with H, K, R, A, G, I, L, S, T, M, V, N, Q, F, W, Y, P, or C; I176 replaced with D, E, H, K, R, N, Q, F, W, Y, P, or C; E177 replaced with H, K, R, A, G, I, L, S, T, M, V, N, Q, F, W, Y, P, or C; C178 replaced with D, E, H, K, R, A, G, I, L, S, T, M, V, N, Q, F, W, Y, or P; V179 replaced with D, E, H, K, R, N, Q, F, W, Y, P, or C; H180 replaced with D, E, A, G, I, L, S, T, M, V, N, Q, F, W, Y, P, or C; K181 replaced with D, E, A, G, I, L, S, T, M, V, N, Q, F, W, Y, P, or C; E182 replaced with H, K, R, A, G, I, L, S, T, M, V, N, Q, F, W, Y, P, or C; S183 replaced with D, E, H, K, R, N, Q, F, W, Y, P, or C; G184 replaced with D, E, H, K, R, N, Q, F, W, Y, P, or C; I185 replaced with D, E, H, K, R, N, Q, F, W, Y, P, or C; I186 replaced with D, E, H, K, R, N, Q, F, W, Y, P, or C; I187 replaced with D, E, H, K, R, N, Q, F, W, Y, P, or C; G188 replaced with D, E, H, K, R, N, Q, F, W, Y, P, or C; V189 replaced with D, E, H, K, R, N, Q, F, W, Y, P, or C; T190 replaced with D, E, H, K, R, N, Q, F, W, Y, P, or C; V191 replaced with D, E, H, K, R, N, Q, F, W, Y, P, or C; A192 replaced with D, E, H, K, R, N, Q, F, W, Y, P, or C; A193 replaced with D, E, H, K, R, N, Q, F, W, Y, P, or C; V194 replaced with D, E, H, K, R, N, Q, F, W, Y, P, or C; V195 replaced with D, E, H, K, R, N, Q, F, W, Y, P, or C; L196 replaced with D, E, H, K, R, N, Q, F, W, Y, P, or C; I197 replaced with D, E, H, K, R, N, Q, F, W, Y, P, or C; V198 replaced with D, E, H, K, R, N, Q, F, W, Y, P, or C; A199 replaced with D, E, H, K, R, N, Q, F, W, Y, P, or C; V200 replaced with D, E, H, K, R, N, Q, F, W, Y, P, or C; F201 replaced with D, E, H, K, R, N, Q, A, G, I, L, S, T, M, V, P, or C; V202 replaced with D, E, H, K, R, N, Q, F, W, Y, P, or C; C203 replaced with D, E, H, K, R, A, G, I, L, S, T, M, V, N, Q, F, W, Y, or P; K204 replaced with D, E, A, G, I, L, S, T, M, V, N, Q, F, W, Y, P, or C; S205 replaced with D, E, H, K, R, N, Q, F, W, Y, P, or C; L206 replaced with D, E, H, K, R, N, Q, F, W, Y, P, or C; L207 replaced with D, E, H, K, R, N, Q, F, W, Y, P, or C; W208 replaced with D, E, H, K, R, N, Q, A, G, I, L, S, T, M, V, P, or C; K209 replaced with D, E, A, G, I, L, S, T, M, V, N, Q, F, W, Y, P, or C; K210 replaced with D, E, A, G, I, L, S, T, M, V, N, Q, F, W, Y, P, or C; V211 replaced with D, E, H, K, R, N, Q, F, W, Y, P, or C; L212 replaced with D, E, H, K, R, N, Q, F, W, Y, P, or C; P213 replaced with D, E, H, K, R, A, G, I, L, S, T, M, V, N, Q, F, W, Y, or C; Y214 replaced with D, E, H, K, R, N, Q, A, G, I, L, S, T, M, V, P, or C; L215 replaced with D, E, H, K, R, N, Q, F, W, Y, P, or C; K216 replaced with D, E, A, G, I, L, S, T, M, V, N, Q, F, W, Y, P, or C; G217 replaced with D, E, H, K, R, N, Q, F, W, Y, P, or C; I218 replaced with D, E, H, K, R, N, Q, F, W, Y, P, or C; C219 replaced with D, E, H, K, R, A, G, I, L, S, T, M, V, N, Q, F, W, Y, or P; S220 replaced with D, E, H, K, R, N, Q, F, W, Y, P, or C; G221 replaced with D, E, H, K, R, N, Q, F, W, Y, P, or C; G222 replaced with D, E, H, K, R, N, Q, F, W, Y, P, or C; G223 replaced with D, E, H, K, R, N, Q, F, W, Y, P, or C; G224 replaced with D, E, H, K, R, N, Q, F, W, Y, P, or C; D225 replaced with H, K, R, A, G, I, L, S, T, M, V, N, Q, F, W, Y, P, or C; P226 replaced with D, E, H, K, R, A, G, I, L, S, T, M, V, N, Q, F, W, Y, or C; E227 replaced with H, K, R, A, G, I, L, S, T, M, V, N, Q, F, W, Y, P, or C; R228 replaced with D, E, A, G, I, L, S, T, M, V, N, Q, F, W, Y, P, or C; V229 replaced with D, E, H, K, R, N, Q, F, W, Y, P, or C; D230 replaced with H, K, R, A, G, I, L, S, T, M, V, N, Q, F, W, Y, P, or C; R231 replaced with D, E, A, G, I, L, S, T, M, V, N, Q, F, W, Y, P, or C; S232 replaced with D, E, H, K, R, N, Q, F, W, Y, P, or C; S233 replaced with D, E, H, K, R, N, Q, F, W, Y, P, or C; Q234 replaced with D, E, H, K, R, A, G, I, L, S, T, M, V, F, W, Y, P, or C; R235 replaced with D, E, A, G, I, L, S, T, M, V, N, Q, F, W, Y, P, or C; P236 replaced with D, E, H, K, R, A, G, I, L, S, T, M, V, N, Q, F, W, Y, or C; G237 replaced with D, E, H, K, R, N, Q, F, W, Y, P, or C; A238 replaced with D, E, H, K, R, N, Q, F, W, Y, P, or C; E239 replaced with H, K, R, A, G, I, L, S, T, M, V, N, Q, F, W, Y, P, or C; D240 replaced with H, K, R, A, G, I, L, S, T, M, V, N, Q, F, W, Y, P, or C; N241 replaced with D, E, H, K, R, A, G, I, L, S, T, M, V, F, W, Y, P, or C; V242 replaced with D, E, H, K, R, N, Q, F, W, Y, P, or C; L243 replaced with D, E, H, K, R, N, Q, F, W, Y, P, or C; N244 replaced with D, E, H, K, R, A, G, I, L, S, T, M, V, F, W, Y, P, or C; E245 replaced with H, K, R, A, G, I, L, S, T, M, V, N, Q, F, W, Y, P, or C; I246 replaced with D, E, H, K, R, N, Q, F, W, Y, P, or C; V247 replaced with D, E, H, K, R, N, Q, F, W, Y, P, or C; S248 replaced with D, E, H, K, R, N, Q, F, W, Y, P, or C; I249 replaced with D, E, H, K, R, N, Q, F, W, Y, P, or C; L250 replaced with D, E, H, K, R, N, Q, F, W, Y, P, or C; Q251 replaced with D, E, H, K, R, A, G, I, L, S, T, M, V, F, W, Y, P, or C; P252 replaced with D, E, H, K, R, A, G, I, L, S, T, M, V, N, Q, F, W, Y, or C; T253 replaced with D, E, H, K, R, N, Q, F, W, Y, P, or C; Q254 replaced with D, E, H, K, R, A, G, I, L, S, T, M, V, F, W, Y, P, or C; V255 replaced with D, E, H, K, R, N, Q, F, W, Y, P, or C; P256 replaced with D, E, H, K, R, A, G, I, L, S, T, M, V, N, Q, F, W, Y, or C; E257 replaced with H, K, R, A, G, I, L, S, T, M, V, N, Q, F, W, Y, P, or C; Q258 replaced with D, E, H, K, R, A, G, I, L, S, T, M, V, F, W, Y, P, or C; E259 replaced with H, K, R, A, G, I, L, S, T, M, V, N, Q, F, W, Y, P, or C; M260 replaced with D, E, H, K, R, N, Q, F, W, Y, P, or C; E261 replaced with H, K, R, A, G, I, L, S, T, M, V, N, Q, F, W, Y, P, or C; V262 replaced with D, E, H, K, R, N, Q, F, W, Y, P, or C; Q263 replaced with D, E, H, K, R, A, G, I, L, S, T, M, V, F, W, Y, P, or C; E264 replaced with H, K, R, A, G, I, L, S, T, M, V, N, Q, F, W, Y, P, or C; P265 replaced with D, E, H, K, R, A, G, I, L, S, T, M, V, N, Q, F, W, Y, or C; A266 replaced with D, E, H, K, R, N, Q, F, W, Y, P, or C; E267 replaced with H, K, R, A, G, I, L, S, T, M, V, N, Q, F, W, Y, P, or C; P268 replaced with D, E, H, K, R, A, G, I, L, S, T, M, V, N, Q, F, W, Y, or C; T269 replaced with D, E, H, K, R, N, Q, F, W, Y, P, or C; G270 replaced with D, E, H, K, R, N, Q, F, W, Y, P, or C; V271 replaced with D, E, H, K, R, N, Q, F, W, Y, P, or C; N272 replaced with D, E, H, K, R, A, G, I, L, S, T, M, V, F, W, Y, P, or C; M273 replaced with D, E, H, K, R, N, Q, F, W, Y, P, or C; L274 replaced with D, E, H, K, R, N, Q, F, W, Y, P, or C; S275 replaced with D, E, H, K, R, N, Q, F, W, Y, P, or C; P276 replaced with D, E, H, K, R, A, G, I, L, S, T, M, V, N, Q, F, W, Y, or C; G277 replaced with D, E, H, K, R, N, Q, F, W, Y, P, or C; E278 replaced with H, K, R, A, G, I, L, S, T, M, V, N, Q, F, W, Y, P, or C; S279 replaced with D, E, H, K, R, N, Q, F, W, Y, P, or C; E280 replaced with H, K, R, A, G, I, L, S, T, M, V, N, Q, F, W, Y, P, or C; H281 replaced with D, E, A, G, I, L, S, T, M, V, N, Q, F, W, Y, P, or C; L282 replaced with D, E, H, K, R, N, Q, F, W, Y, P, or C; L283 replaced with D, E, H, K, R, N, Q, F, W, Y, P, or C; E284 replaced with H, K, R, A, G, I, L, S, T, M, V, N, Q, F, W, Y, P, or C; P285 replaced with D, E, H, K, R, A, G, I, L, S, T, M, V, N, Q, F, W, Y, or C; A286 replaced with D, E, H, K, R, N, Q, F, W, Y, P, or C; E287 replaced with H, K, R, A, G, I, L, S, T, M, V, N, Q, F, W, Y, P, or C; A288 replaced with D, E, H, K, R, N, Q, F, W, Y, P, or C; E289 replaced with H, K, R, A, G, I, L, S, T, M, V, N, Q, F, W, Y, P, or C; R290 replaced with D, E, A, G, I, L, S, T, M, V, N, Q, F, W, Y, P, or C; S291 replaced with D, E, H, K, R, N, Q, F, W, Y, P, or C; Q292 replaced with D, E, H, K, R, A, G, I, L, S, T, M, V, F, W, Y, P, or C; R293 replaced with D, E, A, G, I, L, S, T, M, V, N, Q, F, W, Y, P, or C; R294 replaced with D, E, A, G, I, L, S, T, M, V, N, Q, F, W, Y, P, or C; R295 replaced with D, E, A, G, I, L, S, T, M, V, N, Q, F, W, Y, P, or C; L296 replaced with D, E, H, K, R, N, Q, F, W, Y, P, or C; L297 replaced with D, E, H, K, R, N, Q, F, W, Y, P, or C; V298 replaced with D, E, H, K, R, N, Q, F, W, Y, P, or C; P299 replaced with D, E, H, K, R, A, G, I, L, S, T, M, V, N, Q, F, W, Y, or C; A300 replaced with D, E, H, K, R, N, Q, F, W, Y, P, or C; N301 replaced with D, E, H, K, R, A, G, I, L, S, T, M, V, F, W, Y, P, or C; E302 replaced with H, K, R, A, G, I, L, S, T, M, V, N, Q, F, W, Y, P, or C; G303 replaced with D, E, H, K, R, N, Q, F, W, Y, P, or C; D304 replaced with H, K, R, A, G, I, L, S, T, M, V, N, Q, F, W, Y, P, or C; P305 replaced with D, E, H, K, R, A, G, I, L, S, T, M, V, N, Q, F, W, Y, or C; T306 replaced with D, E, H, K, R, N, Q, F, W, Y, P, or C; E307 replaced with H, K, R, A, G, I, L, S, T, M, V, N, Q, F, W, Y, P, or C; T308 replaced with D, E, H, K, R, N, Q, F, W, Y, P, or C; L309 replaced with D, E, H, K, R, N, Q, F, W, Y, P, or C; R310 replaced with D, E, A, G, I, L, S, T, M, V, N, Q, F, W, Y, P, or C; Q311 replaced with D, E, H, K, R, A, G, I, L, S, T, M, V, F, W, Y, P, or C; C312 replaced with D, E, H, K, R, A, G, I, L, S, T, M, V, N, Q, F, W, Y, or P; F313 replaced with D, E, H, K, R, N, Q, A, G, I, L, S, T, M, V, P, or C; D314 replaced with H, K, R, A, G, I, L, S, T, M, V, N, Q, F, W, Y, P, or C; D315 replaced with H, K, R, A, G, I, L, S, T, M, V, N, Q, F, W, Y, P, or C; F316 replaced with D, E, H, K, R, N, Q, A, G, I, L, S, T, M, V, P, or C; A317 replaced with D, E, H, K, R, N, Q, F, W, Y, P, or C; D318 replaced with H, K, R, A, G, I, L, S, T, M, V, N, Q, F, W, Y, P, or C; L319 replaced with D, E, H, K, R, N, Q, F, W, Y, P, or C; V320 replaced with D, E, H, K, R, N, Q, F, W, Y, P, or C; P321 replaced with D, E, H, K, R, A, G, I, L, S, T, M, V, N, Q, F, W, Y, or C; F322 replaced with D, E, H, K, R, N, Q, A, G, I, L, S, T, M, V, P, or C; D323 replaced with H, K, R, A, G, I, L, S, T, M, V, N, Q, F, W, Y, P, or C; S324 replaced with D, E, H, K, R, N, Q, F, W, Y, P, or C; W325 replaced with D, E, H, K, R, N, Q, A, G, I, L, S, T, M, V, P, or C; E326 replaced with H, K, R, A, G, I, L, S, T, M, V, N, Q, F, W, Y, P, or C; P327 replaced with D, E, H, K, R, A, G, I, L, S, T, M, V, N, Q, F, W, Y, or C; L328 replaced with D, E, H, K, R, N, Q, F, W, Y, P, or C; M329 replaced with D, E, H, K, R, N, Q, F, W, Y, P, or C; R330 replaced with D, E, A, G, I, L, S, T, M, V, N, Q, F, W, Y, P, or C; K331 replaced with D, E, A, G, I, L, S, T, M, V, N, Q, F, W, Y, P, or C; L332 replaced with D, E, H, K, R, N, Q, F, W, Y, P, or C; G333 replaced with D, E, H, K, R, N, Q, F, W, Y, P, or C; L334 replaced with D, E, H, K, R, N, Q, F, W, Y, P, or C; M335 replaced with D, E, H, K, R, N, Q, F, W, Y, P, or C; D336 replaced with H, K, R, A, G, I, L, S, T, M, V, N, Q, F, W, Y, P, or C; N337 replaced with D, E, H, K, R, A, G, I, L, S, T, M, V, F, W, Y, P, or C; E338 replaced with H, K, R, A, G, I, L, S, T, M, V, N, Q, F, W, Y, P, or C; I339 replaced with D, E, H, K, R, N, Q, F, W, Y, P, or C; K340 replaced with D, E, A, G, I, L, S, T, M, V, N, Q, F, W, Y, P, or C; V341 replaced with D, E, H, K, R, N, Q, F, W, Y, P, or C; A342 replaced with D, E, H, K, R, N, Q, F, W, Y, P, or C; K343 replaced with D, E, A, G, I, L, S, T, M, V, N, Q, F, W, Y, P, or C; A344 replaced with D, E, H, K, R, N, Q, F, W, Y, P, or C; E345 replaced with H, K, R, A, G, I, L, S, T, M, V, N, Q, F, W, Y, P, or C; A346 replaced with D, E, H, K, R, N, Q, F, W, Y, P, or C; A347 replaced with D, E, H, K, R, N, Q, F, W, Y, P, or C; G348 replaced with D, E, H, K, R, N, Q, F, W, Y, P, or C; H349 replaced with D, E, A, G, I, L, S, T, M, V, N, Q, F, W, Y, P, or C; R350 replaced with D, E, A, G, I, L, S, T, M, V, N, Q, F, W, Y, P, or C; D351 replaced with H, K, R, A, G, I, L, S, T, M, V, N, Q, F, W, Y, P, or C; T352 replaced with D, E, H, K, R, N, Q, F, W, Y, P, or C; L353 replaced with D, E, H, K, R, N, Q, F, W, Y, P, or C; Y354 replaced with D, E, H, K, R, N, Q, A, G, I, L, S, T, M, V, P, or C; T355 replaced with D, E, H, K, R, N, Q, F, W, Y, P, or C; M356 replaced with D, E, H, K, R, N, Q, F, W, Y, P, or C; L357 replaced with D, E, H, K, R, N, Q, F, W, Y, P, or C; I358 replaced with D, E, H, K, R, N, Q, F, W, Y, P, or C; K359 replaced with D, E, A, G, I, L, S, T, M, V, N, Q, F, W, Y, P, or C; W360 replaced with D, E, H, K, R, N, Q, A, G, I, L, S, T, M, V, P, or C; V361 replaced with D, E, H, K, R, N, Q, F, W, Y, P, or C; N362 replaced with D, E, H, K, R, A, G, I, L, S, T, M, V, F, W, Y, P, or C; K363 replaced with D, E, A, G, I, L, S, T, M, V, N, Q, F, W, Y, P, or C; T364 replaced with D, E, H, K, R, N, Q, F, W, Y, P, or C; G365 replaced with D, E, H, K, R, N, Q, F, W, Y, P, or C; R366 replaced with D, E, A, G, I, L, S, T, M, V, N, Q, F, W, Y, P, or C; D367 replaced with H, K, R, A, G, I, L, S, T, M, V, N, Q, F, W, Y, P, or C; A368 replaced with D, E, H, K, R, N, Q, F, W. Y, P, or C; S369 replaced with D, E, H, K, R, N, Q, F, W, Y, P, or C; V370 replaced with D, E, H, K, R, N, Q, F, W, Y, P, or C; H371 replaced with D, E, A, G, I, L, S, T, M, V, N, Q, F, W, Y, P, or C; T372 replaced with D, E, H, K, R, N, Q, F, W, Y, P, or C; L373 replaced with D, E, H, K, R, N, Q, F, W, Y, P, or C; L374 replaced with D, E, H, K, R, N, Q, F, W, Y, P, or C; D375 replaced with H, K, R, A, G, I, L, S, T, M, V, N, Q, F, W, Y, P, or C; A376 replaced with D, E, H, K, R, N, Q, F, W, Y, P, or C; L377 replaced with D, E, H, K, R, N, Q, F, W, Y, P, or C; E378 replaced with H, K, R, A, G, I, L, S, T, M, V, N, Q, F, W, Y, P, or C; T379 replaced with D, E, H, K, R, N, Q, F, W, Y, P, or C; L380 replaced with D, E, H, K, R, N, Q, F, W, Y, P, or C; G381 replaced with D, E, H, K, R, N, Q, F, W, Y, P, or C; E382 replaced with H, K, R, A, G, I, L, S, T, M, V, N, Q, F, W, Y, P, or C; R383 replaced with D, E, A, G, I, L, S, T, M, V, N, Q, F, W, Y, P, or C; L384 replaced with D, E, H, K, R, N, Q, F, W, Y, P, or C; A385 replaced with D, E, H, K, R, N, Q, F, W, Y, P, or C; K386 replaced with D, E, A, G, I, L, S, T, M, V, N, Q, F, W, Y, P, or C; Q387 replaced with D, E, H, K, R, A, G, I, L, S, T, M, V, F, W, Y, P, or C; K388 replaced with D, E, A, G, I, L, S, T, M, V, N, Q, F, W, Y, P, or C; I389 replaced with D, E, H, K, R, N, Q, F, W, Y, P, or C; E390 replaced with H, K, R, A, G, I, L, S, T, M, V, N, Q, F, W, Y, P, or C; D391 replaced with H, K, R, A, G, I, L, S, T, M, V, N, Q, F, W, Y, P, or C; H392 replaced with D, E, A, G, I, L, S, T, M, V, N, Q, F, W, Y, P, or C; L393 replaced with D, E, H, K, R, N, Q, F, W, Y, P, or C; L394 replaced with D, E, H, K, R, N, Q, F, W, Y, P, or C; S395 replaced with D, E, H, K, R, N, Q, F, W, Y, P, or C; S396 replaced with D, E, H, K, R, N, Q, F, W, Y, P, or C; G397 replaced with D, E, H, K, R, N, Q, F, W, Y, P, or C; K398 replaced with D, E, A, G, I, L, S, T, M, V, N, Q, F, W, Y, P, or C; F399 replaced with D, E, H, K, R, N, Q, A, G, I, L, S, T, M, V, P, or C; M400 replaced with D, E, H, K, R, N, Q, F, W, Y, P, or C; Y401 replaced with D, E, H, K, R, N, Q, A, G, I, L, S, T, M, V, P, or C; L402 replaced with D, E, H, K, R, N, Q, F, W, Y, P, or C; E403 replaced with H, K, R, A, G, I, L, S, T, M, V, N, Q, F, W, Y, P, or C; G404 replaced with D, E, H, K, R, N, Q, F, W, Y, P, or C; N₄O₅ replaced with D, E, H, K, R, A, G, I, L, S, T, M, V, F, W, Y, P, or C; A406 replaced with D, E, H, K, R, N, Q, F, W, Y, P, or C; D407 replaced with H, K, R, A, G, I, L, S, T, M, V, N, Q, F, W, Y, P, or C; S408 replaced with D, E, H, K, R, N, Q, F, W, Y, P, or C; A409 replaced with D, E, H, K, R, N, Q, F, W, Y, P, or C; M410 replaced with D, E, H, K, R, N, Q, F, W, Y, P, or C; and/or S411 replaced with D, E, H, K, R, N, Q, F, W, Y, P, or C of SEQ ID NO:3.

Amino acids in the TR7 protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of TR7 that are essential for TR7 function. In other preferred embodiments, antibodies of the present invention bind regions of TR7 that are essential for TR7 function and inhibit or abolish TR7 function. In other preferred embodiments, antibodies of the present invention bind regions of TR7 that are essential for TR7 function and enhance TR7 function.

Additionally, protein engineering may be employed to improve or alter the characteristics of TR7 polypeptides. Recombinant DNA technology known to those skilled in the art can be used to create novel mutant proteins or polypeptides including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified TR7 polypeptides.

Non-naturally occurring TR7 variants that may be bound by the antibodies of the invention may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res*. 13:4331 (1986); and Zoller et al., *Nucl. Acids Res*. 10:6487 (1982)), cassette mutagenesis (see e.g., Wells et al., *Gene* 34:315 (1985)), restriction selection mutagenesis (see e.g., Wells et al., *Philos. Trans. R. Soc. London Ser A* 317:415 (1986)).

Thus, the invention also encompasses antibodies that bind TR7 derivatives and analogs that have one or more amino acid residues deleted, added, or substituted to generate TR7 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the TR7 polypeptides, and/or an amino acid deletion at the second position of any one or more such recognition sequences will prevent glycosylation of the TR7 at the modified tripeptide sequence (see, e.g., Miyajimo et al., *EMBO J*. 5(6):1193-1197). Additionally, one or more of the amino acid residues of TR7 polypeptides (e.g., arginine and lysine residues) may be deleted or substituted with another residue to eliminate undesired processing by proteases such as, for example, furins or kexins.

The antibodies of the present invention also include antibodies that bind a polypeptide comprising, or alternatively, consisting of the polypeptide encoded by the deposited cDNA (the deposit having ATCC Accession Number 97920) including the leader; the mature polypeptide encoded by the deposited the cDNA minus the leader (i.e., the mature protein); a polypeptide comprising or alternatively, consisting of, amino acids about 1 to about 411 in SEQ ID NO:3; a polypeptide comprising or alternatively, consisting of, amino acids about 2 to about 411 in SEQ ID NO:3; a polypeptide comprising or alternatively, consisting of, amino acids about 52 to about 411 in SEQ ID NO:3; a polypeptide comprising or alternatively, consisting of, the TR7 extracellular domain; a polypeptide comprising or alternatively, consisting of, the TR7 cysteine rich domain; a polypeptide comprising or alternatively, consisting of, the TR7 transmembrane domain; a polypeptide comprising or alternatively, consisting of, the TR7 intracellular domain; a polypeptide comprising or alternatively, consisting of, the extracellular and intracellular domains with all or part of the transmembrane domain deleted; and a polypeptide comprising or alternatively, consisting of, the TR7 death domain; as well as polypeptides which are at least 80% identical, more preferably at least 90% or 95% identical, still more preferably at least 96%, 97%, 98%, or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TR7 polypeptide is intended that the amino acid sequence of the polypeptide is identical to the reference sequence except that the polypeptide sequence may include up to five amino acid alterations per each 100 amino acids of the reference amino acid of the TR7 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A-B (SEQ ID NO:3), the amino acid sequence encoded by deposited cDNA clones, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty-0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are made for the purposes of this embodiment.

The polypeptide of the present invention could be used as a molecular weight marker on SDS-PAGE gels or on molecular sieve gel filtration columns and as a source for generating antibodies that bind the TR7 polypeptides, using methods well known to those of skill in the art.

The present application is also directed to antibodies that bind proteins containing polypeptides at least 90%, 95%, 96%, 97%, 98% or 99% identical to the TR7 polypeptide sequence set forth herein as $n^5$-$m^5$, and/or $n^6$-$m^6$. In preferred embodiments, the application is directed to antibodies that bind proteins containing polypeptides at least 90%, 95%, 96%, 97%, 98% or 99% identical to polypeptides having the amino acid sequence of the specific TR7 N- and C-terminal deletions recited herein.

In certain preferred embodiments, antibodies of the invention bind TR7 proteins of the invention comprise fusion proteins as described above wherein the TR7 polypeptides are those described as $n^5$-$m^5$, and $n^6$-$m^6$, herein.

Antibodies of the Invention May Bind Modified TRAIL Receptor Polypeptides

It is specifically contemplated that antibodies of the present invention may bind modified forms of TR4 proteins SEQ ID NO:1). In those embodimjents where an antibody of the present invention specifically binds both TR4 and TR7 (SEQ ID NO:3), it is also specifically contemplated that those antibodies may bind modified forms of TR4 and/or TR7. Modifiied forms of TR7 would include, for example, modified forms of TR7 that correspond to the modified forms of TR4 described below.

In specific embodiments, antibodies of the present invention bind TR4 polypeptides (such as those decribed above) including, but not limited to naturally purified TR4 polypeptides, TR4 polypeptides produced by chemical synthetic procedures, and TR4 polypeptides produced by recombinant techniques from a prokaryotic or eukaryotic host, including, for example, bacterial, yeast, higher plant, insect and mammalian cells using, for example, the recombinant compositions and methods described above. Depending upon the host employed in a recombinant production procedure, the polypeptides may be glycosylated or non-glycosylated. In addition, TR4 polypeptides may also include an initial modified methionine residue, in some cases as a result of host-mediated processes.

In addition, TR4 proteins that are bound by antibodies of the present invention can be chemically synthesized using techniques known in the art (e.g., see Creighton, Proteins: Structures and Molecular Principles, W. H. Freeman & Co., N.Y. (1983), and Hunkapiller, et al., Nature 310:105-111 (1984)). For example, a peptide corresponding to a fragment of a TR4 polypeptide can be synthesized by use of a peptide synthesizer. Furthermore, if desired, nonclassical amino acids or chemical amino acid analogs can be introduced as a substitution or addition into the TR4 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses antibodies that bind TR4 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications to TR4 polypeptides for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are antibodies that bind chemically modified derivatives of TR4 polypeptides which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each TR4 polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7,6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera Drug Carrier Sys. 9:249-304 (1992).

As mentioned the antibodies of the present invention may bind TR4 polypeptides that are modified by either natural processes, such as posttranslational processing, or by chemical modification techniques which are well known in the art. It will be appreciated that the same type of modification may be present in the same or varying degrees at several sites in a given TR4 polypeptide. TR4 polypeptides may be branched, for example, as a result of ubiquitination, and they may be cyclic, with or without branching. Cyclic, branched, and branched cyclic TR4 polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992)).

Anti-TR4 Antibodies

In one embodiment, the invention provides antibodies (e.g., antibodies comprising two heavy chains and two light chains linked together by disulfide bridges) that immunospecifically bind TR4 (SEQ ID NO:1) or fragments or variants thereof, wherein the amino acid sequence of the heavy chain and the amino acid sequence of the light chain are the same as the amino acid sequence of a heavy chain and a light chain expressed by one or more scFvs or cell lines referred to in Table 1. In another embodiment, the invention provides antibodies (each consisting of two heavy chains and two light chains linked together by disulfide bridges to form an antibody) that immunospecifically bind TR4 or fragments or variants thereof, wherein the amino acid sequence of the heavy chain or the amino acid sequence of the light chain are the same as the amino acid sequence of a heavy chain or a light chain expressed by one or more scFvs or cell lines referred to in Table 1. Immunospecific binding to TR4 polypeptides may be determined by immunoassays known in the art or described herein for assaying specific antibody-antigen binding. Molecules comprising, or alternatively consisting of, fragments or variants of these antibodies that immunospecifically bind to TR4 are also encompassed by the invention, as are nucleic acid molecules encoding these antibodies molecules, fragments and/or variants (e.g., SEQ ID NOs:54-65).

In one embodiment of the present invention, antibodies that immunospecifically bind to a TR4 or a fragment or variant thereof, comprise a polypeptide having the amino acid sequence of any one of the heavy chains expressed by at least one of the scFvs or cell lines referred to in Table 1 and/or any one of the light chains expressed by at least one of the scFvs or cell lines referred to in Table 1.

In another embodiment of the present invention, antibodies that immunospecifically bind to TR4 or a fragment or variant thereof, comprise a polypeptide having the amino acid sequence of any one of the VH domains of at least one of the scFvs referred to in Table 1 and/or any one of the VL domains of at least one of the scFvs referred to in Table 1. In preferred embodiments, antibodies of the present invention comprise the amino acid sequence of a VH domain and VL domain from a single scFv referred to in Table 1. In alternative embodiments, antibodies of the present invention comprise the amino acid sequence of a VH domain and a VL domain from different scFvs referred to in Table 1. Molecules comprising, or alternatively consisting of, antibody fragments or variants of the VH and/or VL domains of at least one of the scFvs referred to in Table 1 that immunospecifically bind to a TR4 are also encompassed by the invention, as are nucleic acid molecules encoding these VH and VL domains, molecules, fragments and/or variants.

The present invention also provides antibodies that immunospecifically bind to a polypeptide, or polypeptide fragment or variant of TR4, wherein said antibodies comprise, or alternatively consist of, a polypeptide having an amino acid sequence of any one, two, three, or more of the VH CDRs contained in a VH domain of one or more scFvs referred to in Table 1. In particular, the invention provides antibodies that immunospecifically bind a TRAIL receptor, comprising, or alternatively consisting of, a polypeptide having the amino acid sequence of a VH CDR1 contained in a VH domain of one or more scFvs referred to in Table 1. In another embodiment, antibodies that immunospecifically bind TR4, comprise, or alternatively consist of, a polypeptide having the amino acid sequence of a VH CDR2 contained in a VH domain of one or more scFvs referred to in Table 1. In a preferred embodiment, antibodies that immunospecifically bind TR4, comprise, or alternatively consist of a polypeptide having the amino acid sequence of a VH CDR3 contained in a VH domain of one or more scFvs referred to in Table 1. Molecules comprising, or alternatively consisting of, these antibodies, or antibody fragments or variants thereof, that immunospecifically bind to TR4 or a TR4 fragment or variant thereof are also encompassed by the invention, as are nucleic acid molecules encoding these antibodies, molecules, fragments and/or variants (e.g., SEQ ID NOs:54-65).

The present invention also provides antibodies that immunospecifically bind to a polypeptide, or polypeptide fragment or variant of TR4, wherein said antibodies comprise, or alternatively consist of, a polypeptide having an amino acid sequence of any one, two, three, or more of the VL CDRs contained in a VL domain of one or more scFvs referred to in Table 1. In particular, the invention provides antibodies that immunospecifically bind TR4, comprising, or alternatively consisting of, a polypeptide having the amino acid sequence of a VL CDR1 contained in a VL domain of one or more scFvs referred to in Table 1. In another embodiment, antibodies that immunospecifically bind TR4, comprise, or alternatively consist of, a polypeptide having the amino acid sequence of a VL CDR2 contained in a VL domain of one or more scFvs referred to in Table 1. In a preferred embodiment, antibodies that immunospecifically bind TR4, comprise, or alternatively consist of a polypeptide having the amino acid sequence of a VL CDR3 contained in a VL domain of one or more scFvs referred to in Table 1. Molecules comprising, or alternatively consisting of, these antibodies, or antibody fragments or variants thereof, that immunospecifically bind to TR4 or a TR4 fragment or variant thereof are also encompassed by the invention, as are nucleic acid molecules encoding these antibodies, molecules, fragments and/or variants (e.g., SEQ ID NOs:54-65).

The present invention also provides antibodies (including molecules comprising, or alternatively consisting of, antibody fragments or variants) that immunospecifically bind to TR4 polypeptide or a fragment or variant of a TR4, wherein said antibodies comprise, or alternatively consist of, one, two, three, or more VH CDRs and one, two, three or more VL CDRs, as contained in a VH domain or VL domain of one or more scFvs referred to in Table 1. In particular, the invention provides for antibodies that immunospecifically bind to a polypeptide or polypeptide fragment or variant of TR4, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a VH domain or VL domain of one or more scFvs referred to in Table 1. In a preferred embodiment, one or more of these combinations are from the same scFv as disclosed in Table 1. Molecules comprising, or alternatively consisting of, fragments or variants of these antibodies, that immunospecifically bind to TR4 are also encompassed by the invention, as are nucleic acid molecules encoding these antibodies, molecules, fragments or variants (e.g., SEQ ID NOs:54-65).

Nucleic Acid Molecules Encoding Anti-TR4 Antibodies

The present invention also provides for nucleic acid molecules, generally isolated, encoding an antibody of the invention (including molecules comprising, or alternatively consisting of, antibody fragments or variants thereof). In specific embodiments, the nucleic acid molecules encoding an antibody of the invention comprise, or alternatively consist of SEQ ID NOs:54-65 or fragments or variants thereof.

In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 and a VL domain having an amino acid sequence of VL domain of at least one of the scFvs referred to in Table 1. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 or a VL domain having an amino acid sequence of a VL domain of at least one of the scFvs referred to in Table 1.

The present invention also provides antibodies that comprise, or alternatively consist of, variants (including derivatives) of the antibody molecules (e.g., the VH domains and/or VL domains) described herein, which antibodies immunospecifically bind to TR4 or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid subsitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind TR4).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybriodma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g, improvements in antigen binding activity or change in antibody specificity). Following mutagenesis, the encoded protein may routinely be expressed and the functional and/or biological activity of the encoded protein, (e.g., ability to immunospecifically bind TR4) can be determined using techniques described herein or by routinely modifying techniques known in the art.

In a specific embodiment, an antibody of the invention (including a molecule comprising, or alternatively consisting of, an antibody fragment or variant thereof), that immunospecifically binds TR4 or a fragment or variant thereof, comprises, or alternatively consists of, an amino acid sequence encoded by a nucleotide sequence that hybridizes to a nucleotide sequence that is complementary to that encoding one of the VH or VL domains of one or more scFvs referred to in Table 1. under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that immunospecifically binds to TR4 or fragments or variants of TR4, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of at least one of the scFvs referred to in Table 1.

In another embodiment, an antibody (including a molecule comprising, or alternatively consisting of, an antibody fragment or variant thereof), that immunospecifically binds to TR4 or a fragment or variant of TR4, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of at least one of the scFvs referred to in Table 1.

Methods of Producing Antibodies

Antibodies in accordance with the invention are preferably prepared the utilization of a phage scFv display library. Technologies utilized for achieving the same are disclosed in the patents, applications, and references disclosed herein.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a TRAIL receotor polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280

(1994); PCT application No. PCT/GB91/01 134; PCT publications WO 90/02809; WO 91/10737; WO 92/01047; WO 92/18719; WO 93/11236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

For some uses, such as for in vitro affinity maturation of an antibody of the invention, it may be useful to express the VH and VL domains of one or more scFvs referred to in Table 1 as single schain antibodies or Fab fragments in a phage display library. For example, the cDNAs encoding the VH and VL domains of the scFvs referred to in Table 1 may be expressed in all possible combinations using a phage display library, allowing for the selection of VH/VL combinations that bind TR4 polypeptides with preferred binding characteristics such as improved affinity or improved off rates. Additionally, VH and VL segments—the CDR regions of the VH and VL domains of the scFvs referred to in Table 1, in particular, may be mutated in vitro. Expression of VH and VL domains with "mutant" CDRs in a phage display library allows for the selection of VH/VL combinations that bind TR4 polypeptides with preferred binding characteristics such as improved affinity or improved off rates.

Additional Methods of Producing Antibodies

Antibodies of the invention (including antibody fragments or variants) can be produced by any method known in the art. For example, it will be appreciated that antibodies in accordance with the present invention can be expressed in cell lines including but not limited to myeloma cell lines and hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains of the scFvs referred to in Table 1. In order to isolate the VH and VL domains from bacteria transfected with a vector containing the scFv, PCR primers complementary to VH or VL nucleotide sequences (See Example 5), may be used to amplify the VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art. Alternatively, the VH and VL domains may be amplified using vector specific primers designed to amplify the entire scFv, (i.e. the VH doamin, linker and VL domain.)

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. If the amino acid sequences of the VH domains, VL domains and CDRs thereof, are known, nucleotide sequences encoding these antibodies can be determined using methods well known in the art, i.e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells or Epstein Barr virus transformed B cell lines that express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, VH and VL domains of one or more scFvs referred to in Table 1, or fragments or variants thereof, are inserted within framework regions using recombinant DNA techniques known in the art. In a specific embodiment, one, two, three, four, five, six, or more of the CDRs of VH and/or VL domains of one or more scFvs referred to in Table 1, or fragments or variants thereof, is inserted within framework regions using recombinant DNA techniques known in the art. The framework regions may be naturally occurring or consensus framework regions, and preferably human framework regions (see, e.g., Chothia et al., J. Mol. Biol. 278: 457-479 (1998) for a listing of human framework regions, the contents of which are hereby incorporated by reference in its entirety). Preferably, the polynucleotides generated by the combination of the framework regions and CDRs encode an antibody (including molecules comprising, or alternatively consisting of, antibody fragments or variants thereof) that specifically binds to a TRAIL receptor. Preferably, as discussed supra, polynucleotides encoding variants of antibodies or antibody fragments having one or more amino acid substitutions may be made within the framework regions, and, preferably, the amino acid substitutions do not significantly alter binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J Exp. Med.* 188:483-495 (1998), Green, *Journal of Immunological Methods* 231:11-23 (1999) and U.S. patent application Ser. No. 08/759,620, filed Dec. 3, 1996, now abandoned, the disclosures of which are hereby incorporated by reference.

Such approach is further discussed and delineated in U.S. patent application Ser. Nos. 07/466,008, filed Jan. 12, 1990, now abandoned, 07/710,515, filed Nov. 8, 1990, now U.S. Pat. No. 5,258,492, 07/919,297, filed Jul. 24, 1992, now abandoned, 07/922,649, filed Jul. 30, 1992, now U.S. Pat. No. 5,939,598, 08/031,801, filed Mar. 15, 1993, now U.S. Pat. No. 6,673,986, 08/112,848, filed Aug. 27, 1993, now abandoned, 08/234,145, filed Apr. 28, 1994, now abandoned, 08/376,279, filed Jan. 20, 1995, now abandoned, 08/430,938, filed Apr. 27, 1995, now abandoned, 08/464,584, filed Jun. 5, 1995, now abandoned, 08/464,582, filed Jun. 5, 1995, now U.S. Pat. No. 6,114,598, 08/471,191, filed Jun. 5, 1995, now abandoned, 08/462,837, filed Jun. 5, 1995, now abandoned, 08/486,853, filed Jun. 5, 1995, now abandoned, 08/486,857, filed Jun. 5, 1995, now U.S. Pat. No.

6,075,181, 08/486,859, filed Jun. 5, 1995, now abandoned, 08/462,513, filed Jun. 5, 1995, now U.S. Pat. No. 6,162,963, 08/724,752, filed Oct. 2, 1996, now U.S. Pat. No. 6,150,584, and 08/759,620, filed Dec. 3, 1996, now abandoned. See also Mendez et al. *Nature Genetics* 15:146-156 (1997) and Green and Jakobovits *J Exp. Med.* 188:483 495 (1998). See also European Patent No., EP 0 471 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against TR4 polypeptides in order to vitiate concerns and/or effects of HAMA or HACA responses.

Monoclonal antibodies specific for TR4 polypeptides may be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). Briefly, XenoMouse™ mice may be immunized with TR4 polypeptides. After immunization, the splenocytes of such mice were extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the TR4 polypetides.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50435, WO 98/24893, WO98/16654, WO 96/34096, WO 96/35735, and WO 91/10741; each of which is incorporated herein by reference in its entirety. In a specific embodiment, antibodies of the present invention comprise one or more VH and VL domains of the invention and constant regions from another immunoglobulin molecule, preferably a human immunoglobulin molecule. In a specific embodiment, antibodies of the present invention comprise one or more CDRs corresponding to the VH and VL domains of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the VH or VL domains of one or more scFvs referred to in Table 1, or fragments or variants thereof, and framework regions (and, optionally one or more CDRs not present in the antibodies expressed by scFvs referred to in Table 1) from a human immunoglobulin molecule. In a preferred embodiment, an antibody of the present invention comprises a VH CDR3, VL CDR3, or both, corresponding to the same scFv, or different scFvs selected from the scFvs referred to in Table 1, or fragments or variants thereof, and framework regions from a human immunoglobulin.

A chimeric antibody is a molecule in which different portions of the antibody are derived from different immunoglobulin molecules such as antibodies having a human variable region and a non-human (e.g., murine) immunoglobulin constant region or vice versa. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a murine, canine or feline immunoglobulin molecule) (or vice versa) can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352). In a preferred embodiment, chimeric antibodies comprise a human CDR3 having an amino acid sequence of any one of the VH CDR3 s or VL CDR3s of a VH or VL domain of one or more of the scFvs referred to in Table 1, or a variant thereof, and non-human framework regions or human framework regions different from those of the frameworks in the corresponding scFv disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 352:323 (1988), which are incorporated herein by reference in their entireties.)

Intrabodies are antibodies, often scFvs, that are expressed from a recombinant nucleic aicd molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595-601 (1994); Marasco, W. A., *Gene Ther.* 4:11-15 (1997); Rondon and Marasco, *Annu. Rev. Microbiol.* 51:257-283 (1997); Proba et al., *J. Mol. Biol.* 275:245-253 (1998); Cohen et al., *Oncogene* 17:2445-2456 (1998); Ohage and Steipe, *J. Mol. Biol.* 291:1119-1128 (1999); Ohage et al., *J. Mol. Biol.* 291:1129-1134 (1999); Wirtz and Steipe, *Protein Sci.* 8:2245-2250 (1999); Zhu et al., *J. Immunol. Methods* 231:207-222 (1999); and references cited therein.

Recombinant expression of an antibody of the invention (including antibody fragments or variants thereof (e.g., a heavy or light chain of an antibody of the invention), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is(are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants teherof (single chain antibodies), microorganisms such as bacteria (e.g., *E. coli*, *B. subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990); Bebbington et al., Bio/Techniques 10:169 (1992); Keen and Hale, Cytotechnology 18:207 (1996)). These references are incorporated in their entirities by refernce herein.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g. glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578T, HTB2, BT20 and T47D, and normal mammary gland cell line such as, for example, CRL7O3O and HsS78Bst.

For long-term, high-yield production of recombinant proteins, stable expression is preferred. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62: 191-217 (1993); TIB TECH 11(5):155-215 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al, J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" in *DNA Cloning, Vol.* 3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NS0) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from supliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310:105-111). For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, $^{213}$Bi, or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin.

In specific embodiments, antibodies of the invention may be labeled with Europium. For example, antibodies of the invention may be labelled with Europium using the DELFIA Eu-labeling kit (catalog# 1244-302, Perkin Elmer Life Sciences, Boston, Mass.) following manufacturer's instructions.

In specific embodiments, antibodies of the invention are attached to macrocyclic chelators useful for conjugating radiometal ions, including but not limited to, $^{111}$In, $^{177}$Lu, $^{90}$Y, $^{166}$Ho, $^{153}$Sm, $^{215}$Bi and $^{225}$Ac to polypeptides. In a preferred embodiment, the radiometal ion associated with the macrocyclic chelators attached to antibodies of the invention is $^{111}$In. In another preferred embodiment, the radiometal ion associated with the macrocyclic chelator attached to antibodies polypeptides of the invention is $^{90}$Y. In specific embodiments, the macrocyclic chelator is 1,4,7, 10-tetraazacyclododecane-N,N',N",N'"-tetraacetic acid (DOTA). In specific embodiments, the macrocyclic chelator is α-(5-isothiocyanato-2-methoxyphenyl)-1,4,7,10-tetraazacyclododecane-1,4,7,10-tetraacetic acid. In other specific embodiments, the DOTA is attached to the antibody of the invention via a linker molecule. Examples of linker molecules useful for conjugating a macrocyclic chelator such as DOTA to a polypeptide are commonly known in the art—see, for example, DeNardo et al., Clin Cancer Res. 4(10): 2483-90, 1998; Peterson et al., Bioconjug. Chem. 10(4): 553-7, 1999; and Zimmerman et al, Nucl. Med. Biol. 26(8): 943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

In one embodiment, antibodies of the invention are labeled with biotin. In other related embodiments, biotinylated antibodies of the invention may be used, for example, as an imaging agent or as a means of identifying one or more TRAIL receptor coreceptor or ligand molecules.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire antibodies chemically modified at the N-terminus of either the heavy chain or the light chain or both. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the antibodies of the invention may be accomplished by any number of means. For example, polyethylene glycol may be attached to the antibody either directly or by an intervening linker. Linkerless systems for attaching polyethylene glycol to proteins are described in Delgado et al., Crit. Rev. Thera Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of antibodies without an intervening linker employs tresylated MPEG, which is produced by the modification of monmethoxy polyethylene glycol (MPEG) using tresylchloride (ClSO2CH2CF3). Upon reaction of protein with tresylated MPEG, polyethylene glycol is directly attached to amine groups of the protein. Thus, the invention includes antibody-polyethylene glycol conjugates produced by reacting antibodies of the invention with a polyethylene glycol molecule having a 2,2,2-trifluoreothane sulphonyl group.

Polyethylene glycol can also be attached to antibodies using a number of different intervening linkers. For example, U.S. Pat. No. 5,612,460, the entire disclosure of which is incorporated herein by reference, discloses urethane linkers for connecting polyethylene glycol to proteins. Antibody-polyethylene glycol conjugates wherein the polyethylene glycol is attached to the antibody by a linker can also be produced by reaction of antibodies with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated antibody products produced using the reaction chemistries set out herein are included within the scope of the invention.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., Crit. Rev. Thera Drug Carrier Sys. 9:249-304 (1992).

Characterization of Anti-TR4 Antibodies

Antibodies of the present invention (including molecules comprising, or alternatively consisting of, antibody fragments or variants thereof) may also be described or specified in terms of their binding to TR4 polypeptides or fragments or variants of TR4 polypeptides. In specific embodiments, antibodies of the invention bind TR4 polypeptides, or fragments or variants thereof, with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind TR4 polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind TR4 polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. The invention encompasses antibodies that bind TR4 polypeptides with a dissociation constant or $K_D$ that is within any one of the ranges that are between each of the individual recited values.

In specific embodiments, antibodies of the invention bind TR4 polypeptides or fragments or variants thereof with an off rate ($k_{off}$) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, antibodies of the invention bind TR4 polypeptides or fragments or variants thereof with an off rate ($k_{off}$) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$. The invention encompasses antibodies that bind TR4 polypeptides with an off rate ($k_{off}$) that is within any one of the ranges that are between each of the individual recited values.

In other embodiments, antibodies of the invention bind TR4 polypeptides or fragments or variants thereof with an on rate ($k_{on}$) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, antibodies of the invention bind TR4 polypeptides or fragments or variants thereof with an on rate ($k_{on}$) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$. The invention encompasses antibodies that bind TR4 polypeptides with on rate ($k_{on}$) that is within any one of the ranges that are between each of the individual recited values.

The antibodies of the invention (including molecules comprising, or alternatively consisting of, antibody fragments or variants thereof) immunospecifically bind to a polypeptide or polypeptide fragment or variant of human TR4 polypeptides (SEQ ID NOS:1). In another embodiment, the antibodies of the invention immunospecifically bind to a polypeptide or polypeptide fragment or variant of simian TR4 polypeptides. In yet another embodiment, the antibodies of the invention immunospecifically bind to a polypeptide or polypeptide fragment or variant of murine TR4 polypeptides. In one embodiment, the antibodies of the invention bind immunospecifically to human and simian TR4 polypeptides. In another embodiment, the antibodies of the invention bind immunospecifically to human TR4 polypeptides and murine TR4 polypeptides. More preferably, antibodies of the invention, preferentially bind to human TR4 polypeptides compared to murine TR4 polypeptides.

In preferred embodiments, the antibodies of the present invention (including molecules comprising, or alternatively consisting of, antibody fragments or variants thereof), immunospecifically bind to TR4 polypeptides and do not cross-react with any other antigens. In preferred embodiments, the antibodies of the invention immunospecifically bind to TR4 polypeptides (e.g., SEQ ID NOS:1 or fragments or variants thereof) and do not cross-react with one or more additional members of the Tumor Necrosis Factor Tumor Necrosis Factor Receptor Family polypeptides (e.g., TR1, TR5, TR10 BCMA, TACI, CD30, CD27, OX40, 4-1BB, CD40, NGFR, TNFR1, TNFR2, Fas, and NGFR).

In another embodiment, the antibodies of the present invention (including molecules comprising, or alternatively consisting of, antibody fragments or variants thereof), immunospecifically bind to TR4 polypeptides and cross-react with other antigens. In other embodiments, the antibodies of the invention immunospecifically bind to TR4 polypeptides (e.g., SEQ ID NOS:1 or fragments or variants thereof) and cross-react with one or more additional members of the Tumor Necrosis Factor Receptor Family polypeptides (e.g., TR1, TR5, TR10 BCMA, TACI, CD30, CD27, OX40, 4-1BB, CD40, NGFR, TNFR1, TNFR2, Fas, and NGFR).

In a preferred embodiment, antibodies of the invention preferentially bind TR4 (SEQ ID NO:1), or fragments and variants thereof relative to their ability to bind TR1, TR5, TR7, or TR10 (SEQ ID NOS:2-5) or fragments or variants thereof. In other preferred embodiments, the antibodies of the invention preferentially bind to TR4 and TR7 (SEQ ID NOS:1 and 3), or fragments and variants thereof relative to their ability to bind TR1, TR5 or TR10 (SEQ ID NOS:5, 2 and 4) or fragments or variants thereof. In other preferred embodiments, the antibodies of the invention bind TR1, TR4, TR5, TR7 and TR10 (SEQ ID NOS:5, 1, 2, 3 and 4). An antibody's ability to preferentially bind one antigen compared to another antigen may be determined using any method known in the art.

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to TR4 polypeptides (e.g., membrane-embedded TRAIL receptors), the ability to stimulate TR4 mediated biological activity (e.g., to stimulate apoptosis of TR4 expressing cells, see Example 4); the ability to substantially block TR4 ligand (e.g. TRAIL (SEQ ID NO:66), also known as AIM-I, International Application No. WO 97/35899 and U.S. patent application 5,771,223), or a fragment, variant or fusion protein thereof, binding to TRAIL receptor, see Example 3; or the ability to upregulate TR4 expression on the surface of cells. Other biological activities that antibodies against TR4 polypeptides may have, include, but are not limited to, the ability to inhibit TR4 mediated biological activity (e.g., to inhibit apoptosis of TR4 expressing cells) or the ability to downregulate TR4 expression on the surface of cells. Optionally, the antibodies of the invention will bind to the same or closely associated (e.g., overlapping) epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that stimulate TR4 mediated biological activities. In one embodiment, an antibody that stimulates TR4 mediated biological activities comprises, or alternatively consists of a VH and/or a VL domain of at least one of the scFvs referred to in Table 1, or fragment or variant thereof. In a specific embodiment, an antibody that stimulates TR4 mediated biological activities comprises, or alternatively consists of a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that stimulate apoptosis of TR4 expressing cells (see Example 4). In one embodiment, an antibody that stimulates apoptosis of TR4 expressing cells comprises, or alternatively consists of a VH and/or a VL domain of at least one of the scFvs referred to in Table 1, or fragment or variant thereof. In a specific embodiment, an antibody that stimulates apoptosis of TR4 expressing cells comprises, or alternatively consists of a VH and a VL domain of any one of the scFvs referred to in Table 1, or fragment or variant thereof. Nucleic acid molecules encoding these antibodies are also encompassed by the invention.

In preferred embodiments, the present invention also provides for antibodies (including molecules comprising, or alternatively consisting of, antibody fragments or variants thereof), that stimulate apoptosis of TR4 expressing cells equally well in the presence or absence of antibody cross-linking reagents, such as for example anti-Ig Fc reagents cells (See, for example, Example 4). In a specific embodiment, antibodies of the present invention stimulate apoptosis of HeLa cells, equally well in the presence or absence of an anti-Ig Fc antibody cross-linking reagent. In another specific embodiment, antibodies of the present invention stimulate apoptosis of HeLa cells, equally well in the presence or absence of an anti-Ig Fc antibody cross-linking reagent in the presence of 2 micrograms/milliliter of cycloheximide. In another embodiment, antibodies of the present invention stimulate apoptosis of SW480 cells, equally well in the presence or absence of an anti Ig Fc antibody cross-linking reagent. In another specific embodiment, antibodies of the present invention stimulate apoptosis of SW480 cells, equally well in the presence or absence of an anti-Ig Fc antibody cross-linking reagent in the presence of 2 micrograms/milliliter of cycloheximide.

In other preferred embodiments, the present invention also provides for antibodies (including molecules comprising, or alternatively consisting of, antibody fragments or variants thereof), that stimulate apoptosis of TR4 expressing cells at least as well as an equal concentration (in terms of, for example, nanograms/milliliter) of TRAIL polypeptide (including TRAIL polypeptide fragments, variants or fusion proteins) stimulates apoptosis of TR4 expressing cells (See, for example, Example 4). In a specific embodiment, antibodies of the invention stimulate apoptosis of TR4 expressing cells better than an equal concentration (in terms of, for example, nanograms/milliliter) of TRAIL polypeptide (including TRAIL polypeptide fragments, variants or fusion proteins) stimulates apoptosis of TR4 expressing cells. In a specific embodiment, antibodies of the invention stimulate apoptosis of HeLa cells better than an equal concentration (in terms of, for example, nanograms/milliliter) of TRAIL polypeptide (including TRAIL polypeptide fragments, variants or fusion proteins) stimulates apoptosis of TR4 expressing cells. In another specific embodiment, antibodies of the present invention stimulate apoptosis of HeLa cells better than an equal concentration (in terms of, for example, nanograms/milliliter) of TRAIL polypeptide (including TRAIL polypeptide fragments, variants or fusion proteins) stimulates apoptosis of TR4 expressing cells in the presence of 2 micrograms/milliliter of cycloheximide.

In other preferred embodiments, the present invention also provides for antibodies (including molecules comprising, or alternatively consisting of, antibody fragments or variants thereof), that stimulate more apoptosis of TR4 expressing cells when administered in combination with a chemotherapeutic drug (or other therapeutic agents useful in the treatment of cancers), than either the chemotherapeutic drug (or other therapeutic agents useful in the treatment of cancers) or the antibodies alone stimulate apoptosis of receptor expressing cells. In specific embodiments, antibodies of the present invention, stimulate more apoptosis of TR4 expressing cells when administered in combination with Topotecan, than either Topotecan or the antibodies alone stimulate apoptosis of receptor expressing cells. In specific embodiments, antibodies of the present invention, stimulate more apoptosis of TR4 expressing cells when administered in combination with cycloheximide, than either cycloheximide or the antibodies alone stimulate apoptosis of receptor expressing cells.

The present invention also provides for antibodies (including molecules comprising, or alternatively consisting of, antibody fragments or variants thereof), that block or inhibit the binding of TRAIL to a TR4 polypeptide (see Example 3). In one embodiment, an antibody that blocks or inhibits the binding of TRAIL to TR4 comprises, or alternatively consists of a VH and/or a VL domain of at least one of the scFvs referred to in Table 1, or fragment or variant thereof. In a specific embodiment, an antibody that blocks or inhibits the binding of TRAIL to TR4 comprises, or alternatively consists of a VH and a VL domain of any one of the scFvs referred to in Table 1, or fragment or variant thereof. Nucleic acid molecules encoding these antibodies are also encompassed by the invention.

The present invention also provides for fusion proteins comprising, or alternatively consisting of, an antibody (including molecules comprising, or alternatively consisting of, antibody fragments or variants thereof), that immunospecifically binds to TR4, and a heterologous polypeptide. Preferably, the heterologous polypeptide to which the antibody is fused to is useful for function or is useful to target the TR4 expressing cells. In specific embodiments the invention encompasses bispecific antibodies that in which one antibody binding site is specific for TR4 and the second antibody binding site is specific for a heterologous polypeptide such as TR7 or a tumor specific antigen. In an alternative preferred embodiment, the heterologous polypeptide to which the antibody is fused to is useful to target the antibody to a tumor cell. In one embodiment, a fusion protein of the invention comprises, or alternatively consists of, a polypeptide having the amino acid sequence of any one or more of the VH domains of an antibody of the invention or the amino acid sequence of any one or more of the VL domains of an antibody of the invention or fragments or variants thereof, and a heterologous polypeptide sequence. In another embodiment, a fusion protein of the present invention comprises, or alternatively consists of, a polypeptide having the amino acid sequence of any one, two, three, or more of the VH CDRs of an antibody of the invention, or the amino acid sequence of any one, two, three, or more of the VL CDRs of an antibody of the invention, or fragments or variants thereof, and a heterologous polypeptide sequence. In a preferred embodiment, the fusion protein comprises, or alternatively consists of, a polypeptide having the amino acid sequence of a VH CDR3 of an antibody of the invention, or fragment or variant thereof, and a heterologous polypeptide sequence, which fusion protein immunospecifically binds to TR4. In another embodiment, a fusion protein comprises, or alternatively consists of a polypeptide having the amino acid sequence of at least one VH domain of an antibody of the invention and the amino acid sequence of at least one VL domain of an antibody of the invention or fragments or variants thereof, and a heterologous polypeptide sequence. Preferably, the VH and VL domains of the fusion protein correspond to a single antibody (or scFv or Fab fragment) of the invention. In yet another embodiment, a fusion protein of the invention comprises, or alternatively consists of a polypeptide having the amino acid sequence of any one, two, three or more of the VH CDRs of an antibody of the invention and the amino acid sequence of any one, two, three or more of the VL CDRs of an antibody of the invention, or fragments or variants thereof, and a heterologous polypeptide sequence. Preferably, two, three, four, five, six, or more of the VHCDR(s) or VLCDR(s) correspond to single antibody (or scFv or Fab fragment) of the invention. Nucleic acid molecules encoding these fusion proteins are also encompassed by the invention.

Antibodies of the present invention (including antibody fragments or variants thereof) may be characterized in a variety of ways. In particular, antibodies and related molecules of the invention may be assayed for the ability to immunospecifically bind to TR4 or a fragment or variant of TR4, using techniques described herein or routinely modifying techniques known in the art. Assays for the ability of the antibodies of the invention to immunospecifically bind TR4 or a fragment or variant of TR4, may be performed in solution (e.g., Houghten, Bio/Techniques 13:412-421 (1992)), on beads (e.g., Lam, Nature 354:82-84 (1991)), on chips (e.g, Fodor, Nature 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249: 386-390 (1990); Devlin, Science 249:404-406 (1990); Cwirla et al., Proc. Natl. Acad. Sci. USA 87:7178-7182 (1990); and Felici, J. Mol. Biol. 222:301-310 (1991)) (each of these references is incorporated herein in its entirety by reference). Antibodies that have been identified to immunospecifically bind to TR4 or a fragment or variant of TR4 can then be assayed for their specificity and affinity for TR4 or a fragment or variant of TR4, using or routinely modifying techniques described herein or otherwise known in the art.

The antibodies of the invention may be assayed for immunospecific binding to TR4 polypeptides and cross-reactivity with other antigens by any method known in the art. Immunoassays which can be used to analyze immunospecific binding and cross-reactivity include, but are not limited to, competitive and non-competitive assay systems using techniques such as BIAcore analysis (See, e.g., Example 2), FACS (fluorescence activated cell sorter) analysis, immunofluorescence, immunocytochemistry, radioimmunoassays, ELISA (enzyme linked immunosorbent assay), "sandwich" immunoassays, immunoprecipitation assays, western blots, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs, the antibody of interest does not have to be conjugated to a detectable compound; instead, a second antibody (which recognizes the antibody of interest) conjugated to a detectable compound may be added to the well. Alternatively, the antigen need not be directly coated to the well; instead the ELISA plates may be coated with an anti-Ig Fc antibody, and the antigen in the form or a TRAIL receptor-Fc fusion protein, may be bound to the anti-Ig Fc coated to the plate. This may be desirable so as to maintain the antigen protein (e.g., the TR4 polypeptides) in a more native conformation than it may have when it is directly coated to a plate. In another alternative, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., antigen labeled with $^3$H or $^{125}$I), or fragment or variant thereof with the antibody of interest in the presence of increasing amounts of unlabeled antigen, and the detection of the antibody bound to the labeled antigen. The affinity of the antibody of the present invention for TR4 and the binding off-rates can be determined from the data by Scatchard plot analysis. Competition with a second antibody can also be determined using radioimmunoassays. In this case, a TR4 polypeptide is incubated with an antibody of the present invention conjugated to a labeled compound (e.g., compound labeled with $^3$H or $^{125}$I) in the presence of increasing amounts of an unlabeled second anti-TR4 antibody. This kind of competitive assay between two antibodies, may also be used to determine if two antibodies bind the same, closely associated (e.g., overlapping) or different epitopes.

In a preferred embodiment, BIAcore kinetic analysis is used to determine the binding on and off rates of antibodies (including antibody fragments or variants thereof) to a TRAIL receptor, or fragments of a TRAIL receptor. BIAcore kinetic analysis comprises analyzing the binding and dissociation of antibodies from chips with immobilized TRAIL receptors on their surface as described in detail in Example 2.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

Antibody Conjugates

Figure 2:
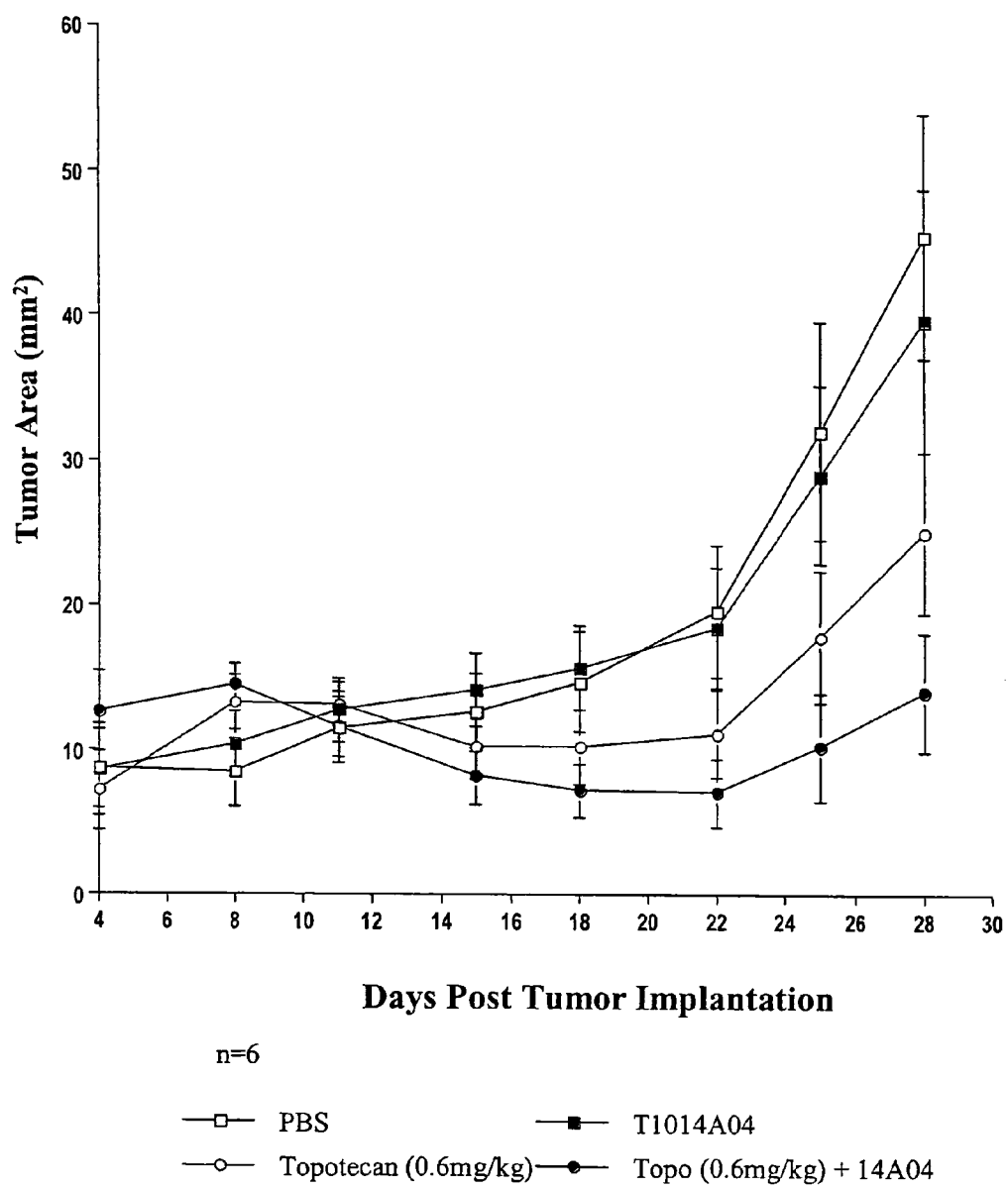
FIG. 2 shows the effect of T1014A04 treatment on SW480 tumor growth in Swiss nu/nu mice with or without Topotecan treatment at 0.6 mg/kg.

The present invention encompasses antibodies (including antibody fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types (e.g., cancer cells), either in vitro or in vivo, by fusing or conjugating the heterologous polypeptides to antibodies of the invention that are specific for particular cell surface antigens or which bind antigens that bind particular cell surface receptors. Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention. Such fusion proteins may, for example, facilitate purification and may increase half-life in vivo. Antibodies fused or conjugated to heterologous polypeptides may also be used in in vitro immunoassays and purification methods using methods known in the art. See e.g., Harbor et al., supra, and PCT publication WO 93/2 1232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146: 2446-2452 (1991), which are incorporated by reference in their entireties.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab)$_2$ fragment, or a portion thereof. Methods for fusing or conjugating polypeptides to antibody portions are known in the art. See, e.g., U.S. Pat. Nos. 5,356,603; 5,622,929; 5,359,046; 5,349,053; 5,447,851; 5,112,946; EP 307,434; EP 367,166; PCT publications WO 96/04388; WO 9 1/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11357-11341 (1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al., Curr. Opinion Biotechnol. 8:724-35 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions immunospecifically bind to TR4 may be recombined with one or more components, motifs, sections, parts, domains, fragments, etc. of one or more heterologous molecules.

Moreover, the antibodies of the present invention (including antibody fragments or variants thereof), can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the FLAG® tag (Stratagene, La Jolla, Calif.).

The present invention further encompasses antibodies (including antibody fragments or variants thereof), conjugated to a diagnostic or therapeutic agent. The antibodies can be used diagnostically to, for example, monitor or prognose the development or progression of a tumor as part of a clinical testing procedure to, e.g., determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not lmited to, luciferase, luciferin, and aequorin; and examples of suitable radioactive material include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody of the invention (including an scFv or other molecule comprising, or alternatively consisting of, antibody fragments or variants thereof), may be coupled or conjugated to a therapeutic moiety such as a cytotoxin, e.g., a cytostatic or cytocidal agent, a therapeutic agent or a radioactive metal ion, e.g, alpha-emitters such as, for example, $^{213}$Bi, or other radioisotopes such as, for example, $^{103}$Pd, $^{135}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al., Nucl. Med. Biol. 26(8):943-50, 1999 which are hereby incorporated by reference in their entirety.

Additional chelating agents are known in the art. Chelating agents may be attached to antibodies of the invention to facilitate labeling said antibodies with metal ions including, but not limited to, radionuclides or fluorescent labels. For example, see Subramanian, R. and Meares, C. F., "Bifunctional Chelating Agents for Radiometal-labeled monoclonal Antibodies," in *Cancer Imaging with Radiolabeled Antibodies* (D. M. Goldenberg, Ed.) Kluwer Academic Publications, Boston; Saji, H., "Targeted delivery of radiolabeled imaging and therapeutic agents: bifunctional radiopharmaceuticals." Crit. Rev. Ther. Drug Carrier Syst. 16:209-244 (1999); Srivastava S. C. and Mease R. C., "Progress in research on ligands, nuclides and techniques for labeling monoclonal antibodies." *Int. J. Rad. Appl. Instrum.* B 18:589-603 (1991); and Liu, S. and Edwards, D. S., "Bifunctional chelators for therapeutic lanthanide radiopharmaceuticals." *Bioconjug. Chem.* 12:7-34 (2001). Any chelator which can be covalently bound to an antibody may be used according to the present invention. The chelator may further comprise a linker moiety that connects the chelating moiety to the antibody.

In one embodiment, antibodies of the invention are attached to an acyclic chelator such as diethylene triamine-N,N,N',N'',N''-pentaacetic acid (DPTA), analogues of DPTA, and/or derivatives of DPTA. As non-limiting examples, the chelator may be 2-(p-isothiocyanatobenzyl)-6-methyldiethylenetriaminepentaacetic acid (1B4M-DPTA, also known as MX-DPTA), 2-methyl-6-(rho-nitrobenzyl)-1,4,7-triazaheptane-N,N,N',N'',N''-pentaacetic acid (nitro-1B4M-DPTA or nitro-MX-DPTA); 2-(p-isothiocyanatobenzyl)-cyclohexyldiethylenetriaminepentaacetic acid (CHX- DTPA), or N-[2-amino-3-(rho-nitrophenyl)propyl]-trans-cyclohexane-1,2-diamine-N,N',N"-pentaacetic acid (nitro-CHX-A-DTPA).

In another embodiment, antibodies of the invention are attached to an acyclic terpyridine chelator such as 6,6"-bis [[N,N,N",N"'-tetra(carboxymethyl)amino]methyl]-4'-(3-amino-4-methoxyphenyl)-2,2':6',2"-terpyridine (TMT-amine).

In specific embodiments, the macrocyclic chelator which is attached to the antibody of the invention is 1,4,7,10-tetraazacyclododecane-N,N',N",N'''-tetraacetic acid (DOTA). In other specific embodiments, the DOTA is attached to an antibody of the invention via a linker molecule. Examples of linker molecules useful for conjugating DOTA to a polypeptide are commonly known in the art— see, for example, DeNardo et al., Clin. Cancer Res. 4(10): 2483-90, 1998; Peterson et al., Bioconjug. Chem. 10(4):553-7, 1999; and Zimmerman et al., Nucl. Med. Biol. 26(8):943-50, 1999 which are hereby incorporated by reference in their entirety. In addition, U.S. Pat. Nos. 5,652,361 and 5,756, 065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the method disclosed therein in order to conjugate chelating agents to other polypeptides.

Bifunctional chelators based on macrocyclic ligands in which conjugation is via an activated arm, or functional group, attached to the carbon backbone of the ligand can be employed using techniques described in the art, such as those described by M. Moi et al., J. Amer. Chem. Soc. 49:2639 (1989) (2-p-nitrobenzyl-1,4,7,10-tetraazacyclododecane-N,N',N",N'''-tetraacetic acid); S. V. Deshpande et al., J. Nucl. Med. 31:473 (1990); G. Ruser et al., Bioconj. Chem. 1:345 (1990); C. J. Broan et al., J. C. S. Chem. Comm. 23:1739 (1990); and C. J. Anderson et al., J. Nucl. Med 36:850 (1995).

In one embodiment, a macrocyclic chelator, such as polyazamacrocyclic chelators, optionally containing one or more carboxy, amino, hydroxamate, phosphonate, or phosphate groups, are attached to antibodies of the invention. In another embodiment, the chelator is a chelator selected from the group consisting of DOTA, analogues of DOTA, and derivatives of DOTA.

In one embodiment, a suitable chelator molecule that may be attached to the antibodies of the invention include a chelator selected from the group: DOXA (1-oxa-4,7,10-triazacyclododecanetriacetic acid), NOTA (1,4,7-triazacyclononanetriacetic acid), TETA (1,4,8,11-tetraazacyclotetradecanetetraacetic acid), and THT (4'-(3-amino-4-methoxy-phenyl)-6,6"-bis(N',N'-dicarboxymethyl-N-methylhydrazino)-2,2':6',2"-terpyridine), and analogs and derivatives thereof. See, e.g. Ohmono et al., J. Med. Chem. 35: 157-162 (1992); Kung et al., J. Nucl. Med. 25: 326-332 (1984); Jurisson et al., Chem. Rev. 93:1137-1156 (1993); and U.S. Pat. No. 5,367,080. Other suitable chelators include chelating agents disclosed in U.S. Pat. Nos. 4,647, 447; 4,687,659; 4,885,363; EP-A-71564; WO89/00557; and EP-A-232751.

In another embodiment, suitable macrocyclic carboxylic acid chelators which can be used in the present invention include a chelator selected from the group: 1,4,7,10-tetraazacyclododecane-N, N', N",N'''-tetraacetic acid (DOTA); 1,4,8,12-tetraazacyclopentadecane-N,N',N',N'''-tetraacetic acid (15N4); 1,4,7-triazacyclononane-N,N',N"-triacetic acid (9N3); 1,5,9-triazacyclododecane-N,N',N"-triacetic acid (12N3); and 6-bromoacetamido-benzyl-1,4,8,11-tetraazacyclotetradecane-N, N',N",N'''-tetraacetic acid (BAT).

A preferred chelator that can be attached to the antibodies of the invention is α-(5-isothiocyanato-2-methoxyphenyl)-1,4,7,10-tetraazacyclododecane-1,4,7,10-tetraacetic acid, which is also known as MeO-DOTA-NCS. A salt or ester of α-(5-isothiocyanato-2-methoxyphenyl)-1,4,7,10-tetraazacyclododecane-1,4,7,10-tetraacetic acid may also be used.

Antibodies of the invention to which chelators such as those described are covalently attached may be labeled (via the coordination site of the chelator) with radionuclides that are suitable for therapeutic, diagnostic, or both therapeutic and diagnostic purposes. Examples of appropriate metals include, but are not limited to, Ag, At, Au, Bi, Cu, Ga, Ho, In, Lu, Pb, Pd, Pm, Pr, Rb, Re, Rh, Sc, Sr, Tc, Ti, Y, and Yb. Examples of the radionuclide used for diagnostic purposes include, but are not limited to, Fe, Gd, $^{111}$In, $^{67}$Ga, or $^{68}$Ga. In another embodiment, the radionuclide used for diagnostic purposes is $^{111}$In or $^{67}$Ga Examples of the radionuclide used for therapeutic purposes include, but are not limited to, $^{166}$Ho, $^{165}$Dy, $^{90}$Y, $^{115m}$In, $^{52}$Fe, or $^{72}$Ga. In one embodiment, the radionuclide used for diagnostic purposes is $^{166}$Ho or $^{90}$Y. Examples of the radionuclides used for both therapeutic and diagnostic purposes include, but are not limited to, $^{153}$Sm, $^{177}$Lu, $^{159}$Gd, $^{175}$Yb, or $^{47}$Sc. In one embodiment, the radionuclide is $^{153}$Sm, $^{177}$Lu, $^{175}$Yb, or $^{59}$Gd.

Preferred metal radionuclides that may be used according to the present invention include a radionuclide selected from $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{47}$Sc, $^{67}$Ga, $^{51}$Cr, $^{177m}$Sn, $^{67}$Cu, $^{167}$Tm, $^{95}$Ru, $^{188}$Re, $^{177}$Lu, $^{199}$Au, $^{203}$Pb and $^{141}$Ce.

In a particular embodiment, antibodies of the invention to which chelators are covalently attached may be labeled with a metal ion selected from the group consisting of $^{90}$Y, $^{111}$In, $^{177}$Lu, $^{166}$Ho, $^{215}$Bi, and $^{225}$Ac.

Moreover, γ-emitting radionuclides, such as $^{99m}$Tc, $^{111}$In, $^{67}$Ga, and $^{169}$Yb have may be used for diagnostic imaging, while β-emitters, such as $^{67}$Cu, $^{111}$Ag, $^{186}$Re, and $^{90}$Y are useful for the applications in tumor therapy. Also other useful radionuclides include γ-emitters, such as $^{99m}$Tc, $^{111}$In, $^{67}$Ga, and $^{169}$Yb, and β-emitters, such as $^{67}$Cu, $^{111}$Ag, $^{186}$Re, $^{188}$Re and $^{90}$Y, as well as other radionuclides of interest such as $^{211}$At, $^{212}$Bi, $^{177}$Lu, $^{86}$Rb, $^{105}$Rh, $^{153}$Sm, $^{198}$Au, $^{149}$Pm, $^{85}$Sr, $^{142}$Pr, $^{214}$Pb, $^{109}$Pd, $^{66}$Ho, $^{208}$Tl, and $^{44}$Sc. Antibodies of the invention to which chelators are covalently attached may be labeled with the radionuclides described above or others known in the art.

In another embodiment, antibodies of the invention to which chelators are covalently attached may be labeled with paramagnetic metal ions including ions of transition and lanthanide metal, such as metals having atomic numbers of 21-29, 42, 43, 44, or 57-71, in particular ions of metals selected from Cr, V, Mn, Fe, Co, Ni, Cu, La, Ce, Pr, Nd, Pm, Sm, Eu, Gd, Th, Dy, Ho, Er, Tm, Yb, and Lu. The paramagnetic metals used in compositions for magnetic resonance imaging include the elements having atomic numbers of 22 to 29, 42, 44 and 58-70.

In another embodiment, antibodies of the invention to which chelators are covalently attached may be labeled with fluorescent metal ions including lanthanides, in particular a member selected from La, Ce, Pr, Nd, Pm, Sm, Eu (e.g., $^{152}$Eu), Gd, Th, Dy, Ho, Er, Tm, Yb, and Lu.

In another embodiment, antibodies of the invention to which chelators are covalently attached may be labeled with heavy metal-containing reporters including atoms of a metal selected from Mo, Bi, Si, and W.

Radiolabeled antibodies of the invention may be used not only to kill cells to which they bind, but also may be useful to kill neighboring cells. For example, expression of TR4 may not be universal on all the cells of the tumor. However, because the energy from certain radioactive decay events can span more than a single cell diameter, radiolabeled antibodies of the invention may be used to kill cells that do not express TR4, e.g., cancerous cells, but which are in close proximity to cells that do express TR4.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and frragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label antibodies of the invention. Such techniques include, but are not limited to, the use of bifunctional conjugating agents (see e.g., U.S. Pat. Nos. 5,756,065; 5,714,711; 5,696,239; 5,652,371; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/35899), AIM II (see, International Publication No. WO 97/34911), Fas Ligand (Takahashi et al., *Int. Immunol.*, 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In specific embodiments antibodies of the invention are conjugated with a a polypeptide cytotoxin. An example of a suitable polypeptide cytotoxin is a ribosome-inactivating protein. Type I ribosome-inactivating proteins are single-chain proteins, while type II ribosome-inactivating proteins consist of two nonidentical subunits (A and B chains) joined by a disulfide bond (for a review, see Soria et al., Targeted Diagn. Ther. 7:193 (1992)). Useful type I ribosome-inactivating proteins include polypeptides from Saponaria officinalis (e.g., saporin-1, saporin-2, saporin-3, saporin-6), Momordica charantia (e.g, momordin), Byronia dioica (e.g., bryodin, bryodin-2), Trichosanthes kirilowii (e.g., trichosanthin, trichokirin), Gelonium multiflorum (e.g., gelonin), Phytolacca americana (e.g., pokeweed antiviral protein, pokeweed antiviral protein-II, pokeweed antiviral protein-S), Phytolacca dodecandra (e.g., dodecandrin, Mirabilis antiviral protein), and the like. Ribosome-inactivating proteins are described, for example, by Walsh et al., U.S. Pat. No. 5,635,384.

Suitable type II ribosome-inactivating proteins include polypeptides from Ricinus communis (e.g., ricin), Abrus precatorius (e.g., abrin), Adenia digitata (e.g., modeccin), and the like. Since type II ribosome-inactivating proteins include a B chain that binds galactosides and a toxic A chain that depurinates adensoine, type II ribosome-inactivating protein conjugates should include the A chain. Additional useful ribosome-inactivating proteins include bouganin, clavin, maize ribosome-inactivating proteins, Vaccaria pyramidata ribosome-inactivating proteins, nigrine b, basic nigrine 1, ebuline, racemosine b, luffin-a, luffin-b, luffin-S, and other ribosome-inactivating proteins known to those of skill in the art. See, for example, Bolognesi and Stirpe, International Publication No. WO98/55623, Colnaghi et al., International Publication No. WO97/49726, Hey et al., U.S. Pat. No. 5,635,384, Bolognesi and Stirpe, International Publication No. WO95/07297, Arias et al., International Publication No. WO94/20540, Watanabe et al., J. Biochem. 106:6 977 (1989); Islam et al., Agric. Biol. Chem. 55:229 (1991), and Gao et al., FEBS Lett. 347:257 (1994).

Antibodies of the invention (including antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an other molecules comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Uses of Antibodies of the Invention

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of TR4 polypeptides in biological samples. See, e.g., Harlow et al., Antibodies: A Laboratory Manual, (Cold Spring Harbor Laboratory Press, 2nd ed. 1988) (incorporated by reference herein in its entirety).

Immunophenotyping

The antibodies of the invention may be utilized for immunophenotyping of cell lines and biological samples (See, for example, Example 4). The translation product of the gene of the present invention may be useful as a cell specific marker, or more specifically as a cellular marker that is differentially expressed at various stages of differentiation and/or maturation of particular cell types, particularly of tumors and cancer cells. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:73749 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Epitope Mapping

The present invention provides antibodies (including antibody fragments or variants thereof), that can be used to identify epitopes of a TR4 polypeptide. In particular, the antibodies of the present invention can be used to identify epitopes of a human TR4 polypeptide (e.g., SEQ ID NOS:1) or a TR4 polypeptide expressed on human cells; a murine TR4 or a TR4 polypeptide expressed on murine cells; a rat TR4 polypeptide receptor or a TR4 polypeptide expressed on rat cells; or a monkey TR4 polypeptide or a TR4 polypeptide expressed on monkey cells, using techniques described herein or otherwise known in the art. Fragments which function as epitopes may be produced by any conventional means. (See, e.g., Houghten, Proc. Natl. Acad. Sci. USA 82:5131-5135 (1985), further described in U.S. Pat. No. 4,711,211.) Identified epitopes of antibodies of the present invention may, for example, be used as vaccine candidates, i.e., to immunize an individual to elicit antibodies against the naturally occuring forms of TR4 polypeptides.

Diagnostic Uses of Antibodies

Labeled antibodies of the invention (including molecules comprising, or alternatively consisting of, antibody fragments or variants thereof) which specifically bind to a TR4 polypeptide can be used for diagnostic purposes to detect, diagnose, prognose, or monitor diseases and/or disorders. In specific embodiments, labeled antibodies of the invention (including molecules comprising, or alternatively consisting of, antibody fragments or variants thereof) which specifically bind to a TR4 polypeptide can be used for diagnostic purposes to detect, diagnose, prognose, or monitor diseases and/or disorders associated with the aberrant expression and/or activity of TR4.

The invention provides for the detection of expression of a TR4 polypeptide comprising: (a) assaying the expression of a TR4 polypeptide in a biological sample from an individual using one or more antibodies of the invention that immunospecifically binds to TR4; and (b) comparing the level of TR4 polypeptide in the biological sample with a standard level of TR4 polypeptide, (e.g., the level in normal biological samples).

The invention provides for the detection of aberrant expression of a TR4 polypeptide comprising: (a) assaying the expression of a TR4 polypeptide in a biological sample from an individual using one or more antibodies of the invention that immunospecifically binds to TR4; and (b) comparing the level of a TR4 polypeptide in the biological sample with a standard level of a TR4 polypeptide, e.g., in normal biological samples, whereby an increase or decrease in the assayed level of a TR4 polypeptide compared to the standard level of a TR4 polypeptide is indicative of aberrant expression.

By "biological sample" is intended any fluids and/or cells obtained from an individual, body fluid, body tissue, body cell, cell line, tissue culture, or other source which may contain a TR4 polypeptide protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

Antibodies of the invention (including molecules comprising, or alternatively consisting of, antibody fragments or variants thereof) which specifically bind to a TR4 polypeptide can be used for diagnostic purposes to detect, diagnose, prognose, or monitor cancers and other hyperproliferative disorders, and/or diseases or conditions associated therewith. The invention provides for the detection of aberrant expression of TR4 polypeptide comprising: (a) assaying the expression of TR4 polypeptide in a biological sample from an individual using one or more antibodies of the invention that immunospecifically binds to a TR4 polypeptide; and (b) comparing the level of a TR4 polypeptide with a standard level of TR4 polypeptide, e.g., in normal biological samples, whereby an increase or decrease in the assayed level of TR4 polypeptide compared to the standard level of TR4 polypeptide is indicative of a cancer and/or a hyperproliferative disorder.

TRAIL has been shown in some instances to selectively kill tumor cells (See, for example, Oncogene 19:3363-71 (2000)). This may be a result of differential expression of TRAIL receptors on normal and cancerous cells. Thus, in specific embodiments, an increase in the assayed level of a TR4 polypeptide is indicative of a cancer and/or a hyperproliferative disorder.

Other reports suggest that decreased TR4 expression by tumor cells may be a mechanism by which tumor cells evade the immune system (See, for example, Int. J. Oncol. 16:917-25 (2000)) Thus, in other specific embodiments, a decrease in the assayed level of TR4 polypeptide is indicative of a cancer and/or a hyperproliferative disorder.

One aspect of the invention is the detection and diagnosis of a disease or disorder associated with aberrant expression of TR4 in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that immunospecifically binds to a TR4 polypeptide; b) waiting for a time interval following the administering for permitting the labeled antibody to preferentially concentrate at sites in the subject where TR4 polypeptide is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of TR4 polypeptide. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment, the time interval following administration is 5 to 20 days or 5 to 10 days.

In one embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Therapeutic Uses of Antibodies

One or more antibodies of the present invention (including molecules comprising, or alternatively consisting of, antibody fragments or variants thereof) that immunospecifically bind to TR4 may be used locally or systemically in the body as a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for preventing or treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. In one embodiment, the antibodies of the invention can be used to treat, ameliorate or prevent diseases, disorders or conditions, including, but not limited to, any one or more of the diseases, disorders, or conditions described herein. The treatment and/or prevention of diseases, disorders, or conditions includes, but is not limited to, alleviating symptoms associated with those diseases, disorders or conditions. Antibodies of the invention may be provided in pharmaceutically acceptable compositions as known in the art or as described herein. In certain embodiments, properties of the antibodies of the present invention, as detailed in the Examples below, make the antibodies better therapeutic agents than previously described TR4 binding antibodies.

Therapeutic Uses of Antibodies for Treating Cancers

In highly preferred embodiments, antibodies of the invention that bind TR4 and stimulate apoptosis of TR4 expressing cells are used to treat, prevent or ameliorate cancer. In other highly preferred embodiments, antibodies of the invention that bind a TR4 polypeptide are used to treat, prevent or ameliorate cancer. In specific embodiments, antibodies of the invention are used to inhibit the progression or metastasis of cancers and other related disorders. Cancers and related disorders, include, but are not limited to, colon cancer, cervical cancer, leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In highly preferred embodiments, antibodies of the invention that bind TR4 and stimulate apoptosis of TR4 expressing cells are used to treat, prevent or ameliorate renal cancer.

In other preferred embodiments, antibodies of the invention that bind TR4 are used to treat, prevent or ameliorate renal cancer.

In highly preferred embodiments, antibodies of the invention that bind TR4 and stimulate apoptosis of TR4 expressing cells are used to treat, prevent or ameliorate melanoma.

In other preferred embodiments, antibodies of the invention that bind TR4 are used to treat, prevent or ameliorate melanoma.

In highly preferred embodiments, antibodies of the invention that bind TR4 and stimulate apoptosis of TR4 expressing cells are used to treat, prevent or ameliorate cancers of the liver such as hepatomas.

In other preferred embodiments, antibodies of the invention that bind TR4 are used to treat, prevent or ameliorate cancers of the liver such as hepatomas.

In highly preferred embodiments, antibodies of the invention that bind TR4 and stimulate apoptosis of TR4 expressing cells are used to treat, prevent or ameliorate cancers of the central nervous system such as medulloblastoma, neuroblastoma, and glioblastoma.

In other preferred embodiments, antibodies of the invention that bind TR4 are used to treat, prevent or ameliorate cancers of the central nervous system such as medulloblastoma, neuroblastoma, and glioblastoma.

In other preferred embodiments, antibodies of the invention that bind TR4 are used to treat, prevent or hematological cancers such as multiple myeloma, non-Hodgkin's lymphoma, chronic lymphocytic leukemia and chronic myelgenous leukemia.

In highly preferred embodiments, antibodies of the invention that bind TR4 and stimulate apoptosis of TR4 expressing cells are used to treat, prevent or ameliorate multiple myeloma.

In other preferred embodiments, antibodies of the invention that bind TR4 are used to treat, prevent or ameliorate multiple myleoma.

In other highly preferred embodiments, antibodies of the invention that bind TR4 and stimulate apoptosis of TR4 expressing cells are used to treat, prevent or ameliorate non-Hodgkin's lymphoma.

In other preferred embodiments, antibodies of the invention that bind TR4 are used to treat, prevent or ameliorate non-Hodgkin's lymphoma Non hodgkin's lymphomas, include but are not limited to, B cell lymphomas such as precursor B lymphoblastic lymphoma, small lymphocytic lymphoma, B-cell prolymphocytic lymphoma, lymphoplasmacytic lymphoma, splenic marginal zone lymphoma, extranodal marginal zone—MALT lymphoma, nodal marginal zone lymphoma, follicular lymphoma, mantle cell lymphoma, diffuse large B-cell lymphoma, primary mediastinal large B-cell lymphoma, primary effusion lymphoma and Burkitt's lymphoma) and T-cell lymphomas such as precursor (peripheral) T-cell lymphoblastic lymphoma, adult T-cell lymphoma, extranodal Natural Killer/T-cell, nasal type lymphoma, enteropathy type T-cell lymphoma, hepatosplenic T-cell lymphoma, subcutaneous panniculitis like T-cell lymphoma, skin (cutaneous) lymphomas (including mycosis fungoides and Sezary syndrome), anaplastic large cell lymphoma, peripheral T-cell, not otherwise specified lymphoma, and angioimmunoblastic T-cell lymphoma.

In other highly preferred embodiments, antibodies of the invention that bind TR4 and stimulate apoptosis of TR4 expressing cells are used to treat, prevent or ameliorate chronic lymphocytic leukemia (CLL).

In other preferred embodiments, antibodies of the invention that bind TR4 are used to treat, prevent or ameliorate chronic lymphocytic leukemia (CLL).

In other highly preferred embodiments, antibodies of the invention that bind TR4 and stimulate apoptosis of TR4 expressing cells are used to treat, prevent or ameliorate chronic myelogenous leukemia (CML).

In other preferred embodiments, antibodies of the invention that bind TR4 are used to treat, prevent or ameliorate chronic myelogenous leukemia (CML).

In highly preferred embodiments, antibodies of the invention that bind TR4 and stimulate apoptosis of TR4 expressing cells are used to treat, prevent or ameliorate prostate cancer and/or metastatic prostate cancer.

In other preferred embodiments, antibodies of the invention that bind TR4 are used to treat, prevent or ameliorate prostate cancer and/or metastatic prostate cancer.

It has been demonstrated, in accordance with the present invention that the expression of TRAIL receptor TR4 on lung carcinoma tissue, bladder carcinoma tissue and Ovarian carcinoma tissue. Additionally, it has been demonstrated, in accordance with the present invention that TRAIL receptor TR4 is expressed on primary breast, colon, lung, and stomach tumor tissue. (See Example 9).

Thus, in highly preferred embodiments, antibodies of the invention that bind TR4 and stimulate apoptosis of TR4 expressing cells are used to treat lung cancer, including but not limited to non-small cell lung cancer.

In other preferred embodiments, antibodies of the invention that bind TR4 are used to treat lung cancer, including but not limited to non-small cell lung cancer.

In other highly preferred embodiments, antibodies of the invention that bind TR4 and stimulate apoptosis of TR4 expressing cells are used to treat bladder cancer.

In other preferred embodiments, antibodies of the invention that bind TR4 are used to treat bladder cancer.

In other highly preferred embodiments, antibodies of the invention that bind TR4 and stimulate apoptosis of TR4 expressing cells are used to treat ovarian cancer.

In other preferred embodiments, antibodies of the invention that bind TR4 are used to treat ovarian cancer.

In other highly preferred embodiments, antibodies of the invention that bind TR4 and stimulate apoptosis of TR4 expressing cells are used to treat breast cancer and/or breast cancers that have metastasized.

In other preferred embodiments, antibodies of the invention that bind TR4 are used to treat breast cancer and/or breast cancers that have metastasized.

In other highly preferred embodiments, antibodies of the invention that bind TR4 and stimulate apoptosis of TR4 expressing cells are used to treat colon cancer and/or colorectal cancer.

In other preferred embodiments, antibodies of the invention that bind TR4 are used to treat colon cancer and/or colorectal cancer.

In other highly preferred embodiments, antibodies of the invention that bind TR4 and stimulate apoptosis of TR4 expressing cells are used to treat stomach cancer.

In other preferred embodiments, antibodies of the invention that bind TR4 are used to treat stomach cancer.

In other highly preferred embodiments, antibodies of the invention that bind TR4 and stimulate apoptosis of TR4 expressing cells are used to treat, prevent or ameliorate renal cancer, melanoma, pancreatic cancer and cancers of the liver such as hepatomas. In other preferred embodiments, antibodies of the invention that bind TR4 are used to treat, prevent or ameliorate renal cancer, melanoma, pancreatic cancer and cancers of the liver such as hepatomas.

In other highly preferred embodiments, antibodies of the invention that bind TR4 and stimulate apoptosis of TR4 expressing cells are used to treat, prevent or ameliorate leukemia.

In other preferred embodiments, antibodies of the invention that bind TR4 are used to treat, prevent or ameliorate leukemia.

In other highly preferred embodiments, antibodies of the invention that bind TR4 and stimulate apoptosis of TR4 expressing cells are used to treat, prevent or ameliorate myelodysplastic syndrome.

In other preferred embodiments, antibodies of the invention that bind TR4 are used to treat, prevent or ameliorate myelodysplastic syndrome.

In other highly preferred embodiments, antibodies of the invention that bind TR4 and stimulate apoptosis of TR4 expressing cells are used to treat, prevent or ameliorate bone cancers including but not limited to Ewing's sarcoma and osteosarcoma.

In other preferred embodiments, antibodies of the invention that bind TR4 are used to treat, prevent or ameliorate bone cancers including but not limited to Ewing's sarcoma and osteosarcoma.

In other highly preferred embodiments, antibodies of the invention that bind TR4 and stimulate apoptosis of TR4 expressing cells are used to treat, prevent or ameliorate bone cancers including but not limited to Ewing's sarcoma and rhabdomyosarcoma.

In other preferred embodiments, antibodies of the invention that bind TR4 are used to treat, prevent or ameliorate bone cancers including but not limited to Ewing's sarcoma and rhabdomyosarcoma.

In another embodiment, antibodies of the invention that bind TR4 and, optionally, stimulate apoptosis of TR4 expressing cells, are used to treat diseases and/or disorders associated with increased cell survival, or the inhibition of apoptosis, including cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostrate cancer, Kaposi's sarcoma and ovarian cancer); autoimmune disorders (such as multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. In preferred embodiments, the antibodies and antibody compositions of the invention are used to inhibit growth, progression, and/or metastasis of cancers, in particular those listed above. In preferred embodiments the antibodies and antibody compositions of the invention are not hepatotoxic, in vitro or in vivo.

In preferred embodiments, the antibodies of the invention that are used to treat, prevent or ameliorate the cancers described above specifically and/or preferentially bind TR4. In other preferred embodiments, the antibodies of the invention that are used to treat, prevent or ameliorate the cancers described above specifically and/or preferentially bind TR4 and TR7.

In preferred embodiments, the antibodies of the invention are used to treat, prevent or ameliorate radiation resistant cancers and/or cancers that are resistant to one or more chemotherapeutic agents or other therapeutic agents useful in the treatment of cancers.

Additional Therapeutic Uses of Antibodies

In another embodiment, the invention provides methods and compositions for inhibiting the growth of or killing TR4 expressing cells, comprising, or alternatively consisting of, administering to an animal in which such inhibition of growth or killing of TR4 expressing cells is desired, antibody or antibody compositions of the invention (e.g., antibody fragments and variants, antibody mixtures, antibody multimers, fusion proteins of the invention, and antibodies in combination with other therapeutic compounds such as chemotherapeutic agents) in an amount effective to inhibit the growth of or kill TR4 expressing cells.

In one aspect, the present invention is directed to a method for enhancing apoptosis induced by a TNF-family ligand (especially TRAIL (SEQ ID NO:66)), which involves contacting a cell which expresses a TR4 polypeptide with an effective amount of an antibody or antibody composition of the invention, preferably an agonistic anti-TR4 antibody, capable of inducing or increasing TR4 mediated signaling. In another aspect, the present invention is directed to a method for enhancing apoptosis induced by a TNF-family ligand (especially TRAIL (SEQ ID NO:66)), which involves contacting a cell which expresses a TR4 and/or TR7 polypeptide with an effective amount of an antibody or antibody composition of the invention, preferably an agonistic antibody that specifically binds both TR4 and TR7, capable of inducing or increasing TR4 and/or TR7 mediated signaling. Preferably, TR4 and/or TR7 mediated signaling is increased or induced by an antibody of the invention to treat a disease wherein decreased apoptosis or decreased cytokine and adhesion molecule expression is exhibited.

In one aspect, the present invention is directed to a method for inducing apoptosis of TR4 and/or TR7 expressing cells, which involves contacting a cell which expresses TR4 and/or TR7, with an effective amount of an antibody or antibody composition of the invention, preferably an agonistic anti-TR4, and/or an anti-TR4 and TR7 antibody (i.e., an antibody that immunospecifically binds both TR4 and TR7), capable of inducing or increasing TRAIL receptor mediated signaling, especially TR4 and TR7 mediated signalling.

In a further aspect, the present invention is directed to a method for inhibiting apoptosis induced by a TNF-family ligand (especially TRAIL (SEQ ID NO:66)), which involves contacting a cell which expresses a TR4 polypeptide, with an effective amount of an antibody or antibody composition of the invention, preferably an antagonistic anti-TR4 antibody, capable of decreasing TR4 mediated signaling. In another aspect, the present invention is directed to a method for inhibiting apoptosis induced by a TNF-family ligand (especially TRAIL (SEQ ID NO:66)), which involves contacting a cell which expresses a TR4 and/or TR7 polypeptide, with an effective amount of an antibody or antibody composition of the invention, preferably an antagonistic antibody that specifically binds both TR4 and TR7, capable of decreasing TR4 and/or TR7 mediated signaling. Preferably, TR4 and/or TR7 mediated signaling is decreased to treat a disease wherein increased apoptosis or NFκB expression is exhibited.

In one aspect, the present invention is directed to a method for inhibiting apoptosis of TR4 and/or TR7 expressing cells, which involves contacting a cell which expresses TR4 and/or TR7, with an effective amount of an antibody or antibody composition of the invention, preferably an antagonistic anti-TR4, and/or an anti-TR4 and TR7 antibody (i.e., an antibody that immunospecifically binds both TR4 and TR7), capable of decreasing TRAIL receptor mediated signaling, especially TR4 and TR7 mediated signalling.

By TR4 "agonist" is intended naturally occurring and synthetic compounds capable of enhancing or potentiating apoptosis mediated by TRAIL receptor. By TR4 "antagonist" is intended naturally occurring and synthetic compounds capable of inhibiting apoptosis mediated by TRAIL receptor. Whether any candidate "agonist" or "antagonist" of the present invention can enhance or inhibit, respectively, apoptosis can be determined using art-known TNF-family ligand/receptor cellular response assays, including those described in more detail below.

The antibodies of the invention can be used to treat, ameliorate or prevent diseases, disorders or conditions associated with aberrant expression and/or activity of TR4 or TR4 ligand, including, but not limited to, any one or more of the diseases, disorders, or conditions described herein. The treatment and/or prevention of diseases, disorders, or conditions associated with aberrant TR4 expression and/or activity or aberrant TR4 ligand expression and/or activity includes, but is not limited to, alleviating symptoms associated with those diseases, disorders or conditions. Antibodies of the invention may be provided in pharmaceutically acceptable compositions as known in the art or as described herein.

Further, antibodies of the present invention (including molecules comprising, or alternatively consisting of, antibody fragments or variants thereof) which activate TRAIL receptor-mediated biological activities (e.g., the induction of apoptosis in TRAIL receptor expressing cells) can be administered to an animal to treat, prevent or ameliorate a disease or disorder described herein, particularly cancers and other hyperproliferative disorders. These antibodies may potentiate or activate either all or a subset of the biological activities of TRAIL receptor, for example, by inducing a conformational change in TRAIL receptor. In a specific embodiment, an antibody of the present invention that increases TR4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to TR4 activity in absence of the antibody is administered to an animal to treat, prevent or ameliorate a disease or disorder. In another embodiment, a combination of antibodies, a combination of antibody fragments, a combination of antibody variants, or a combination of antibodies, antibody fragments and/or antibody variants that increase TR4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to TR4 activity in absence of the said antibodies or antibody fragments and/or antibody variants, is administered to an animal to treat, prevent or ameliorate a disease or disorder.

Further, antibodies of the present invention (including molecules comprising, or alternatively consisting of, antibody fragments or variants thereof) which activate TR4-mediated biological activities (e.g., the induction of apoptosis in TR4 expressing cells) can be administered to an animal to treat, prevent or ameliorate a disease or disorder associated with aberrant TR4 expression, lack of TR4 function, aberrant TR4 ligand expression, or lack of TR4 ligand function. These antibodies may potentiate or activate either all or a subset of the biological activities of TRAIL receptor, for example, by inducing a conformational change in TRAIL receptor. In a specific embodiment, an antibody of the present invention that increases TR4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to TR4 activity in absence of the antibody is administered to an animal to treat, prevent or ameliorate a disease or disorder associated with aberrant TR4 expression, lack of TR4 function, aberrant TR4 ligand expression, or lack of TR4 ligand function. In another embodiment, a combination of antibodies, a combination of antibody fragments, a combination of antibody variants, or a combination of antibodies, antibody fragments and/or antibody variants that increase TR4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to TR4 activity in absence of the said antibodies or antibody fragments and/or antibody variants, is administered to an animal to treat, prevent or ameliorate a disease or disorder associated with aberrant TR4 expression or lack of TR4 function or aberrant TR4 ligand expression or lack of TR4 ligand function.

Antibodies of the present invention (including molecules comprising, or alternatively consisting of, antibody fragments or variants thereof) that function as agonists or antagonists of a TRAIL receptor, preferably of TR4 signal transduction, can be administered to an animal to treat, prevent or ameliorate a disease or disorder associated with aberrant TR4 expression, lack of TR4 function, aberrant TR4 ligand expression, or lack of TR4 ligand function. For example, antibodies of the invention which mimic the action of TRAIL binding to TR4, in full or in part, TR4 agonists, may be administered to an animal to treat, prevent or ameliorate a disease or disorder associated with aberrant TR4 expression, lack of TR4 function, aberrant TR4 ligand expression, or lack of TR4 ligand function. As an alternative example, antibodies of the invention which disrupt or prevent the interaction between TR4 and its ligand or inhibit, reduce, or prevent signal transduction through TR4, may be administered to an animal to treat, prevent or ameliorate a disease or disorder associated with aberrant TR4 expression, lack of TR4 function, aberrant TR4 ligand expression, or lack of TR4 ligand function. Antibodies of the invention which do not prevent TR4 from binding its ligand but inhibit or downregulate TR4 signal transduction can be administered to an animal to treat, prevent or ameliorate a disease or disorder associated with aberrant TR4 expression, lack of TR4 function, aberrant TR4 ligand expression, or lack of TR4 ligand function. The ability of an antibody of the invention to enhance, inhibit, upregulate or downregulate TR4 signal transduction may be determined by techniques described herein or otherwise known in the art. For example, TRAIL-induced receptor activation and the activation of signaling molecules can be determined by detecting the association of adaptor proteins such as FADD and TRADD with TR4, by immunoprecipitation followed by western blot analysis (for example, as described herein).

Further, antibodies of the present invention (including molecules comprising, or alternatively consisting of, antibody fragments or variants thereof) which activate TR4-mediated biological activities (e.g., the induction of apoptosis in TR4 expressing cells) can be administered to an animal to treat, prevent or ameliorate a disease or disorder associated with aberrant TR4 expression, lack of TR4 function, aberrant TR4 ligand expression, or lack of TR4 ligand function. These antibodies may potentiate or activate either all or a subset of the biological activities of TRAIL receptor, for example, by inducing a conformational change in TRAIL receptor. In a specific embodiment, an antibody of the present invention that increases TR4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to TR4 activity in absence of the antibody is administered to an animal to treat, prevent or ameliorate a disease or disorder associated with aberrant TR4 expression, lack of TR4 function, aberrant TR4 ligand expression, or lack of TR4 ligand function. In another embodiment, a combination of antibodies, a combination of antibody fragments, a combination of antibody variants, or a combination of antibodies, antibody fragments and/or antibody variants that increase TR4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to TR4 activity in absence of the said antibodies or antibody fragments and/or antibody variants is administered to an animal to treat, prevent or ameliorate a disease or disorder associated with aberrant TR4 expression or lack of TR4 function or aberrant TR4 ligand expression or lack of TR4 ligand function.

In a specific embodiment, an antibody of the present invention (including molecules comprising, or alternatively consisting of, antibody fragments or variants thereof) that inhibits or downregulates, in full or in part, TR4 activity (e.g., stimulation of apoptosis) by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to TR4 activity in absence of the antibody is administered to an animal to treat, prevent or ameliorate a disease or disorder associated with aberrant TR4 expression, excessive TR4 function, aberrant TR4 ligand expression, or excessive TR4 ligand function. In another embodiment, a combination of antibodies, a combination of antibody fragments, a combination of antibody variants, or a combination of antibodies, antibody fragments, and/or variants that inhibit or downregulate TR4 activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to TR4 activity in absence of said antibodies, antibody fragments, and/or antibody variants, are administered to an animal to treat, prevent or ameliorate a disease or disorder associated with aberrant TR4 expression, excessive TR4 function, aberrant TR4 ligand expression, or excessive TR4 ligand function.

In one embodiment, therapeutic or pharmaceutical compositions of the invention are administered to an animal to treat, prevent or ameliorate a disease or disorder diseases associated with increased apoptosis including, but not limited to, AIDS, neurodegenerative disorders (such as Alzheimer's disease, Parkinson's disease, Amyotrophic lateral sclerosis, Retinitis pigmentosa, Cerebellar degeneration), myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. In another embodiment, therapeutic or pharmaceutical compositions of the invention are administered to an animal to treat, prevent or ameliorate bone marrow failure, for example, aplastic anemia and myelodysplastic syndrome.

Therapeutic or pharmaceutical compositions of the invention, may also be administered to treat, prevent, or ameliorate organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. Cellular death induced by immune cell effector functions is apoptotic death. Thus, the administration of antibodies of the invention, (e.g., those that inhibit apoptosis), may be an effective therapy in preventing organ rejection or GVHD.

In another embodiment, therapeutic or pharmaceutical compositions of the invention are administered to an animal to treat, prevent or ameliorate infectious diseases. Infectious diseases include diseases associated with yeast, fungal, viral and bacterial infections. Viruses associated with viral infections which can be treated or prevented in accordance with this invention include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and *cytomegalovirus*), arenavirues (e.g., lassa fever virus), paramyxoviruses (e.g., *morbillivirus* virus, human respiratory syncytial virus, mumps, and *pneumovirus*), adenoviruses, bunyaviruses (e.g., *hantavirus*), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C), papovaviruses (e.g., papillomavirues), picomaviruses (e.g., rhinoviruses, enteroviruses and hepatitis A viruses), poxviruses, reoviruses (e.g., rotavirues), togaviruses (e.g., rubella virus), rhabdoviruses (e.g., rabies virus). Microbial pathogens associated with bacterial infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (*Vibrio*) *fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori.*

In another embodiments, antibodies and antibody compositions of the present invention are used to treat, prevent, or ameliorate diseases associated with increased apoptosis including, but not limited to, AIDS, neurodegenerative disorders (such as Alzheimer's disease, Parkinson's disease, Amyotrophic lateral sclerosis, Retinitis pigmentosa, Cerebellar degeneration), brain tumor or prion associated disease); autoimmune disorders (such as, multiple sclerosis, Rheumatoid Arthritis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, anti-TR4 antagonistic antibodies, prevent TRAIL from binding to the TRAIL receptors to which the antibodies are bound, but do not transduce the biological signal that results in apoptosis) are used to treat the diseases and disorders listed above.

Many of the pathologies associated with HIV are mediated by apoptosis, including HIV-induced nephropathy and HIV encephalitis. Thus, in additional preferred embodiments, antibodies, preferably antagonistic anti-TR4 antibodies, of the invention are used to treat AIDS and pathologies associated with AIDS. Another embodiment of the present invention is directed to the use of antibodies of the invention to reduce TRAIL-mediated death of T cells in HIV-infected patients.

In additional embodiments, antibodies of the present invention, particularly antagonistic anti-TR4 antibodies, are administered in combination with other inhibitors of T cell apoptosis. For example, Fas-mediated apoptosis has been implicated in loss of T cells in HIV individuals (Katsikis et al., *J Exp. Med.* 181:2029-2036, 1995). Thus, a patient susceptible to both Fas ligand mediated and TRAIL mediated T cell death may be treated with both an agent that blocks TRAIL/TR4 interactions and an agent that blocks Fas-ligand/Fas interactions. Suitable agents for blocking binding of Fas-ligand to Fas include, but are not limited to, soluble Fas polypeptides; mulitmeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in International application publication number WO 95/10540, hereby incorporated by reference.

Suitable agents, which also block binding of TRAIL to a TR4 that may be administered with the antibodies of the present invention include, but are not limited to, soluble TR4 polypeptides (e.g., a soluble form of OPG, TR5 (International application publication number WO 98/30693); a soluble form of TR4 (International publication number WO 98/32856); TR7/DR5 (International application publication number WO 98/41629); and TR10 (International application publication number WO 98/54202)); multimeric forms of soluble TR4 polypeptides; and TR4 antibodies that bind the TR4 without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Antibodies of the present invention (e.g., agonistic antibodies of the invention) are able to suppress the immune response to both allografts and xenografts because lymphocytes activated and differentiated into effector cells will express the TR4 polypeptides, and thereby are susceptible to compounds which enhance apoptosis. Thus, the present invention further provides a method for creating immune privileged tissues. Antagonist of the invention can further be used in the treatment of Inflammatory Bowel-Disease.

Antibodies and antibody compositions of the invention may be useful for treating inflammatory diseases, such as rheumatoid arthritis, osteoarthritis, psoriasis, septicemia, and inflammatory bowel disease.

In addition, due to lymphoblast expression of TR4 polypeptides, antibodies and antibody compositions of the invention may be used to treat this form of cancer. Further, antibodies and antibody compositions of the invention may be used to treat various chronic and acute forms of inflammation such as rheumatoid arthritis, osteoarthritis, psoriasis, septicemia, and inflammatory bowel disease.

In one embodiment, antibodies and antibody compositions of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic venoocclusive disease, hypertension, hypotension, ischemia, peripheral vascular diseases, phlebitis, pulmonary venoocclusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In one embodiment, antibodies and antibody compositions of the invention is used to treat thrombotic microangiopathies. One such disorder is thrombotic thrombocytopenic purpura (TTP) (Kwaan, H. C., *Semin. Hematol.* 24:71 (1987); Thompson et al., *Blood* 80:1890 (1992)). Increasing TTP-associated mortality rates have been reported by the U.S. Centers for Disease Control (Torok et al., *Am. J. Hematol.* 50:84 (1995)). Plasma from patients afflicted with TTP (including HIV+ and HIV− patients) induces apoptosis of human endothelial cells of dermal microvascular origin, but not large vessel origin (Laurence et al., *Blood* 87:3245 (1996)). Plasma of TTP patients thus is thought to contain one or more factors that directly or indirectly induce apoptosis. As described in International patent application number WO 97/01715 (hereby incorporated by reference), TRAIL is present in the serum of TTP patients, and is likely to play a role in inducing apoptosis of microvascular endothelial cells. Another thrombotic microangiopathy is hemolytic-uremic syndrome (HUS) (Moake, J. L., *Lancet*, 343:393 (1994); Melnyk et al., (*Arch. Intern. Med.*, 155:2077 (1995); Thompson et al., supra). Thus, in one embodiment, the invention is directed to use of antibodies and antibody compositions of the invention to treat the condition that is often referred to as "adult HUS" (even though it can strike children as well). A disorder known as childhood/diarrhea-associated HUS differs in etiology from adult HUS. In another embodiment, conditions characterized by clotting of small blood vessels may be treated using of antibodies and antibody compositions of the invention. Such conditions include, but are not limited to, those described herein. For example, cardiac problems seen in about 5-10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated. In one embodiment, antibodies and antibody compositions of the invention, preferably antagonistic anti-TR4 antibodies of the invention, may be administered in vivo to a patient afflicted with a thrombotic microangiopathy. Thus, the present invention provides a method for treating a thrombotic microangiopathy, involving use of an effective amount of an antibody or antibody composition of the invention.

Antibodies and antibody compositions of the invention may be employed in combination with other agents useful in treating a particular disorder. For example, in an in vitro study reported by Laurence et al. (Blood 87:3245 (1996)), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated with an antibody or antibody composition of the invention in combination with an agent that inhibits Fas-ligand-mediated apoptosis of endothelial cells, such as, for example, an agent described above. In one embodiment, antibodies of the invention and an anti-FAS blocking antibody are both administered to a patient afflicted with a disorder characterized by thrombotic microangiopathy, such as TTP or HUS. Examples of blocking monoclonal antibodies directed against Fas antigen (CD95) are described in International patent application publication number WO 95/10540, hereby incorporated by reference.

The naturally occurring balance between endogenous stimulators and inhibitors of angiogenesis is one in which inhibitory influences predominate (Rastinejad et al., *Cell* 56:345-355 (1989)). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:710-714 (1991); Folkman et al., *N. Engl. J. Med.*, 353:1757-1771 (1995); Auerbach et al., *J. Microvasc. Res.* 29:401-411 (1985); Folkman, *Advances in Cancer Research*, eds. Klein and Weinhouse, Academic Press, New York, pp. 175-203 (1985); Patz, *Am. J. Opthalmol.* 94:715-743 (1982); and Folkman et al., *Science* 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442447 (1987).

The present invention provides for treatment of diseases or disorders associated with neovascularization by administration of an antibody or antibody compositions of the invention. Malignant and metastatic conditions which can be treated with the polynucleotides and polypeptides of the invention include, but are not limited to those malignancies, solid tumors, and cancers described herein and otherwise known in the art (for a review of such disorders, see Fishman et al., *Medicine*, 2d Ed., J. B. Lippincott Co., Philadelphia (1985)).

Additionally, ocular disorders associated with neovascularization which can be treated with an antibody or antibody composition of the invention include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Additionally, disorders which can be treated with an antibody or antibody composition of the invention include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Antibodies and antibody compositions of the invention are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.))), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, autoimmune lymphoproliferative syndrome (ALPS), immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Antibodies and antibody compositions of the invention are useful in promoting angiogenesis, wound healing (e.g., wounds, burns, and bone fractures).

Antibodies and antibody compositions of the invention are also useful as an adjuvant to enhance immune responsiveness to specific antigen, such as in anti-viral immune responses.

More generally, antibodies and antibody compositions of the invention are useful in regulating (i.e., elevating or reducing) immune response. For example, antibodies and antibody compositions of the invention may be useful in preparation or recovery from surgery, trauma, radiation therapy, chemotherapy, and transplantation, or may be used to boost immune response and/or recovery in the elderly and immunocompromised individuals. Alternatively, antibodies and antibody compositions of the invention are useful as immunosuppressive agents, for example in the treatment or prevention of autoimmune disorders. In specific embodiments, antibodies and antibody compositions of the invention are used to treat or prevent chronic inflammatory, allergic or autoimmune conditions, such as those described herein or are otherwise known in the art.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer antibody or fragment or variant thereof of the invention, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, intracerebral, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g, in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1535 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the composition can be delivered in a controlled release system. In one embodiment, a pump may be used (see Langer, supra; Sefton, CRC Crit. Ref Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:71 (1983); see also Levy et al., Science 228:190 (1985); During et al., Ann. Neurol. 25:35 1 (1989); Howard et al., J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1535 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg (e.g., 3 mg/kg or 5 mg/kg) of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

Antibodies of the invention may be formulated in pharmaceutically acceptable carriers. A formulation of an antibody of the invention may comprise a buffer. Buffers are well-known in the art and may be routinely applied to maintain the desired pH of the solution compositions of the invention. Suitable buffers for use in the preparation of a pharmaceutical composition of the invention include, for example, those described below.

Suitable buffers for use in the preparation of a antibody composition of the invention may include, but are not limited to, citrate, acetate, phosphate, carbonate, diphosphate, glycyl-glycine-piperazine-2HCl—NaOH; MES-NaOH—NaCl; TRIS-malic acid-NaOH; MES-NaOH; ACES-NaOH—NaCl; BES-NaOH—NaCl; MOPS-NaOH—NaCl; TES-NaOH—NaCl; MOPS-KOH; HEPES-NaOH—NaCl; TRIS-HCl; HEPPSO-NaOH; TAPS-NaOH—NaCl; HEPPS (EPPS)-NaOH; citric acid-disodiumhydrogenphosphate; boric acid-citric acid-potassium dihydrogen phosphate-Diethyl-barbituric acid-NaOH; citric acid-sodium citrate; sodium acetate-acetic acid; histidine; phosphate; potassium hydrogenphthalate-NaOH; cacodylic acid sodium salt-HCl; potassium dihydrogen phosphate-disodium hydrogenphosphate; potassium dihydrogen-phosphate-NaOH; sodium dihydrogen phosphate-disodium hydrogen phosphate; imidazole-HCl; sodium tetraborate-boric acid; 2-amino-2-methyl-1,3-propanediol-HCl; diethanolamine-HCl; potassium chloride-boric acid-NaOH; boric acid-NaOH—KCl; glycine-NaOH; and sodium carbonate-sodium hydrogen carbonate.

In one embodiment, the buffer is a citrate buffer or an acetate buffer. In another embodiment, the buffer includes an acetate buffer having a concentration of about 1 to about 50 mM and having a NaCl concentration of about 1 to about 500 mM. In another embodiment, the buffer includes an acetate buffer having a concentration of about 10 mM and having a NaCl concentration of about 140 mM. Suitable acetate buffers include acetate buffers having a concentration of about 1, 20, 25, 50, 75, 100, 200, 250, 300, 400, or 500 mM. Suitable buffers and solutions include those having a NaCl concentration of about 1, 50, 75, 100, 125, 140, 150, 175, 200, 225, 250, 275, 300, 350, 400, 450, or 500 mM. An additional suitable buffer is a HEPES buffer, in particular a HEPES buffer having a concentration of about 10, 20, 30, 40, 50, 60, 70, 80, 90, or 100 mM. In an additional embodiment, the solution comprises a HEPES buffer having a concentration of about 50 mM.

In other embodiments, antibodies of the invention are formulated in a citrate buffered solution that has a pH in the range of 5.5 to 6.5. In further embodiments, antibodies of the invention are formulated in a citrate buffered solution that has a pH of approximately or exactly 6.0. In other embodiments, antibodies of the invention are formulated in a citrate buffered solution that has a pH in the range of 5.5 to 6.5 and which also contains between 0 and 2.0%, preferably between 0 and 0.1% and more preferably less than 0.05%, of a surfactant such as Tween 80 or polysorbate 80.

In one embodiment, antibodies of the invention are formulated in 10 mM sodium citrate, 1.9% glycine, 0.5% sucrose, 0.02% polysorbate 80, pH 6.5.

In other embodiments, antibodies of the invention are formulated in a histidine buffered solution that has a pH in the range of 6.5 to 7.5. In other embodiments, antibodies of the invention are formulated in a histidine buffered solution that has a pH in the range of 6.5 to 7.5 and which also contains between 0 and 2.0%, preferably between 0 and 0.1% and more preferably less than 0.05%, of a surfactant such as Tween 80 or polysorbate 80.

In other embodiments, antibodies of the invention are formulated in a phosphate buffered solution that has a pH in the range of 7.0 to 8.0. In other embodiments, antibodies of the invention are formulated in a phosphate buffered solution that has a pH in the range of 7.0 to 8.0 and which also contains between 0 and 2.0%, preferably between 0 and 0.1% and more preferably less than 0.05%, of a surfactant such as Tween 80 or polysorbate 80.

Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent in vivo inhibiting and/or neutralizing antibodies of the invention (including molecules comprising, or alternatively consisting of, antibody fragments or variants thereof) that immunospecifically bind to TR4, or polynucleotides encoding antibodies that immunospecifically bind to TR4, for both immunoassays and therapy of disorders related to TR4 polynucleotides or polypeptides, including fragments thereof. Such antibodies will preferably have an affinity for TR4 and/or TR4 polypeptide fragments. Preferred binding affinities include those with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind TR4 polypeptides or fragments or variants thereof with a dissociation constant or $K_D$ less than or equal to $5\times10^{-6}$ M, $10^{-6}$ M, $5\times10^{-7}$ M, $10^{-7}$M, $5\times10^{-8}$ M, or $10^{-8}$ M. Even more preferably, antibodies of the invention bind TR4 polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In a preferred embodiment, antibodies of the invention induce apoptosis of TR4 expressing cells.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibody and antibody compositions of the invention may be administered alone or in combination with other therapeutic agents, including but not limited to chemotherapeutic agents, antibiotics, antivirals, anti-retroviral agents, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In preferred embodiments, antibodies of the invention that are administered to an animal, preferably a human, for therapeutic uses are multimeric antibodies. In specific embodiments, antibodies of the invention are homodimeric IgG molecules. In other specific embodiments, antibodies of the invention are homodimeric IgG1 molecules. In specific embodiments, antibodies of the invention are homotrimeric IgG molecules. In other specific embodiments, antibodies of the invention are trimeric IgG1 molecules. In other specific embodiments, antibodies of the invention are higher-order multimers of IgG molecules (e.g., tetramers, penatmers and hexamers]. In still further specific embodiments, antibodies of the IgG molecules comprising the higher order multimers of IgG molecules are IgG1 molecules.

Alternatively, antibodies of the invention for therapeutic uses may be administered in combination with crosslinking agents known in the art, including but not limited to, anti-IgG antibodies.

Combination Therapies with Anti-TR4 Antibodies, TRAIL, Apoptosis Inducing Peptides and/or Chemotherapeutic Agents Anti-TR4 antibodies may be administered in combination with other anti-TR4 antibodies, TRAIL, chemotherapeutics and/or other therapeutic agents useful in the treatment of cancers.

In specific embodiments, an antibody of the invention that specifically binds TR4 is used or administered in combination with a second antibody that specifically binds TR7. In another embodiment, the antibodies specific for TR4 and TR7 are agonistic antibodies that induce apoptosis of TR4 expressing cells (e.g., cells that express TR4 and TR7). In a specific embodiment, the combination of anti-TR4 treatment and anti-TR7 treatment induces more apoptosis of TR4 and TR7 expressing cells than either anti-TR4 antibody treatment or anti-TR7 antibody treatment alone. The anti-TR4 and anti-TR7 antibodies can be administered either simultaneously, sequentially, or a combination of simultaneous or sequential administration throughout the dosage regimen. In another specific embodiment anti-TR4 and anti-TR7 antibodies are used or administered in combination with a chemotherapeutic drug, such as those described herein (see, for example, below and Example 4). In a particular embodiment, the synergistic induction of apoptosis resulting from anti-TR4 and anti-TR7 antibody treatment, is more evident or more pronounced when the anti-TR4 and anti-TR7 antibodies are used or administered in combination with a chemotherapeutic agent and/or a cross-linking reagent.

In a specific embodiment, antibodies or antibody compositions of the invention are administered in combination with $DAB_{389}EGF$, a diphtheria toxin fused to Epidermal Growth Factor. $DAB_{389}EGF$ is described in Shaw et al., (1991) *The Journal of Biological Chemistry*, 266:21118-24, which is hereby incorporated by reference in its entirety. In a specific embodiment, antibodies or antibody compositions of the invention are administered in combination with $DAB_{389}EGF$ for the treatment of cancer, such as brain cancers and epithelial cancers. In a specific embodiment, antibodies or antibody compositions of the invention are administered in combination with $DAB_{389}EGF$ for the treatment of astrocytomas. In a specific embodiment, antibodies or antibody compositions of the invention are administered in combination with DAB$_{389}$EGF for the treatment of glioblastyoma multiforme (GBM).

In a preferred embodiment, compositions of the invention are administered in combination with a chemotherapeutic agent. Chemotherapeutic agents that may be administered with the compositions of the invention include, but are not limited to, antibiotic derivatives (e.g., doxorubicin (adriamycin), bleomycin, daunorubicin, and dactinomycin); anti-estrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, etoposide, Topotecan, 5-Fluorouracil, paclitaxel (Taxol), Cisplatin, Cytarabine, and IFN-gamma, irinotecan (Camptosar, CPT-11), irinotecan analogs, gemcitabine ((GEMZAR™), and oxaliplatin, ifosamide, nitosourea compounds).

Therapeutic agents, useful in the treatment, prevention, amelioration and/or cure of cancers, with which antibodies of the present invention may be administered, include, for example, biological agents (e.g., inhibitors of signaling pathways, inhibitors of gene transcription, inhibitors of multi-drug resistance (MDR) mechanisms, inhibitors of angiogenesis, inhibitors of matrix metalloproteinases, proteasome inhibitors, hormones and hormone antagonists, and compounds of unknown mechanism), chemotherapeutic agents (e.g., alkylating agents, antimetabolites, farnesyl transferase inhibitors, mitotic spindle inhibitors (plant-derived alkaloids), nucleotide analogs, platinum analogs, and topoisomerase inhibitors), corticosteroids, gene therapies, immunotherapeutic agents (e.g., monoclonal antibodies, cytokines and vaccines), phototherapy, radiosensitizing agents, treatment support agents (e.g., anti-emetic agents, analgesic agents and hematopoietic agents), and other miscellaneous drug types. Therapeutic procedures, useful in the treatment, prevention, amelioration and/or cure of cancers, with which agonistic antibodies of the present invention may be administered, include, for example, but are not limited to, surgical procedures and radiation therapies.

In preferred embodiments, agonistic antibodies of the invention are administered in combination with one or more of the above-described therapeutic agents in the treatment, prevention, amelioration and/or cure of cancers.

In specific embodiments, antibodies of the present invention may be administered in combination with one or more chemotherapeutic or other therapeutic agents useful in the treatment, prevention, amelioration and/or cure of cancers including, but not limited to, 81C6 (Anti-tenascin monoclonal antibody), 2-chiorodeoxyadenosine, A007 (4-4'-dihydroxybenzophenone-2, 4-dinitrophenyihydrazone), Abarelix (Abarelix-Depot-M®, PPI-149, R-3827); Abiraterone acetate (CB-7598, CB-7630), ABT-627 (ET-1 inhibitor), ABX-EGF (anti-EGFr MAb), Acetyldinaline (CI-994, GOE-5549, GOR-5549, PD-130636), AG-2034 (AG-2024, AG-2032, GARFT [glycinamide ribonucleoside transformylase] inhibitor), Alanosine, Aldesleukin (IL-2, Proleukin®), Alemtuzumab (Campath®), Alitretinoin (Panretin®, LGN-1057), Allopurinol (Aloprim®, Zyloprim®), Altretamine (Hexalen®, hexamethylmelamine, Hexastat®), Amifostine (Ethyol®), Aminocamptothecin (9-AC, 9-Aminocamptothecin, NSC 603071), Aminoglutethimide (Cytadren®), Aminolevulinic acid (Levulan®, Kerastick®), Aminopterin, Amsacrine, Anastrozole (Arimidex®), Angiostatin, Annamycin (AR-522, annamycin LF, Aronex®), Anti-idiotype therapy (BsAb), Anti-CD19/CD3 MAb (anti-CD19/CD3 scFv, anti-NHL MAb), APC-8015 (Provenge®, Dendritic cell therapy), Aplidine (Aplidin®, Aplidina®), Arabinosylguanine (Ara-G, GW506U78, Nelzarabine, Compound 506U78), Arsenic trioxide (Trisenox®, ATO, Atrivex®), Avorelin (Meterelin®, MF-6001, EP-23904), B43-Genistein (anti-CD19 Ab/genistein conjugate), B43-PAP (anti-CD19 Ab/pokeweed antiviral protein conjugate), B7 antibody conjugates, BAY 43-9006 (Raf kinase inhibitor), BBR 3464, Betathine (Beta-LT), Bevacizumab (Anti-VEGF monoclonal antibody, rhuMAb-VEGF), Bexarotene (Targretin®, LGD1069), BIBH-1 (Anti-FAP MAb), BIBX-1382, Biclutamide (Casodex®), Biricodar dicitrate (Incel®, Incel MDR Inhibitor), Bleomycin (Blenoxane®), BLP-25 (MUC-1 peptide), BLyS antagonists, BMS-214662 (BMS-192331, BMS-193269, BMS-206635), BNP-1350 (BNPI-1100, Karenitecins), Boronated Protoporphyrin Compound (PDIT, Photodynamic Immunotherapy), Bryostatin-1, (BMY-45618, NSC-339555), Budesonide (Rhinocort®), Busulfan (Busulfex®, Myleran®), C225 (IMC-225, EGFR inhibitor, Anti-EGFr MAb, Cetuximab), C242-DM1 (huC242-DM1), Cabergoline (Dostinex®), Capecitabine (Xeloda®, Doxifluridine, oral 5-FU), Carbendazin® (FB-642), Carboplatin (Paraplatin®, CBDCA), Carboxyamidotriazole (NSC 609974, CAI, L-651582), Carmustine (DTI-015, BCNU, BiCNU, Gliadel Wafer®), CC49-zeta gene therapy, CEA-cide® (Labetuzumab, Anti-CEA monoclonal antibody, hMN-14), CeaVac® (MAb 3H1), Celecoxib (Celebrex®), CEP-701 (KT-5555), Cereport® (Lobradimil, RMP-7), Chlorambucil (Leukeran®), CHML (Cytotropic Heterogeneous Molecular Lipids), Cholecaliferol, CI-1033 (Pan-erbB RTK inhibitor), Cilengitide (EMD-121974, integrin alphavbeta3 antagonist), Cisplatin (Platinol®, CDDP), Cisplatin-epinephrine gel (IntraDose®, FocaCist®), Cisplatin-liposomal (SPI-077), 9-cis retinoic acid (9-cRA), Cladribine (2-CdA, Leustatin®), Clofarabine (chloro-fluoro-araA), Clonadine hydrochloride (Duraclon®), CMB-401 (Anti-PEM MAb/calicheamycin), CMT-3 (COL-3, Metastat®), Cordycepin, Cotara® (chTNT-1/B, [$^{131}$I]chTNT-1/B), CN-706, CP-358774 (Tarceva®, OSI-774, EGFR inhibitor), CP-609754, CP IL-4-toxin (IL-4 fusion toxin), CS-682, CT-2584 (Apra®, CT-2583, CT-2586, CT-3536), CTP-37 (Avicine®, hCG blocking vaccine), Cyclophosphamide (Cytoxan®, Neosar®, CTX), Cytarabine (Cytosar-U®, ara-C, cytosine arabinoside, DepoCyt®), D-limonene, DAB389-EGF (EGF fusion toxin), Dacarbazine (DTIC), Daclizumab® (Zenapax®), Dactinomycin (Cosmegen®), Daunomycin (Daunorubicin®, Cerubidine®), Daunorubicin (DaunoXome®, Daunorubicin®, Cerubidine®), DeaVac® (CEA anti-idiotype vaccine), Decitabine (5-aza-2'-deoxyytidine), Declopramide (Oxi-104), Denileukin diftitox (Ontak®), Depsipeptide (FR901228, FK228), Dexamethasone (Decadron®), Dexrazoxane (Zinecard®), Diethylnorspermine (DENSPM), Diethylstilbestrol (DES), Dihydro-5-azacytidine, Docetaxel (Taxotere®, Taxane®), Dolasetron mesylate (Anzemet®), Dolastatin-10 (DOLA-10, NSC-376128), Doxorubicin (Adriamycin®, Doxil®, Rubex®), DPPE, DX-8951f (DX-8951), Edatrexate, EGF-P64k Vaccine, Elliott's B Solution®, EMD-121974, Endostatin, Eniluracil (776c85), EO9 (EO1, EO4, EO68, EO70, EO72), Epirubicin (Ellence®, EPI, 4' epi-doxorubicin), Epratuzumab (Lymphocide®, humanized anti-CD22, HAT), Erythropoietin (EPO®, Epogen®, Procrit®), Estramustine (Emcyt®), Etanidazole (Radinyl®), Etoposide phosphate (Etopophos®), Etoposide (VP-16, Vepesid®), Exemestane (Aromasin®, Nikidess®), Exetecan mesylate (DX-8951, DX-8951 f), Exisulind (SAAND, Aptosyn®, cGMP-PDE2 and 5 inhibitor), F19 (Anti-FAP monoclonal antibody, iodinated anti-FAP MAb), Fadrozole (Afema®, Fadrozole hydrochloride, Arensin®), Fenretinide® (4HPR), Fentanyl citrate (Actiq®), Filgrastim (Neupogen®, G-CSF), FK-317 (FR-157471, FR-70496), Flavopiridol (HMR-1275), Fly3/flk2 ligand (Mobista®), Fluasterone, Fludarabine (Fludara®, FAMP), Fludeoxyglucose (F-18®), Fluorouracil (5-FU, Adrucil®, Fluoroplex®, Efudex®), Flutamide (Eulexin®), FMdC (KW-2331, MDL-101731), Formestane (Lentaron®), Fotemustine (Muphoran®, Mustophoran®), FUDR (Floxuridine®), Fulvestrant (Faslodex®), G3139 (Genasense®, GentaAnticode®, Bcl-2 antisense), Gadolinium texaphyrin (Motexafin gadolinium, Gd-Tex®, Xcytrin®), Galarubicin hydrochloride (DA-125), GBC-590, Gastrimmune® (Anti-gastrin-17 immunogen, anti-g17), Gemcitabine (Gemto®, Gemzar®), Gentuzumab-ozogamicin (Mylotarg®), GL331, Globo H hexasaccharide (Globo H-KLH®), Glufosfamide® (β-D-glucosyl-isofosfamide mustard, D19575, INN), Goserelin acetate (Zoladex®), Granisetron (Kytril®), GVAX (GM-CSF gene therapy), Her-2/Neu vaccine, Herceptin® (Trastuzumab, Anti-HER-2 monoclonal antibody, Anti-EGFR-2 MAb), HSPPC-96 (HSP cancer vaccine, gp96 heat shock protein-peptide complex), Hu1D10 (anti-HLA-DR MAb, SMART 1D10), HumaLYM (anti-CD20 MAb), Hydrocortisone, Hydroxyurea (Hydrea®), Hypericin (VIMRxyn®), I-131 Lipidiol, Ibritumomab tiuxetan (Zevalin®), Idarubicin (Idamycin®, DMDR, IDA), Ifosfamide (IFEX®), Imatinib mesylate (STI-571, Imatinib®, Glivec®, Gleevec®, Ab1 tyrosine kinase inhibitor), INGN-101 (p53 gene therapy/retrovirus), INGN-201 (p53 gene therapy/adenovirus), Interferon alpha (Alfaferone®, Alpha-IF®), Interferon alpha 2a (Intron A®), Interferon gamma (Gamma-interferon, Gamma 100®, Gamma-IF), Interleukin-2 (ProleiukinR®), Intoplicine (RP 60475), Irinotecan (Camptosar®, CPT-11, Topotecin®, CaptoCPT-1), Irofulven (MGI-114, Ivofulvan, Acylfulvene analogue), ISIS-2053 (PKC-alpha antisense), ISIS-2503 (Ras antisense), ISIS-3521 (PKC-alpha antisense), ISIS-5132 (K-ras/raf antisense), Isotretinoin (13-CRA, 13-cis retinoic acid, Accutane®), Ketoconazole (Nizoral®), KRN-8602 (MX, MY-5, NSC-619003, MX-2), L-778123 (Ras inhibitors), L-asparaginase (Elspar®, Crastinin®, Asparaginase medac®, Kidrolase®), Leflunomide (SU-101, SU-0200), Letrozole (Femara®), Leucovorin (Leucovorin®, Wellcovorin®), Leuprolide acetate (Viadur®, Lupron®, Leuprogel®, Eligard®), Leuvectin® (cytofectin+IL-2 gene, IL-2 gene therapy), Levamisole (Ergamisol®), Liarozole (Liazal, Liazol, R-75251, R-85246, Ro-85264), Lmb-2 immunotoxin (anti-CD25 recombinant immuno toxin, anti-Tac(Fv)-PE38), Lometrexol (T-64, T-904064), Lomustine (CCNU®, CeeNU®), LY-335979, Lym-1 (131-I LYM-1), Lymphoma vaccine (Genitope), Mannan-MUC1 vaccine, Marimastat® (BB-2516, TA-2516, MMP inhibitor), MDX-447 (MDX-220, BAB-447, EMD-82633, H-447, anti-EGFr/FcGammaR1r), Mechlorethamine (Nitrogen Mustard, $HN_2$, Mustargen®), Megestrol acetate (Megace®, Pallace®), Melphalan (L-PAM, Alkeran®, Phenylalanine mustard), Mercaptopurine (6-mercaptopurine, 6-MIP), Mesna (Mesnex®), Methotrexate (MTX, Mexate®, Folex®), Methoxsalen (Uvadex®), 2-Methoxyestradiol (2-ME, 2-ME2), Methylprednisolone (Solumedrol®), Methyltestosterone (Android-10®, Testred®, Virilon®), MGV, Mitomycin C (Mitomycin®, Mutamycin®, Mito Extra®), Mitoxantrone (Novantrone®, DHAD), Mitumomab (BEC-2, EMD-60205), Mivobulin isethionate (CI-980), MN-14 (Anti-CEA immunoradiotherapy, $^{131}$I-MN-14, $^{188}$Re-MN-14), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Nelarabine (Compound 506, U78), Neovastat® (AE-941, MMP inhibitor), Neugene compounds (Oncomyc-NG, Resten-NG, myc antisense), Nilutamide (Nilandron®), NovoMAb-G2 scFv (NovoMAb-G2 IgM), 06-benzylguanine (BG, Procept®), Octreotide acetate (Sandostatin LAR® Depot), Odansetron (Zofran®), Onconase (Ranpirnase®), OncoVAX-CL, OncoVAX-CL Jenner (GA-733-2 vaccine), OncoVAX-P (OncoVAX-PrPSA), Onyx-015 (p53 gene therapy), Oprelvekin (Neumage®), Orzel (Tegafur+Uracil+Leucovorin), Oxaliplatin (Eloxatine®, Eloxatin®), Pacis® (BCG, live), Paclitaxel (Paxene®, Taxol®), Paclitaxel-DHA (Taxoprexin®), Pamidronate (Aredia®), PC SPES, Pegademase (Adagen®, Pegademase bovine), Pegaspargase (Oncospar®), Peldesine (BCX-34, PNP inhibitor), Pemetrexed disodium (Alimta®, MTA, multitargeted antifolate, LY 231514), Pentostatin (Nipent®, 2-deoxycoformycin), Perfosfamide (4-hydroperoxycyclophosphamide, 4-HC), Perillyl alcohol (perilla alcohol, perillic alcohol, perillol, NSC-641066), Phenylbutyrate, Pirarubicin (THP), Pivaloyloxymethyl butyrate (AN-9, Pivanex®), Porfimer sodium (Photofrin®), Prednisone, Prinomastat® (AG-3340, MMP inhibitor), Procarbazine (Matulane®), PROSTVAC, Providence Portland Medical Center Breast Cancer Vaccine, PS-341 (LDP-341, 26S proteasome inhibitor), PSMA MAb (Prostate Specific Membrane Antigen monoclonal antibody), Pyrazoloacridine (NSC-366140, PD-115934), Quinine, R115777 (Zarnestra®), Raloxifene hydrochloride (Evista®, Keoxifene hydrochloride), Raltitrexed (Tomudex®, ZD-1694), Rebeccamycin, Retinoic acid, R-flurbiprofen (Flurizan®, E-7869, MPC-7869), RFS-2000 (9-nitrocamptothecan, 9-NC, rubitecan®), Rituximab (Rituxan®, anti-CD20 MAb), RSR-13 (GSJ-61), Satraplatin (BMS-182751, JM-216), SCH 6636, SCH-66336, Sizofilan (SPG, Sizofiran, Schizophyllan, Sonifilan), SKI-2053R (NSC-D644591), Sobuzoxane (MST-16, Perazolin®), Squalamine (MSI-1256F), SR-49059 (vasopressin receptor inhibitor, V1a), Streptozocin (Zanosar®), SU5416 (Semaxanib®, VEGF inhibitor), SU6668 (PDGF-TK inhibitor), T-67 (T-138067, T-607), Talc (Sclerosol®), Tamoxifen (Nolvadex®), Taurolidine (Taurolin®), Temozolamide (Temodar®, NSC 362856), Teniposide (VM-26, Vumon®), TER-286, Testosterone (Andro®, Androderm®, Testoderm TTS®, Testoderm®, Depo-Testosterone®, Androgel®, depoAndro®), Tf-CRM 107 (Transferrin-CRM-107), Thalidomide, Theratope, Thioguanine (6-thioguanine, 6-TG), Thiotepa (triethylenethiophosphaoramide, Thioplex®), Thymosin alpha I (Zadaxin®, Thymalfasin®), Tiazofurin (Tiazole®), Tirapazamine (SR-259075, SR-4233, Tirazone®, Win-59075), TNP-470 (AGM-1470, Fumagillin), Tocladesine (8-Cl-cAMP), Topotecan (Hycamtin®, SK&F-104864, NSC-609699, Evotopin®), Toremifene (Estrimex®, Fareston®), Tositumomab (Bexxar®), Tretinoin (Retin-A®, Atragen®, ATRA, Vesanoid®), TriAb® (antiidiotype antibody immune stimulator), Trilostane (Modrefen®), Triptorelin pamoate (Trelstar Depot®, Decapeptyl®), Trimetrexate (Neutrexin®), Troxacitabine (BCH-204, BCH-4556, Troxatyl®), TS-1, UCN-01 (7-hydroxystaurosporine), Valrubicin (Valstar®), Valspodar (PSC 833), Vapreotide® (BMY-41606), Vaxid (B-cell lymphoma DNA vaccine), Vinblastine (Velban®, VLB), Vincristine (Oncovin®, Onco TCS®, VCR, Leurocristine®), Vindesine (Eldisine®, Fildesin®), Vinorelbine (Navelbine®), Vitaxin® (LM-609, integrin alphavbeta3 antagonistic MAb), WF10 (macrophage regulator), WHI-P131, WT1 Vaccine, XR-5000 (DACA), XR-9576 (XR-9351, P-glycoprotein/MDR inhibitor), ZD-9331, ZD-1839 (IRESSA®), and Zoledronate (Zometa®).

In one embodiment, antibodies of the present invention may be administered in combination with a taxane. In another embodiment, antibodies of the present invention may be administered in combination with a taxane for the treatment of cancers that are resistant to individual chemotherapies. In a specific embodiment, antibodies of the present invention may be administered in combination with Docetaxel (Taxotere®). In a specific embodiment, antibodies of the present invention may be administered in combination with Docetaxel (Taxotere®) for the treatment of cancers that are resistant to individual chemotherapies.

In one embodiment, agonistic antibodies of the present invention may be administered in combination with a taxane. In another embodiment, agonistic antibodies of the present invention may be administered in combination with a taxane for the treatment of cancers that are resistant to individual chemotherapies. In a specific embodiment, agonistic antibodies of the present invention may be administered in combination with Docetaxel (Taxotere®). In a specific embodiment, agonistic antibodies of the present invention may be administered in combination with Docetaxel (Taxotere®) for the treatment of cancers that are resistant to individual chemotherapies.

In one embodiment, antibodies of the present invention may be administered in combination with a platinum-based chemotherapeutic. In another embodiment, antibodies of the present invention may be administered in combination with a platinum-based chemotherapeutic for the treatment of cancers that are resistant to individual chemotherapies. In another specific embodiment, antibodies of the invention may be administered in combination with Carboplatin (Paraplatin®, CBDCA). In another specific embodiment, antibodies of the present invention may be administered in combination with Carboplatin (Paraplatin®, CBDCA) for the treatment of cancers that are resistant to individual chemotherapies.

In one embodiment, agonistic antibodies of the present invention may be administered in combination with a platinum-based chemotherapeutic. In another embodiment, agonistic antibodies of the present invention may be administered in combination with a platinum-based chemotherapeutic for the treatment of cancers that are resistant to individual chemotherapies. In another specific embodiment, agonistic antibodies of the invention may be administered in combination with Carboplatin (Paraplatin®, CBDCA). In another specific embodiment, agonistic antibodies of the present invention may be administered in combination with Carboplatin (Paraplatin®, CBDCA) for the treatment of cancers that are resistant to individual chemotherapies.

In one embodiment, antibodies of the present invention may be administered in combination with a topoisomerase inhibitor. In another embodiment, antibodies of the present invention may be administered in combination with a topoisomerase inhibitor for the treatment of cancers that are resistant to individual chemotherapies. In a specific embodiment, antibodies of the present invention may be administered in combination with Irinotecan (Camptosar®, CPT-11, Topotecin®, CaptoCPT-1). In a specific embodiment, antibodies of the present invention may be administered in combination with Irinotecan (Camptosar®, CPT-11, Topotecin®, CaptoCPT-1) for the treatment of cancers that are resistant to individual chemotherapies.

In one embodiment, agonistic antibodies of the present invention may be administered in combination with a topoisomerase inhibitor. In another embodiment, agonistic antibodies of the present invention may be administered in combination with a topoisomerase inhibitor for the treatment of cancers that are resistant to individual chemotherapies. In a specific embodiment, agonistic antibodies of the present invention may be administered in combination with Irinotecan (Camptosar®, CPT-11, Topotecin®, CaptoCPT-1). In a specific embodiment, agonistic antibodies of the present invention may be administered in combination with Irinotecan (Camptosar®, CPT-11, Topotecin®, CaptoCPT-1) for the treatment of cancers that are resistant to individual chemotherapies.

In one embodiment, antibodies of the present invention may be administered in combination with a fluoropyrimidine. In another embodiment, antibodies of the present invention may be administered in combination with a fluoropyrimidine for the treatment of cancers that are resistant to individual chemotherapies. In another specific embodiment, antibodies of the invention may be administered in combination with Fluorouracil (5-FU, Adrucil®). In another specific embodiment, antibodies of the present invention may be administered in combination with Fluorouracil (5-FU, Adrucil®) for the treatment of cancers that are resistant to individual chemotherapies.

In one embodiment, agonistic antibodies of the present invention may be administered in combination with a fluoropyrimidine. In another embodiment, agonistic antibodies of the present invention may be administered in combination with a fluoropyrimidine for the treatment of cancers that are resistant to individual chemotherapies. In another specific embodiment, agonistic antibodies of the invention may be administered in combination with Fluorouracil (5-FU, Adrucil®). In another specific embodiment, agonistic antibodies of the present invention may be administered in combination with Fluorouracil (5-FU, Adrucil®) for the treatment of cancers that are resistant to individual chemotherapies.

In preferred embodiments, agonistic antibodies of the invention are administered in combination with one or more of the above-described therapeutic agents in the treatment, prevention, amelioration and/or cure of cancers.

In further specific embodiments, antibodies of the present invention may be administered in combination with one or more combinations of therapeutic agents useful in the treatment, prevention, amelioration and/or cure of cancers including, but not limited to, 9-aminocamptothecin+G-CSF, Adriamycin® (Doxorubicin)+Blenoxane+Vinblastine+Dacarbazine (ABVD), BCNU (Carmustine)+Etoposide+Ara-C (Cytarabine)+Melphalen (BEAM), Bevacizumab+Leucovorin, Bleomycin+Etoposide+Platinol (Cisplatin) (BEP), Bleomycin+Etoposide+Adriamycin+Cyclophosphamide+Vincristine+Procarbazine+Prednisone (BEACOPP), Bryostatin+Vincristine, Busulfan+Melphalan, Carboplatin+Cereport (Lobradimil), Carboplatin+Cyclophosphamide, Carboplatin+Paclitaxel, Carboplatin+Etoposide+Bleomycin (CEB), Carboplatin+Etoposide+Thiotepa, Cisplatin+Cyclophosphamide, Cisplatin+Docetaxel, Cisplatin+Doxorubicin, Cisplatin+Etoposide, Cisplatin+Gemcitabine, Cisplatin+Interferon alpha, Cisplatin+Irinotecan, Cisplatin+Paclitaxel, Cisplatin+Teniposide, Cisplatin+Vinblastine, Cisplatin+Vindesine, Cisplatin+Vinorelbine, Cisplatin+Cytarabine+Ifosfarnide, Cisplatin+Ifosfamide+Vinblastine, Cisplatin+Vinblastine+Mitomycin C, Cisplatin+Vincristine+Fluorouracil, Cisplatin+Vincristine+Lomustine, Cisplatin+Vinorelbine+Gemcitabine, Cisplatin+Carmustine+Dacarbazine+Tamoxifen, Cisplatin+Cyclophosphamide+Etoposide+Vincristine, Cisplatin (Platinol®)+Oncovin® (Vincristine)+Doxorubicin (Adriarnycin®)+Etoposide (CODE), Cisplatin+Cytarabine+Ifosfamide+Etoposide+Methotrexate, Cyclophosphamide+Adriamycin® (Doxorubicin), Cyclophosphamide+Melphalan, Cyclophosphamide+SCH 6636, Cyclophosphamide+Adriamycin® (Doxorubicin)+Cisplatin (Platinol®) (CAP), Cyclophosphamide+Adriamycin® (Doxorubicin)+Vincristine (CAV), Cyclophosphamide+Doxorubicin+Teniposide+Prednisone, Cyclophosphamide+Doxorubicin+Teniposide+Prednisone+Interferon alpha, Cyclophosphamide+Epirubicin+Cisplatin (Platinol®) (CEP), Cyclophosphamide+Epirubicin+Fluorouracil, Cyclophosphamide+Methotrexate+Fluoruracil (CMF), Cyclophosphamide+Methotrexate+Vincristine (CMV), Cyclophosphamide+Adriamycin® (Doxorubicin)+Methotrexate +Fluorouracil (CAMF), Cyclophosphamide+Adriamycin® (Doxorubicin)+Methotrexate+Procarbazine (CAMP), Cyclophosphamide+Adriamycin® (Doxorubicin)+Vincristine+Etoposide (CAV-E), Cyclophospharnide+Adriamycin® (Doxorubicin)+Vincristine+Prednisone (CHOP), Cyclophosphamide+Novantrone® (Mitoxantrone)+Vincristine (Oncovorin)+Prednisone (CNOP), Cyclophosphamide+Adriamycin® (Doxorubicin)+Vincristine+Prednisone+Rituximab (CHOP+Rituximab), Cyclophosphamide+Adriamycin® (Doxorubicin)+Vincristine+Teniposide (CAV-T), Cyclophosphamide+Adriamycin+Vincristine alternating with Platinol (Cisplatin)+Etoposide (CAV/PE), Cyclophosphamide+BCNU (Carmustine)+VP-16 (Etoposide) (CBV), Cyclophospharnide+Vincristine+Prednisone (CVP), Cyclophosphamide+Oncovin® (Vincristine)+Methotrexate+Fluorouracil (COMF), Cytarabine+Methotrexate, Cytarabine+Bleomycin+Vincristine+Methotrexate (CytaBOM), Dactinomycin+Vincristine, Dexamethasone+Cytarabine+Cisplatin (DHAP), Dexamethasone+Ifosfamide+Cisplatin+Etoposide (DICE), Docetaxel+Gemcitabine, Docetaxel+Vinorelbine, Doxorubicin+Vinbiastine+Mechiorethamine+Vincristine+Bleomycin+Etoposide+Prednisone (Stanford V), Epirubicin+Gemeitabine, Estramustine+Docetaxel, Estramustine+Navelbine, Estramustine+Paclitaxel, Estramustine+Vinbiastine, Etoposide (Vepesid®)+Ifosfarnide+Cisplatin (Platinol®) (VIP), Etoposide+Vinbiastine+Adriamycin (EVA), Etoposide (Vepesid®)+Ifosfamide+Cisplatin+Epirubicin (VIC-E), Etoposide+Methyiprednisone+Cytarabine+Cisplatin (ESHAP), Etoposide+Prednisone+Ifosfarnide+Cisplatin (EPIC), Eludarabine+Mitoxantrone+Dexarnethasone (FMD), Fludarabine+Dexamethasone+Cytarabine (ara-C)+Cisplatin (Platinol®) (FluDAP), Fluorouracil+Bevacizumab, Fluorouracil+CeaVac® (MAb 3H1), Fluorouracil+Leucovorin, Fluorouracil+Levamisole, Fluorouracil+Oxaliplatin, Fluorouracil+Raltitrexed, Fluorouracil+SCH 6636, Fluorouracil+Trimetrexate, Fluorouracil+Leucovorin+Bevacizumab, Fluorouracil+Leucovorin+Oxaliplatin, Fluorouracil+Leucovorin+Trimetrexate, Fluorouracil+Oncovin+Mitomycin C (FOMi), Hydrazine+Adriamycin® (Doxorubicin)+Methotrexate (HAM), Ifosfamide+Docetaxel, Ifosfamide+Etoposide, Ifosfarnide+Gemcitabine, Ifosfamide+Paclitaxel, Ifosfamide+Vinorelbine, Ifosfamide+Carboplatin+Etoposide (ICE), Ifosfarnide+Cisplatin+Doxorubicin, Irinotecan+C225 (Cetuximab), Irinotecan+Docetaxel, Irinotecan+Etoposide, Irinotecan+Fluorouracil, Irinotecan+Gemcitabine, Mechlorethaniine+Oncovin® (Vincristine)+Procarbazine (MOP), Mechiorethamine+Oncovin® (Vincristine)+Procarbazine+Prednisone (MOPP), Mesna+Ifosfamide+Idarubicin+Etoposide (MIZE), Methotrexate+Interferon alpha, Methotrexate+Vinblastine, Methotrexate+Cisplatin, Methotrexate with leucovorin rescue+Bleomycin+Adriamycin+Cyclophosphamide+Oncovorin+Dexamethasone (m-BACOD), Mitomycin C+Ifosfamide+Cisplatin (Platinol®) (MIP), Mitomycin C+Vinbiastine+Paraplatin® (Carboplatin) (MVP), Mitoxantrone+Hydrocortisone, Mitoxantrone+Prednisone, Oncovin® (Vincristine)+SCH 6636, Oxaliplatin+Leucovorin, Paclitaxel+Doxorubicin, Paclitaxel+SCH 6636, Paraplatin® (Carboplatin)+Docetaxel, Paraplatin® (Carboplatin)+Etoposide, Paraplatin® (Carboplatin)+Gemcitabine, Paraplatin® (Carboplatin)+Interferon alpha, Paraplatin® (Carboplatin)+Jrinotecan, Paraplatin® (Carboplatin)+Paclitaxel, Paraplatin® (Carboplatin)+Vinbiastine, Carboplatin (Paraplatin®)+Vincristine, Paraplatin® (Carboplatin)+Vindesine, Paraplatin® (Carboplatin)+Vinorelbine, Pemetrexed disodium+Gemcitabine, Platinol® (Cisplatin)+Vinbiastine+Bleomycin (PVB), Prednisone+Methotrexate+Adriamycin+Cyclophosphamide+Etoposide (ProMACE), Procarbazine+Lomustine, Procarbazine+Lomustine+Vincristine, Procarbazine+Lomustine+Vincristine+Thioguanine, Procarbazine+Oncovin® Vincristine+CCNU® Lomustine+Cyclophosphamide (POCC), Quinine+Doxorubicin, Quinine+Mitoxantrone+Cytarabine, Thiotepa+Etoposide, Thiotepa+Busulfan+Cyclophosphamide, Thiotepa+Busulfan+Melphalan, Thiotepa+Etoposide+Carmustine, Thiotepa+Etoposide+Carboplatin, Topotecan+Paclitaxel, Trimetrexate+Leucovorin, Vinbiastine+Doxorubicin+Thiotepa, Vinbiastine+Bleomycin+Etoposide+Carboplatin, Vincristine+Lomustine+Prednisone, Vincristine (Oncovin®)+Adriamycin® (Doxorubicin)+Dexamethasone (VAD), Vincristine (Oncovin®)+Adriamycin® (Doxorubicin)+Procarbazine (VAP), Vincristine+Dactinomycin+Cyclophosphamide, and Vinorelbine+Gemcitabine.

In one embodiment, antibodies of the present invention may be administered in combination with a taxane and a platinum-based chemotherapeutic. In another embodiment, antibodies of the present invention may be administered in combination with a taxane and a platinum-based chemotherapeutic for the treatment of cancers that are resistant to individual chemotherapies. In a specific embodiment, antibodies of the present invention may be administered in combination with Docetaxel (Taxotere®) and Carboplatin (Paraplatin®, CBDCA). In another specific embodiment, antibodies of the present invention may be administered in combination with Docetaxel (Taxotere®) and Carboplatin (Paraplatin®, CBDCA) for the treatment of cancers that are resistant to individual chemotherapies.

In one embodiment, agonistic antibodies of the present invention may be administered in combination with a taxane and a platinum-based chemotherapeutic. In another embodiment, agonistic antibodies of the present invention may be administered in combination with a taxane and a platinum-based chemotherapeutic for the treatment of cancers that are resistant to individual chemotherapies. In a specific embodiment, agonistic antibodies of the present invention may be administered in combination with Docetaxel (Taxotere®) and Carboplatin (Paraplatin®, CBDCA). In another specific embodiment, agonistic antibodies of the present invention may be administered in combination with Docetaxel (Taxotere®) and Carboplatin (Paraplatin®, CBDCA) for the treatment of cancers that are resistant to individual chemotherapies.

In one embodiment, antibodies of the present invention may be administered in combination with a topoisomerase inhibitor and a fluoropyrimidine. In another embodiment, antibodies of the present invention may be administered in combination with a topoisomerase inhibitor and a fluoropyrimidine for the treatment of cancers that are resistant to individual chemotherapies. In a specific embodiment, antibodies of the present invention may be administered in combination with Irinotecan (Camptosar®, CPT-11, Topotecin®, CaptoCPT-1) and Fluorouracil (5-FU, Adrucil®). In another specific embodiment, antibodies of the present invention may be administered in combination with Irinotecan (Camptosar®, CPT-11, Topotecin®, CaptoCPT-1) and Fluorouracil (5-FU, Adrucil®) for the treatment of cancers that are resistant to individual chemotherapies.

In one embodiment, agonistic antibodies of the present invention may be administered in combination with a topoisomerase inhibitor and a fluoropyrimidine. In another embodiment, agonistic antibodies of the present invention may be administered in combination with a topoisomerase inhibitor and a fluoropyrimidine for the treatment of cancers that are resistant to individual chemotherapies. In a specific embodiment, agonistic antibodies of the present invention may be administered in combination with Irinotecan (Camptosar®, CPT-11, Topotecin®, CaptoCPT-1) and Fluorouracil (5-FU, Adrucil®). In another specific embodiment, agonistic antibodies of the present invention may be administered in combination with Irinotecan (Camptosar®, CPT-11, Topotecin®, CaptoCPT-1) and Fluorouracil (5-FU, Adrucil®) for the treatment of cancers that are resistant to individual chemotherapies.

In preferred embodiments, agonistic antibodies of the invention are administered in combination with one or more of the above-described combinations of therapeutic agents in the treatment, prevention, amelioration and/or cure of cancers.

In a specific embodiment, antibody and antibody compositions of the invention are administered in combination with CHOP (cyclophosphamide, doxorubicin, vincristine, and prednisone) or any combination of the components of CHOP. In another embodiment, antibody and antibody compositions of the invention are administered in combination with Rituximab. In a further embodiment, antibody and antibody compositions of the invention are administered with Rituximab and CHOP, or lymphomaRituximab and any combination of the components of CHOP.

In additional preferred embodiments, antibody compositions of the invention are administered in combination with Rituximab (Rituxan™) and/or Ibritumomab Tiuxetan (Zevalin™, e.g., either (In-111) Ibritumomab Tiuxetan or (Y-90) Ibritumomab Tiuxetan). In a specific embodiment, antibody compositions of the invention are administered in combination with Rituximab and/or Ibritumomab Tiuxetan for the treatment of non-Hodgkin's lymphoma.

In additional preferred embodiments, antibody compositions of the invention are administered in combination with imatinib mesylate (Gleevec®: 4-[(4-Methyl-1-piperazinyl)methyl]-N-[4-methyl-3-[[4-(3-pyridinyl)-2-pyrimidinyl]amino]-phenyl]benzamide methanesulfonate). In a specific embodiment, antibody compositions of the invention are administered in combination with imatinib mesylate for the treatment of chronic myelogenous leukemia.

In additional preferred embodiments, antibody compositions of the invention are administered in combination with bortezomib (Velcade™ [(1R)-3-methyl-1-[[(2S)-1-oxo-3-phenyl-2-[(pyrazinylcarbonyl)amino]propyl]amino]butyl] boronic acid). In a specific embodiment, antibody compositions of the invention are administered in combination with bortezomib for the treatment of multiple myeloma.

In additional preferred embodiments, antibody compositions of the invention are administered in combination with Alemtuzumab (Campath®). In a specific embodiment, antibody compositions of the invention are administered in combination with Alemtuzumab for the treatment of chronic lymphocytic leukemia.

In additional preferred embodiments, antibody compositions of the invention are administered in combination with fludarabine phosphate (Fludara®: 9$\underline{H}$-Purin-6-amine, 2-fluoro-9-(5-$\underline{O}$-phosphono-β-D-arabinofuranosyl) (2-fluoro-ara-AMP)). In a specific embodiment, antibody compositions of the invention are administered in combination with fludarabine phosphate for the treatment of chronic lymphocytic leukemia.

In additional preferred embodiments, the compositions of the invention are administered in combination with TRAIL polypeptides or fragments or variants thereof, particularly of the extracellular soluble domain of TRAIL.

In one embodiment, the compositions of the invention are administered in combination with other members of the TNF family or antibodies specific for TNF receptor family members. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (J. Exp. Med. 188(6):1185-1190), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-1BB, TR2 (International Publication No. WO 96/34095), DR3 (International Publication No. WO 97/35904), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In one embodiment, the antibody compositions of the invention are administered in combination with apoptosis inducing polypeptides. In a specific embodiment, antibodies of the invention are administered in combination with Smac (second mitochondria-derived activator of caspases) proteins, also known as DIABLO (direct IAP (inhibitor of apoptosis) binding protein with low pI) (GenBank Accession No. :NP_063940 which is hereby incorporated by reference in its entirety). Smac is a 239 amino acid protein. The N-terminal 55 amino acids serve as a mitochondrial targeting sequence which is cleaved after import to the mitochondria Apoptosis inducing polypeptides may be delivered using techniques known in the art. For example, one way to deliver Smac protein would be through the delivery of a nucleic acid encoding either the full length or mature form of Smac (amino acids 56-239 of GenBank Accession No. : NP_063940, a cytosolic form that bypasses mitochondrial processing). Alternatively, antibody compositions of the invention may be administered in combination with cell permeable, synthetic Smac peptides which are capable of inhibiting IAP proteins (e.g., those containing amino acid residues 56-62 of GenBank Accession No. :NP_063940; AVPIAQK as described in Chai et al., (2000) *Nature* 406: 855-862 and Fulda et al., (2002) *Nature Medicine* 8:808-815, both of which are hereby incorporated by reference in their entireties.

In one embodiment, an antibody composition of the invention is administered in combination with a histone deacetylase inhibitor (e.g., depsipeptide (e.g., FK-288 and FR901228), MS-275, and the triterpenoid 2-cyano-3,12-dioxooleana-1,9-dien-28-oic acid (CDDO) or other molecules related to CDDO, valproic acid, suberoylanilide hydroxamic acid (SAHA), pyroxamide, trapoxin, (depsipeptide), and N-acetyl dinaline (CI-994).

In another embodiment, an antibody compositions of the invention is administered in combination with inhibitors of ERK1/2.

In another embodiment, an antibody compositions of the invention is administered in combination with proteasome inhibitors such as PS-341 (LDP-341, 26S proteasome inhibitor).

In another embodiment, an antibody compositions of the invention is administered in combination with a COX-2 inhibitor.

In specific embodiments antibodies of the present invention may be administered in combination with one or more therapeutic agents, as described above, in the treatment, prevention, amelioration and/or cure of hematological cancer (e.g., leukemia, acute lymphocytic leukemia, chronic lymphocytic leukemia, non-Hodgkin's lymphoma, multiple myeloma), colorectal cancer, lung cancer, brain cancer, skin cancer, breast cancer, prostate cancer, pancreatic cancer, hepatic cancer, ovarian cancer, as well as endothelioma, osteoblastoma, osteoclastoma, Ewing's sarcoma, and Kaposi's sarcoma.

In further particular embodiments, antibodies of the present invention are used to treat, ameliorate and/or prevent hematological cancers. Antibodies of the present invention may be used in combination with one or more surgical and/or radiological procedures and/or therapeutic agents to treat, ameliorate and/or prevent hematological cancers. Hematological cancers which may be treated using antibodies of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In preferred embodiments, agonistic antibodies of the present invention are used to treat, ameliorate and/or prevent hematological cancers. Agonistic antibodies of the present invention may be used in combination with one or more surgical and/or radiological procedures and/or therapeutic agents to treat, ameliorate and/or prevent hematological cancers. Hematological cancers which may be treated using agonistic antibodies of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In one preferred embodiment, agonistic antibodies of the invention are used to treat plasma cell neoplasms. In a specific embodiment, that plasma cell neoplasm is multiple myeloma.

In another preferred embodiment, agonistic antibodies of the invention are used to treat non-Hodgkin's lymphoma.

In another preferred embodiment, agonistic antibodies of the invention are used to treat leukemia. In a specific embodiment, that leukemia is acute lymphocytic leukemia In another specific embodiment, that leukemia is chronic lymphocytic leukemia.

Antibodies of the present invention may be administered in combination with one or more surgical and/or radiological procedures useful in the treatment of hematological cancer including, but not limited to, bone marrow transplantation, external beam radiation and total body irradiation.

In preferred embodiments, agonistic antibodies of the invention are administered in combination with one or more surgical and/or radiological procedures useful in the treatment of hematological cancer including, but not limited to, bone marrow transplantation, external beam radiation and total body irradiation.

In one preferred embodiment, agonistic antibodies of the present invention may be administered in combination with one or more surgical and/or radiological procedures useful in the treatment of multiple myeloma including, but not limited to, allogeneic bone marrow transplantation and peripheral stem cell support.

In another preferred embodiment, agonistic antibodies of the present invention may be administered in combination with one or more surgical and/or radiological procedures useful in the treatment of non-Hodgkin's lymphoma including, but not limited to, allogeneic bone marrow transplantation and peripheral stem cell support.

In further specific embodiments, agonistic antibodies of the present invention may be administered in combination with one or more surgical and/or radiological procedures useful in the treatment of leukemia including, but not limited to, allogeneic bone marrow transplantation and peripheral stem cell support. In one specific preferred embodiment, agonistic antibodies of the invention are used to treat acute lymphocytic leukemia (ALL). In another specific preferred embodiment, agonistic antibodies of the invention are used to treat chronic lymphocytic leukemia (CLL).

Antibodies of the present invention may be administered in combination with one or more therapeutic agents useful in the treatment of multiple myeloma including, but not limited to, Alkylating agents, Anthracyclines, Carmustine (DTI-015, BCNU, BiCNU, Gliadel Wafers®), Cyclophosphamide (Cytoxan®, Neosar®, CTX), Dexamethasone (Decadron®), Doxorubicin (Adriamycin®, Doxil®, Rubex®), Melphalan (L-PAM, Alkeran®, Phenylalanine mustard), Prednisone, Thalidomide and Vincristine (Oncovorin®, Onco TCS®, VCR, Leurocristine®).

In preferred embodiments, agonistic antibodies of the invention are administered in combination with one or more of the above-described therapeutic agents in the treatment, amelioration and/or prevention of multiple myeloma.

Preferred combinations of therapeutic agents useful in the treatment of multiple myeloma which may be administered in combination with antibodies of the present invention include, but are not limited to, Cyclophosphamide+Prednisone, Melphalan+Prednisone (MP), Vincristine+Adriamycin® (Doxorubicin)+Dexamethasone (VAD), Vincristine+

Carmustine+Melphalan+Cyclophosphamide+Prednisone (VBMCP; the M2 protocol), and Vincristine+Melphalan+Cyclophosphamide+Prednisone alternating with Vincristine Carmustine+Doxorubicin+Prednisone (VMCP/VBAP).

In preferred embodiments, agonistic antibodies of the invention are administered in combination with one or more of the above-described therapeutic agent combinations in the treatment, amelioration and/or prevention of multiple myeloma.

Antibodies of the present invention may be administered in combination with one or more therapeutic agents useful in the treatment of non-Hodgkin's lymphoma including, but not limited to, 2-chlorodeoxyadenosine, Amifostine (Ethyol®, Ethiofos®, WR-272), Bexarotene (Targretin®, Targretin gel®, Targretin oral®, LGD 1069), Bleomycin (Blenoxane®), Busulfan (Busulfex®, Myleran®), Carboplatin (Paraplatin®, CBDCA), Carmustine (DTI-015, BCNU, BiCNU, Gliadel Wafer®), Chlorambucil (Leukeran®), Cisplatin (Platinol®, CDDP), Cladribine (2-CdA, Leustatin®), Cyclophosphamide (Cytoxan®, Neosar®, CTX), Cytarabine (Cytosar-U®, ara-C, cytosine arabinoside, DepoCyt®), Dacarbazine (DTIC), Daunorubicin (Daunomycin, DaunoXome®, Daunorubicin®, Cerubidine®), Denileukin diftitox (Ontak®), Dexamethasone (Decadron®), Dolasetron mesylate (Anzemet®), Doxorubicin (Adriamycin®, Doxil®, Rubex®), Erythropoietin (EPO®, Epogen®, Procrit®), Etoposide phosphate (Etopophos®), Etoposide (VP-16, Vepesid®), Fludarabine (Fludara®, FAMP), Granisetron (Kytril®), Hydrocortisone, Idarubicin (Idamycin®, DMDR, IDA), Ifosfamide (IFEX®), Interferon alpha (Alfaferone®, Alpha-IF®), Interferon alpha 2a (Intron A®), Mechlorethamine (Nitrogen Mustard, $HN_2$, Mustargen®), Melphalan (L-PAM, Alkeran®, Phenylalanine mustard), Methotrexate (MTX, Mexate®, Folex), Methylprednisolone (Solumedrol®), Mitoxantrone (Novantrone®, DHAD), Ondansetron (Zofran®), Pentostatin (Nipent®, 2-deoxycoformycin), Perfosfamide (4-hydroperoxycyclophosphamide, 4-HC), Prednisone, Procarbazine (Matulane®), Rituximab (Rituxan®, anti-CD20 MAb), Thiotepa (triethylenethiophosphaoramide, Thioplex®), Topotecan (Hycamtin®, SK&F-104864, NSC-609699, Evotopin®), Vinblastine (Velban®, VLB), Vincristine (Oncovin®, Onco TCS®, VCR, Leurocristine®) and Vindesine (Eldisine®, Fildesin®).

In preferred embodiments, agonistic antibodies of the invention are administered in combination with one or more of the above-described therapeutic agents in the treatment, amelioration and/or prevention of non-Hodgkin's lymphoma.

Preferred combinations of therapeutic agents useful in the treatment of non-Hodgkin's lymphoma which may be administered in combination with antibodies of the present invention include, but are not limited to, Adriamycin® (Doxorubicin)+Blenoxane+Vinblastine Dacarbazine (ABVD), Anti-idiotype therapy (BsAb)+Interferon alpha, Anti-idiotype therapy (BsAb)+Chlorambucil, Anti-idiotype therapy (BsAb) Interleukin-2, BCNU (Carmustine)+Etoposide Ara-C (Cytarabine)+Melphalen (BEAM), Bleomycin+Etoposide+Adriamycin® (Doxorubicin)+Cyclophosphamide+Vincristine+Procarbazine+Prednisone (BEACOPP), Bryostatin+Vincristine, Cyclophosphamide+BCNU (Carrnustine)+VP-16 (Etoposide) (CBV), Cyclophosphamide+Vincristine+Prednisone (CVP), Cyclophosphamide+Adriamycin® (Hydroxyldaunomycin)+Vincristine (Oncovin®)+Prednisone (CHOP), Cyclophosphamide+Novantrone® (Mitoxantrone)+Vincristine (Oncovin®)+Prednisone (CNOP), Cyclophosphamide+Doxorubicin+Teniposide+Prednisone, Cyclophosphamide+Adriamycin® (Hydroxyldaunomycin)+Vincristine (Oncovin®)+Prednisone+Rituximab (CHOP+Rituximab), Cyclophosphamide+Doxorubicin+Teniposide+Prednisone+Interferon alpha, Cytarabine+Bleomycin+Vincristine+Methotrexate (CytaBOM), Dexamethasone+Cytarabine+Cisplatin (DHAP), Dexamethasone+Ifosfamide+Cisplatin+Etoposide (DICE), Doxorubicin Vinblastine+Mechlorethamine+Vincristine+Bleomycin+Etoposide+Prednisone (Stanford V), Etoposide+Vinblastine+Adriamycin® (Doxorubicin) (EVA), Etoposide+Methylprednisone+Cytarabine+Cisplatin (ESHAP), Etoposide+Prednisone+Ifosfamide+Cisplatin (EPIC), Fludarabine, Mitoxantrone+Dexamethasone (FMD), Fludarabine, Dexamethasone, Cytarabine (ara-C),+Cisplatin (Platinol®) (FluDAP), Ifosfamide+Cisplatin+Etoposide (ICE), Mechlorethamine+Oncovin® (Vincristine)+Procarbazine+Prednisone (MOPP), Mesna+Ifosfamide+Idarubicin+Etoposide (MIZE), Methotrexate with leucovorin rescue+Bleomycin+Adriamycin+Cyclophosphamide+Oncovorin+Dexamethasone (m-BACOD), Prednisone+Methotrexate+Adriamycin® (Doxorubicin)+Cyclophosphamide+Etoposide (ProMACE), Thiotepa+Busulfan+Cyclophosphamide, Thiotepa+Busulfan+Melphalan, Topotecan+Paclitaxel, and Vincristine (Oncovin®)+Adriamycin® (Doxorubicin)+Dexamethasone (VAD).

In preferred embodiments, agonistic antibodies of the invention are administered in combination with one or more of the above-described therapeutic agent combinations in the treatment, amelioration and/or prevention of non-Hodgkin's lymphoma.

Further examples of therapeutic agents useful in the treatment of non-Hodgkin's lymphoma which may be administered in combination with antibodies of the present invention include, but are not limited to, A007 (4-4'-dihydroxybenzophenone-2, 4-dinitrophenylhydrazone), AG-2034 (AG-2024, AG-2032, GARET [glycinamide ribonucleoside transformylase] inhibitor), Aldesleukin (IL-2, Proleukin®), Alemtuzumab (Campath®), Alitretinoin (Panretin®, LGN-1057), Altretamine (Hexalen®, hexamethylmelamine, Hexastat®), Aminocamptothecin (9-AC, 9-Aminocamptothecin, NSC 603071), Anti-CD19/CD3 MAb (anti-CD19/CD3 scFv, anti-NHL MAb), Anti-idiotype therapy (BsAb), Arabinosylguanine (Ara-G, GW506U78), Arsenic trioxide (Trisenox®, ATO), B43-Genistein (anti-CD19 Ab/genistein conjugate), B7 antibody conjugates, Betathine (Beta-LT), BLyS antagonists, Bryostatin-1 (BMY-45618, NSC-339555), CHML (Cytotropic Heterogeneous Molecular Lipids), Clofarabine (chloro-fluoro-araA), Daclizumab (Zenapax®), Depsipeptide (FR901228, FK228), Dolastatin-10 (DOLA-10, NSC-376128), Epirubicin (Ellence®, EPI, 4'epi-doxorubicin), Epratuzumab (Lymphocide®, humanized anti-CD22, HAT), Fly3/flk2 ligand (Mobista®), G3139 (Genasense®, GentaAnticode®, Bcl-2 antisense), Hu1D10(anti-HLA-DR MAb, SMART 1D10), HumaLYM (anti-CD20 MAb), Ibritumomab tiuxetan (Zevalin®), Interferon gamma (Gamma-interferon, Gamma 100®, Gamma-IF), Irinotecan (Camptosar®, CPT-11, Topotecin®, CaptoCPT-1), ISIS-2053, ISIS-3521 (PKC-alpha antisense), Lmb-2 immunotoxin (anti-CD25 recombinant immuno toxin, anti-Tac(Fv)-PE38), Leuvectin® (cytofectin+IL-2 gene, IL-2 gene therapy), Lym-1 (131-I LYM-1), Lymphoma vaccine (Genitope), Nelarabine (Compound 506, U78), Neugene compounds (Oncomyc-NG®, Resten-NG®, myc antisense), NovoMAb-G2 scFv (NovoMAb-G2IgM), O6-benzylguanine (BG, Procept®), Oxaliplatin (Eloxatine®, Eloxatin®), Paclitaxel (Paxene®, Taxol®), Paclitaxel-DHA (Taxoprexin®), Peldesine (BCX-34, PNP inhibitor), Rebeccamycin and Rebeccamycin analogues, SCH-66336, Sobuzoxane (MST-16, Perazolin®), SU5416 (Semaxanib®, VEGF inhibitor), TER-286, Thalidomide, TNP-470 (AGM-1470), Tositumomab (Bexxar®), Vaispodar (PSC 833), Vaxid (B-cell lymphoma DNA vaccine), Vinorelbine (Navelbine®), WF10 (macrophage regulator) and XR-9576 (XR-9351, P-glycoprotein/MDR inhibitor).

In preferred embodiments, agonistic antibodies of the invention are administered in combination with one or more of the above-described therapeutic agents in the treatment, amelioration and/or prevention of non-Hodgkin's lymphoma.

Antibodies of the present invention may be administered in combination with one or more therapeutic agents useful in the treatment of acute lymphocytic leukemia including, but not limited to, Amsacrine, Carboplatin (Paraplatin®, CBDCA), Carmustine (DTI-015, BCNU, BiCNU, Gliadel Wafer®), Cholecaliferol, Cyclophosphamide (Cytoxan®, Neosar®, CTX), Cytarabine (Cytosar-U®, ara-C, cytosine arabinoside, DepoCyt®), Daunorubicin (Daunomycin, DaunoXome®, Daunorubicin®, Cerubidine®), Dexamethasone (Decadron®), Doxorubicin (Adriamycin®, Doxil®, Rubex®), Etoposide (VP-16, Vepesid®), Filgrastam® (Neupogen®, G-CSF, Leukine®), Fludarabine (Fludara®, FAMP), Idarubicin (Idamycin®, DMDR, IDA), Ifosfamide (IFEX®), Imatinib mesylate (STI-571, Imatinib®, Glivec®, Gleevec®, Ab1 tyrosine kinase inhibitor), Interferon gamma (Gamma-interferon, Gamma 100®, Gamma-IF), L-asparaginase (Elspar®, Crastinin®, Asparaginase medac®, Kidrolase®), Mercaptopurine (6-mercaptopurine, 6-MP), Methotrexate (MTX, Mexate®, Folex®), Mitoxantrone (Novantrone®, DHAD), Pegaspargase (Oncospar®), Prednisone, Retinoic acid, Teniposide (VM-26, Vumon®), Thioguanine (6-thioguanine, 6-TG), Topotecan (Hycamtin®, SK&F-104864, NSC-609699, Evotopin®), Tretinoin (Retin-A®, Atragen®, ATRA, Vesanoid®) and Vincristine, (Oncorvin®, Onco TCS®, VCR, Leurocristine®).

In preferred embodiments, agonistic antibodies of the invention are administered in combination with one or more of the above-described therapeutic agents in the treatment, amelioration and/or prevention of acute lymphocytic leukemia.

Further examples of therapeutic agents useful in the treatment of acute lymphocytic leukemia which may be administered in combination with antibodies of the present invention include, but are not limited to, Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®), Arsenic trioxide (Trisenox®, ATO, Atrivex®), B43-Genistein (anti-CD19 Ab/genistein conjugate), B43-PAP (anti-CD19 Ab/pokeweed antiviral protein conjugate), Cordycepin, CS-682, Decitabine (5-aza-2'-deoxyytidine), Dolastatin-10 (DOLA-10, NSC-376128), G3139 (Genasense®, GentaAnticode®, Bcl-2 antisense), Irofulven (MGI-114, Ivofulvan, Acylfulvene analogue), MS-209, Phenylbutyrate, Quinine, TNP-470 (AGM-1470, Fumagillin), Trimetrexate (Neutrexin®), Troxacitabine (BCH-204, BCH-4556, Troxatyl®), UCN-01 (7-hydroxystaurosporine), WHI-P131 and WT1 Vaccine.

In preferred embodiments, agonistic antibodies of the invention are administered in combination with one or more of the above-described therapeutic agents in the treatment, amelioration and/or prevention of acute lymphocytic leukemia.

Preferred combinations of therapeutic agents useful in the treatment of acute lymphocytic leukemia which may be administered in combination with antibodies of the present invention include, but are not limited to, Carboplatin+Mitoxantrone, Carmustine+Cyclophosphamide+Etoposide, Cytarabine+Daunorubicin, Cytarabine+Doxorubicin, Cytarabine+Idarubicin, Cytarabine+Interferon gamma, Cytarabine+L-asparaginase, Cytarabine+Mitoxantrone, Cytarabine+Fludarabine and Mitoxantrone, Etoposide+Cytarabine, Etoposide+Ifosfamide, Etoposide+Mitoxantrone, Ifosfamide+Etoposide+Mitoxantrone, Ifosfamide+Teniposide, Methotrexate+Mercaptopurine, Methotrexate+Mercaptopurine+Vincristine+Prednisone, Phenylbutyrate+Cytarabine, Phenylbutyrate+Etoposide, Phenylbutyrate+Topotecan, Phenylbutyrate+Tretinoin, Quinine+Doxorubicin, Quinine+Mitoxantrone+Cytarabine, Thioguanine+Cytarabine+Amsacrine, Thioguanine+Etoposide+Idarubicin, Thioguanine+Retinoic acid+Cholecaliferol, Vincristine+Prednisone, Vincristine+Prednisone and L-asparaginase, Vincristine+Dexamethasone/Prednisone+Asparaginase+Daunorubicin/Doxorubicin, Vincristine+Dexamethasone/Prednisone+Asparaginase+Daunorubicin/Doxorubicin+Filgrastim, Vincristine+Dexamethasone/Prednisone+Asparaginase+Daunorubicin/Doxorubicin+Cyclophosphamide+Methotrexate, and Vincristine+Dexamethasone/Prednisone+Asparaginase+Daunorubicin/Doxorubicin+Cyclophosphamide+Methotrexate+Filgrastim.

In preferred embodiments, agonistic antibodies of the invention are administered in combination with one or more of the above-described therapeutic agent combinations in the treatment, amelioration and/or prevention of acute lymphocytic leukemia.

Antibodies of the present invention may be administered in combination with one or more therapeutic agents useful in the treatment of chronic lymphocytic leukemia including, but not limited to, Chlorambucil (Leukeran®), Cladribine (2-CdA, Leustatin®), Cyclophosphamide (Cytoxan®, Neosar®, CTX), Cytarabine (Cytosar-U®, ara-C, cytosine arabinoside, DepoCyt®, cytarabine ocfosfate, ara-CMP), Doxorubicin (Adriamycin®, Doxil®, Rubex®), Fludarabine (Fludara®, FAMP), Pentostatin (Nipent®, 2-deoxycoformycin), Prednisone and Vincristine (Oncovorin®, Onco TCS®, VCR, Leurocristine®).

In preferred embodiments, agonistic antibodies of the invention are administered in combination with one or more of the above-described therapeutic agents in the treatment, amelioration and/or prevention of chronic lymphocytic leukemia.

Further examples of therapeutic agents useful in the treatment of chronic lymphocytic leukemia which may be administered in combination with antibodies of the present invention include, but are not limited to, Alemtuzumab (Campath®), Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®, Compound 506U78), Arsenic trioxide (Trisenox®, ATO, Atrivex®), Bryostatin-1 (Bryostatin®, BMY-45618, NSC-339555), CS-682, Dolastatin-10 (DOLA-10, NSC-376128), Filgrastim (Neupogen®, G-CSF, Leukine), Flavopiridol (NSC-649890, HMR-1275), G3139 (Genasense®, GentaAnticode®, Bcl-2 antisense), Irofulven (MGI-114, Ivofulvan, Acylfulvene analogue), MS-209, Phenylbutyrate, Rituximab (Rituxan®, anti-CD20 MAb), Thalidomide, Theophylline, TNP-470 (AGM-1470, Fumagillin), UCN-01 (7-hydroxystaurosporine) and WHI-P 131.

In preferred embodiments, agonistic antibodies of the invention are administered in combination with one or more of the above-described therapeutic agents in the treatment, amelioration and/or prevention of chronic lymphocytic leukemia.

Preferred combinations of therapeutic agents useful in the treatment of chronic lymphocytic leukemia which may be administered in combination with antibodies of the present invention include, but are not limited to, Fludarabine+Prednisone, and Cyclophosphamide+Doxorubicin+Vincristine+Prednisone (CHOP).

In preferred embodiments, agonistic antibodies of the invention are administered in combination with one or more of the above-described therapeutic agent combinations in the treatment, amelioration and/or prevention of chronic lymphocytic leukemia.

In further particular embodiments, antibodies of the present invention are used to treat, ameliorate and/or prevent colorectal cancer. Antibodies of the present invention may be used in combination with one or more surgical and/or radiological procedures and/or therapeutic agents to treat, ameliorate and/or prevent colorectal cancer. Colorectal cancers which may be treated using antibodies of the present invention include, but are not limited to, colon cancer (e.g., early stage colon cancer (stage I and II), lymph node positive colon cancer (stage III), metastatic colon cancer (stage IV)) and rectal cancer.

In preferred embodiments, agonistic antibodies of the present invention are used to treat, ameliorate and/or prevent colorectal cancer. Agonistic antibodies of the present invention may be used in combination with one or more surgical and/or radiological procedures and/or therapeutic agents to treat, ameliorate and/or prevent colorectal cancer. Colorectal cancers which may be treated using agonistic antibodies of the present invention include, but are not limited to, colon cancer (e.g., early stage colon cancer (stage I and I), lymph node positive colon cancer (stage III), metastatic colon cancer (stage IV)) and rectal cancer.

In one preferred embodiment, agonistic antibodies of the invention are used to treat colon cancer.

Antibodies of the present invention may be administered in combination with one or more therapeutic agents useful in the treatment of colorectal cancer including, but not limited to, Capecitabine (Xeloda®, Doxifluridine®, oral 5-FU), Fluorouracil (5-FU, Adrucil®, Fluoroplex®, Efudex®), Irinotecan (Camptosar®, CPT-11, Topotecin®, CaptoCPT-1), Leucovorin (Leucovorin®, Wellcovorin®), and Levamisole (Ergamisol®).

In one embodiment, antibodies of the present invention may be administered in combination with a topoisomerase inhibitor. In another embodiment, antibodies of the present invention may be administered in combination with a topoisomerase inhibitor for the treatment of colon cancer that is resistant to individual chemotherapies. In a specific embodiment, antibodies of the present invention may be administered in combination with Irinotecan (Camptosar®, CPT-11, Topotecin®, CaptoCPT-1). In a specific embodiment, antibodies of the present invention may be administered in combination with Irinotecan (Camptosar®, CPT-11, Topotecin®, CaptoCPT-1) for the treatment of colon cancer that is resistant to individual chemotherapies.

In one embodiment, agonistic antibodies of the present invention may be administered in combination with a topoisomerase inhibitor. In another embodiment, agonistic antibodies of the present invention may be administered in combination with a topoisomerase inhibitor for the treatment of colon cancer that is resistant to individual chemotherapies. In a specific embodiment, agonistic antibodies of the present invention may be administered in combination with Irinotecan (Camptosar®, CPT-11, Topotecin®, CaptoCPT-1). In a specific embodiment, agonistic antibodies of the present invention may be administered in combination with Irinotecan (Camptosar®, CPT-11, Topotecin®, CaptoCPT-1) for the treatment of colon cancer that is resistant to individual chemotherapies.

In one embodiment, antibodies of the present invention may be administered in combination with a fluoropyrimidine. In another embodiment, antibodies of the present invention may be administered in combination with a fluoropyrimidine for the treatment of colon cancer that is resistant to individual chemotherapies. In another specific embodiment, antibodies of the invention may be administered in combination with Fluorouracil (5-FU, Adrucil®). In another specific embodiment, antibodies of the present invention may be administered in combination with Fluorouracil (5-FU, Adrucil®) for the treatment of colon cancer that is resistant to individual chemotherapies.

In one embodiment, agonistic antibodies of the present invention may be administered in combination with a fluoropyrimidine. In another embodiment, agonistic antibodies of the present invention may be administered in combination with a fluoropyrimidine for the treatment of colon cancer that is resistant to individual chemotherapies. In another specific embodiment, agonistic antibodies of the invention may be administered in combination with Fluorouracil (5-FU, Adrucil®). In another specific embodiment, agonistic antibodies of the present invention may be administered in combination with Fluorouracil (5-FU, Adrucil®) for the treatment of colon cancer that is resistant to individual chemotherapies.

In preferred embodiments, agonistic antibodies of the invention are administered in combination with one or more of the above-described therapeutic agents in the treatment, amelioration and/or prevention of colorectal cancers.

Preferred combinations of therapeutic agents useful in the treatment of colorectal cancer which may be administered in combination with antibodies of the present invention include, but are not limited to, Fluorouracil+Leucovorin, and Fluorouracil+Levamisole.

In one embodiment, antibodies of the present invention may be administered in combination with a topoisomerase inhibitor and a fluoropyrimidine. In another embodiment, antibodies of the present invention may be administered in combination with a topoisomerase inhibitor and a fluoropyrimidine for the treatment of colon cancer, that are resistant to individual chemotherapies. In a specific embodiment, antibodies of the present invention may be administered in combination with Irinotecan (Camptosar®, CPT-11, Topotecin®, CaptoCPT-1) and Fluorouracil (5-FU, Adrucil®). In another specific embodiment, antibodies of the present invention may be administered in combination with Irinotecan (Camptosar®, CPT-11, Topotecin®, CaptoCPT-1) and Fluorouracil (5-FU, Adrucil®) for the treatment of colon cancer that is resistant to individual chemotherapies.

In one embodiment, agonistic antibodies of the present invention may be administered in combination with a topoisomerase inhibitor and a fluoropyrimidine. In another embodiment, agonistic antibodies of the present invention may be administered in combination with a topoisomerase inhibitor and a fluoropyrimidine for the treatment of colon cancer, that are resistant to individual chemotherapies. In a specific embodiment, agonistic antibodies of the present invention may be administered in combination with Irinotecan (Camptosar®, CPT-11, Topotecin®, CaptoCPT-1) and Fluorouracil (5-FU, Adrucil®). In another specific embodiment, agonistic antibodies of the present invention may be administered in combination with Irinotecan (Camptosar®, CPT-11, Topotecin®, CaptoCPT-1) and Fluorouracil (5-FU, Adrucil®) for the treatment of colon cancer, that are resistant to individual chemotherapies.

In preferred embodiments, agonistic antibodies of the invention are administered in combination with one or more of the above-described therapeutic agent combinations in the treatment, amelioration and/or prevention of colorectal cancers.

Further examples of therapeutic agents useful in the treatment of colorectal cancer which may be administered in combination with antibodies of the present invention include, but are not limited to, Aminocamptothecin (9-AC, 9-Aminocamptothecin, NSC 603071), Aplidine (Aplidin®, Aplidina®), Bevacizumab (Anti-VEGF monoclonal antibody, rhuMAb-VEGF), C225 (IMC-225, EGFR inhibitor, Anti-EGFr MAb, Cetuximab®), C242-DM1 (huC242-DM1), CC49-zeta gene therapy, CEA-cide® (Labetuzumab, Anti-CEA monoclonal antibody, hMN-14), CeaVac® (MAb 3H1), CP-609754, CTP-37 (Avicine®, hCG blocking vaccine), Declopramide (Oxi-104), Eniluracil (776c85), F19 (Anti-FAP monoclonal antibody, iodinated anti-FAP MAb), FMdC (KW-2331, MDL-101731), FUDR (Floxuridine®), Gemcitabine (Gemto®, Gemzar®), Herceptin® (Trastuzumab, Anti-HER-2 monoclonal antibody, Anti-EGFR-2 MAb), Intoplicine (RP 60475), L-778123 (Ras inhibitors), Leuvectin® (cytofectin+IL-2 gene, IL-2 gene therapy), MN-14 (Anti-CEA immunoradiotherapy, $^{131}$I-MN-14, $^{188}$Re-MN-14), OncoVAX-CL, OncoVAX-CL-Jenner (GA-733-2 vaccine).Orzel® (Tegafur+Uracil+Leucovorin), Oxaliplatin (Eloxatine®, Eloxatin®), Paclitaxel-DHA (Taxoprexin®), Pemetrexed disodium (Alimta®, MTA, multitargeted antifolate, LY 231514), R115777 (Zarnestra®), Raltitrexed (Tomudex®, ZD-1694), SCH 66336, SU5416 (Semaxanib®, VEGF inhibitor), Tocladesine (8-Cl-cAMP), Trimetrexate (Neutrexin®), TS-1, and ZD-9331.

In preferred embodiments, agonistic antibodies of the invention are administered in combination with one or more of the above-described therapeutic agents in the treatment, amelioration and/or prevention of colorectal cancers.

Further exemplary combinations of therapeutic agents useful in the treatment of colorectal cancer which may be administered in combination with antibodies of the present invention include, but are not limited to, Aminocamptothecin+G-CSF, Bevacizumabli+Fluorouracil, Bevacizumab+Leucovorin, Bevacizumab+Fluorouracil+Leucovorin, Cyclophosphamide+SCH 6636, Fluorouracil+CeaVac® (MAb 3H1), Fluorouracil+Oxaliplatin, Fluorouracil+Raltitrexed, Fluorouracil+SCH 6636, Fluorouracil+Trimetrexate, Fluorouracil+Leucovorin+Oxaliplatin, Fluorouracil+Leucovorin+Trimetrexate, Irinotecan+C225 (Cetuximablill), Oncovin® (Vincristine)+SCH 6636, Oxaliplatin+Leucovorin, Paclitaxel+SCH 6636, Pemetrexed disodium+Gemcitabine, and Trimetrexate+Leucovorin.

In preferred embodiments, agonistic antibodies of the invention are administered in combination with one or more of the above-described therapeutic agent combinations in the treatment, amelioration and/or prevention of colorectal cancers.

In further particular embodiments, antibodies of the present invention are used to treat, ameliorate and/or prevent lung cancer. Antibodies of the present invention may be used in combination with one or more surgical and/or radiological procedures and/or therapeutic agents to treat, ameliorate and/or prevent lung cancer. Lung cancer which may be treated using antibodies of the present invention includes, but is not limited to, non-small cell lung cancer (NSCLC) including early stage NSCLC (i.e., Stage IA/IB and Stage IIA/IIB), Stage IIIA NSCLC, Stage IIA(unresectable)/IIIB NSCLC and Stage 1V NSCLC, small cell lung cancer (SCLC) including limited stage SCLC and extensive stage SCLC as well as Malignant Pleural Mesothelioma.

In preferred embodiments, agonistic antibodies of the present invention are used to treat, ameliorate and/or prevent lung cancer. Agonistic antibodies of the present invention may be used in combination with one or more surgical and/or radiological procedures and/or therapeutic agents to treat, ameliorate and/or prevent lung cancer. Lung cancer which may be treated using agonistic antibodies of the present invention includes, but is not limited to, non-small cell lung cancer (NSCLC) including early stage NSCLC (i.e., Stage IA/IB and Stage IIA/IIB), Stage IIIA NSCLC, Stage IIA(unresectable)/IIIB NSCLC and Stage IV NSCLC, small cell lung cancer (SCLC) including limited stage SCLC and extensive stage SCLC as well as Malignant Pleural Mesothelioma.

In one preferred embodiment, agonistic antibodies of the invention are used to treat non-small cell lung cancers.

Antibodies of the present invention may be administered in combination with one or more therapeutic agents useful in the treatment of lung cancer including, but not limited to, BAY 43-9006 (Raf kinase inhibitor), Carboplatin (Paraplatin®, CBDCA), Chlorambucil (Leukeran®), Cisplatin (Platinol®, CDDP), Cisplatin-epinephrine gel (IntraDose®, FocaCist®), Cyclophosphamide (Cytoxan®, Neosar®, CTX), Docetaxel (Taxotere®, Taxane®), Doxorubicin (Adriamycin®, Doxil®, Rubex®), Edatrexate, Epirubicin (Ellence®, EPI, 4'epi-doxorubicin), Etoposide phosphate (Etopophos®), Etoposide (VP-16, Vepesid®), Gemcitabine (Gemto®, Gernzar®), Herceptin® (Trastuzumab, Anti-HIER-2 monoclonal antibody, Anti-EGFR-2 MAb), Ifosfamide (IFEX®), Irinotecan (Camptosar®, CPT-11, Topotecin®, CaptoCPT-1), Lomustine (CCNU®, CeeNU®), Mechlorethamine (Nitrogen Mustard, $HN_2$, Mustargen®), Melphalan (L-PAM, Alkeran®, Phenylalanine mustard), Methotrexate (MTX, Mexate®, Folex®), Mitomycin C (Mitomycin®, Mutamycin®, Mito Extra®), Paclitaxel (Paxene®, Taxol®), Paclitaxel-DHA (Taxoprexin®), Porfimer sodium (Photofrin®), Procarbazine (Matulane®), SKI-2053R (NSC-D644591), Teniposide (VM-26, Vumon®), Topotecan (Hycamtin®, SK&F-104864, NSC-609699, Evotopin®), Vinblastine (Velban®, VLB), Vincristine (Oncovin®, Onco TCS®, VCR, Leurocristine®), Vindesine (Fldisine®, Fildesin®), and Vinorelbine (Navelbine®).

In preferred embodiments, agonistic antibodies of the invention are administered in combination with one or more of the above-described therapeutic agents in the treatment, amelioration and/or prevention of lung cancers.

In one embodiment, antibodies of the present invention may be administered in combination with a taxane. In another embodiment, antibodies of the present invention may be administered in combination with a taxane for the treatment of lung cancers, such as non-small cell lung cancer, that are resistant to individual chemotherapies. In a specific embodiment, antibodies of the present invention may be administered in combination with Docetaxel (Taxotere®). In a specific embodiment, antibodies of the present invention may be administered in combination with Docetaxel (Taxotere®) for the treatment of lung cancers, such as non-small cell lung cancer, that are resistant to individual chemotherapies.

In one embodiment, agonistic antibodies of the present invention may be administered in combination with a taxane. In another embodiment, agonistic antibodies of the present invention may be administered in combination with a taxane for the treatment of lung cancers, such as non-small cell lung cancer, that are resistant to individual chemotherapies. In a specific embodiment, agonistic antibodies of the present invention may be administered in combination with Docetaxel (Taxotere®). In a specific embodiment, agonistic antibodies of the present invention may be administered in combination with Docetaxel (Taxotere®) for the treatment of lung cancers, such as non-small cell lung cancer, that are resistant to individual chemotherapies.

In one embodiment, antibodies of the present invention may be administered in combination with a platinum-based chemotherapeutic. In another embodiment, antibodies of the present invention may be administered in combination with a platinum-based chemotherapeutic for the treatment of lung cancers, such as non-small cell lung cancer, that are resistant to individual chemotherapies. In another specific embodiment, antibodies of the invention may be administered in combination with Carboplatin (Paraplatin®, CBDCA). In another specific embodiment, antibodies of the present invention may be administered in combination with Carboplatin (Paraplatin®, CBDCA) for the treatment of lung cancers, such as non-small cell lung cancer, that are resistant to individual chemotherapies.

In one embodiment, agonistic antibodies of the present invention may be administered in combination with a platinum-based chemotherapeutic. In another embodiment, agonistic antibodies of the present invention may be administered in combination with a platinum-based chemotherapeutic for the treatment of lung cancers, such as non-small cell lung cancer, that are resistant to individual chemotherapies. In another specific embodiment, agonistic antibodies of the invention may be administered in combination with Carboplatin (Paraplatin®, CBDCA). In another specific embodiment, agonistic antibodies of the present invention may be administered in combination with Carboplatin (Paraplatin®, CBDCA) for the treatment of lung cancers, such as non-small cell lung cancer, that are resistant to individual chemotherapies.

Further examples of therapeutic agents useful in the treatment of lung cancer which may be administered in combination with antibodies of the present invention include, but are not limited to, ABX-EGF (anti-EGFr MAb), Acetyldinaline (CI-994), AG-2034 (AG-2024, AG-2032, GARFT [glycinamide ribonucleoside transformylase] inhibitor), Alanosine, Aminocamptothecin (9-AC, 9-Aminocamptothecin, NSC 603071), Angiostatin, Aplidine (Aplidin®, Aplidina®), BBR 3464, Bexarotene (Taigretin®, LGD1O69), BIBH-1 (Anti-FAP MAb), BT.BX-1382, BLP-25 (MUC-1 peptide), Bryostatin-1 (Bryostatin®, BMY-45618, NSC-339555), Budesonide (Rhinocort®), C225 (IMC-225, EGFR inhibitor, Anti-EGFr MAb, Cetuximab), Capecitabine (Xeloda®, Doxifluridine®, oral 5-FU), Carboxyamidotriazole (NSC 609974, CAI, L-651582), CEA-cide® (Labetuzumab, Anti-CEA monoclonal antibody, hMN-14), Cereport® (Lobradimil®, RMP-7), CI-1033 (Pan-erbB RTK inhibitor), Cilengitide® (EMD-121974, integrin alphavbeta3 antagonist), 9-cis retinoic acid (9-cRA), Cisplatin-liposomal (SPI-077), CNTB-401 (Anti-PEM MAb/calicheamycin), CMT-3 (Metastat®), CP-358774 (Tarceva®, OSI-774, EGFR inhibitor), CT-2584 (Apra®), DAB389-EGF (EGF fusion toxin), DeaVac® (CEA anti-idiotype vaccine), Decitabine (5-aza-2'-deoxyytidine), Diethylnorsperrnine (DENSPM), Dihydro-5-azacytidine, EGF-P64k Vaccine, Endostatin, Etanidazole (Radinyl®), Exetecan mesylate (DX-8951, DX-8951f), Exisulind (SAAND, Aptosyn®, cGMP-PDE2 and 5 inhibitor), FK-317 (FR-157471, FR-70496), Flavopiridol (HMR-1275), Fotemustine (Muphoran®, Mustophoran®), G3139 (Genasense®, GentaAnticode®, Bcl-2 antisense), Gadolinium texaphyrin (Motexafin gadolinium, Gd-Tex®, Xcytrin®), GBC-590, GL331, Galarubicin hydrochloride (DA-125), Glufosfamide® (β-D-glucosyl-isofosfamide mustard, D19575, INN), GVAX (GM-CSF gene therapy), INGN-101 (p53 gene therapy/retrovirus), INGN-201 (p53 gene therapy/adenovirus), Irofulven (MGI-114), ISIS-2053, ISIS-3521 (PKC-alpha antisense), ISIS-5132 (K-ras/raf antisense), Isotretinoin (13-CRA, 13-cis retinoic acid, Accutane®), Lometrexol (T-64, T-904064), Marimastat® (BB-2516, TA-2516, MMP inhibitor), MDX-447 (BAB-447, EMD-82633, H-447, anti-EGFr/EcGammaR1r), MGV, Mitumomab (BEC-2, EMD-60205), Mivobulin isethionate (CI-980), Neovastat® (AE-941, MMP inhibitor), Onconase (Ranpimase®), Onyx-015 (p53 gene therapy), Pemetrexed disodium (Alimta®, MTA, multitargeted antifolate, LY 231514), Pivaloyloxymethyl butyrate (AN-9, Pivanex®), Prinomastat® (AG-3340, MMP inhibitor), PS-341 (LDP-341, 26S proteasome inhibitor), Pyrazoloacridine (NSC-366140, PD-115934), R115777 (Zarnestra®), Raltitrexed (Tomudex®, ZD-1694), R-flurbiprofen (Flurizan®, E-7869, MPC-7869), RFS-2000 (9-nitrocamptothecan, 9-NC, rubitecan®), RSR-i3 (GSJ-61), Satraplatin (BMS-182751, JM-216), SCH-66336, Sizofilan (SPG, Sizofiran, Schizophyllan, Sonifilan), Squalamine (MSI-1256F), SR-49059 (vasopressin receptor inhibitor, V1a), SU5416 (Semaxanib®, VEGF inhibitor), Taurolidine (Taurolin®), Temozolamide (Temodar®, NSC 362856), Thalidomide, Thymosin alpha I (Zadaxin®, Thymalfasin®), Tirapazamine (SR-259075, SR-4233, Tirazone®, Win-59075), TNIP-470 (AGM-1470), TriAb® (anti-idiotype antibody immune stimulator), Tretinoin (Retin-A®, Atragen®, ATRA, Vesanoid®), Troxacitabine (BCH-204, BCH-4556, Troxatyl®), Vitaxin® (LM-609, integrin alphavbeta3 antagonistic MAb), XR-9576 (P-glycoprotein/MDR inhibitor), and ZD-1839 (IRESSA®).

In preferred embodiments, agonistic antibodies of the invention are administered in combination with one or more of the above-described therapeutic agents in the treatment, amelioration and/or prevention of lung cancers.

Preferred combinations of therapeutic agents useful in the treatment of lung cancer which may be administered in combination with antibodies of the present invention include, but are not limited to, Cisplatin+Docetaxel, Cisplatin+Etoposide, Cisplatin+Gemcitabine, Cisplatin+Interferon alpha, Cisplatin+Irinotecan, Cisplatin+Paclitaxel, Cisplatin+Teniposide, Cisplatin+Vinblastine, Cisplatin+Vindesine, Cisplatin+Vinorelbine, Cisplatin+Vinblastine+Mitomycin C, Cisplatin+Vinorelbine+Gemcitabine, Cisplatin (Platinol®)+Oncovin® (Vincristine)+Doxorubicin (Adriamycin®)+Etoposide (CODE), Cyclophospharnide+Adriamycin® (Doxorubicin)+Cisplatin (Platinol®) (CAP), Cyclophosphamide+Adriamycin® (Doxorubicin)+Vincristine (CAV), Cyclophospharnide+Epirubicin+Cisplatin (Platinol®) (CEP), Cyclophosphamide+Methotrexate Vincristine (CMV), Cyclophosphamide+Adriamycin® (Doxorubicin), Methotrexate+Fluorouracil (CAMF), Cyclophosphamide Adriamycin® (Doxorubicin), Methotrexate+Procarbazine (CAMP), Cyclophosphamide+Adriamycin® (Doxorubicin), Vincristine+Etoposide (CAV-E),Cyclophosphamide+Adriamycin® (Doxorubicin), Vincristine+Teniposide (CAV-T), Cyclophosphamide+Oncovin® (Vincristine), Methotrexate+Fluorouracil (COMF), Cyclophosphamide+Adriamycin® (Doxorubicin)+Vincristine, alternating with Cisplatin+Etoposide (CAV/PE), Docetaxel+Gemcitabine, Docetaxel+Vinorelbine, Etoposide (Vepesid®)+Ifosfamide+Cisplatin (Platinol®) (VIP), Etoposide (Vepesid®)+Ifosfarnide, Cisplatin+Epirubicin (VIC-E), Fluorouracil+Oncovin®+Mitomycin C (FOMi), Ilydrazine+Adriamycin® (Doxorubicin)+Methotrexate (HAM), Ifosfamide+Docetaxel, Ifosfamide+Etoposide, Ifosfamide+Gemcitabine, Ifosfamide+Paclitaxel, ifosfamide+Vinorelbine, Ifosfamide+Carboplatin+Etoposide (ICE), Irinotecan+Docetaxel, Irinotecan+Etoposide, Irinotecan+Gemcitabine, Methotrexate+Cisplatin, Methotrexate+Interferon alpha, Methotrexate+Vinbiastine, Mitomycin C+Ifosfamide+Cisplatin (Platinol®) (MIP), Mitomycin C+Vinbiastine+Paraplatin® (Carboplatin) (MVP), Paraplatin® (Carboplatin)+Docetaxel, Paraplatin® (Carboplatin)+Etoposide, Paraplatin® (Carboplatin)+Gemcitabine, Paraplatin® (Carboplatin)+Interferon alpha, Paraplatin® (Carboplatin)+Irinotecan, Pairaplatin® (Carboplatin)+Paclitaxel, Paraplatin® (Carboplatin)+Vinbiastine, Paraplatin® (Carboplatin)+Vindesine, Paraplatin® (Carboplatin)+Vinorelbine, Procarbazine+Oncovin® (Vincristine)+CCNU® (Lomustine)+Cyclophosphamide (POCC), Vincristine (Oncovin®)+Adriamycin® (Doxorubicin)+Procarbazine (VAP), and Vinorelbine+Gemcitabine.

In preferred embodiments, agonistic antibodies of the invention are administered in combination with one or more of the above-described therapeutic agent combinations in the treatment, amelioration and/or prevention of lung cancers.

In one embodiment, antibodies of the present invention may be administered in combination with a taxane and a platinum-based chemotherapeutic. In another embodiment, antibodies of the present invention may be administered in combination with a taxane and a platinum-based chemotherapeutic for the treatment of lung cancers, such as non-small cell lung cancer, that are resistant to individual chemotheraries. In a specific embodiment, antibodies of the present invention may be administered in combination with Docetaxel (Taxotere®) and Carboplatin (Paraplatin®, CBDCA). In another specific embodiment, antibodies of the present invention may be administered in combination with Docetaxel (Taxotere®) and Carboplatin (Paraplatin®, CBDCA) for the treatment of lung cancers, such as non-small cell lung cancer, that are resistant to individual chemotherapies.

In one embodiment, agonistic antibodies of the present invention may be administered in combination with a taxane and a platinum-based chemotherapeutic. In another embodiment, agonistic antibodies of the present invention may be administered in combination with a taxane and a platinum-based chemotherapeutic for the treatment of lung cancers, such as non-small cell lung cancer, that are resistant to individual chemotherapies. In a specific embodiment, agonistic antibodies of the present invention may be administered in combination with Docetaxel (Taxotere®) and Carboplatin (Paraplatin®, CBDCA). In another specific embodiment, agonistic antibodies of the present invention may be administered in combination with Docetaxel (Taxotere®) and Carboplatin (Paraplatin®, CBDCA) for the treatment of lung cancers, such as non-small cell lung cancer, that are resistant to individual chemotherapies.

In further particular embodiments, antibodies of the present invention are used to treat, ameliorate and/or prevent head and neck cancers including brain cancers. Antibodies of the present invention may be used in combination with one or more surgical and/or radiological procedures and/or therapeutic agents to treat, ameliorate and/or prevent head and neck cancers including brain cancers. Brain cancers which may be treated using antibodies of the present invention include, but are not limited to, gliomas such as astrocytomas and oligodendromas, non-glial tumors such as neuronal, meningeal, ependymal and choroid plexus cell tumors, and metastatic brain tumors such as those originating as breast, lung, prostate and skin cancers.

In further preferred embodiments, agonistic antibodies of the present invention are used to treat, ameliorate and/or prevent head and neck cancers including brain cancers. Agonistic antibodies of the present invention may be used in combination with one or more surgical and/or radiological procedures and/or therapeutic agents to treat, ameliorate and/or prevent head and neck cancers including brain cancers. Brain cancers which may be treated using agonistic antibodies of the present invention include, but are not limited to, gliomas such as astrocytomas and oligodendromas, non-glial tumors such as neuronal, meningeal, ependymal and choroid plexus cell tumors, and metastatic brain tumors such as those originating as breast, lung, prostate and skin cancers.

In one preferred embodiment, agonistic antibodies of the invention are used to treat brain tumors. In a further preferred embodiment, agonistic antibodies of the invention are used to treat glioblastoma multiforme.

Antibodies of the present invention may be administered in combination with one or more radiological procedures useful in the treatment of brain cancers including, but not limited to, external beam radiation therapy, stereotactic radiation therapy, conformal radiation therapy, intensity-modulated radiation therapy (IMRT), and radiosurgery.

In preferred embodiments, agonistic antibodies of the invention are administered in combination with one or more radiological procedures useful in the treatment of brain cancers including, but not limited to, external beam radiation therapy, stereotactic radiation therapy, conformal radiation therapy, intensity-modulated radiation therapy (IMRT), and radiosurgery.

Antibodies of the present invention may be administered in combination with one or more therapeutic agents useful in the treatment of brain cancers including, but not limited to, Bleomycin (Blenoxane®), Busulfan (Busulfex®, Myleran®), Carboplatin (Paraplatin®, CBDCA), Carmustine (DTJ-015, BCNU, BiCNU, Gliadel Wafer®), Cisplatin (Platinol®, CDDP), Cisplatin-epinephrine gel (IntraDose®, FocaCist®), Cyclophosphamide (Cytoxan®, CTX), Cytarabine (Cytosar-U®, ara-C, cytosine arabinoside, DepoCyt®), Dacarbazine (DTIC®), Dactinomycin (Cosmegen®), Daunorubicin (Daunomycin, DaunoXome®, Daunorubicin®, Cerubidine®), Docetaxel (Taxotere®, Taxane®), Dexamethasone (Decadron®), Etoposide phosphate (Etopophos®), Etoposide (VP-16, Vepesid®), Fluorouracil (5-EU, Adrucil®), Hydroxyurea (Hydrea®), Ifosfamide (IFEX®), Lomustine (CCNU®, CeeNU®), Melphalan (L-PAM, Alkeran®, Phenylalanine mustard), Mercaptopurine (6-mercaptopurine, 6-MIP), Methchlorethamine (Nitrogen Mustard, $HN_2$, Mustargen®), Methotrexate (MTX, Mexate®, Folex®), Paclitaxel (Paxene®, Taxol®), Paclitaxel-DHA (Taxoprexin®), Procarbazine (Matulane®), Temozolamide (Temodar®, NSC 362856), Teniposide (VM-26, Vumon®), Thioguanine (6-thioguanine, 6-TG), Thiotepa (triethylenethiophosphaoramide), Topotecan (Hycamtin®, SK&F-104864, NSC-609699, Evotopin®), and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of brain cancers.

Further examples of therapeutic agents useful in the treatment of brain cancers which may be administered in combination with antibodies of the present invention include, but are not limited to, 81C6 (Anti-tenascin monoclonal antibody), BIBX-1382, Cereport® (Lobradimil®, RMP-7), Cilengitide® (EMD-121974, integrin alphavbeta3 antagonist), CMT-3 (Metastat®), Cotara® (chTNT-1/B, [$^{131}$I]-chTNT-1/B), CP IL-4-toxin (IL-4 fusion toxin), Fenretinide® (4HPR), Fotemustine (Muphoran®, Mustophoran®), Gemcitabine (Gemto®, Gemzar®), Hypericin (VIM-Rxyn®), Imatinib mesylate (STI-571, Imatinib®, Glivec®, Gleevec®, Ab1 tyrosine kinase inhibitor), Irinotecan (Camptosar®, CPT-11, Topotecin®, CaptoCPT-1), Leflunomide (SU-101, SU-0200), Mivobulin isethionate (CI-980), O6-benzylguanine (BG, Procept®), Prinomastat® (AG-3340, MMP inhibitor), R115777 (Zarnestra®), SU6668 (PDGF-TK inhibitor), T-67 (T-138067, T-607), Tamoxifen (Nolvadex®), Tf-CRM107 (Transferrin-CRM-107), Thalidomide, Tiazofurin (Tiazole®), Vapreotide® (BMY-41606), Vinorelbine (Navelbine®), and XR-5000 (DACA).

In preferred embodiments, agonistic antibodies of the invention are administered in combination with one or more of the above-described therapeutic agents in the treatment, amelioration and/or prevention of brain cancers.

Further examples of therapeutic agents useful in the treatment of brain cancers which may be administered in combination with antibodies of the present invention include, but are not limited to, 81C6 (Anti-tenascin monoclonal antibody), BIBX-1382, Cereport® (Lobradimil, RMP-7), Cilengitide® (EMD-121974, integrin alphavbeta3 antagonist), CMT-3 (Metastat®), Cotara® (chTNT-1/B, [$^{131}$I]-chTNT-1/B), CP IL-4-toxin (IL-4 fusion toxin), Fenretinide® (4HPR), Fotemustine (Muphoran®, Mustophoran®), Gemcitabine (Gemto®, Gemzar®), Hypericin (VIM-Rxyn®), Irnatinib mesylate (STI-571, Imatinib®, Glivec®, Gleevec®, Ab1 tyrosine kinase inhibitor), Irinotecan (Camptosar®, CPT-11, Topotecin®, CaptoCPT-1), Leflunomide (SU-101, SU-0200), Mivobulin isethionate (CI-980), O6-benzylguanine (BG, Procept®), Prinomastat® (AG-3340, MMP inhibitor), R115777 (Zarnestra®), SU6668 (PDGF-TK inhibitor), T-67 (T-138067, T-607), Tamoxifen (Nolvadex®), Tf-CRM107 (Transferrin-CRM-107), Thalidomide, Tiazofurin (Tiazole®), Vapreotide (BMY-41606), Vinorelbine (Navelbine®), and XR-5000 (DACA).

In preferred embodiments, agonistic antibodies of the invention are administered in combination with one or more of the above-described combinations of therapeutic agents in the treatment, amelioration and/or prevention of brain cancers.

In specific embodiments antibodies of the present invention are used to treat, ameliorate and/or prevent skin cancers including basal cell carcinoma, squamous cell carcinoma and malignant melanoma Antibodies of the present invention may be used in combination with one or more surgical and/or radiological procedures and/or therapeutic agents to treat, ameliorate and/or prevent skin cancers.

In preferred embodiments agonistic antibodies of the present invention are used to treat, ameliorate and/or prevent skin cancers including basal cell carcinoma, squamous cell carcinoma and malignant melanoma Agonistic antibodies of the present invention may be used in combination with one or more surgical and/or radiological procedures and/or therapeutic agents to treat, ameliorate and/or prevent skin cancers.

Antibodies of the present invention may be administered in combination with one or more therapeutic agents useful in the treatment of skin cancers including, but not limited to, Bleomycin (Blenoxane®, Carmustine (DTI-015, BCNU, BiCNU, Gliadel Wafer®), Cisplatin (Platinol®, CDDP), Dacarbazine (DTIC), Interferon alpha 2b (Intron A®), Interleukin-2 (ProleiukinR®), Tamoxifen (Nolvadex®), Temozolamide (Temodar®, NSC 362856), Vinblastine (Velban®, VLB), Vincristine (Oncovin®, Onco TCS®, VCR, Leurocristine®), and Vindesine (Eldisine®, Fildesin®). Combinations of therapeutic agents useful in the treatment of skin cancers include, but are not limited to, Cisplatin+Carmustine+Dacarbazine+Tamoxifen.

In preferred embodiments, agonistic antibodies of the invention are administered in combination with one or more of the above-described therapeutic agents in the treatment, amelioration and/or prevention of skin cancers.

In further particular embodiments, antibodies of the present invention are used to treat, ameliorate and/or prevent breast cancer. Antibodies of the present invention may be used in combination with one or more surgical and/or radiological procedures and/or therapeutic agents to treat, ameliorate and/or prevent breast cancer. Breast cancers which may be treated using antibodies of the present invention include, but are not limited to, ductal carcinoma, stage I, stage II, stage III and stage IV breast cancers as well as invasive breast cancer and metastatic breast cancer.

In preferred embodiments, agonistic antibodies of the present invention are used to treat, ameliorate and/or prevent breast cancer. Agonistic antibodies of the present invention may be used in combination with one or more surgical and/or radiological procedures and/or therapeutic agents to treat, ameliorate and/or prevent breast cancer. Breast cancers which may be treated using agonistic antibodies of the present invention include, but are not limited to, ductal carcinoma, stage I, stage II, stage III and stage IV breast cancers as well as invasive breast cancer and metastatic breast cancer.

In one preferred embodiment, agonistic antibodies of the invention are used to treat metastatic breast cancer.

Antibodies of the present invention may be administered in combination with one or more surgical and/or radiological procedures useful in the treatment of breast cancer.

In preferred embodiments, agonistic antibodies of the present invention may be administered in combination with one or more surgical and/or radiological procedures useful in the treatment of breast cancer.

Antibodies of the present invention may be administered in combination with one or more therapeutic agents useful in the treatment of breast cancer including, but not limited to, Amifostine (Ethyol®), Aminoglutethimide (Cytadren®), Anastrozole (Arimidex®), Bleomycin (Blenoxane®), Capecitabine (Xeloda®, Doxifluridine®, oral 5-FU), Cisplatin (Platinol®, CDDP), Cisplatin-epinephrine gel (IntraDose®, FocaCist®), Cyclophosphamide (Cytoxan®, Neosar®, CTX), Docetaxel (Taxotere®, Taxane®), Doxorubicin (Adriamycin®, Doxil®, Rubex®), Epirubicin (Ellence®, EPI, 4' epi-doxorubicin), Exemestane (Aromasin®, Nikidess®), Fadrozole (Afema®, Fadrozole hydrochloride, Arensin®), Fluorouracil (5-FU, Adrucil®, Fluoroplex®, Efudex®), Herceptin® (Trastuzumab, Anti-HER-2 monoclonal antibody, Anti-EGFR-2 MAb), Ifosfamide (IFEX®), Letrozole (Femara®), Leucovorin (Leucovorin®, Wellcovorin®), Mechiorethamine (Nitrogen Mustard, HN$_2$, Mustargen®), Megestrol acetate (Megace®, Pallace®), Meiphalan (L-PAM, Alkeran®, Phenylalanine mustard), Methotrexate (MTX, Mexate®, Folex®), Methyltestosterone (Android-10®, Testred®, Virilon®), Mitomycin C (Mitomycin®, Mutamycin®, Mito Extra®), Orzel® (Tegafur+Uracil+Leucovorin), Paclitaxel (Paxene®, Taxol®), Sobuzoxane (MST- 16, Perazolin®), Tamoxifen (Nolvadex®), Testosterone (Andro®, Androderm®, Testoderm TTS®, Testoderm®, Depo-Testosterone®, Androgel®, depoAndro®), Vinbiastine (Velban®, VLB), Vincristine (Oncovin®, Onco TCS®, VCR, Leurocristine®), and Vinorelbine (Navelbine®).

In preferred embodiments, agonistic antibodies of the invention are administered in combination with one or more of the above-described therapeutic agents in the treatment, amelioration and/or prevention of breast cancers.

Further examples of therapeutic agents useful in the treatment of breast cancer which may be administered in combination with antibodies of the present invention include, but are not limited to, Aldesleukin (IL-2, Proleukin®), Altretamine (Hexylen®, hexamethylmelamine, Hexastat®), Angiostatin, Annamycin (AR-522, annamycin LF, Aronex®), Biricodar dicitrate (Incel®, Incel MDR Inhibitor), Boronated Protoporphyrin Compound (PDIT, Photodynamic Immunotherapy), Bryostatin-1 (Bryostatin, BMY-45618, NSC-339555), Busulfan (Busulfex®, Myleran®), Carmustine (DTI-015, BCNU, BiCNU, Gliadel Wafer®), D-limonene, Dacarbazine (DTIC), Daunorubicin (Daunomycin, DaunoXome®, Daunorubicin®, Cerubidine®), Dolastatin-10 (DOLA-10, NSC-376128), DPPE, DX-8951f (DX-8951), EMD-121974, Endostatin, EO9 (EO1, EO4, EO68, EO70, EO72), Etoposide phosphate (Etopophos®), Etoposide (VP-16, Vepesid®), Fluasterone, Fludarabine (Fludara®, FAMP), Flutamide (Eulexin®), Formestane (Lentaron®), Fulvestrant (Faslodex®), Galarubicin hydrochloride (DA-125), Gemcitabine (Gemto®, Gemzar®), Her-2/Neu vaccine, Hydroxyurea (Hydrea®), Idarubicin (Idamycin®, DMDR, IDA), Interferon alpha 2a (Intron A®), Interferon gamma (Gamma-interferon, Gamma 100®, Gamma-IF), Irinotecan (Camptosar®, CPT-11, Topotecin®, CaptoCPT-1), Ketoconazole (Nizoral®), KRN-8602 (MX, MY-5, NSC-619003, MX-2), L-asparaginase (Elspar®), Leuprolide acetate (Viadur®, Lupron®), Lomustine (CCNU®, CeeNU®), LY-335979, Mannan-MUC1 vaccine, 2-Methoxyestradiol (2-ME, 2-ME-2), Mitoxantrone (Novantrone®, DHAD), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Perillyl alcohol (perilla alcohol, perillic alcohol, perillol, NSC-641066), Pirarubicin (THP), Procarbazine (Matulane®), Providence Portland Medical Center Breast Cancer Vaccine, Pyrazoloacridine (NSC-366140, PD-115934), Raloxifene hydrochloride (Evista®, Keoxifene hydrochloride), Raltitrexed (Tomudex®, ZD-1694), Rebeccamycin, Streptozocin (Zanosar®), Temozolamide (Temodar®, NSC 362856), Theratope, Thiotepa (triethylenethiophosphaoramide, Thioplex®), Topotecan (Hycamtin®, SK&F-104864, NSC-609699, Evotopin®), Toremifene (Estrimex®, Fareston®), Trilostane (Modrefen®), and XR-9576 (XR-9351, P-glycoprotein/MDR inhibitor).

In preferred embodiments, agonistic antibodies of the invention are administered in combination with one or more of the above-described therapeutic agents in the treatment, amelioration and/or prevention of breast cancers.

Preferred combinations of therapeutic agents useful in the treatment of breast cancer which may be administered in combination with antibodies of the present invention include, but are not limited to, Cyclophosphamide+Adriamycin® (Doxorubicin), Cyclophosphamide+Epirubicin+Fluorouracil, Cyclophosphamide+Methotrexate+Fluorouracil (CMF), Paclitaxel+Doxorubicin, and Vinblastine+Doxorubicin+Thiotepa.

In preferred embodiments, agonistic antibodies of the invention are administered in combination with one or more of the above-described therapeutic agent combinations in the treatment, amelioration and/or prevention of breast cancers.

In further particular embodiments, antibodies of the present invention are used to treat, ameliorate and/or prevent prostate cancer. Antibodies of the present invention may be used in combination with one or more surgical and/or radiological procedures and/or therapeutic agents to treat, ameliorate and/or prevent prostate cancer. Prostate cancer which may be treated using antibodies of the present invention includes, but is not limited to, benign prostatic hyperplasia, malignant prostate cancer (e.g., stage I, stage II, stage III or stage IV) and metastatic prostate cancer.

In preferred embodiments, agonistic antibodies of the present invention are used to treat, ameliorate and/or prevent prostate cancer. Agonistic antibodies of the present invention may be used in combination with one or more surgical and/or radiological procedures and/or therapeutic agents to treat, ameliorate and/or prevent prostate cancer. Prostate cancer which may be treated using agonistic antibodies of the present invention includes, but is not limited to, benign prostatic hyperplasia, malignant prostate cancer (e.g., stage I, stage II, stage III or stage IV) and metastatic prostate cancer.

In one preferred embodiment, agonistic antibodies of the invention are used to treat malignant prostate cancer. In a further preferred embodiment, agonistic antibodies of the invention are used to treat metastatic prostate cancer.

Antibodies of the present invention may be administered in combination with one or more surgical, radiological and/or hormonal procedures useful in the treatment of prostate cancer including, but not limited to, prostatectomy (e.g., radical retropubic prostatectomy), external beam radiation therapy, brachytherapy, orchiectomy and hormone treatment (e.g., LHRH agonists, androgen receptor inhibitors).

In preferred embodiments, agonistic antibodies of the present invention may be administered in combination with one or more surgical, radiological and/or hormonal procedures useful in the treatment of prostate cancer including, but not limited to, prostatectomy (e.g., radical retropubic prostatectomy), external beam radiation therapy, brachytherapy, orchiectomy and hormone treatment (e.g., LHRH agonists, androgen receptor inhibitors).

Antibodies of the present invention may be administered in combination with one or more therapeutic agents useful in the treatment of prostate cancer including, but not limited to, Aminoglutethimide (Cytadren®), Biclutamide (Casodex®), Cyclophosphamide (Cytoxan®, Neosar®, CTX), Diethylstilbestrol (DES), Doxorubicin (Adriamycin®, Doxil®, Rubex®), Flutamide (Eulexin®), Hydrocortisone, Ketoconazole (Nizoral®), Leuprolide acetate (Viadur®, Lupron®, Leuprogel®, Eligard®), Mitoxantrone (Novantrone®, DHAD), Nilutamide (Nilandron®), Paclitaxel (Paxene®, Taxol®), Paclitaxel-DHA (Taxoprexin®), PC SPES, Prednisone, Triptorelin pamoate (Trelstar Depot®, Decapeptyl®), and Vinblastine (Velban®, VLB).

In preferred embodiments, agonistic antibodies of the invention are administered in combination with one or more of the above-described therapeutic agents in the treatment, amelioration and/or prevention of prostate cancers.

Further examples of therapeutic agents useful in the treatment of prostate cancer which may be administered in combination with antibodies of the present invention include, but are not limited to, Abarelix (Abarelix-Depot-M®, PPI-149, R-3827); Abiraterone acetate® (CB-7598, CB-7630), ABT-627 (ET-1 inhibitor), APC-8015 (Provenge®, Dendritic cell therapy), Avorelin (Meterelin®, MF-6001, EP-23904), CEP-701 (KT-5555), CN-706, CT-2584 (Apra®, CT-2583, CT-2586, CT-3536), GBC-590, Globo H hexasaccharide (Globo H-KLH®), Interferon alpha 2a (Intron A®), Liarozole (Liazal, Liazol, R-75251, R-85246, Ro-85264), MDX-447 (MDX-220, BAB-447, EMD-82633, H-447, anti-EGFr/FcGammaR1r), Onco-VAX-P (OncoVAX-PrPSA), PROSTVAC, PS-341 (LDP-341, 26S proteasome inhibitor), PSMA MAb (Prostate Specific Membrane Antigen monoclonal antibody), and R-flurbiprofen (Flurizan®, E-7869, MPC-7869).

In preferred embodiments, agonistic antibodies of the invention are administered in combination with one or more of the above-described therapeutic agents in the treatment, amelioration and/or prevention of prostate cancers.

Preferred combinations of therapeutic agents useful in the treatment of prostate cancer which may be administered in combination with antibodies of the present invention include, but are not limited to, Docetaxel+Estramustine, Mitoxantrone+Hydrocortisone, Mitoxantrone+Prednisone, Navelbine+Estramustine, Paclitaxel+Estramustine, and Vinblastine+Estramustine.

In preferred embodiments, agonistic antibodies of the invention are administered in combination with one or more of the above-described therapeutic agent combinations in the treatment, amelioration and/or prevention of prostate cancers.

In further particular embodiments, antibodies of the present invention are used to treat, ameliorate and/or prevent pancreatic cancer. Antibodies of the present invention may be used in combination with one or more surgical and/or radiological procedures and/or therapeutic agents to treat, ameliorate and/or prevent pancreatic cancer. Pancreatic cancers which may be treated using antibodies of the present invention include, but are not limited to, adenocarcinoma, endocrine (islet cell) tumors, tumors confined to the pancreas, locally advanced pancreatic cancer and metastatic pancreatic cancer.

In preferred embodiments, agonistic antibodies of the present invention are used to treat, ameliorate and/or prevent pancreatic cancer. Agonistic antibodies of the present invention may be used in combination with one or more surgical and/or radiological procedures and/or therapeutic agents to treat, ameliorate and/or prevent pancreatic cancer. Pancreatic cancers which may be treated using agonistic antibodies of the present invention include, but are not limited to, adenocarcinoma, endocrine (islet cell) tumors, tumors confined to the pancreas, locally advanced pancreatic cancer and metastatic pancreatic cancer.

In one preferred embodiment, agonistic antibodies of the invention are used to treat locally advanced pancreatic cancer. In a further preferred embodiment, agonistic antibodies of the invention are used to treat metastatic pancreatic cancer.

Antibodies of the present invention may be administered in combination with one or more surgical and/or radiological procedures useful in the treatment of pancreatic cancer including, but not limited to, pancreaticoduodenumectomy (Whipple resection).

In preferred embodiments, agonistic antibodies of the present invention may be administered in combination with one or more surgical and/or radiological procedures useful in the treatment of pancreatic cancer including, but not limited to, pancreaticoduodenumectomy (Whipple resection).

Antibodies of the present invention may be administered in combination with one or more therapeutic agents useful in the treatment of pancreatic cancer including, but not limited to, Capecitabine (Xeloda®, Doxifluridine®, oral 5-FU), Cisplatin (Platinol®, CDDP), Fluorouracil (5-FU, Adrucil®, Fluoroplex®, Efudex®, Gemcitabine (Gemto®, Gemzar®), and Irinotecan (Camptosar®, CPT-11, Topotecin®, CaptoCPT-1).

In preferred embodiments, agonistic antibodies of the invention are administered in combination with one or more of the above-described therapeutic agents in the treatment, amelioration and/or prevention of pancreatic cancers.

Preferred combinations of therapeutic agents useful in the treatment of pancreatic cancer which may be administered in combination with antibodies of the present invention include, but are not limited to, Cisplatin+Gemcitabine, CP-358774+Gemcitabine, Docetaxel+Gemcitabine, Irinotecan+Fluorouracil, Irinotecan+Gemcitabine, and Paclitaxel+Gemcitabine.

In preferred embodiments, agonistic antibodies of the invention are administered in combination with one or more of the above-described therapeutic agent combinations in the treatment, amelioration and/or prevention of pancreatic cancers.

Further examples of therapeutic agents useful in the treatment of pancreatic cancer which may be administered in combination with antibodies of the present invention include, but are not limited to, ABX-EGF (anti-EGFr MAb), Acetyldinaline (CJ-994, GOE-5549, GOR-5549, PD-130636), BMS-214662 (BMS-192331, BMS-193269, BMS-206635), BNP-1350 (BNPI-1100, Karenitecins), C225 (IMC-225, EGFR inhibitor, Anti-EGFr MAb, Cetuximab), C242-DM1 (huC242-DM1, SB-408075), Carbendazin® (FB-642), Carmustine (DTI-015, BCNU, BiCNU, Gliadel Wafer®), CMT-3 (COL-3, Metastat®), CP-358774 (Tarceva®, OSI-774, EGER inhibitor), Docetaxel (Taxotere®, Taxane®), Exetecan mesylate (DX-8951, DX-895 if), Flavopiridol (HMR-1275), Gastrimmune® (Anti-gastrin-17 imrnunogen, anti-g17), GBC-590, Herceptin® (Trastuzumab, Anti-HER-2 monoclonal antibody, Anti-EGFR-2 MAb), HSPPC-96 (HSP cancer vaccine, gp96 heat shock protein-peptide complex), Irofulven (MGI-114), ISIS-2503 (Ras antisense), Onyx-OlS (p53 gene therapy), Paclitaxel (Paxene®, Taxol®), Pemetrexed disodium (Alimta®, MTA, multitargeted antifolate, LY 231514), Perillyl alcohol (perilla alcohol, perillic alcohol, perillol, NSC-641066), RFS-2000 (9-nitrocamptothecan, 9-NC, rubitecan®), and Rituximab (Rituxan®, anti-CD20 MAb).

In preferred embodiments, agonistic antibodies of the invention are administered in combination with one or more of the above-described therapeutic agents in the treatment, amelioration and/or prevention of pancreatic cancers.

In further particular embodiments, antibodies of the present invention are used to treat, ameliorate and/or prevent hepatic cancer. Antibodies of the present invention may be used in combination with one or more surgical and/or radiological procedures and/or therapeutic agents to treat, ameliorate and/or prevent hepatic cancer. Hepatic cancers which may be treated using antibodies of the present invention include, but are not limited to, hepatocellular carcinoma, malignant hepatoma, cholangiocarcinoma, mixed hepatocellular cholangiocarcinoma or hepatoblastoma.

In preferred embodiments, agonistic antibodies of the present invention are used to treat, ameliorate and/or prevent hepatic cancer. Agonistic antibodies of the present invention may be used in combination with one or more surgical and/or radiological procedures and/or therapeutic agents to treat, ameliorate and/or prevent hepatic cancer. Hepatic cancers which may be treated using agonistic antibodies of the present invention include, but are not limited to, hepatocellular carcinoma, malignant hepatoma, cholangiocarcinoma, mixed hepatocellular cholangiocarcinoma or hepatoblastoma.

In one preferred embodiment, agonistic antibodies of the invention are used to treat hepatoblastoma. In one further preferred embodiment, agonistic antibodies of the invention are used to treat hepatocellular carcinoma.

Antibodies of the present invention may be administered in combination with one or more surgical and/or radiological procedures useful in the treatment of hepatic cancers including, but not limited to, partial hepatectomy, liver transplant, radiofrequency ablation, laser therapy, microwave therapy, cryosurgery, percutaneous ethanol injection, hepatic arterial infusion, hepatic artery ligation, chemoembolization and external beam radiation therapy.

In preferred embodiments, agonistic antibodies of the present invention may be administered in combination with one or more surgical and/or radiological procedures useful in the treatment of hepatic cancers including, but not limited to, partial hepatectomy, liver transplant, radiofrequency ablation, laser therapy, microwave therapy, cryosurgery, percutaneous ethanol injection, hepatic arterial infusion, hepatic artery ligation, chemoembolization and external beam radiation therapy.

Antibodies of the present invention may be administered in combination with one or more therapeutic agents useful in the treatment of hepatic cancer including, but not limited to, Aldesleukin (IL-2, Proleukin®), Cisplatin (Platinol®, CDDP), Doxorubicin (Adriamycin®, Doxil®, Rubex®), Etoposide phosphate (Etopophos®), Etoposide (VP-16, Vepesid®), Fluorouracil (5-FU, Adrucil®, Fluoroplex®, Efudex®), I-131 Lipidiol®, Ifosfamide (IFEX®), Megestrol acetate (Megace®, Pallace®), Pravastatin sodium (Pravachol®), and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of hepatic cancers.

Preferred combinations of therapeutic agents useful in the treatment of hepatic cancer which may be administered in combination with antibodies of the present invention include, but are not limited to, Cisplatin+Doxorubicin, Cisplatin+Etoposide, Cisplatin+Vincristine+Fluorouracil, and Ifosfamide+Cisplatin+Doxorubicin.

In preferred embodiments, agonistic antibodies of the invention are administered in combination with one or more of the above-described therapeutic agent combinations in the treatment, amelioration and/or prevention of hepatic cancers.

In further particular embodiments, antibodies of the present invention are used to treat, ameliorate and/or prevent ovarian cancer. Antibodies of the present invention may be used in combination with one or more surgical and/or radiological procedures and/or therapeutic agents to treat, ameliorate and/or prevent ovarian cancer. Ovarian cancers which may be treated using antibodies of the present invention include, but are not limited to, epithelial carcinoma, germ cell tumors and stromal tumors.

In preferred embodiments, agonistic antibodies of the present invention are used to treat, ameliorate and/or prevent ovarian cancer. Agonistic antibodies of the present invention may be used in combination with one or more surgical and/or radiological procedures and/or therapeutic agents to treat, ameliorate and/or prevent ovarian cancer. Ovarian cancers which may be treated using agonistic antibodies of the present invention include, but are not limited to, epithelial carcinoma, germ cell tumors and stromal tumors.

In one preferred embodiment, agonistic antibodies of the invention are used to treat germ cell tumors. In one further preferred embodiment, agonistic antibodies of the invention are used to treat epithelial carcinoma.

Antibodies of the present invention may be administered in combination with one or more surgical and/or radiological procedures useful in the treatment of ovarian cancer including, but not limited to, hysterectomy, oophorectomy, hysterectomy with bilateral salpingo-oophorectomy, omentectomy, tumor debulking, external beam radiation therapy and intraperitoneal radiation therapy.

In preferred embodiments, agonistic antibodies of the present invention may be administered in combination with one or more surgical and/or radiological procedures useful in the treatment of ovarian cancer including, but not limited to, hysterectomy, oophorectomy, hysterectomy with bilateral salpingo-oophorectomy, omentectomy, tumor debulking, external beam radiation therapy and intraperitoneal radiation therapy.

Antibodies of the present invention may be administered in combination with one or more therapeutic agents useful in the treatment of ovarian cancer including, but not limited to, Altretamine (Hexylen®, hexamethylmelamine, Hexastat®, Bleomycin (Blenoxane®), Carboplatin (Paraplatin®, CBDCA), Cisplatin (Platinol®, CDDP), Cyclophosphamide (Cytoxan®, Neosar®, CTX), Dactinomycin (Cosmegen®), Doxorubicin (Adriamycin®, Doxil®, Rubex®), Etoposide phosphate (Etopophos®), Etoposide (VP-16, Vepesid®), Fluorouracil (5-FU, Adrucil®, Fluoroplex®, Efudex®), Gemcitabine (Gemto®, Gemzar®), Ifosfamide (IFEX®), Irinotecan (Camptosar®, CPT-11, Topotecin®, CaptoCPT-1), Leucovorin (Leucovorin®, Wellcovorin®), Melphalan (L-PAM, Alkeran®, Phenylalanine mustard), Paclitaxel (Paxene®, Taxol®), Tamoxifen (Nolvadex®), Vinblastine (Velban®, VLB) and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of ovcarian cancers.

Preferred combinations of therapeutic agents useful in the treatment of ovarian cancer which may be administered in combination with antibodies of the present invention include, but are not limited to, Bleomycin+Etoposide+Platinol® (Cisplatin) (BEP), Carboplatin+Cyclophosphamide, Carboplatin+Paclitaxel, Carboplatin+Etoposide+Bleomycin (CEB), Cisplatin+Cyclophosphamide, Cisplatin+Etoposide, Cisplatin+Paclitaxel, Cisplatin+Ifosfamide+Vinblastine, Fluorouracil+Leucovorin, Platinol® (Cisplatin)+Vinblastine+Bleomycin (PVB), and Vincristine+Dactinomycin+Cyclophosphamide.

In preferred embodiments, agonistic antibodies of the invention are administered in combination with one or more of the above-described therapeutic agent combinations in the treatment, amelioration and/or prevention of ovarian cancers.

In further particular embodiments, antibodies of the present invention are used to treat, ameliorate and/or prevent Ewing's sarcoma Antibodies of the present invention may be used in combination with one or more surgical and/or radiological procedures and/or therapeutic agents to treat, ameliorate and/or prevent Ewing's sarcoma Ewing's sarcoma family tumors which may be treated using antibodies of the present invention include, but are not limited to, Ewing's tumor of bone (ETB), extraosseus Ewing's (EOE), primitive neuroectodermal tumors (PNET or peripheral neuroepithelioma) and Askin's tumor.

In preferred embodiments, agonistic antibodies of the present invention are used to treat, ameliorate and/or prevent Ewing's sarcoma Agonistic antibodies of the present invention may be used in combination with one or more surgical and/or radiological procedures and/or therapeutic agents to treat, ameliorate and/or prevent Ewing's sarcoma. Ewing's sarcoma family tumors which may be treated using agonistic antibodies of the present invention include, but are not limited to, Ewing's tumor of bone (ETB), extraosseus Ewing's (EOE), primitive neuroectodermal tumors (PNET or peripheral neuroepithelioma) and Askin's tumor.

In one preferred embodiment, agonistic antibodies of the invention are used to treat Ewing's tumor of bone. In one further preferred embodiment, agonistic antibodies of the invention are used to treat peripheral neuroepithelioma.

Antibodies of the present invention may be administered in combination with one or more surgical and/or radiological procedures useful in the treatment of Ewing's sarcoma family tumors.

In preferred embodiments, agonistic antibodies of the invention are administered in combination with one or more surgical and/or radiological procedures useful in the treatment of Ewing's sarcoma family tumors.

Antibodies of the present invention may be administered in combination with one or more therapeutic agents useful in the treatment of Ewing's sarcoma family tumors including, but not limited to, Cyclophosphamide (Cytoxan®, Neosar®, CTX), Doxorubicin (Adriamycin®, Doxil®, Rubex®), Etoposide phosphate (Etopophos®), Etoposide (VP-16, Vepesid®), Filgrastim (Neupogen®, G-CSF), Ifosfamide (IFEX®), Topotecan (Hycamtin®, SK&F-104864, NSC-609699, Evotopin®), and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of Ewing's sarcoma family tumors.

Preferred combinations of therapeutic agents useful in the treatment of Ewing's sarcoma family tumors which may be administered in combination with antibodies of the present invention include, but are not limited to, Cyclophosphamide+Topotecan, Cyclophosphamide+Doxorubicin+Vincristine, Cyclophosphamide+Doxorubicin+Vincristine, alternating with Ifosfamide+Etoposide and Cyclophosphamide+Doxorubicin+Vincristine, alternating with Filgrastim+Ifosfamide+Etoposide.

In preferred embodiments, agonistic antibodies of the invention are administered in combination with one or more of the above-described therapeutic agent combinations in the treatment, amelioration and/or prevention of Ewing's sarcoma family tumors.

Additional Combination Therapies

In a more preferred embodiment, the antibody and antibody compositions of the invention are administered in combination with an antimalarial, methotrexate, anti-TNF antibody, ENBREL™ (Etanercept) and/or suflasalazine. In one embodiment, the antibody and antibody compositions of the invention are administered in combination with methotrexate. In another embodiment, the antibody and antibody compositions of the invention are administered in combination with anti-TNF antibody. In another embodiment, the antibody and antibody compositions of the invention are administered in combination with methotrexate and anti-TNF antibody. In another embodiment, the antibody and antibody compositions of the invention are administered in combination with suflasalazine. In another specific embodiment, the antibody and antibody compositions of the invention are administered in combination with methotrexate, anti-TNF anilibody, and suflasalazine. In another embodiment, the antibody and antibody compositions of the invention are administered in combination ENBREL™ (Etanercept). In another embodiment, the antibody and antibody compositions of the invention are administered in combination with ENBREL™ (Etanercept) and methotrexate. In another embodiment, the antibody and antibody compositions of the invention are administered in combination with ENBREL™ (Etanercept), methotrexate and suflasalazine. In another embodiment, the antibody and antibody compositions of the invention are administered in combination with ENBREL™ (Etanercept), methotrexate and suflasalazine. In other embodiments, one or more antimalarials is combined with one of the above-recited combinations. In a specfic embodiment, the antibody and antibody compositions of the invention are administered in combination with an antimalarial (e.g., hydroxychloroquine), ENBREL™ (Etanercept), methotrexate and suflasalazine. In another specfic embodiment, the antibody and antibody compositions of the invention are administered in combination with an antimalarial (e.g., hydroxychioroquine), sulfasalazine, anti-TNF antibody, and methotrexate.

The antibodies of the invention (including molecules comprising, or alternatively consisting of, antibody fragments or variants thereof) may be administered alone or in combination with other therapeutic or prophylactic regimens (e.g., radiation therapy, chemotherapy, hormonal therapy, immunotherapy, anti-tumor agents, anti-angiogenesis and anti-inflammatory agents). Such combinatorial therapy may be administered sequentially and/or concomitantly.

Conventional nonspecific immunosuppressive agents, that may be administered in combination with the antibody and antibody compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, antibody and antibody compositions of the invention are administered in combination with immunosuppressants. Immunosuppressants preparations that may be administered with the antibody and antibody compositions of the invention include, but are not limited to, ORTHOCLONE™ (OKT3), SANDMMUNE™/NEORAL™/SANGDYA™ (cyclosporin), PROGRAF™ (tacrolimus), CELLCEP™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the antibody and antibody compositions of the invention are administered in combination with steroid therapy. Steroids that may be administered in combination with the antibody and antibody compositions of the invention, include, but are not limited to, oral corticosteroids, prednisone, and methylprednisolone (e.g., IV methylprednisolone). In a specific embodiment, antibody and antibody compositions of the invention are administered in combination with prednisone. In a further specific embodiment, the antibody and antibody compositions of the invention are administered in combination with prednisone and an immunosuppressive agent. Immunosuppressive agents that may be administered with the antibody and antibody compositions of the invention and prednisone are those described herein, and include, but are not limited to, azathioprine, cylophosphamide, and cyclophosphamide IV. In another specific embodiment, antibody and antibody compositions of the invention are administered in combination with methylprednisolone. In a further specific embodiment, the antibody and antibody compositions of the invention are administered in combination with methylprednisolone and an immunosuppressive agent. Immunosuppressive agents that may be administered with the antibody and antibody compositions of the invention and methylprednisolone are those described herein, and include, but are not limited to, azathioprine, cylophosphamide, and cyclophosphamide IV.

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the antibody and antibody compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., Panminerva Medica, 23:243-248 (1981); Kurtz, FEBS Letters, 14a:105-108 (1982); McGonigle et al., Kidney Int., 25:437-444 (1984); and Pavlovic-Kantera, Expt. Hematol., 8(supp. 8) 283-291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, Kidney Int., 22:383-391 (1982); Shahidi, New Eng. J. Med., 289:72-80 (1973); Urabe et al., J. Exp. Med., 149:1314-1325 (1979); Billat et al., Expt. Hematol., 10:135-140 (1982); Naughton et al., Acta Haemat, 69:171-179 (1983); Cognote et al. in abstract 364, Proceedings 7th Intl. Cong. of Endocrinology (Quebec City, Quebec, Jul. 1-7, 1984); and Rothman et al., 1982, J. Surg. Oncol., 20:105-108 (1982). Methods for stimulating hematopoiesis comprise administering a hematopoietically effective amount (i.e., an amount which effects the formation of blood cells) of a pharmaceutical composition containing polynucleotides and/or poylpeptides of the invention (and/or agonists or antagonists thereof) to a patient. The polynucleotides and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In an additional embodiment, the antibody and antibody compositions of the invention are administered in combination with hematopoietic growth factors. Hematopoietic growth factors that may be administered with the antibody and antibody compositions of the invention include, but are not limited to, LEUKINE™ (sargramostim) and NEUPOGEN™ (filgrastim).

In an additional embodiment, the antibody and antibody compositions of the invention are administered alone or in combination with an anti-angiogenic agent(s). Anti-angiogenic agents that may be administered with the antibody and antibody compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-

17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman *J Pediatr. Surg.* 28:445-51 (1993)); an integrin alpha v beta 3 antagonist (C. Storgard et al., *J. Clin. Invest.* 103:47-54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC359555); CGP-41251 (PKC 412); CM11; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3540) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the antibody and antibody compositions of the invention include, but are not limited to, AG-3540 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aeterna, St-Foy, Quebec). Examples of anti-angiogenic inhibitors that act by blocking the function of endothelial cell-extracellular matrix adhesion molecules and which may be administered in combination with the antibody and antibody compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the antibody and antibody compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the antibody and antibody compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of antibody and antibody compositions of the invention in combination with anti-angiogenic agents is contemplated for the treatment, prevention, and/or amelioration of cancers and other hyperproliferative disorders.

In a further embodiment, the antibody and antibody compositions of the invention are administered in combination with an antiviral agent. Antiviral agents that may be administered with the antibody and antibody compositions of the invention include, but are not limited to, acyclovir, ribavirin, amantadine, and remantidine.

In certain embodiments, Therapeutics of the invention are administered in combination with antiretroviral agents, nucleoside/nucleotide reverse transcriptase inhibitors (NR-TIs), non-nucleoside reverse transcriptase inhibitors (NNR-TIs), and/or protease inhibitors (PIs). NRTIs that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with the Therapeutics of the invention, include, but are not limited to, VIRA™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEP™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In a further embodiment, the antibody and antibody compositions of the invention are administered in combination with an antibiotic agent. Antibiotic agents that may be administered with the antibody and antibody compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

In other embodiments, antibody and antibody compositions of the invention may be administered in combination with anti-opportunistic infection agents. Anti-opportunistic agents that may be administered in combination with the antibody and antibody compositions of the invention, include; but are not limited to, tiimethoprim sulfamethoxazole, dapsone, pentamidin, atovaquone, isoniazid, rifampin, pyrazinamide, ethambutol, rifabutin, clarithromycin, azithromycin, ganciclovir, foscarnet, cidofovir, fluconazole, itraconazole, ketoconazole, acyclovir, famciclovir, pyrimethamine, leucovorin, NEUPOGEN™ (filgrastim/G-CSF), and LEUKINE™ (sargramostim/GM-CSF). In a specific embodiment, antibody and antibody compositions of the invention are used in any combination with trimethoprim sulfamethoxazole,. dapsone, pentarnidine, and/or atovaquone to prophylactically treat, prevent, and/or diagnose an opportunistic *Pneumocystis carinii* pneumonia infection. In another specific embodiment, antibody and antibody compositions of the invention are used in any combination with isoniazid, rifampin, pyrazinamide, and/or ethambutol to prophylactically treat, prevent, and/or diagnose an opportunistic *Mycobacierium avium* complex infection. In another specific embodiment, antibody and antibody compositions of the invention are used in any combination with rifabutin, clarithromycin, and/or azithrornycin to prophylactically treat, prevent, and/or diagnose an opportunistic *Mycobacterium tuberculosis* infection. In another specific embodiment, antibody and antibody compositions of the invention are used in any combination with ganciclovir, foscarnet, and/or cidofovir to prophylactically treat, prevent, and/or diagnose an opportunistic cytomegalovirus infection. In another specific embodiment, antibody and antibody compositions of the invention are used in any combination with fluconazole, itraconazole, and/or ketoconazole to prophylactically treat, prevent, and/or diagnose an opportunistic fungal infection. In another specific embodiment, antibody and antibody compositions of the invention are used in any combination with acyclovir and/or famciclovir to prophylactically treat, prevent, and/or diagnose an opportunistic herpes simplex virus type I and/or type II infection. In another specific embodiment, antibody and antibody compositions of the invention are used in any combination with pyrimethamine and/or leucovorin to prophylactically treat, prevent, and/or diagnose an opportunistic *Toxoplasma gondii* infection. In another specific embodiment, antibody and antibody compositions of the invention are used in any combination with leucovorin and/or NEUPOGEN™ (filgrastim/G-CSF) to prophylactically treat, prevent, and/or diagnose an opportunistic bacterial infection.

In an additional embodiment, the antibody and antibody compositions of the invention are administered alone or in combination with an anti-inflammatory agent. Anti-inflammatory agents that may be administered with the antibody and antibody compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

The antibodies and antibody compositions of the invention may be administered alone or in combination with other adjuvants. Adjuvants that may be administered with the antibody and antibody compositions of the invention include, but are not limited to, alum, alum plus deoxycholate (ImmunoAg), MTP-PE (Biocine Corp.), QS21 (Genentech, Inc.), BCG, and MPL. In a specific embodiment, antibody and antibody compositions of the invention are administered in combination with alum. In another specific embodiment, antibody and antibody compositions of the invention are administered in combination with QS-21. Further adjuvants that may be administered with the antibody and antibody compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the antibody and antibody compositions of the invention include, but are not limited to, vaccines directed toward protection against MIMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, andlor PNEUMOVAX-23™ (Pneumococcal Vaccine Polyvalent). Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, antibody and antibody compositions of the invention are used in combination with PNEUMOVAX-23™ (Pneumococcal Vaccine Polyvalent) to treat, prevent, and/or diagnose infection and/or any disease, disorder, and/or condition associated therewith. In one embodiment, antibody and antibody compositions of the invention are used in combination with PNEUMOVAX-23™ (Pneumococcal Vaccine Polyvalent) to treat, prevent, and/or diagnose any Gram positive bacterial infection and/or any disease, disorder, and/or condition associated therewith. In another embodiment, antibody and antibody compositions of the invention are used in combination with PNEUMOVAX-23™ (Pneumococcal Vaccine Polyvalent) to treat, prevent, and/or diagnose infection and/or any disease, disorder, and/or condition associated with one or more members of the genus *Enterococcus* and/or the genus *Streptococcus*. In another embodiment, antibody and antibody compositions of the invention are used in any combimition with PNEUMOVAX-23™ (Pneumococcal Vaccine Polyvalent) to treat, prevent, and/or diagnose infection and/or any disease, disorder, and/or condition associated with one or more members of the Group B streptococci. In another embodiment, antibody and antibody compositions of the invention are used in combination with PNEUMOVAX-23™ (Pneumococcal Vaccine Polyvalent) to treat, prevent, and/or diagnose infection and/or any disease, disorder, and/or condition associated with *Streptococcus pneumoniae*.

In a preferred embodiment, the antibody and antibody compositions of the invention are administered in combination with CD40 ligand (CD40L), a soluble form of CD40L (e.g., AVREND™), bioloigically active fragments, variants, or derivatives of CD40L, anti-CD40L antibodies (e.g., agonistic or antagonistic antibodies), and/or anti-CD40 antibodies (e.g., agonistic or antagonistic antibodies).

In another embodiment, antibody and antibody compositions of the invention are administered in combination with an anticoagulant. Anticoagulants that may be administered with the antibody and antibody compositions of the invention include, but are not limited to, heparin, warfarin, and aspirin. In a specific embodiment, antibody and antibody compositions of the invention are administered in combination with heparin and/or warfarin. In another specific embodiment, antibody and antibody compositions of the invention are administered in combination with warfarin. In another specific embodiment, antibody and antibody compositions of the invention are administered in combination with warfarin and aspirin. In another specific embodiment, antibody and antibody compositions of the invention are administered in combination with heparin. In another specific embodiment, antibody and antibody compositions of the invention are administered in combination with heparin and aspirin.

In another embodiment, antibody and antibody compositions of the invention are administered in combination with an agent that suppresses the production of anticardiolipin antibodies. In specific embodiments, the polynucleotides of the invention are administered in combination with an agent that blocks and/or reduces the ability of anticardiolipin antibodies to bind phospholipid-binding plasma protein beta 2-glycoprotein I (b2GPI).

In a preferred embodiment, the antibody and antibody compositions of the invention are administered in combination with an antimalarial. Antimalarials that may be administered with the antibody and antibody compositions of the invention include, but are not limited to, hydroxychloroquine, chloroquine, and/or quinacrine.

In a preferred embodiment, the antibody and antibody compositions of the invention are administered in combination with an NSAID. In a preferred embodiment, the antibody and antibody compositions of the invention are administered in combination with indomethacin. In a preferred embodiment, the antibody and antibody compositions of the invention are administered in combination with sodium salicylate.

In a nonexclusive embodiment, the antibody and antibody compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-714 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-671 (Merck), ST-1482 (Sigma-Tau), and butixocort propionate (WarnerLambert).

In a preferred embodiment, the antibody and antibody compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, LJP 394 (La Jolla Pharmaceutical Company, San Diego, Calif.) and prednisolone.

In an additional embodiment, antibody and antibody compositions of the invention are administered alone or in combination with one or more intravenous immune globulin preparations. Intravenous immune globulin preparations that may be administered with the antibody and antibody compositions of the invention include, but not limited to, GAMMAR™, IVEEGAM™, SANDOGLOBULIN™, GAMMAGARD S/D™, and GAMIMUNE™. In a specific embodiment, antibody and antibody compositions of the invention are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the antibody and antibody compositions of the invention are administered in combination with cytokines. Cytokines that may be administered with the antibody and antibody compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In preferred embodiments, antibody and antibody compositions of the invention are administered with TRAIL receptor. In another embodiment, antibody and antibody compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the antibody and antibody compositions of the invention are administered in combination with IL4 and IL10. In other preferred embodiments, the antibody and antibody compositions of the invention are administered in combination with IL2. In preferred embodiments, the antibody and antibody compositions of the invention are administered in combination with G-CSF.

In one embodiment, the antibody and antibody compositions of the invention are administered in combination with one or more chemokines. In specific embodiments, the antibody and antibody compositions of the invention are administered in combination with an $\alpha(C \times C)$ chemokine selected from the group consisting of gamma-interferon inducible protein-10 ($\gamma$IP-10), interleukin-8 (IL-8), platelet factor-4 (PF4), neutrophil activating protein (NAP-2), GRO-$\alpha$, GRO-$\beta$, GRO-$\gamma$, neutrophil-activating peptide (ENA-78), granulocyte chemoattractant protein-2 (GCP-2), and stromal cell-derived factor-1 (SDF-1, or pre-B cell stimulatory factor (PBSF)); and/or a $\beta$(CC) chemokine selected from the group consisting of: RANTES (regulated on activation, normal T expressed and secreted), macrophage inflammatory protein-1 alpha (MIP-1$\alpha$), macrophage inflammatory protein-1 beta (MIP-1$\beta$), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1$\gamma$), macrophage inflammatory protein-3 alpha (MIP-3$\alpha$), macrophage inflammatory protein-3 beta (MIP-3$\beta$), macrophage inflammatory protein-4 (MIP-4/DC-CK-1/PARC), eotaxin, Exodus, and I-309; and/or the $\gamma$(C) chemokine, lymphotactin. In preferred embodiments, the antibody and antibody compositions of the invention are administered in combination with an agent that increases IFN-gamma and/or caspase activity particularly caspase-8 activity.

In another embodiment, the antibody and antibody compositions of the invention are administered with chemokine beta-8, chemokine beta-1, and/or macrophage inflammatory protein-4. In a preferred embodiment, the antibody and antibody compositions of the invention are administered with chemokine beta-8.

In an additional embodiment, the antibody and antibody compositions of the invention are administered in combination with an IL-4 antagonist. IL-4 antagonists that may be administered with the antibody and antibody compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the antibody and antibody compositions of the invention are administered in combination with fibroblast growth factors. Fibroblast growth factors that may be administered with the antibody and antibody compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans.

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

Antibodies or compositions of the invention can be tested for their ability to reduce tumor formation in in vitro, ex vivo and in vivo assays. Antibodies or compositions of the invention can also be tested for their ability to inhibit viral replication or reduce viral load in in vitro and in vivo assays. Antibodies or compositions of the invention can also be tested for their ability to reduce bacterial numbers in in vitro and in vivo assays known to those of skill in the art. Antibodies or compositions of the invention can also be tested for their ability to alleviate of one or more symptoms associated with cancer, an immune disorder (e.g., an inflammatory disease), a neurological disorder or an infectious disease. Antibodies or compositions of the invention can also be tested for their ability to decrease the time course of the infectious disease. Further, antibodies or compositions of the invention can be tested for their ability to increase the survival period of animals suffering from disease or disorder, including cancer, an immune disorder or an infectious disease. Techniques known to those of skill in the art can be used to analyze the function of the antibodies or compositions of the invention in vivo.

Efficacy in treating or preventing viral infection may be demonstrated by detecting the ability of an antibody or composition of the invention to inhibit the replication of the virus, to inhibit transmission or prevent the virus from establishing itself in its host, or to prevent, ameliorate or alleviate the symptoms of disease a progression. The treatment is considered therapeutic if there is, for example, a reduction in viral load, amelioration of one or more symptoms, or a decrease in mortality and/or morbidity following administration of an antibody or composition of the invention.

Antibodies or compositions of the invention can be tested for their ability to modulate the biological activity of immune cells by contacting immune cells, preferably human immune cells (e.g., T-cells, B-cells, and Natural Killer cells), with an antibody or composition of the invention or a control compound and determining the ability of the antibody or compostion of the invention to modulate (i.e, increase or decrease) the biological activity of immune cells. The ability of an antibody or composition of the invention to modulate the biological activity of immune cells can be assessed by detecting the expression of antigens, detecting the proliferation of immune cells (i.e., B-cell proliferation), detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the ability of an antibody or composition of the invention to induce B-cell proliferation is measured. In another preferred embodiment, the ability of an antibody or composition of the invention to modulate immunoglobulin expression is measured.

Panels/Mixtures

The present invention also provides for mixtures of antibodies (including scFvs and other molecules comprising, or alternatively consisting of, antibody fragments or variants thereof) that immunospecifically bind to TR4 or a fragment or variant thereof, wherein the mixture has at least one, two, three, four, five or more different antibodies of the invention. In specific embodiments, the invention provides mixtures of at least 2, preferably at least 4, at least 6, at least 8, at least 10, at least 12, at least 15, at least 20, or at least 25 different antibodies that immunospecifically bind to TR4 or fragments or variants thereof, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that immunospecifically bind to TR4 or a fragment or variant thereof, wherein the panel has at least one, two, three, four, five or more different antibodies of the invention. In specific embodiments, the invention provides for panels of antibodies that have different affinities for TRAIL receptor, different specificities for TRAIL receptor, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention further provides for compositions comprising, one or more antibodies (including molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains of a one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s of a VH domain of one or more of the scFvs referred to in Table 1, or a variant thereof. In another embodiment, a composition of the present invention comprises, one, two, three, four, five or more antibodies that comprise, or alternatively consist of, a polypeptide having an amino acid sequence of any one or more of the VH CDR2s of a VH domain of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s as of a VH domain of one or more of the scFvs referred to in Table 1, or a variant thereof.

Other embodiments of the present invention providing for compositions comprising, one or more antibodies (including molecules comprising, or alternatively consisting of antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s domains of one or more of the scFvs referred to in Table 1, or a variant thereof.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alterative embodiment, a kit comprises an antibody fragment that immunospecifically binds to TR4 polypeptides or fragments or variants thereof. In a specific embodiment, the kits of the present invention contain a substantially isolated TR4 polypeptide or fragment or variant thereof as a control. Preferably, the kits of the present invention further comprise a control antibody which does not react with any, some or all TRAIL receptors. In another specific embodiment, the kits of the present invention contain a means for detecting the binding of an antibody to TR4 polypeptides (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized TRAIL receptor. The TR4 provided in the kit may also be attached to a solid support. In a more specific embodiment the detecting means of the above-described kit includes a solid support to which TR4 is attached. Such a kit may also include a non-attached reporter-labeled anti-human antibody. In this embodiment, binding of the antibody to TR4 can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with a TRAIL receptor, and means for detecting the binding of TR4 polypeptides to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having surface-bound TRAIL receptors obtained by the methods of the present invention. After TR4 polypeptides bind to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-TR4 antibody on the solid support. Typically, the reporter is an enzyme which is detected by incubating the solid phase in the presence of a suitable fluorometric, luminescent or calorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant TRAIL receptor, and a reporter-labeled anti-human antibody for detecting surface-bound anti-TR4 antibody.

Placental Expression of TRAIL Receptors

The expression of tumor necrosis family receptors and ligands in whole placenta and in placental macrophage and trophoblast cell lines have been carefully examined. It has been shown that trophoblasts express TR7 and TR5 but not TR10 are entirely resistant to killing by recombinant TRAIL whereas macrophages, which express TR4, TR7 and TR10 but not TR5, are sensitive (Phillips et al., J. Immunol 15:6053-9 (1999) which is incorporated in its entirety by refrence herein). Thus the methods for using anti-TR4 antibodies described herein, may also be used on placenta and placental cell types (e.g., macrophagges and trophoblast cells) to prevent, treat, diagnose, ameliorate, or monitor diseases and disorders of the placenta placental cell types.

Gene Therapy

In a specific embodiment, nucleic acids comprising sequences encoding antibodies or functional derivatives thereof, are administered to treat, inhibit or prevent a disease or disorder associated with aberrant expression and/or activity of TRAIL Receptors and/or its ligands (e.g., TRAIL), by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06 180; WO 92/22715; WO92/203 16; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651(1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503

(1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

EXAMPLES

Example 1

Isolation and Characterization of scFvs Referred to in Table 1

Rescue of Large scFv Libraries

An scFv library of up to $1 \times 10^{11}$ clones, which is an expanded version of the $1.38 \times 10^{10}$ library described (Vaughan et. al. (1996) *Nature Biotechnology* 14: 309-314), was used to select antibodies specific for TR4. Phage were rescued by taking $3 \times 10^{10}$ cells from a glycerol stock culture and growing in 2YTAG (2YT media supplemented with 100 g/ml ampicillin and 2% (w/v) glucose) at 37° C. for 2 h with shaking. M13K07 helper phage (Stratagene) was added to the culture at a multiplicity of infection (moi) of approximately 10. The culture was incubated stationary at 37° C. for 15 min followed by 45 min with light aeration (200 rpm) at the same temperature. The culture was centrifuged and the cells were resuspended in 500 ml 2YTAK (2YT media supplemented with 100 µg/ml kanamycin), and the culture incubated overnight at 30° C. with good aeration (300 rpm). Phage particles were purified and concentrated by three cycles of polyethylene glycol (PEG) precipitation (20% PEG 6000, 2.5M NaCl) on ice, then resuspended in phosphate buffered saline (PBS) at $10^{12}$ transducing units (tu)/ml, titrated as ampicillin resistant clones.

Panning of scFv Libraries on TR4

Soluble, purified TR4 fusion protein was produced by HGS. Purified phagemids were first deselected on an irrelevant fusion protein to remove any irrelevant binders. To do this, 500 µl of an irrelevant fusion protein was immobilised (10 µg/ml in PBS) on a 75 mm×12 mm immunotube (Nunc; Maxisorp) overnight at 4° C. After washing 3 times with PBS, the tube was filled with 3% MPBS (3% 'Marvel' skimmed milk powder in PBS) and blocked for 2 h at 37° C. The wash was repeated and phagemid particles (1013 tu) in 500 µl 3% MPBS containing 100 µg/ml irrelevant fusion protein were added and the tube incubated stationary at 37° C. for 1 h. The phagemid particles were then transferred to an immunotube which had been coated with TR4 (10 µg/ml in PBS) overnight at 4° C. and blocked for 2 h at 37° C. with 3% MPBS. The tube was incubated stationary at 37° C. for 1 hour and then washed 10 times with PBST (PBS containing 0.1% (v/v) Tween 20), and 10 times with PBS. Bound phagemid particles were eluted with 1 ml 100 mM triethylamine for 10 min at room temperature, then immediately neutralised with 0.5 ml 1M Tris.HCl (pH 7.4). The eluted phage were used to infect 10 ml exponentially growing *E. coli* TG1. Infected cells were grown in 2YT broth for 1 h at 37° C. with light aeration, then streaked onto 2YTAG agar plates (243 mm×243 mm; Nunc) and incubated overnight at 30° C. Colonies were scraped off the plates into 10 ml of 2YT broth and 15% (v/v) glycerol added for storage −70° C.

Glycerol stock cultures from the first round of panning on TR4 fusion protein were then superinfected with helper phage and rescued to give phagemid particles for the second round of panning. 25 μl of glycerol stock was inoculated into 25 ml 2TYAG broth, and incubated at 37° C. with good aeration until the $OD_{600nm}$ reached 0.7. M13K07 helper phage (moi=10) was added to the culture which was then incubated stationary for 15 min at 37° C. then with shaking for 45 min at the same temperature. The culture was centrifuged, the cells were resuspended in 50 ml prewarmed 2YTAK and rescue was performed overnight at 30° C. as before. Phagemid particles were purified and concentrated as before and resuspended in PBS to $10^{13}$ tu/ml. Repertoires harvested at subsequent rounds of selection were superinfected and rescued in the same way.

Four rounds of panning selection were performed and individual colonies screened by phage ELISA for binding to TR4.

Phage ELISA

To determine the specificity of each of the antibodies, a phage ELISA was performed for each antibody against TR4 fusion protein and an irrelevant fusion protein.

Individual E. coli colonies containing phagemid were inoculated into 96 well plates containing 100 μl 2TYAG medium per well. Plates were incubated 37° C. for 4 hours, shaking. M13K07 helper phage was added to each well to an moi of 10 and the plates were incubated for a further 1 hour at 37° C. The plates were centrifuged in a benchtop centrifuge at 2000 rpm for 10 minutes. The supernatant was removed and cell pellets were resuspended in 100 μl 2TYAK and incubated at 30C overnight, shaking. The next day, plates were centrifuged at 2000 rpm for 10 min and 100 μl phage-containing supernatant from each well carefully transferred into a fresh 96-well plate. Twenty μl of 6×MPBS was added to each well, and incubated at room temperature for 1 hour to block the phage prior to ELISA.

Flexible 96-well plates (Falcon) were coated overnight at 4° C. with human TR4 (1 μg/ml) or an irrelevant fusion protein (1 μg/ml). Both antigens were coated in PBS. After coating, the solutions were removed from the wells, and the plates were blocked for 1 hour at room temperature in MPBS. The plates were washed 3 times with PBS and then 50 μl of preblocked phage was added to each well. The plates were incubated at room temperature for 1 hour and then washed with 3 changes of PBST followed by 3 changes of PBS.

To each well, 50 μl of an anti-M13-HRP conjugate (Pharmacia) at a 1 in 5000 dilution in MPBS was added and the plates incubated at room temperature for 1 hour. Each plate was washed three times with PBST followed by three times with PBS.

Fifty μl of TMB substrate was then added to each well, and incubated at room temperature for 30 minutes or until colour development. The reaction was stopped by the addition of 25 μl of 0.5 M $H_2SO_4$. The signal generated was measured by reading the absorbance at 450 nm ($A_{450}$) using a microtitre plate reader (Bio-Rad 3550).

From a panel of 1500 clones which were screened by ELISA, 250 antibodies were identified which bound TR4 fusion protein but not an irrelevant fusion protein. The results of a typical plate of clones are shown in FIG. 1. ninety-five percent of isolated antibodies recognised TR4 fusion protein but not an irrelevant fusion protein.

Specificity Phage ELISA

To determine the specificity of the antibodies which bound TR4, a phage ELISA was performed against human TR4 fusion protein, and a panel of related and unrelated human antigens TR7, TR5, TR10, BlyS (described in International Patent Publication Numbers WO98/18921 and WO00/50597, which are both herein icorprated by reference in their entireties), irrelevant fusion protein and BSA.

Individual E. coli colonies containing phagemid were inoculated into 5 ml 2YTAG and incubated at 37° C. for 4 hours, shaking. M13K07 helper phage (Pharmacia) was added to each tube to an moi of 10 and incubated for 30 min at 37° C. for 1 hour, the first 30 minutes static and the final 30 minutes with gentle shaking. Cells were pelleted by centrifugation at 3,500 rpm for 10 minutes. The phage containing supernatant (5 ml) was carefully transferred to a fresh tube, 1 ml of 6 MPBS added and then incubated at room temperature for 1 hour to pre-block the phage prior to ELISA.

Flexible 96-well plates (Falcon) were coated overnight at 4° C. with each antigen (1 μg/ml). All antigens were coated in PBS. After coating, the solutions were removed from the wells, and the plates were blocked for 1 hour at room temperature in MPBS. The plates were washed 3 times with PBS and then 50 μl of pre-blocked phage was added to each well. The plates were incubated at room temperature for 1 hour and then washed with 3 changes of PBST followed by 3 changes of PBS.

To each well, 50 μl of an anti-M13-HRP conjugate (Pharmacia) at a 1 in 5000 dilution in MPBS was added and the plates incubated at room temperature for 1 hour. Each plate was washed three times with PBST followed by three times with PBS.

Fifty μl of TMB substrate was then added to each well, and incubated at room temperature for 30 minutes or until colour development. The reaction was stopped by the addition of 25 μl of 0.5 M $H_2SO_4$. The signal generated was measured by reading the absorbance at 450 nm ($A_{450nm}$) using a microtitre plate reader (Bio-Rad 3550).

Using this assay, scFVs T1014F08, T1014G03, T1014A04, T1014G04, T1014B11, T1017D09 were shown to bind TR4 but not TR7, TR5, TR10, BLyS, or an irrelevant fusion protein, indicating that the antibodies specifically recognise TR4.

Example 2

Biacore Analysis of the Affinity of TR4 Binding Polypeptides

Materials
  BIAcore 2000 instrument
  BIAcore 2000 control software, version 3.1.1
  BIAevaluation, version 3.1
  BIAcore CM5 Sensor Chip, Cat # BR-1000-14 Lot# 0364 (BIAcore)
  HBS-EP Buffer
  Amine Coupling Kit Cat# BR-1000-50 (BIAcore)
    EDC, #1048-950345(BIAcore)
    NHS, #1048-950345(BIAcore)
    Ethanolamine, #1048-950345(BIAcore)
  10 mM Acetate, pH 4.0 Cat# BR1003-50 Lot#1821-9503844(BIAcore)
  TRAIL-FLAG (Alexis Biochemicals Cat# 522-003-C010 #L04793/a)
  The temperature was 25° C. for all experiments.

General Methods

TR4, TR5, TR7 and TR10 (in the form of Fc fusion proteins) are immobilized on individual flow cells of a BIAcore sensor chip. The TR4-Fc fusion protein comprises residues M1-1240 of TR4 (SEQ ID NO:1). Post translational processing of this fusion protein results in a TR4-Fc fusion protein that comprises residues A109-1240 of TR4 (SEQ ID NO:1). The TR5-Fc fusion protein comprises residues R70-S282 of TR5 (SEQ ID NO:2). This protein is expressed in a baculovirus expression system that utilizes the GP signal peptide. Thus, post-translational processing of this fusion protein results in a TR5-Fc fusion protein that comprises the last 3 residues of the GP signal peptide (Ala-Asp-Pro) fused to R70-S282 of TR5 (SEQ ID NO:2) fused to the Fc region. The TR7-Fc fusion protein comprises residues E-52-G184 of TR7 (SEQ ID NO:3). This protein is expressed in a baculovirus expression system that utilizes the GP signal peptide. Thus, post-translational processing of this fusion protein results in a TR7-Fc fusion protein that comprises the last 3 residues of the GP signal peptide (Ala-Asp-Pro) fused to E-52-G184 of TR5 (SEQ ID NO:3) fused to the Fc region. The TR10-Fc fusion protein comprises residues M1-G204 of TR10 (SEQ ID NO:4). Post translational processing of this fusion protein results in a TR10-Fc fusion protein that comprises residues A56-G204 of TR10 (SEQ ID NO:4).

Amine coupling is used to covalently bind each receptor (Fc) to the dextran matrix on the CM5 sensor chip. The optimal pH for this coupling is analyzed using preconcentration experiments ranging from pH 4-7 and is determined based on the slope of the binding.

The actual coupling is performed using the manual injection mode. A target level of ~2000 RU is set as the goal for all flow cells. (This may vary from 2000-3100 depending on the molecular weight of the receptor). The concentration of all receptors for immobilization was 10 ug/ml in 10 mM acetate, pH 4.0. The entire immobilization experiment is performed at 5 microliters/min. Contact time for the EDC/NHS injection is 7 minutes. The ethanolamine is injected for 7 minutes.

The screening may be performed with the following procedures. The flow rate for the entire binding cycle is 25 microliters/minute. Antibodies corresponding to scFvs are diluted in HBS-EP and flown through all four cells with immobilized TRAIL receptors. Each sample is in contact with the receptors for 4 minutes. Regeneration is performed using 15 microliters of 25 mM NaOH. Successful regeneration is considered as not only removing the antibody, but also not denaturing the immobilized receptor.

The positive control for this screening experiment is an identical (in flow rate and length of time) injection of the soluble TRAIL ligand. The concentration is 1 microgram/mL. The negative control is a 1:10 dilution in HBS-EP of the antibody diluent. Data may be analyzed using the BIAevaluation software package.

Biacore Analysis of Anti-TR4 Antibodies

In the following experiment based on the general methods described above, the affinties of certain antibodies (corresponding to the scFvs of the invention) for TR4 were determined using a "double reference subtraction" method using TR4:Fc receptor in the experimental flow cell and TR2:Fc (comprising aminos acids 1-240 of TR2 as disclosed in WO96/34095) as a negative control.

Immobilization:

The optimal pH for this coupling was analyzed using preconcentration experiments ranging from pH 4-7 and was determined to be pH 4.0 for both the TR4 and the TR2 receptor. Amine coupling was used to covalently bind each receptor (fc) to the dextran matrix on the CM5 sensor chip. The immobilization experiment was performed using the manual injection mode. The entire immobilization experiment was performed at 5 µL/min. A 3-minute injection of EDC/NHS (1:1) was applied to each flow cell to active esters. A target level of ~200 RU was set as the goal for all each flow cell. Fc-fusion receptors, TR4 and TR2 at 5 µg/mL, were immobilized onto individual flow cells of a sensor chip. The amount applied varied from 8-14 µL. A 3-minute ethanolamine injection completed the immobilization experiment by inactivating the esters.

Kinetics:

The kinetics cycles were performed as follows: The flow rate for the entire cycle was 25 µL/minute with the flow path including both the control (TR2) and experimental (TR4) flow cell at all times. A 1-minute buffer injection was applied to stabilize the baseline. The purified antibody (IgG1 antibody comprising the VH and VL domains of each of the T1014A04, T1014G03, T1014F08, and T14G04 scFvs) was diluted from 10 µg/mL (65 nM) to 0.115 µg/mL (0.75 nM) in running buffer and tested in duplicate. Each concentration was in contact with the control (TR2) and the experimental (TR4) flow cell during a 4-minute association and a 10-minute dissociation phase. Regeneration was performed using 25 mM NaOH from 5-12 µL depending on the sample concentration.

Evaluation:

A double-reference subtraction was performed, which refers to the control flow cell subtraction for every cycle, in addition to a buffer cycle subtraction. The 1:1 Langmuir model was used for all evaluation fitting. Results of these experiments are shown in Table 5 below.

TABLE 5

Affinity of antibodies for TR4

| Clone | ka | kd | $K_D$ | $Chi^2$ |
|---|---|---|---|---|
| T1014A04 | $5.67 \times 10^5$ | $2.65 \times 10^{-4}$ | $4.68 \times 10^{-10}$ | 2 |
| T1014G03 | $3.50 \times 10^5$ | $1.94 \times 10^{-4}$ | $5.54 \times 10^{-10}$ | 0.76 |
| T1014F08 | $1.23 \times 10^6$ | $1.02 \times 10^{-4}$ | $8.27 \times 10^{-10}$ | 1.83 |
| T1014G04 | $6.05 \times 10^5$ | $1.18 \times 10^{-4}$ | $1.94 \times 10^{-10}$ | 1.14 |

Example 3

Inhibition of Binding of Biotinylated-TRAIL to TR4

I. Materials:
   10×PBS (Quality Biological Cat 130-069-161, Lot 708712)
   Immulon 4 microplate (Dynex Cat 3855, Lot ND540319)
      Bovine Serum Albumin fraction V (Sigma, #58H0456)
   Tri Hydroxy Methyl Amino Methane (TRIS BASE)
   Tween 20 (Sigma)
      Goat anti-human Fc (Sigma, I-2136, #89H4871)
   TR-4:Fc (as described above)
      Biotinylated TRAIL (AM100200-Peprotech)
   HRP-Streptavidin (Vector, #L0328)
      TMB Peroxidase Microwell Substrate System (KPL, Kirkegaard & Perry Laboratories, Inc.)
   $H_2SO_4$ (Fisher)
      96 well dilution plate (Costar)

II. Buffers:
   Coating buffer (1× PBS)
   Blocking buffer (3% BSA in PBS)
   All-purpose Diluent (1% BSA in PBST)
   Washing buffer (0.1% Tween 20 and 1× PBS)

III. Methods

Goat anti-human Fc is diluted to 0.1 micrograms/ml in coating buffer. An Immulon 4 microplate is coated with 100 microliters per well of the Goat anti-human Fc solution and incubated overnight at 4° C. The coating solution is decanted from the plate, and blocking solution is dispensed at 200 microliters per well. The plate is incubated at room temperature for 1 hour. After the 1 hour incubation period, the blocking solution is decanted from the plate and 1 microgram/mL of TR4-Fc is dispensed at 100 microliters/well and incubated for 2 hours at room temperature. After the incubation, the plate is washed five times manually using a Wheaton manifold.

Antibodies corresponding to scFvs of the present invention are (previously) prepared in a low binding dilution plate using diluent. The antibodies are prepared in duplicate and are diluted from the stock concentration with 2.5 fold dilutions for the 7 subsequent wells. If a purified form of the antibody is available, the starting concentration is 5 micrograms/mL. The positive control (TR4-Fc) is diluted from 5 micrograms/mL. 100 microliters is transferred into the ELISA plate and pre-incubated for 30 minutes at room temperature. 20 microliters of biotinylated TRAIL is added at 5 micrograms/mL to the 100 µL of the supernatant and mixed. The combined 120 microliters is incubated for 2 hours at RT.

After the two-hour incubation, the washing cycle is repeated and the plate decanted and blotted. HRP-streptavidin is diluted 1:2000 and 100 microliters per well is dispensed. Incubation is for one hour at room temperature. Meanwhile, equal amounts of the TMB peroxidase substrate and the peroxidase solution B are withdrawn and the solutions are equilibrated to room temperature.

After the one-hour incubation, the plate is decanted and washed with PBST five times and blotted. The TMB peroxidase substrate and the peroxidase solution B are combined and 100 microliters is dispensed to each well. The color developed at room temperature for 15 minutes. The color development is quenched by adding 50 microliters of the 1 M $H_2SO_4$ to each well. The plate is immediately read at 450 nm using the spectrometer from Molecular Devices.

The IC-50, i.e, the concentration of purified antibody that resulted in 50% inhibition of plateau binding, is then measured. For comparison purposes, a TR4 polypeptide is used as a sample in this assay.

Example 4

Assay for Ability of Anti-TRAIL-R1 (TR4) Antibodies to Induce Apoptosis

General Methods:

Anti-TR4 antibodies are tested for their ability to induce apoptosis of TR4 expressing cells, alone or in combination with chemotherapeutic or cross-linking agents. Briefly, antibodies are tested for activity to induce TR4 mediated apoptosis of TR4 expressing cell lines, SW480 and HeLa. HT1080 fibrosarcoma cell line, which does not express TR4, is used as a negative control.

To induce apoptosis, either HeLa or SW480 cells are incubated with the indicated concentration of monoclonal antibodies or a human IgG2a control antibody. One day prior to assay, cells (0.3×10⁶ cells/ml; 100 ul/well) are seeded into wells of a 96-well plate and allowed to adhere overnight. The following day, the test antibody is added either in the presence or absence of 2.0 micrograms/ml cycloheximide (Sigma R75010-7). In some experiments, the potency of anti-TR4 monoclonal antibody is compared to rhuTRAIL-FLAG protein (Alexis Biochemicals). rhuTRAIL is used at the indicated concentrations in the presence of anti-FLAG enhancer antibody at 2 micrograms/ml. The effect of secondary crosslinking is also assessed by measuring the ability of the monoclonal antibodies to kill cells alone, or in the presence of a secondary goat-anti-human Ig Fc specific antibody (SIGMA). The secondary crosslinking antibody is added to cells at an equivalent concentration as the test monoclonal antibody. The ability of a chemotherapeutic agent to sensitize cells to killing via the monoclonal antibody is assessed by treating either Hela or SW480 cells with monoclonal antibody in the presence of Topotecan (Hycamtin, SmithKline Beecham NDC 0007-4201-01).

Assays are performed for 16-18 hrs at 37° C., after which viability is revealed using the reagent, Alamar Blue (Biosource, cat. # DAL1100) using conditions suggested by the manufacturer. Alamar Blue fluorescence is detected using the CytoFluor fluorescence reader at 530 nm excitation and 590 emission. Results are expressed as a percent viability compared to untreated cells. Cell viability may also be measured using other methods described herein or otherwise known in the art. For example, cell viability may be measured using the CellTiter-Glo® Luminescent Cell Viability Assay available from Promega according to the manufacturer's instructions.

Other chemotherapeutics that may be tested in this assay (and used in treatment regimens in conjunction with the antibodies of the present invention) include, for example, 5-Fluorouracil, Etoposide, Taxol, Cisplatin, Cytabarine (Cytosar), IFN gamma, camptothecin, irinotecan (camptosar, CPT-11), adraimycin (doxorubicin), methotrexate, paraplatinin, interferon-alpha, paclitaxel, docetaxel, the NF-kappa-B inhibitor SN50, and gemcitabine (Gemzar™). Other cell lines that may be tested in this assay include, for example, the human Burkitt lymphoma line ST486, human breast carcinoma cell line MDA-MB-231, the human uterine carcinoma cell line RL-95, the human lung carcinoma cell line SK-MES-1, human colon cancer cell lines, LS174T, HT29, and HCT116, the su.86.86 and CFPAC pancreatic cancer cell lines, the human ovarian cancer cell line TOV21G, and the human heptocellular cancer cell line SNU449. Cancers of the tissues corresponding to the tissues from which these cancer cell lines were derived may be treated with the therapeutic compositions in accordance with the invention.

Analysis of Anti-TR4 Antibodies

Using the assay above, several scFVs of the present invention that had been converted to whole IgG1 molecules were tested for the ability to induce apoptosis of TR4 1 (TR4) expressing cells. The IgG1 format of T1014A04 induces apotosis of SW480 cells in the presence of a cross-linking agent, but in the absence of cycloheximide. In the presence of cycloheximide, but with or without a crosslinking reagent, the IgG1 format of T1014A04 induces apoptosis of SW480 and HeLa cells. Killing of SW480 and HeLa cells by treatment with the IgG1 format of T1014A04 in the presence of cyclohexomide is greater when crosslinking reagent is also used. In fact in the presence of crosslinking reagent, and cycloheximide, the IgG1 format of T1014A01 is able to induce more apoptosis than an equal concentration (in ng/ml) of soluble TRAIL. The IgG1 format of T1015A02 does not induce killing in the absence of the sensitizing agent cycloheximide. In the presence of cycloheximide, with or without a crosslinking reagent, the IgG1 format of T1015A02 induces apoptosis of SW480 cells but not HeLa cells. Killing of SW480 by treatment with the IgG1 format of T1015A02 is greater in the presence of a crosslinking reagent.

In addition, the assay described in this example may also be used to test the effect of more than one anti-TR4 antibody on TR4 expressing cells. For example, cells may be treated with both an antibody that specifically binds TR4 and an antibody that specifically binds TR7. As above, this experiment may be performed in the presence of absence of one or more chemotherapeutic agents or crosslinking agents. In another variation of the present experiment antibodies of the invention may tested for the apoptosis inducing effect when used in the presence of TRAIL. The amount of apoptosis induced by dual treatment with anti-TR4 and anti-TR7 may be synergistic compared to treatment with either anti-TR4 or anti-TR7 alone. Such an effect may be more pronounced when the experiment is performed in the presence of chemotherapeutic and/or crosslinking agents.

Example 5

Identification and Cloning of VH and VL Domains

One method to identfy and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL-domains of the antibodies expressed by the EBV cell lines. Cells may lysed in the TRIzol® reagent (Life Technologies, Rockville. MD) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Follwing washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can be determined using optical density measurements.

cDNA may be synthesized, according to methods well-known in the art, from 1.5-2.5 micrograms of RNA using reverse transciptase and random hexamer primers. cDNA is then used as a template for PCR amplification of VH and VL domains. Primers used to amplify VH and VL genes are shown in Table 6. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1×PCR buffer, 2 mM of each dNTP, 0.7 units of High Fidelity Taq polymerse, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 6

Primer Sequences Used to Amplify VH and VL domains.

| Primer name | SEQ ID NO | Primer Sequence (5'-3') |
| --- | --- | --- |
| VH Primers | | |
| Hu VH1-5' | 6 | CAGGTGCAGCTGGTGCAGTCTGG |
| Hu VH2-5' | 7 | CAGGTCAACTTAAGGGAGTCTGG |
| Hu VH3-5' | 8 | GAGGTGCAGCTGGTGGAGTCTGG |
| Hu VH4-5' | 9 | CAGGTGCAGCTGCAGGAGTCGGG |
| Hu VH5-5' | 10 | GAGGTGCAGCTGTTGCAGTCTGC |
| Hu VH6-5' | 11 | CAGGTACAGCTGCAGCAGTCAGG |
| Hu JH1,2-5' | 12 | TGAGGAGACGGTGACCAGGGTGCC |
| Hu JH3-5' | 13 | TGAAGAGACGGTGACCATTGTCCC |
| Hu JH4,5-5' | 14 | TGAGGAGACGGTGACCAGGGTTCC |
| Hu JH6-5' | 15 | TGAGGAGACGGTGACCGTGGTCCC |
| VL Primers | | |
| Hu Vkappa1-5' | 16 | GACATCCAGATGACCCAGTCTCC |
| Hu Vkappa2a-5' | 17 | GATGTTGTGATGACTCAGTCTCC |
| Hu Vkappa2b-5' | 18 | GATATTGTGATGACTCAGTCTCC |
| Hu Vkappa3-5' | 19 | GAAATTGTGTTGACGCAGTCTCC |
| Hu Vkappa4-5' | 20 | GACATCGTGATGACCCAGTCTCC |
| Hu Vkappa5-5' | 21 | GAAACGACACTCACGCAGTCTCC |
| Hu Vkappa6-5' | 22 | GAAATTGTGCTGACTCAGTCTCC |
| Hu Vlambda1-5' | 23 | CAGTCTGTGTTGACGCAGCCGCC |
| Hu Vlambda2-5' | 24 | CAGTCTGCCCTGACTCAGCCTGC |
| Hu Vlambda3-5' | 25 | TCCTATGTGCTGACTCAGCCACC |
| Hu Vlambda3b-5' | 26 | TCTTCTGAGCTGACTCAGGACCC |
| Hu Vlambda4-5' | 27 | CACGTTATACTGACTCAACCGCC |
| Hu Vlambda5-5' | 28 | CAGGCTGTGCTCACTCAGCCGTC |
| Hu Vlambda6-5' | 29 | AATTTTATGCTGACTCAGCCCCA |
| Hu Jkappa1-3' | 30 | ACGTTTGATTTCCACCTTGGTCCC |
| Hu Jkappa2-3' | 31 | ACGTTTGATCTCCAGCTTGGTCCC |
| Hu Jkappa3-3' | 32 | ACGTTTGATATCCACTTTGGTCCC |
| Hu Jkappa4-3' | 33 | ACGTTTGATCTCCACCTTGGTCCC |
| Hu Jkappa5-3' | 34 | ACGTTTAATCTCCAGTCGTGTCCC |
| Hu Jlambda1-3' | 35 | CAGTCTGTGTTGACGCAGCCGCC |
| Hu Jlambda2-3' | 36 | CAGTCTGCCCTGACTCAGCCTGC |
| Hu Jlambda3--3' | 37 | TCCTATGTGCTGACTCAGCCACC |
| Hu Jlambda3b-3' | 38 | TCTTCTGAGCTGACTCAGGACCC |
| Hu Jlambda4-3' | 39 | CACGTTATACTGACTCAACCGCC |
| Hu Jlambda5-3' | 40 | CAGGCTGTGCTCACTCAGCCGTC |
| Hu Jlambda6-3' | 41 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of *E. coli* and blue/white color selection. Cloned PCR products may then be sequenced using methods commonly known in the art.

Example 6

Anti-TR4 Antibodies Retard the Growth of Tumor Cells in Nude Mice

SW480 (colorectal adenocarcinoma) tumor cell line was maintained in vitro in Leibovitz's L-15 medium supplemented with fetal bovine serum, glutamine and antibiotics as per the instructions received from American Type Culture Collection. Cells at passage 3-10 were used for the in vivo studies. The tumor cells were harvested from the T-150 flasks, rinsed with sterile PBS and then resuspended in sterile saline at a density of 5(10$^4$) cells/ul. Tumor cells were implanted subcutaneously on the upper back or flanks of Swiss athymic mice at a density of $10^7$ cells per site, 2 sites per animal. In preventive (de novo) tumor models, chemotherapeutic agents and antibody treatments were initiated 24 hr post-tumor cell inoculation.

The antibody treatment, with an antibody comprising the VH and VL domain from either T1014A04 or T1014G03 (in this example hereinafter "T114A04" or "T1014G03"), was as follows: loading dose: 20 mg/kg, intavenously 24 hours post injection of tumor cells with maintenance doses of 10 mg/kg, intraperitoneally. Maintenance doses of T1014A04 were given on days four, seven, ten, thirteen and sixteen. Maintenance doses of T1014G03 were given on days four, seven, ten, fourteen, twenty-two and twenty-five. Topotecan was the chemotherapeutic agent used in this experiment. In the experiment with T1014A04, the dose and dosing frequency of Topotecan was as follows: either 0.3 or 0.6 mg/kg, intraperitoneally on the first, second, third, fourth, seventh, tenth, fourteenth, eighteenth, twenty-second, and twenty fifth days of the experiment. In the experiment with T1014G03, the dose and dosing frequency of Topotecan was as follows: either 0.3 or 0.6 mg/kg, intraperitoneally on the first, second, third, fourth, seventh, tenth, thirteenth, and sixteenth days of the experiment.

Figure 3:
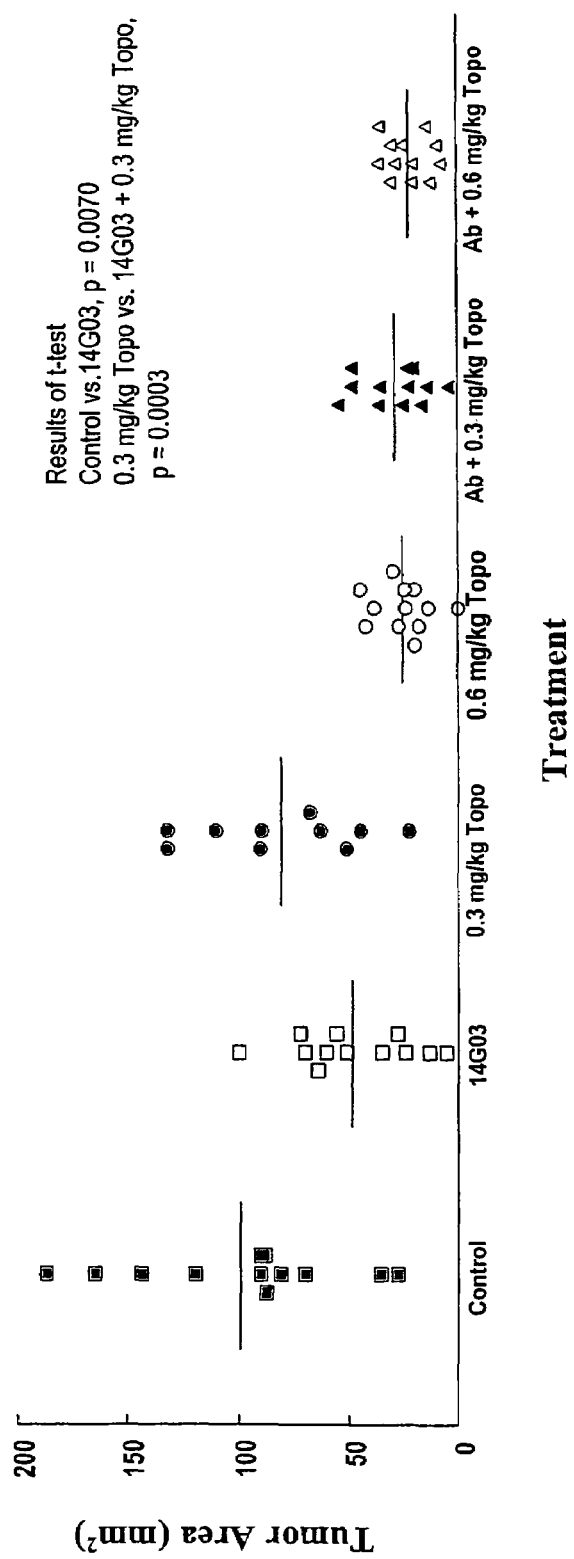
FIG. 3 shows the effect of 14G03 treatment on the growth of SW480 tumors in vivo after 28 days with and without Topotecan treatment.

When T1014A04 or T1014G03 was administered with topotecan a significant reduction in tumor size was observed. Treatment with the antibody alone may reduce tumor growth at the later time points. (See FIGS. 1-3).

The above described assay may also be used to test the effect of treatment with more than one anti-TR4 antibody on the growth of tumor cells in vivo. For example, animals into which tumor cells have been injected may be treated with both an antibody that specifically binds TR4 and an antibody that specifically binds TR7. As above, this experiment may be performed in the presence of absence of one or more chemotherapeutic agents. In another variation of the present experiment antibodies of the invention may administered in combination with TRAIL. The ability of such combination therapy to inhibit the growth of tumor cells as compared to treatment with either an antibody alone can be assayed using the methods detailed above, and comparing the results obtained between the combination therapy with the results obtained from treatment with either and anti-TR4 or an anti-TR7 antibody alone.

Example 7

Effect of Anti-TR4 Antibodies on Human Hepatocytes

The effect of T1014G03 (lot AB22125-M2) in human primary hepatocytes was determined by measuring either caspase activation or cell viability. Human hepatocytes were treated with 15.6, 62.5, 250 or 1000 ng/mL of TRAIL (amino acid residues 114-281, Biomol Research Laboratories Inc, Plymouth Meeting, Pa.), 62.5, 125, 250, or 1000 ng/ml of isotype control mAb (hIgG$_1$, CAT002) or 62.5, 125, 250, or 1000 ng/ml T1014G03. Caspase activation was determined at 6 hrs following treatment, while viability was determined at 24 hrs following treatment.

Caspase activity was measured using a fluorimetric assay utilizing the caspase substrate Rhodamine conjugated DEVD, (e.g., Homogeneous Fluorimetric Caspases Assay available from Roche Molecular Biochemicals (Indianapolis, Ind.)). Cell viability was determined using an ALAMAR Blue™ (Biosource International, Camarillo, Calif.) assay. TRAIL reduced cell viability at all concentrations tested, and induced caspase activity at the highest concentration tested. In contrast to TRAIL, T1014G03 treatment was found not to effect either caspase or cell viability in human hepatocytes.

Apoptotic signaling may be measured by any assay described herein or otherwise known in the art. For example, apoptosis or apoptotic signaling, such as that induced by agonistic anti-TR4 antibodies, may also be measured or monitored using terminal dUTP nick end labeling (TUNEL) assay, immunohistochemistry, Western blot analysis, real-time RT-PCR, and enzyme activity assay. One such Western Blot analysis that could be performed is described below. Approximately $2 \times 10^6$ cells are plated in 150-mm cell culture plates and cultured overnight. Cells are then treated with various concentrations of chemotherapeutic drugs, antibody crosslinking agent (such as a goat anti-human IgG antibody) and or agonistic antibody for a given length of time (e.g., minutes, hours or days). After stimulation, the cells are a=scraped from the plate in ice-cold PBS and lysed with 1% NP40 lysis buffer (1 mM HEPES) pH7.5, 0.15 mM NaCl, 10% glycerol, protease inhibityor cocktail and 1 mM EDTA). The protein concentration of the lysates is determined, for example, by the CBA method (Pierce) and equalized with lysis buffer. The proteins are separated using a 10% or a 4-20% gradient polyacrylamide SDS gel electrophoresis and transferred to nitrocellulose memebrane. The membranes are immunoblotted with antibodies to different protins according to standard western blotting protocols. Proteins involved associated with cell survival and/or apoptosis that may be assessed include, but are not limited to Poly(ADP-ribose) polymerase (PARP), caspase-8, caspase-3, caspase 9, and BID. Upon induction of an apoptosis signaling cascade, PARP is cleaved to a lower molecular weight form as are caspases-3, -8 and 9. Upon induction of an apoptosis signaling cascade caspase 8 cleaves BID and the COOH-terminal part of BID translocates to mitochondria where it triggers cytochrome c release. Each of the cleavage events may be monitored by western blotting.

Example 8

RL95-2 Uterine Carcinoma Xenograft Model

The objective of this experiment was to examine whether T1014G03 is able to alter the growth pattern of the RL95-2 tumor in athymic mice when T1014G03 is used as a single agent.

RL95-2 is a uterine adenocarcinoma cell line that forms solid tumors when injected subcutaneously in athymic mice. RL95-2 cells have been demonstrated to express TRAIL-R1 and are sensitive in vitro to T1014G03-induced apoptosis in the absence of any sensitizing agent. Based on these findings, the RL95-2 model in athymic mice was selected to test the in vivo efficacy of T1014G03 on reduction of pre-existing tumors. In these experiments, T1014F08 served as a negative control (huIgGλ). T1014F08 binds TRAIL-R1, but was not observed to have agonist activity.

RL95-2 cells in log phase were injected SC (10 million cells/mouse) in nude mice. After 3 days, the tumor size was determined and the animals were segregated into various treatment groups (6 animals/treatment group) such that all the treatment groups had 5×5 mm size tumor. Mice were injected (IP) with T1014G03 or T1014F08 antibodies at 0.2, 2.0, and 20 mg/Kg doses on days 4, 8, 12, and 16. Tumor size was monitored twice a week from day 3 to day 43. Mice receiving injection vehicle (saline) served as the control.

Data were analyzed by non-parametric Mann-Whitney test and are expressed as fold increase in tumor size relative to the day 3-tumor size. The growth of tumor was significantly retarded in mice T1014G03 antibody treatment at 20 mg/Kg compared to the control and T1014F08 treated animals. The effect of T1014G03 antibody at 0.2 and 2.0 mg/Kg was not significantly different from the control. The data demonstrate the ability of T1014G03 to inhibit growth of a pre-established tumor cells.

The above described assay may also be used to test the effect of treatment with more than one anti-TR4 antibody on the growth of pre-established tumors in vivo. For example, animals into which tumor cells have been injected may be treated with both an antibody that specifically binds TR4 and an antibody that specifically binds TR7. As above, this experiment may be performed in the presence of absence of one or more chemotherapeutic agents. In another variation of the present experiment antibodies of the invention may administered in combination with TRAIL. The ability of such combination therapy to inhibit the growth of tumors or even eliminate tumors as compared to treatment with either an antibody alone can be assayed using the methods detailed above, and comparing the results obtained between the combination therapy with the results obtained from treatment with either and anti-TR4 or an anti-TR7 antibody alone.

Example 9

Immunohistochemistry of Primary Tumor Tissue for Expression of TRAIL R1 (TR4) Expression Primary human tumor tissues of the bladder, breast, colon, liver lung ovary and pancreas were stained with a goat anti-human TRAIL-R1 polyclonal antibody (R&D Systems). This antibody stains cells transfected with TRAIL-R1 expression constructs, but not vector control transfected cells. Staining data are presented below in Table 7 below. Positive staining was observed in certain breast, colon, lung, and stomach carcinoma tissues. In contrast, normal human tissue samples from the same organs, had no specific staining. In addition, no specific staining was observed in normal human and monkey liver and spleen samples.

TABLE 7

Immunohistochemical staining of Human tumor and Normal Tissues

| | # Evaluated | Positive | +/− | Negative |
|---|---|---|---|---|
| Tumor Tissue | | | | |
| Bladder | 2 | 0 | 1 | 1 |
| Breast | 2 | 1 | 0 | 1 |
| Colon | 2 | 1 | 1 | 0 |
| Liver | 2 | 0 | 1 | 1 |
| Lung | 2 | 2 | 0 | 1 |
| Ovary | 1 | 0 | 0 | 1 |
| Pancreas | 2 | 0 | 0 | 2 |
| Stomach | 1 | 1 | 0 | 0 |
| Totals | 14 | 5 | 3 | 6 |
| Normal Tissue | | | | |
| Bladder | 1 | 0 | 0 | 1 |
| Breast | 0 | 0 | 0 | 0 |
| Colon | 1 | 0 | 0 | 1 |
| Liver | 1 | 0 | 1 | 0 |
| Lung | 1 | 0 | 0 | 1 |
| Ovary | 1 | 0 | 0 | 1 |

TABLE 7-continued

Immunohistochemical staining of Human tumor and Normal Tissues

| | # Evaluated | Positive | +/− | Negative |
|---|---|---|---|---|
| Pancreas | 1 | 0 | 0 | 1 |
| Stomach | 0 | 0 | 0 | 0 |
| Totals | 6 | 0 | 1 | 5 |

Example 10

Antibody Production and Purification

The following example describes a large scale antibody production and purification methods that may be used to make antibodies of the present invention. One of skill in the art will be aware of routine modifications to the protocol described below, for example, as regards column choice, column, loading, wash, and elution buffers, and pH.

Cell Culture Scale-Up and Antibody Production

A serum-free and animal source-free growth medium (HGS-NS0SF) is used from thawing cells through scale-up to the production bioreactor. The HGS-NS0SF growth medium is prepared by adding 20 mL/L GS supplement and 1 mL/L cholesterol (synthetic) lipid concentrate into 1 L CD hybridoma media without 1-glutamine (Invitrogen/Life technologies). The media are stored at 2-8° C. until use.

Thawing Cells from MCB Vial(s)

Approximately $16 \times 10^6$ cells are thawed at 37° C. in a water bath. The cells are transferred into T-225 culture flask(s) to yield approximately 50 mL working volume with an inoculation density of approximately $3.0 \times 10^5$ cells/mL. The culture flask(s) is then placed in a humidified $CO_2$ incubator at 37° C. with 5% $CO_2$ for 4 days.

First Expansion(s) of Culture in Spinner Flask

The culture is aseptically expanded into a 500 mL spinner flask to give approximately 300 mL working volume, at an inoculation cell density of approximately $2.2 \times 10^5$ cells/mL. The spinner flask is then placed on magnetic stirrers in a humidified $CO_2$ incubator at 37° C. with 5% $CO_2$ for 4 days. The agitation rate for the spinner flask is 80 rpm.

The culture is again expanded aseptically into one 3000 mL spinner flask to give approximately 1500 mL working volume, at an inoculation cell density of approximately $2.2 \times 10^5$ cells/mL. The spinner flask is then placed on magnetic stirrers in a humidified $CO_2$ incubator at 37° C. with 5% $CO_2$ for 4 days. The agitation rate for the spinner flasks is 80 rpm. If a sufficient amount of cell culture is accumulated to inoculate the seed bioreactor, proceed to Step 4. If not, the culture is expanded aseptically into multiple 3000 mL spinner flasks for a total of 3 to 4 expansions, until a sufficient amount of cell culture is accumulated to inoculate the seed bioreactor.

Seed Culture

The seed bioreactor is equipped with 2 impellers for mixing, a dissolved oxygen probe, a temperature probe, a pH probe, aseptic sampling and additional systems. The first step of the cell cultivation process is the addition of HGS-NS0SF media into the bioreactor. After the HGS-NS0SF media temperature reaches 37±0.5° C., the dissolved oxygen (DO) and pH levels are stabilized by addition of $N_2$ and $CO_2$ to decrease dissolved oxygen concentration to 30±5% air saturation, and obtain a pH of 7.20±0.10. The agitation rate is 80 rpm. The pooled cell culture is transferred aseptically to a 15 L seed bioreactor containing sterile HGS-NS0SF growth media to yield a culture with an inoculation cell density of approximately $2.2 \times 10^5$ cells/mL. During the cultivation process the temperature is maintained via a heat blanket and a cooling finger, the oxygen concentration is maintained via sparger and surface aeration, and pH is controlled by addition of $CO_2$ gas to lower the pH. The cultivation period is 5-6 days. The bioreactor air vents are protected by hydrophobic 0.2 μm vent filters.

Production Culture

The production bioreactor is equipped with 2 impellers for mixing, 2 dissolved oxygen probes, a temperature probe, 2 pH probes, aseptic sampling and additional systems. 80 L of HGS-NS0SF growth media is aseptically transferred into the 100 L production bioreactor. After the HGS-NS0SF growth media temperature reaches 37±0.5° C., the DO and pH levels are stabilized by addition of $N_2$ and $CO_2$ to decrease dissolved oxygen concentration to 30±5% air saturation, and obtain a pH of 7.20±0.10. The agitation rate is 45 rpm. The 15 L seed culture is aseptically transferred into the production bioreactor to yield a culture with an inoculation cell density of approximately $2.2 \times 10^5$ cells/mL. During the cultivation process the temperature is maintained via a heat exchanger, the oxygen concentration is maintained via sparger and surface aeration, and pH is controlled by addition of $CO_2$ gas to lower the pH. On day 3 after inoculation when cell density reaches approximately $1.0 \times 10^6$ cells/mL, approximately 6 L of HGS-NS0SF fed-batch media was fed into the production bioreactor. The production culture containing the antibody was harvested on Day 5 after feeding.

Recovery and Purification

Harvest of Cell Supernatant

Cell supernatant, (e.g., culture supernatant from NS0 cells expressing antibodies of the invention) is harvested on day 5 or 6 post final feeding in the final production bioreactor using a fed-batch cell culture process. The harvest process is started when the antibody concentration of at least 400 mg/L is attained. Cell culture temperature in the production bioreactor is cooled down to 15° C. at the time of harvest and maintained at that temperature during the recovery. A depth filtration process is used for cell removal and antibody recovery. The filtration process train consists of 4.5 μm, 0.45 μm and 0.2 μm pore size filters connected in series. A constant flow rate of 1.00 L/min is maintained during the operation with a cross-filter-pressure control of up to 15 psi. The 0.2 μm filtered culture supernatant is collected in a process bag and transferred for purification.

The purification process is conducted at 22 to 26° C.

Chromatography on MEP HyperCEL HCIC Column

The culture supernatant is loaded onto a MEP HyperCEL™ (4-Mercapto-Ethyl-Pyridine-linked cellulose matrix) column, a Hydrophobic charge interaction chromatography, HCIC, available from Ciphergen Biosystems, or equivalent column that is equilibrated in 50 mM Tris, 0.5 M sodium chloride, pH 7.5. The MEP column is washed with 25 mM sodium citrate, 0.15 M sodium chloride, pH 6.4 and eluted with 25 mM sodium citrate, 0.15 M sodium chloride, pH 4.4. The elution is monitored by ultraviolet (UV) absorbance at 280 nm. The peak fractions are collected, analyzed by $A_{280}$ and SDS-PAGE. Appropriate fractions are pooled. Alternatively, the chromatography on the MEP HyperCEL™ (4-Mercapto-Ethyl-Pyridine-linked cellulose matrix) may be substituted with affinity chromatography over a recombinant protein A column.

Virus Inactivation

The eluate from the MEP column is adjusted with 1 M citric acid to pH 3.4±0.2 and allowed to stand for 45-60 minutes for viral inactivation. The solution is then re-adjusted to pH 5.0 with 1 M Tris base.

Chromatography on SP Sepharose FF Column

The inactivated eluate from the MEP column is diluted with water for injection (WFI) to a conductivity of 5 mS/cm, and loaded onto a SP Sepharose FF (cation exchange chromatography, Amersham-Pharmacia) column, or equivalent column equilibrated with 65 mM sodium acetate, pH 5.0. The antibody is eluted from the SP column with 20 mM sodium citrate, 0.15 M sodium chloride, 1.9% glycine, pH 7.1. The elution is monitored by ultraviolet (UV) absorbance at 280 nm. Peak fractions are collected and analyzed by $A_{280}$ and SDS-PAGE. Appropriate fractions are pooled.

Virus Removal Filtration, Diafiltration and Concentration

The eluate from the SP Sepharose FF column is filtered through a sequentially connected 0.2 μm filter and a Pall DV50 viral removal filter. The DV50 filtrate is placed into a 30 kD MW cut-off membrane device (Millipore Pellicon) to concentrate to a target concentration of 35-40 mg/mL, and diafiltered against 10 mM sodium citrate, 1.9% glycine, 0.5% sucrose, pH 6.5. The diafiltered material is monitored by $A_{280}$. The diafiltered bulk is 0.2 μm filtered and stored at 2-8° C. up to 24 hours.

Chromatography on Q Sepharose FF Column

The diafiltered TRM-1 solution is passed over a Q Sepharose FF column (anion exchange chromatography, Amersham-Pharmacia) or equivalent column equilibrated with 10 mM sodium citrate, 1.9% glycine, 0.5% sucrose, pH 6.5. The antibody is collected in the flow-through and monitored by $A_{280}$. Appropriate fractions are pooled and the final target concentration is 25 mg/mL.

Bulk Formulation, Filtration and Bulk Drug Substance Fill

Polysorbate 80 (2% stock solution) is pre-filtered through a 0.2 μm filter and added to the antibody solution from step 7 to a final concentration of 0.02%. The purified antibody is aseptically filtered under a laminar flow hood through a 0.2 μm filter and filled into polypropylene containers.

Storage of Bulk Drug Substance

The bulk drug substance is stored at 2-8° C. (short-term storage) or at or below −65° C. (long-term storage) prior to the release of the product. In-process testing of the unprocessed production bioreactor culture at harvest for each batch and in-process testing during the purification process are performed. The bioreactor is sampled aseptically and the culture is tested at various times throughout cultivation for cell density, viability and nutrient determination to ensure consistency of material being supplied for purification. The purification process is monitored at each step. Appearance is checked by vuisual inspection. The protein concentration is determined by Absorbance at 280 nm. The pH of the material is checked. Purity is checked, for example, by SDS-PAGE and size exclusion chromatography. An ELISA may be performed to check the ability of the antibody to bind its antigen. The biological activity of the antibody is also monitored. Residual DNA content, Endotoxin levels, and the bioburden (the number of viable organisms present in the antibody preparation) are all monitored and kept at or below standard acceptable levels. Additionally, the oligosaccharide content may be analyzed; the peptide sequence of the antibody chains may also be analyzed using N-terminal sequencing and peptide mapping. Short and long-term studies of antibody stability may also be performed.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Further, the Sequence Listing submitted herewith, in both computer and paper forms, is hereby incorporated by reference in its entirety.

The entire disclosure (including the specification, sequence listing, and drawings) of each of the following U.S. and International Patent applications are herein incorporated by reference in their entirety: U.S. Provisional Patent Application Ser. Nos. 60/608,362 filed Sep. 10, 2004; 60/468,050 filed May 6, 2003; 60/425,730 filed Nov. 13, 2002; 60/403,382 filed Aug. 15, 2002; 60/369,860 filed Apr. 5, 2002; 60/341,237 filed Dec. 20, 2001; 60/331,310 filed Nov. 14, 2001; 60/331,044 filed Nov. 7, 2001; 60/327,364 filed Oct. 9, 2001; 60/323,807 filed Sep. 21, 2001; 60/309,176 filed Aug. 2, 2001; 60/294,981 filed Jun. 4, 2001; and 60/293,473 filed May 25, 2001; U.S. patent application Ser. No. 10/139,785 filed May 7, 2002, now U.S. Pat. No. 7,064,189, issued Jun. 20, 2006, International Patent Application Number PCT/US02/14268 filed May 7, 2002 and International Patent Application Number PCT/US03/25457 filed Aug. 15, 2003.

What is claimed is:

1. A method of treating a TR4 expressing cancer comprising administering to an animal an isolated antibody or fragment thereof comprising the amino acid sequence selected from the group consisting of:

(a) an amino acid sequence that is at least 95% identical to the VH and VL domains of SEQ ID NO:42;
   (b) an amino acid sequence that is at least 95% identical to the VH and VL domains of SEQ ID NO:43; and
   (c) an amino acid sequence that is at least 95% identical to the VH and VL domains of SEQ ID NO:47;

wherein said antibody or fragment thereof immunospecifically binds a TR4 protein selected from the group consisting of:

(i) a polypeptide having the amino acid sequence of any one of amino acid residues 1 to 468 of SEQ ID NO:1, amino acid residues 24 to 468 of SEQ ID NO:1, amino acid residues 24 to 238 of SEQ ID NO:1, and amino acid residues 109 to 240 of SEQ ID NO:1;
   (ii) a multimer of the polypeptide of (i);
   (iii) the polypeptide of (i) expressed on the surface of a cell; and
   (iv) the multimer of (ii) expressed on the surface of a cell;

or a composition containing said antibody or fragment thereof.

2. The method of claim 1 wherein the animal is a human.

3. The method of claim 1 wherein the cancer is colon cancer.

4. The method of claim 1 wherein the cancer is breast cancer.

5. The method of claim 1 wherein the cancer is uterine cancer.

6. The method of claim 1 wherein the cancer is pancreatic cancer.

7. The method of claim 1 wherein the cancer is lung cancer.

8. The method of claim 1 wherein the cancer is gastrointestinal cancer.

9. The method of claim 1 wherein the cancer is Kaposi's sarcoma.

10. The method of claim 1 wherein the cancer is a cancer of the central nervous system.

11. The method of claim 10 wherein the cancer of the central nervous system is a neuroblastoma.

12. The method of claim 10 wherein the cancer of the central nervous system is a glioblastoma.

13. The method of claim 1, wherein the antibody or fragment thereof is administered in combination with a chemotherapeutic agent.

14. The method of claim 13, wherein chemotherapeutic agent is selected from the group consisting of:
(a) irinotecan;
(b) paclitaxel; and
(c) gemcitabine.

15. A method of inhibiting the growth of or killing TR4 expressing cells, comprising administering to an animal in which such inhibition of growth or killing of TR4 receptor expressing cells is desired, an isolated antibody or fragment thereof comprising the amino acid sequence selected from the group consisting of:
(a) an amino acid sequence that is at least 95% identical to the VH and VL domains of SEQ ID NO:42;
(b) an amino acid sequence that is at least 95% identical to the VH and VL domains of SEQ ID NO:43; and
(c) an amino acid sequence that is at least 95% identical to the VH and VL domains of SEQ ID NO:47;
wherein said antibody or fragment thereof immunospecifically binds a TR4 protein selected from the group consisting of:
(i) a polypeptide having the amino acid sequence of any one of amino acid residues 1 to 468 of SEQ ID NO:1, amino acid residues 24 to 468of SEQ ID NO:1, amino acid residues 24 to 238 of SEQ ID NO:1, and amino acid residues 109 to 240 of SEQ ID NO:1;
(ii) a multimer of the polypeptide of (i);
(iii) the polypeptide of (i) expressed on the surface of a cell; and
(iv) the multimer of (ii)expressed on the surface of a cell;
or a composition containing said antibody or fragment thereof in an amount effective to inhibit the growth of or kill TR4 expressing cells.

16. The method of claim 15, wherein said antibody or fragment thereof comprises a VH domain having the amino acid sequence of the VH domain of SEQ ID NO:42 and a VL domain having the amino acid sequence of the VL domain of SEQ ID NO:42.

17. The method of claim 15, wherein said antibody or fragment thereof comprises a VH domain having the amino acid sequence of the VH domain of SEQ ID NO:43 and a VL domain having the amino acid sequence of the VL domain of SEQ ID NO:43.

18. The method of claim 15, wherein said antibody is expressed by the cell line of ATCC Deposit PTA-3570.

19. The method of claim 15, wherein said antibody is expressed by the cell line of ATCC Deposit PTA-3571.

20. The method of claim 15, wherein said antibody or fragment thereof is selected from the group consisting of:
(a) a whole immunoglobulin molecule;
(b) an scFv;
(c) a monoclonal antibody;
(d) a human antibody;
(e) a chimeric antibody;
(f) a Fab fragment;
(g) an Fab' fragment;
(h) an F(ab')2;
(i) an Fv; and
(j) a disulfide linked Fv.

21. The method of claim 15, wherein the animal is a human.

22. The method of claim 15, wherein said TR4 expressing cells are cancer cells.

23. The method of claim 22 wherein the cancer cells are colon cancer cells.

24. The method of claim 22 wherein the cancer cells are breast cancer cells.

25. The method of claim 22 wherein the cancer cells are uterine cancer cells.

26. The method of claim 22 wherein the cancer cells are pancreatic cancer cells.

27. The method of claim 22 wherein the cancer cells are lung cancer cells.

28. The method of claim 22 wherein the cancer cells are gastrointestinal cancer cells.

29. The method of claim 22 wherein the cancer cells are Kaposi's sarcoma cells.

30. The method of claim 22 wherein the cancer cells are central nervous system cancer cells.

31. The method of claim 30 wherein the central nervous system cancer cells are neuroblastoma cells.

32. The method of claim 30 wherein the central nervous system cancer cells are glioblastoma cells.

33. The method of claim 15, wherein the antibody or fragment thereof is administered in combination with a chemotherapetuic agent.

34. The method of claim 33, wherein the chemotherapeutic agent is selected from the group consisting of:
(a) irinotecan;
(b) paclitaxel; and
(c) gemcitabine.

35. The method of claim 1, wherein said antibody or fragment thereof comprises a VH domain having the amino acid sequence of the VH domain of SEQ ID NO:42 and a VL domain having the amino acid sequence of the VL domain of SEQ ID NO:42.

36. The method of claim 15, wherein said antibody or fragment thereof comprises a VH domain having the amino acid sequence of the VH domain of SEQ ID NO:43 and a VL domain having the amino acid sequence of the VL domain of SEQ ID NO:43.

37. The method of claim 1, wherein said antibody is expressed by the cell line of ATCC Deposit PTA-3570.

38. The method of claim 1, wherein said antibody is expressed by the cell line of ATCC Deposit PTA-3571.

39. The method of claim 1, wherein said antibody or fragment thereof is selected from the group consisting of:
- (a) a whole immunoglobulin molecule;
- (b) an scFv;
- (c) a monoclonal antibody;
- (d) a human antibody;
- (e) a chimeric antibody;
- (f) a Fab fragment;
- (g) an Fab' fragment;
- (h) an F(ab')2;
- (i) an Fv; and
- (j) a disulfide linked Fv.

40. The method of claim 1, wherein said antibody or fragment thereof comprises a VH domain having the amino acid sequence of the VH domain of SEQ ID NO:47 and a VL domain having the amino acid sequence of the VL domain of SEQ ID NO:47.

41. The method of claim 15, wherein said antibody or fragment thereof comprises a VH domain having the amino acid sequence of the VH domain of SEQ ID NO:47 and a VL domain having the amino acid sequence of the VL domain of SEQ ID NO:47.

42. A method of treating a TR4 expressing cancer comprising administering to an animal an isolated antibody or fragment thereof comprising amino acid residues 26-35, 50-66, 99-107, 157-170, 186-192, and 225-234 of the amino acid sequence selected from the group consisting of:
- (a) SEQ ID NO:42;
- (b) SEQ ID NO:43; and
- (c) SEQ ID NO:47;

wherein said antibody or fragment thereof immunospecifically binds a TR4 protein selected from the group consisting of:
- (i) a polypeptide having the amino acid sequence of any one of amino acid residues 1 to 468 of SEQ ID NO:1; amino acid residues 24 to 468 of SEQ ID NO:1; amino acid residues 24 to 238 of SEQ ID NQ:1; and amino acid residues 109 to 240 of SEQ ID NO:1;
- (ii) a multimer of the polypeptide of (i);
- (iii) the polypeptide of (i) expressed on the surface of a cell; and
- (iv) the multimer of (ii) expressed on the surface of a cell.

43. A method of inhibiting the growth of or killing TR4 expressing cells, comprising administering to an animal in which such inhibition of growth or killing of TR4 receptor expressing cells is desired, an isolated antibody or fragment thereof comprising amino acid residues 26-35, 50-66, 99-107, 157-170, 186-192, and 225-234 of the amino acid sequence selected from the group consisting of:
- (a) SEQ ID NO:42;
- (b) SEQ ID NO:43; and
- (c) SEQ ID NO:47;

wherein said antibody or fragment thereof immunospecifically binds a TR4 protein selected from the group consisting of:
- (i) a polypeptide having the amino acid sequence of any one of amino acid residues 1 to 468 of SEQ ID NO:1; amino acid residues 24 to 468 of SEQ ID NO:1; amino acid residues 24 to 238 of SEQ ID NO:1; and amino acid residues 109 to 240 of SEQ ID NO:1;
- (ii) a multimer of the polypeptide of (i);
- (iii) the polypeptide of (i) expressed on the surface of a cell; and
- (iv) the multimer of (ii) expressed on the surface of a cell.

* * * * *

UNITED STATES PATENT AND TRADEMARK OFFICE
CERTIFICATE OF CORRECTION

| | | |
|---|---|---|
| PATENT NO. | : 7,348,003 B2 | Page 1 of 1 |
| APPLICATION NO. | : 10/986047 | |
| DATED | : March 25, 2008 | |
| INVENTOR(S) | : Salcedo et al. | |

It is certified that error appears in the above-identified patent and that said Letters Patent is hereby corrected as shown below:

On the Cover Page:

Item (63) Under "Related U.S. Application Data," delete "Continuation-in-part of application No. PCT/US03/25457, filed on Aug. 15, 2003, which is a continuation-in-part of application No. 10/139,785, filed on May 7, 2002, now Pat. No. 7,064,189." and insert --Continuation-in-part of application No. PCT/US03/25457, filed on Aug. 15, 2003. This application is also a continuation-in-part of application No. 10/139,785, filed on May 7, 2002, now Pat. No. 7,064,189.--

In the Claims:

Col. 281, Ln 50, In Claim 15(c)(i), line 3, insert a space between "468" and "of";

Col. 281, Ln 56, In Claim 15(c)(iv), line 1, insert a space between "(ii)" and "expressed."

Signed and Sealed this

Seventh Day of October, 2008

JON W. DUDAS
*Director of the United States Patent and Trademark Office*

SEQUENCE LISTING

```
<160> NUMBER OF SEQ ID NOS: 70

<210> SEQ ID NO 1
<211> LENGTH: 468
<212> TYPE: PRT
<213> ORGANISM: Homo sapiens

<400> SEQUENCE: 1

Met Ala Pro Pro Ala Arg Val His Leu Gly Ala Phe Leu Ala Val
 1               5                  10                  15

Thr Pro Asn Pro Gly Ser Ala Ala Ser Gly Thr Glu Ala Ala Ala
                20                  25                  30

Thr Pro Ser Lys Val Trp Gly Ser Ser Ala Gly Arg Ile Glu Pro Arg
            35                  40                  45

Gly Gly Gly Arg Gly Ala Leu Pro Thr Ser Met Gly Gln His Gly Pro
        50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
                100                 105                 110

Leu His Asp Gln Ser Ile Gly Thr Gln Gln Trp Glu His Ser Pro Leu
            115                 120                 125

Gly Glu Leu Cys Pro Pro Gly Ser His Arg Ser Glu Arg Pro Gly Ala
        130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Thr Gly Cys Pro Arg Gly Met Val Lys Val Lys Asp Cys Thr Pro Trp
    210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
```

```
                245                 250                 255
Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
        275                 280                 285

Pro Gly Ala Glu Asp Asn Ala His Asn Glu Ile Leu Ser Asn Ala Asp
    290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Leu Leu
            340                 345                 350

Val Pro Ala Asn Gly Ala Asp Pro Thr Glu Thr Leu Met Leu Phe Phe
        355                 360                 365

Asp Lys Phe Ala Asn Ile Val Pro Phe Asp Ser Trp Asp Gln Leu Met
    370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Lys Glu Lys Ile Gln Asp Leu Leu
        435                 440                 445

Val Asp Ser Gly Lys Phe Ile Tyr Leu Glu Asp Gly Thr Gly Ser Ala
    450                 455                 460

Val Ser Leu Glu
465

<210> SEQ ID NO 2
<211> LENGTH: 299
<212> TYPE: PRT
<213> ORGANISM: Homo sapiens

<400> SEQUENCE: 2

Met Gln Gly Val Lys Glu Arg Phe Leu Pro Leu Gly Asn Ser Gly Asp
  1               5                  10                  15

Arg Ala Pro Arg Pro Asp Gly Arg Gly Arg Val Arg Pro Arg Thr
             20                  25                  30

Gln Asp Gly Val Gly Asn His Thr Met Ala Arg Ile Pro Lys Thr Leu
         35                  40                  45

Lys Phe Val Val Ile Val Ala Val Leu Leu Pro Val Leu Ala Tyr
     50                  55                  60

Ser Ala Thr Thr Ala Arg Gln Glu Glu Val Pro Gln Gln Thr Val Ala
 65                  70                  75                  80

Pro Gln Gln Gln Arg His Ser Phe Lys Gly Glu Glu Cys Pro Ala Gly
                 85                  90                  95

Ser His Arg Ser Glu His Thr Gly Ala Cys Asn Pro Cys Thr Glu Gly
            100                 105                 110

Val Asp Tyr Thr Asn Ala Ser Asn Asn Glu Pro Ser Cys Phe Pro Cys
        115                 120                 125

Thr Val Cys Lys Ser Asp Gln Lys His Lys Ser Ser Cys Thr Met Thr
    130                 135                 140
```

```
Arg Asp Thr Val Cys Gln Cys Lys Glu Gly Thr Phe Arg Asn Glu Asn
145                 150                 155                 160

Ser Pro Glu Met Cys Arg Lys Cys Ser Arg Cys Pro Ser Gly Glu Val
            165                 170                 175

Gln Val Ser Asn Cys Thr Ser Trp Asp Asp Ile Gln Cys Val Glu Glu
        180                 185                 190

Phe Gly Ala Asn Ala Thr Val Glu Thr Pro Ala Ala Glu Glu Thr Met
    195                 200                 205

Asn Thr Ser Pro Gly Thr Pro Ala Pro Ala Ala Glu Glu Thr Met Asn
210                 215                 220

Thr Ser Pro Gly Thr Pro Ala Pro Ala Ala Glu Glu Thr Met Thr Thr
225                 230                 235                 240

Ser Pro Gly Thr Pro Ala Pro Ala Ala Glu Glu Thr Met Thr Thr Ser
            245                 250                 255

Pro Gly Thr Pro Ala Pro Ala Ala Glu Glu Thr Met Thr Thr Ser Pro
        260                 265                 270

Gly Thr Pro Ala Ser Ser His Tyr Leu Ser Cys Thr Ile Val Gly Ile
    275                 280                 285

Ile Val Leu Ile Val Leu Leu Ile Val Phe Val
290                 295

<210> SEQ ID NO 3
<211> LENGTH: 411
<212> TYPE: PRT
<213> ORGANISM: Homo sapiens

<400> SEQUENCE: 3

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
            85                  90                  95

Cys Lys Tyr Gly Gln Asp Tyr Ser Thr His Trp Asn Asp Leu Leu Phe
        100                 105                 110

Cys Leu Arg Cys Thr Arg Cys Asp Ser Gly Glu Val Glu Leu Ser Pro
    115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
            165                 170                 175

Glu Cys Val His Lys Glu Ser Gly Ile Ile Ile Gly Val Thr Val Ala
        180                 185                 190

Ala Val Val Leu Ile Val Ala Val Phe Val Cys Lys Ser Leu Leu Trp
    195                 200                 205

Lys Lys Val Leu Pro Tyr Leu Lys Gly Ile Cys Ser Gly Gly Gly Gly
210                 215                 220
```

```
Asp Pro Glu Arg Val Asp Arg Ser Ser Gln Arg Pro Gly Ala Glu Asp
225                 230                 235                 240

Asn Val Leu Asn Glu Ile Val Ser Ile Leu Gln Pro Thr Gln Val Pro
            245                 250                 255

Glu Gln Glu Met Glu Val Gln Glu Pro Ala Glu Pro Thr Gly Val Asn
            260                 265                 270

Met Leu Ser Pro Gly Glu Ser Glu His Leu Leu Glu Pro Ala Glu Ala
        275                 280                 285

Glu Arg Ser Gln Arg Arg Arg Leu Leu Val Pro Ala Asn Glu Gly Asp
    290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
                325                 330                 335

Asn Glu Ile Lys Val Ala Lys Ala Glu Ala Ala Gly His Arg Asp Thr
            340                 345                 350

Leu Tyr Thr Met Leu Ile Lys Trp Val Asn Lys Thr Gly Arg Asp Ala
        355                 360                 365

Ser Val His Thr Leu Leu Asp Ala Leu Glu Thr Leu Gly Glu Arg Leu
    370                 375                 380

Ala Lys Gln Lys Ile Glu Asp His Leu Leu Ser Ser Gly Lys Phe Met
385                 390                 395                 400

Tyr Leu Glu Gly Asn Ala Asp Ser Ala Met Ser
                405                 410

<210> SEQ ID NO 4
<211> LENGTH: 386
<212> TYPE: PRT
<213> ORGANISM: Homo sapiens

<400> SEQUENCE: 4

Met Gly Leu Trp Gly Gln Ser Val Pro Thr Ala Ser Ser Ala Arg Ala
1               5                   10                  15

Gly Arg Tyr Pro Gly Ala Arg Thr Ala Ser Gly Thr Arg Pro Trp Leu
            20                  25                  30

Leu Asp Pro Lys Ile Leu Lys Phe Val Val Phe Ile Val Ala Val Leu
        35                  40                  45

Leu Pro Val Arg Val Asp Ser Ala Thr Ile Pro Arg Gln Asp Glu Val
    50                  55                  60

Pro Gln Gln Thr Val Ala Pro Gln Gln Arg Arg Ser Leu Lys Glu
65                  70                  75                  80

Glu Glu Cys Pro Ala Gly Ser His Arg Ser Glu Tyr Thr Gly Ala Cys
                85                  90                  95

Asn Pro Cys Thr Glu Gly Val Asp Tyr Thr Ile Ala Ser Asn Asn Leu
            100                 105                 110

Pro Ser Cys Leu Leu Cys Thr Val Cys Lys Ser Gly Gln Thr Asn Lys
        115                 120                 125

Ser Ser Cys Thr Thr Thr Arg Asp Thr Val Cys Gln Cys Glu Lys Gly
    130                 135                 140

Ser Phe Gln Asp Lys Asn Ser Pro Glu Met Cys Arg Thr Cys Arg Thr
145                 150                 155                 160

Gly Cys Pro Arg Gly Met Val Lys Val Ser Asn Cys Thr Pro Arg Ser
                165                 170                 175

Asp Ile Lys Cys Lys Asn Glu Ser Ala Ala Ser Ser Thr Gly Lys Thr
```

-continued

```
                 180                 185                 190
Pro Ala Ala Glu Glu Thr Val Thr Ile Leu Gly Met Leu Ala Ser
            195                 200                 205
Pro Tyr His Tyr Leu Ile Ile Ile Val Leu Val Ile Ile Leu Ala
        210                 215                 220
Val Val Val Gly Phe Ser Cys Arg Lys Lys Phe Ile Ser Tyr Leu
225                 230                 235                 240
Lys Gly Ile Cys Ser Gly Gly Gly Gly Pro Glu Arg Val His Arg
                245                 250                 255
Val Leu Phe Arg Arg Arg Ser Cys Pro Ser Arg Val Pro Gly Ala Glu
            260                 265                 270
Asp Asn Ala Arg Asn Glu Thr Leu Ser Asn Arg Tyr Leu Gln Pro Thr
        275                 280                 285
Gln Val Ser Glu Gln Glu Ile Gln Gly Gln Glu Leu Ala Glu Leu Thr
    290                 295                 300
Gly Val Thr Val Glu Ser Pro Glu Glu Pro Gln Arg Leu Leu Glu Gln
305                 310                 315                 320
Ala Glu Ala Glu Gly Cys Gln Arg Arg Arg Leu Leu Val Pro Val Asn
                325                 330                 335
Asp Ala Asp Ser Ala Asp Ile Ser Thr Leu Leu Asp Ala Ser Ala Thr
            340                 345                 350
Leu Glu Glu Gly His Ala Lys Glu Thr Ile Gln Asp Gln Leu Val Gly
        355                 360                 365
Ser Glu Lys Leu Phe Tyr Glu Glu Asp Glu Ala Gly Ser Ala Thr Ser
    370                 375                 380
Cys Leu
385

<210> SEQ ID NO 5
<211> LENGTH: 401
<212> TYPE: PRT
<213> ORGANISM: Homo sapiens

<400> SEQUENCE: 5

Met Asn Lys Leu Leu Cys Cys Ala Leu Val Phe Leu Asp Ile Ser Ile
1               5                   10                  15
Lys Trp Thr Thr Gln Glu Thr Phe Pro Pro Lys Tyr Leu His Tyr Asp
            20                  25                  30
Glu Glu Thr Ser His Gln Leu Leu Cys Asp Lys Cys Pro Pro Gly Thr
        35                  40                  45
Tyr Leu Lys Gln His Cys Thr Ala Lys Trp Lys Thr Val Cys Ala Pro
    50                  55                  60
Cys Pro Asp His Tyr Tyr Thr Asp Ser Trp His Thr Ser Asp Glu Cys
65                  70                  75                  80
Leu Tyr Cys Ser Pro Val Cys Lys Glu Leu Gln Tyr Val Lys Gln Glu
                85                  90                  95
Cys Asn Arg Thr His Asn Arg Val Cys Glu Cys Lys Glu Gly Arg Tyr
            100                 105                 110
Leu Glu Ile Glu Phe Cys Leu Lys His Arg Ser Cys Pro Pro Gly Phe
        115                 120                 125
Gly Val Val Gln Ala Gly Thr Pro Glu Arg Asn Thr Val Cys Lys Arg
    130                 135                 140
Cys Pro Asp Gly Phe Phe Ser Asn Glu Thr Ser Ser Lys Ala Pro Cys
145                 150                 155                 160
```

-continued

```
Arg Lys His Thr Asn Cys Ser Val Phe Gly Leu Leu Thr Gln Lys
            165                 170                 175
Gly Asn Ala Thr His Asp Asn Ile Cys Ser Gly Asn Ser Glu Ser Thr
        180                 185                 190
Gln Lys Cys Gly Ile Asp Val Thr Leu Cys Glu Glu Ala Phe Phe Arg
            195                 200                 205
Phe Ala Val Pro Thr Lys Phe Thr Pro Asn Trp Leu Ser Val Leu Val
210                 215                 220
Asp Asn Leu Pro Gly Thr Lys Val Asn Ala Glu Ser Val Glu Arg Ile
225                 230                 235                 240
Lys Arg Gln His Ser Ser Gln Glu Gln Thr Phe Gln Leu Leu Lys Leu
                245                 250                 255
Trp Lys His Gln Asn Lys Asp Gln Asp Ile Val Lys Lys Ile Ile Gln
            260                 265                 270
Asp Ile Asp Leu Cys Glu Asn Ser Val Gln Arg His Ile Gly His Ala
        275                 280                 285
Asn Leu Thr Phe Glu Gln Leu Arg Ser Leu Met Glu Ser Leu Pro Gly
    290                 295                 300
Lys Lys Val Gly Ala Glu Asp Ile Glu Lys Thr Ile Lys Ala Cys Lys
305                 310                 315                 320
Pro Ser Asp Gln Ile Leu Lys Leu Leu Ser Leu Trp Arg Ile Lys Asn
                325                 330                 335
Gly Asp Gln Asp Thr Leu Lys Gly Leu Met His Ala Leu Lys His Ser
            340                 345                 350
Lys Thr Tyr His Phe Pro Lys Thr Val Thr Gln Ser Leu Lys Lys Thr
        355                 360                 365
Ile Arg Phe Leu His Ser Phe Thr Met Tyr Lys Leu Tyr Gln Lys Leu
    370                 375                 380
Phe Leu Glu Met Ile Gly Asn Gln Val Gln Ser Val Lys Ile Ser Cys
385                 390                 395                 400
Leu

<210> SEQ ID NO 6
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 6
caggtgcagc tggtgcagtc tgg                                              23

<210> SEQ ID NO 7
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 7
caggtcaact taagggagtc tgg                                              23

<210> SEQ ID NO 8
<211> LENGTH: 23
<212> TYPE: DNA
<213> ORGANISM: Artificial sequence
<220> FEATURE:
```

<223> OTHER INFORMATION: PCR primer useful for amplifying VH and VL
      domains

<400> SEQUENCE: 8
gaggtgcagc tggtggagtc tgg                                              23

<210> SEQ ID NO 9
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 9
caggtgcagc tgcaggagtc ggg                                              23

<210> SEQ ID NO 10
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 10
gaggtgcagc tgttgcagtc tgc                                              23

<210> SEQ ID NO 11
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 11
caggtacagc tgcagcagtc agg                                              23

<210> SEQ ID NO 12
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 12
tgaggagacg gtgaccaggg tgcc                                             24

<210> SEQ ID NO 13
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 13
tgaagagacg gtgaccattg tccc                                             24

<210> SEQ ID NO 14
<211> LENGTH: 24
<212> TYPE: DNA
<213> ORGANISM: Artificial sequence
<220> FEATURE:
<223> OTHER INFORMATION: PCR primer useful for amplifying VH and VL domains

<400> SEQUENCE: 14
tgaggagacg gtgaccaggg ttcc        24

<210> SEQ ID NO 15
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 15
tgaggagacg gtgaccgtgg tccc        24

<210> SEQ ID NO 16
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 16
gacatccaga tgacccagtc tcc        23

<210> SEQ ID NO 17
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 17
gatgttgtga tgactcagtc tcc        23

<210> SEQ ID NO 18
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 18
gatattgtga tgactcagtc tcc        23

<210> SEQ ID NO 19
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 19
gaaattgtgt tgacgcagtc tcc        23

<210> SEQ ID NO 20
<211> LENGTH: 23
<212> TYPE: DNA
<213> ORGANISM: Artificial sequence
<220> FEATURE:
<223> OTHER INFORMATION: PCR primer useful for amplifying VH and VL
      domains

```
<400> SEQUENCE: 20
gacatcgtga tgacccagtc tcc                                              23

<210> SEQ ID NO 21
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 21
gaaacgacac tcacgcagtc tcc                                              23

<210> SEQ ID NO 22
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 22
gaaattgtgc tgactcagtc tcc                                              23

<210> SEQ ID NO 23
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 23
cagtctgtgt tgacgcagcc gcc                                              23

<210> SEQ ID NO 24
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 24
cagtctgccc tgactcagcc tgc                                              23

<210> SEQ ID NO 25
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 25
tcctatgtgc tgactcagcc acc                                              23

<210> SEQ ID NO 26
<211> LENGTH: 23
<212> TYPE: DNA
<213> ORGANISM: Artificial sequence
<220> FEATURE:
<223> OTHER INFORMATION: PCR primer useful for amplifying VH and VL
      domains
```

```
<400> SEQUENCE: 26
tcttctgagc tgactcagga ccc                                        23

<210> SEQ ID NO 27
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 27
cacgttatac tgactcaacc gcc                                        23

<210> SEQ ID NO 28
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 28
caggctgtgc tcactcagcc gtc                                        23

<210> SEQ ID NO 29
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 29
aattttatgc tgactcagcc cca                                        23

<210> SEQ ID NO 30
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 30
acgtttgatt tccaccttgg tccc                                       24

<210> SEQ ID NO 31
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 31
acgtttgatc tccagcttgg tccc                                       24

<210> SEQ ID NO 32
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 32
```
acgtttgata tccactttgg tccc                                              24

<210> SEQ ID NO 33
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 33
acgtttgatc tccaccttgg tccc                                              24

<210> SEQ ID NO 34
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 34
acgtttaatc tccagtcgtg tccc                                              24

<210> SEQ ID NO 35
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 35
cagtctgtgt tgacgcagcc gcc                                               23

<210> SEQ ID NO 36
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 36
cagtctgccc tgactcagcc tgc                                               23

<210> SEQ ID NO 37
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 37
tcctatgtgc tgactcagcc acc                                               23

<210> SEQ ID NO 38
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 38
tcttctgagc tgactcagga ccc                                              23

<210> SEQ ID NO 39
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 39
cacgttatac tgactcaacc gcc                                              23

<210> SEQ ID NO 40
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 40
caggctgtgc tcactcagcc gtc                                              23

<210> SEQ ID NO 41
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 41
aattttatgc tgactcagcc cca                                              23

<210> SEQ ID NO 42
<211> LENGTH: 245
<212> TYPE: PRT
<213> ORGANISM: Artificial sequence
<220> FEATURE:
<223> OTHER INFORMATION: T1014A04 scFv

<400> SEQUENCE: 42

Glu Val Gln Leu Val Gln Ser Gly Ala Asp Val Lys Arg Pro Gly Ala
 1               5                  10                  15

Ser Val Lys Val Ser Cys Lys Ile Ser Gly Asp Ser Phe Asn Ala Tyr
            20                  25                  30

Phe Ile His Trp Val Arg Gln Ala Pro Gly Gln Gly Leu Glu Trp Met
        35                  40                  45

Gly Trp Phe Asn Pro Asp Ser Gly Thr Ala Asp Ser Ala Gln Lys Phe
    50                  55                  60

His Gly Arg Val Thr Met Thr Arg Asp Thr Ser Ser Thr Ala Phe
 65                  70                  75                  80

Leu Glu Leu Ser Arg Leu Arg Ser Asp Asp Thr Ala Val Tyr Tyr Cys
                85                  90                  95

Val Arg Gln His Arg Gly Asn Thr Phe Ala Pro Trp Gly Arg Gly Thr
            100                 105                 110

Met Val Thr Val Ser Ser Gly Gly Gly Ser Gly Gly Gly Gly Ser
        115                 120                 125

Gly Gly Gly Gly Ser Ala Gln Ser Val Leu Thr Gln Pro Pro Ser Ala
    130                 135                 140

Ser Gly Ser Pro Gly Gln Ser Val Thr Ile Ser Cys Thr Gly Thr Thr

```
                145                 150                 155                 160
Ser Asp Val Gly Gly Tyr Asn Tyr Val Ser Trp Tyr Gln Gln His Pro
                    165                 170                 175
Gly Lys Ala Pro Lys Leu Met Ile Tyr Gly Val Asn Gln Arg Pro Ser
            180                 185                 190
Gly Val Pro Asp Arg Phe Ser Gly Ser Lys Ser Gly Asn Thr Ala Ser
        195                 200                 205
Leu Thr Val Ser Gly Leu Gln Ala Glu Asp Glu Ala Asp Tyr Tyr Cys
    210                 215                 220
Ser Ser Tyr Ala Gly Ser Asn Asn Trp Val Phe Gly Gly Gly Thr Lys
225                 230                 235                 240
Leu Thr Val Leu Gly
                245

<210> SEQ ID NO 43
<211> LENGTH: 245
<212> TYPE: PRT
<213> ORGANISM: Artificial sequence
<220> FEATURE:
<223> OTHER INFORMATION: T1014G03 scFv

<400> SEQUENCE: 43

Glu Val Gln Leu Val Gln Ser Gly Ala Glu Val Lys Met Pro Gly Ala
 1               5                  10                  15
Ser Val Lys Leu Ser Cys Arg Val Ser Gly Asp Thr Phe Thr Ala Tyr
            20                  25                  30
Phe Ile His Trp Val Arg Gln Ala Pro Gly Gln Gly Leu Glu Trp Met
        35                  40                  45
Gly Trp Phe Asn Pro Ile Ser Gly Thr Ala Gly Ser Ala Glu Lys Phe
    50                  55                  60
Arg Gly Arg Val Ala Met Thr Arg Asp Thr Ser Ile Ser Thr Ala Tyr
65                  70                  75                  80
Met Glu Leu Asn Arg Leu Thr Phe Asp Asp Thr Ala Val Tyr Tyr Cys
                85                  90                  95
Ala Arg Gln His Arg Gly Asn Thr Phe Asp Pro Trp Gly Gln Gly Thr
            100                 105                 110
Leu Val Thr Val Ser Ser Gly Gly Gly Gly Ser Gly Gly Gly Gly Ser
        115                 120                 125
Gly Gly Gly Gly Ser Ala Gln Ser Ala Leu Thr Gln Pro Ala Ser Val
    130                 135                 140
Ser Gly Ser Pro Gly Gln Ser Ile Thr Ile Ser Cys Thr Gly Thr Ser
145                 150                 155                 160
Ser Asp Ile Gly Ala Tyr Lys Tyr Val Ser Trp Tyr Gln Gln His Pro
                165                 170                 175
Gly Lys Ala Pro Lys Leu Val Ile Tyr Glu Val Ser Asn Arg Pro Ser
            180                 185                 190
Gly Val Ser Ser Arg Phe Ser Gly Ser Lys Ser Gly Gln Thr Ala Ser
        195                 200                 205
Leu Thr Ile Ser Gly Leu Gln Ala Asp Asp Glu Ala Asp Tyr Tyr Cys
    210                 215                 220
Asn Ser Tyr Gln Gly Tyr Asn Thr Trp Val Phe Gly Gly Gly Thr Lys
225                 230                 235                 240
Val Thr Val Leu Gly
                245
```

```
<210> SEQ ID NO 44
<211> LENGTH: 244
<212> TYPE: PRT
<213> ORGANISM: Artificial sequence
<220> FEATURE:
<223> OTHER INFORMATION: T1014A02 scFv

<400> SEQUENCE: 44

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Asp Tyr
            20                  25                  30

Tyr Trp Ser Trp Val Arg Gln Ser Pro Gly Lys Gly Leu Glu Trp Ile
        35                  40                  45

Gly Ser Ile Asp Tyr Ala Gly Ser Thr Asn Tyr Asn Pro Ser Leu Lys
    50                  55                  60

Ser Arg Val Thr Met Thr Ile Asp Lys Ser Lys Lys Gln Phe Pro Leu
65                  70                  75                  80

Lys Ile Asp Ser Val Thr Ala Ala Asp Thr Ala Met Tyr Tyr Cys Ala
                85                  90                  95

Arg Gln Leu Gly Arg Ile Ser Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ala Leu Ser Tyr Val Leu Thr Gln Pro Pro Ser Ala Ser
    130                 135                 140

Gly Thr Pro Gly Gln Arg Val Thr Ile Ser Cys Ala Gly Ser Ser Ser
145                 150                 155                 160

Asn Ile Gly Gly Asn Thr Val Asn Trp Tyr Gln Gln Leu Pro Ala Thr
                165                 170                 175

Ala Pro Lys Leu Leu Ile Tyr Ser Asn Asn Gln Arg Pro Ser Gly Val
            180                 185                 190

Pro Asp Arg Phe Ser Gly Ser Lys Ser Gly Thr Ser Ala Ser Leu Ala
        195                 200                 205

Ile Ser Gly Leu Gln Ser Glu Asp Glu Ala Asp Tyr Tyr Cys Ala Thr
    210                 215                 220

Trp Asp Ser Arg Gly Gly Trp Val Phe Gly Gly Gly Thr Lys Leu
225                 230                 235                 240

Thr Val Leu Gly

<210> SEQ ID NO 45
<211> LENGTH: 245
<212> TYPE: PRT
<213> ORGANISM: Artificial sequence
<220> FEATURE:
<223> OTHER INFORMATION: T1014A12 scFv

<400> SEQUENCE: 45

Glu Val Gln Leu Val Gln Ser Gly Ala Asp Val Lys Arg Pro Gly Ala
 1               5                  10                  15

Ser Val Lys Val Ser Cys Lys Ile Ser Gly Asp Ser Phe Thr Ala Tyr
            20                  25                  30

Phe Ile His Trp Val Arg Gln Ala Pro Gly Gln Gly Leu Glu Trp Met
        35                  40                  45

Gly Trp Phe Asn Pro Asp Ser Gly Thr Ala Asp Ser Ala Gln Lys Phe
    50                  55                  60

His Gly Arg Val Thr Met Thr Arg Asp Thr Ser Ser Ser Thr Ala Phe
```

-continued

```
                65                  70                  75                  80
Leu Glu Leu Ser Arg Leu Arg Ser Asp Asp Thr Ala Val Tyr Tyr Cys
                    85                  90                  95

Val Arg Gln His Arg Gly Asn Thr Phe Ala Pro Trp Gly Arg Gly Thr
                100                 105                 110

Met Val Thr Val Ser Ser Gly Gly Gly Gly Ser Gly Gly Gly Gly Ser
                115                 120                 125

Gly Gly Gly Gly Ser Ala Gln Ser Ala Leu Thr Gln Pro Ala Ser Val
            130                 135                 140

Ser Gly Pro Pro Gly Gln Ser Ile Thr Ile Ser Cys Thr Gly Ser Ser
145                 150                 155                 160

Ser Asp Val Gly Gly Tyr Lys Tyr Val Ser Trp Tyr Gln Gln His Pro
                    165                 170                 175

Gly Lys Ala Pro Lys Leu Ile Ile His Asp Val Ser Arg Arg Pro Ser
                180                 185                 190

Glu Val Ser Ser Arg Phe Ser Gly Ser Lys Ser Gly Asn Thr Ala Ser
                195                 200                 205

Leu Thr Ile Ser Gly Leu Gln Ala Glu Asp Glu Ala Glu Tyr Tyr Cys
                210                 215                 220

Ser Ser Tyr Ser Ser Thr Asn Ser Trp Val Phe Gly Gly Gly Thr Lys
225                 230                 235                 240

Val Thr Val Leu Gly
                245

<210> SEQ ID NO 46
<211> LENGTH: 245
<212> TYPE: PRT
<213> ORGANISM: Artificial sequence
<220> FEATURE:
<223> OTHER INFORMATION: T1014B01 scFv

<400> SEQUENCE: 46

Gln Val Gln Leu Val Gln Ser Gly Ala Glu Val Lys Lys Pro Gly Ala
  1                   5                  10                  15

Ser Val Lys Val Ser Cys Lys Ile Ser Gly Asp Thr Phe Ala Ala Tyr
                 20                  25                  30

Phe Ile His Trp Val Arg Gln Ala Pro Gly Gln Gly Leu Glu Trp Met
             35                  40                  45

Gly Trp Phe Asn Pro Asn Ser Gly Thr Ala Asp Ser Ser Gln Lys Phe
         50                  55                  60

His Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                     85                  90                  95

Ala Arg Gln His Arg Ser Asn Thr Phe Asp Pro Trp Gly Gln Gly Thr
                100                 105                 110

Met Val Thr Val Ser Ser Gly Gly Gly Gly Ser Gly Gly Gly Gly Ser
                115                 120                 125

Gly Gly Gly Gly Ser Ala Gln Ser Val Val Thr Gln Pro Pro Ser Val
            130                 135                 140

Ser Gly Ser Pro Gly Gln Ser Val Thr Ile Ser Cys Thr Gly Thr Ser
145                 150                 155                 160

Ser Asp Ile Gly Ala Tyr Asn Tyr Val Ser Trp Phe Gln Gln His Pro
                    165                 170                 175

Gly Lys Ala Pro Lys Leu Ile Ile Ser Glu Val Ser Lys Arg Pro Ser
```

-continued

```
            180                 185                 190
Gly Val Pro Asp Arg Leu Ser Gly Ser Lys Ser Gly Asn Thr Ala Ser
            195                 200                 205

Leu Thr Val Ser Gly Leu Gln Ala Glu Asp Glu Ala Asp Tyr Tyr Cys
        210                 215                 220

Gly Ser Tyr Ala Gly Ser Asn Ile Trp Val Phe Gly Gly Gly Thr Lys
225                 230                 235                 240

Val Thr Val Leu Gly
            245

<210> SEQ ID NO 47
<211> LENGTH: 245
<212> TYPE: PRT
<213> ORGANISM: Artificial sequence
<220> FEATURE:
<223> OTHER INFORMATION: T1014B11 scFv

<400> SEQUENCE: 47

Glu Val Gln Leu Val Gln Ser Gly Ala Glu Val Lys Lys Pro Gly Ala
1               5                   10                  15

Ser Val Lys Val Ser Cys Lys Ile Ser Gly Asp Ser Phe Thr Ala Tyr
            20                  25                  30

Phe Ile His Trp Leu Arg Gln Ala Pro Gly Glu Gly Leu Glu Trp Met
        35                  40                  45

Gly Trp Phe Asn Pro Ile Ser Gly Thr Ala Gly Ser Pro Gln Lys Phe
    50                  55                  60

His Gly Arg Val Ala Met Thr Arg Asp Thr Ser Ile Ser Thr Ala Tyr
65              70                  75                  80

Met Glu Leu Thr Arg Leu Ala Ser Asp Asp Thr Ala Ile Tyr Tyr Cys
                85                  90                  95

Ala Arg Gln His His Ser Asn Thr Phe Asp Pro Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Gln Ser Ala Leu Thr Gln Pro Ala Ser Val
    130                 135                 140

Ser Gly Ser Pro Gly Gln Ser Ile Thr Ile Ser Cys Thr Gly Thr Asn
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Glu Val Asn Asn Arg Pro Ser
            180                 185                 190

Gly Val Ser Asn Arg Phe Ser Gly Ser Lys Ser Gly Asn Thr Ala Ser
        195                 200                 205

Leu Thr Ile Ser Gly Leu Gln Ala Asp Asp Glu Ala Asp Tyr Tyr Cys
    210                 215                 220

Ser Ser Tyr Thr Thr Ser Asn Thr Trp Val Phe Gly Gly Gly Thr Lys
225                 230                 235                 240

Leu Thr Val Leu Gly
            245

<210> SEQ ID NO 48
<211> LENGTH: 245
<212> TYPE: PRT
<213> ORGANISM: Artificial sequence
<220> FEATURE:
<223> OTHER INFORMATION: T1014F11 scFv
```

-continued

```
<400> SEQUENCE: 48

Glu Val Gln Leu Val Gln Ser Gly Ala Glu Val Lys Lys Pro Gly Ala
 1               5                  10                  15

Ser Val Lys Leu Ser Cys Arg Val Ser Gly Asp Thr Phe Thr Ala Tyr
             20                  25                  30

Phe Ile His Trp Val Arg Gln Ala Pro Gly Gln Gly Pro Glu Trp Met
         35                  40                  45

Gly Trp Phe Asn Pro Ile Ser Gly Thr Ala Gly Ser Ala Ala Arg Phe
     50                  55                  60

Arg Gly Arg Val Ala Met Thr Arg Asp Thr Ser Ile Ser Thr Ala Tyr
 65                  70                  75                  80

Met Glu Leu Asn Arg Leu Thr Phe Asp Asp Thr Ala Val Tyr Tyr Cys
                 85                  90                  95

Ala Arg Gln His Arg Gly Asn Thr Phe Asp Pro Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Pro Val Leu Thr Gln Pro Pro Ser Ala
    130                 135                 140

Ser Gly Ser Pro Gly Gln Ser Val Thr Ile Ser Cys Thr Gly Thr Ser
145                 150                 155                 160

Ser Asp Val Gly Gly Tyr Lys Tyr Val Ser Trp Tyr Gln Gln His Pro
                165                 170                 175

Gly Lys Ala Pro Lys Leu Met Ile Tyr Glu Val Ser Met Arg Pro Ser
            180                 185                 190

Gly Val Pro Asp Arg Phe Ser Gly Ser Lys Ser Gly Asn Thr Ala Ser
        195                 200                 205

Leu Thr Val Ser Gly Leu Gln Ala Glu Asp Glu Ala Asp Tyr Tyr Cys
    210                 215                 220

Ala Ser Tyr Ala Gly Ser Asn Asn Trp Val Phe Gly Gly Gly Thr Lys
225                 230                 235                 240

Leu Thr Val Leu Gly
                245

<210> SEQ ID NO 49
<211> LENGTH: 245
<212> TYPE: PRT
<213> ORGANISM: Artificial sequence
<220> FEATURE:
<223> OTHER INFORMATION: T1014G04 scFv

<400> SEQUENCE: 49

Glu Val Gln Leu Val Gln Ser Gly Ala Asp Val Lys Arg Pro Gly Ala
 1               5                  10                  15

Ser Val Lys Val Ser Cys Lys Ile Ser Gly Asp Ser Phe Thr Ala Tyr
             20                  25                  30

Phe Ile His Trp Val Arg Gln Ala Pro Gly Gln Gly Leu Glu Trp Met
         35                  40                  45

Gly Trp Phe Asn Pro Asp Ser Gly Thr Ala Asp Ser Ala Gln Lys Phe
     50                  55                  60

His Gly Arg Val Thr Met Thr Arg Asp Thr Ser Ser Ser Thr Ala Phe
 65                  70                  75                  80

Leu Glu Leu Ser Arg Leu Arg Ser Asp Asp Thr Ala Val Tyr Tyr Cys
                 85                  90                  95
```

```
Val Arg Gln His Arg Gly Asn Thr Phe Ala Pro Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Gln Pro Val Leu Thr Gln Pro Pro Ser Ala
    130                 135                 140

Ser Gly Ser Pro Gly Gln Ser Val Thr Ile Ser Cys Thr Gly Thr Ser
145                 150                 155                 160

Ser Asp Val Gly Ser Tyr Glu Tyr Val Ser Trp Tyr Gln Gln His Pro
                165                 170                 175

Gly Lys Ala Pro Arg Leu Met Ile Ser Glu Val Asn Lys Arg Pro Ser
            180                 185                 190

Gly Val Pro Asn Arg Phe Ser Gly Ser Lys Ser Gly Asn Thr Ala Ser
        195                 200                 205

Leu Thr Val Ser Gly Leu Gln Ala Asp Asp Glu Ala Asp Tyr Tyr Cys
    210                 215                 220

Ser Ser Tyr Ala Gly Ser Asn Asn Trp Val Phe Gly Gly Gly Thr Lys
225                 230                 235                 240

Val Thr Val Leu Gly
                245

<210> SEQ ID NO 50
<211> LENGTH: 250
<212> TYPE: PRT
<213> ORGANISM: Artificial sequence
<220> FEATURE:
<223> OTHER INFORMATION: T1015A02 scFv
<220> FEATURE:
<221> NAME/KEY: SITE
<222> LOCATION: (250)
<223> OTHER INFORMATION: Xaa equals either Gly or Ser

<400> SEQUENCE: 50

Gln Val Gln Leu Gln Glu Ser Gly Pro Gly Leu Val Lys Pro Ser Gln
 1               5                  10                  15

Thr Leu Ser Leu Lys Cys Asn Val Ser Gly Gly Ser Ile Gly Thr Gly
            20                  25                  30

Asp Tyr Tyr Trp Ser Trp Ile Arg Gln Pro Pro Gly Lys Gly Leu Glu
        35                  40                  45

Trp Ile Gly Tyr Ile His Ser Ser Gly Ser Thr Tyr Tyr Lys Pro Ser
    50                  55                  60

Leu Arg Ser Arg Leu Thr Val Ser Met Asp Thr Ser Arg Asn Gln Phe
65                  70                  75                  80

Ser Leu Lys Leu Thr Ser Val Thr Ala Ala Asp Thr Ala Leu Tyr Tyr
                85                  90                  95

Cys Val Arg Glu Trp Ala Asn Gly Asp His Trp Ser Ala Phe Asp Leu
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Ala Gln Ala Val Leu Thr
    130                 135                 140

Gln Pro Ser Ser Ala Ser Gly Thr Pro Gly Gln Arg Val Thr Ile Pro
145                 150                 155                 160

Cys Ser Gly Ser Ser Ser Asn Ile Gly Gly Asn Thr Val Asn Trp Tyr
                165                 170                 175

Gln Gln Leu Pro Gly Thr Ala Pro Lys Leu Leu Ile Tyr Gly Asn Asp
            180                 185                 190
```

```
Gln Arg Pro Ser Gly Val Pro Asp Arg Phe Ser Gly Ser Lys Ser Gly
            195                 200                 205

Thr Ser Ala Ser Leu Ala Ile Thr Gly Leu Gln Ser Glu Asp Glu Ala
            210                 215                 220

Asp Tyr Tyr Cys Ala Ala Trp Asp Asp Ser Leu Ile Gly Tyr Val Phe
225                 230                 235                 240

Gly Thr Gly Thr Gln Leu Thr Val Leu Xaa
            245                 250

<210> SEQ ID NO 51
<211> LENGTH: 245
<212> TYPE: PRT
<213> ORGANISM: Artificial sequence
<220> FEATURE:
<223> OTHER INFORMATION: T1015A07 scFv

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ile Ser Gly Asp Ser Phe Thr Ala Tyr
            20                  25                  30

Phe Ile His Trp Leu Arg Gln Ala Pro Gly Glu Gly Leu Glu Trp Met
        35                  40                  45

Gly Trp Phe Asn Pro Ile Ser Gly Thr Ala Asp Ser Pro Gln Lys Phe
    50                  55                  60

His Gly Arg Val Ala Met Thr Arg Asp Thr Ser Ile Ser Thr Ala Tyr
65                  70                  75                  80

Met Glu Leu Thr Arg Leu Ala Ser Asp Asp Thr Ala Ile Tyr Tyr Cys
                85                  90                  95

Ala Arg Gln His His Ser Asn Thr Phe Asp Pro Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Gln Ser Ala Leu Thr Gln Pro Ala Ser Met
    130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Ala Val Thr Asn Arg Pro Ser
            180                 185                 190

Gly Val Ser Asn Arg Phe Ser Ala Ser Lys Ser Gly Asn Thr Ala Ser
        195                 200                 205

Leu Thr Ile Ser Gly Leu Gln Ala Glu Asp Glu Ala Asp Tyr Tyr Cys
    210                 215                 220

Ser Ser Tyr Thr Ser Ser Asn Thr Trp Val Phe Gly Gly Gly Thr Lys
225                 230                 235                 240

Val Thr Val Leu Gly
                245

<210> SEQ ID NO 52
<211> LENGTH: 245
<212> TYPE: PRT
<213> ORGANISM: Artificial sequence
<220> FEATURE:
<223> OTHER INFORMATION: T1015E01 scFv
<220> FEATURE:
```

```
<221> NAME/KEY: SITE
<222> LOCATION: (4)
<223> OTHER INFORMATION: Xaa equals Val or Leu
<220> FEATURE:
<221> NAME/KEY: SITE
<222> LOCATION: (5)
<223> OTHER INFORMATION: Xaa equals Ala or Val
<220> FEATURE:
<221> NAME/KEY: SITE
<222> LOCATION: (7)
<223> OTHER INFORMATION: Xaa equals Ala or Ser
<220> FEATURE:
<221> NAME/KEY: SITE
<222> LOCATION: (10)
<223> OTHER INFORMATION: Xaa equals Asp or Glu
<220> FEATURE:
<221> NAME/KEY: SITE
<222> LOCATION: (12)
<223> OTHER INFORMATION: Xaa equals Asn or Lys
<220> FEATURE:
<221> NAME/KEY: SITE
<222> LOCATION: (23)
<223> OTHER INFORMATION: Xaa Met or Lys

<400> SEQUENCE: 52

Glu Val Gln Xaa Xaa Gln Xaa Gly Ala Xaa Val Xaa Lys Pro Gly Ala
 1               5                  10                  15

Ser Val Lys Val Ser Cys Xaa Ile Ser Gly Asp Ser Phe Thr Ala Tyr
                20                  25                  30

Phe Ile His Trp Leu Arg Gln Ala Pro Gly Glu Gly Leu Glu Trp Met
            35                  40                  45

Gly Trp Phe Asn Pro Ile Ser Gly Thr Ala Asp Ser Pro Gln Lys Phe
    50                  55                  60

His Gly Arg Val Ala Met Thr Arg Asp Thr Ser Ile Ser Thr Ala Tyr
65                  70                  75                  80

Met Glu Leu Thr Arg Leu Ala Ser Asp Asp Thr Ala Ile Tyr Tyr Cys
                85                  90                  95

Ala Arg Gln His His Ser Asn Thr Phe Asp Pro Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Ala Gln Ser Ala Leu Thr Gln Pro Ala Ser Met
    130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Ala Val Thr Asn Arg Pro Ser
            180                 185                 190

Gly Val Ser Asn Arg Phe Ser Ala Ser Lys Ser Gly Asn Thr Ala Ser
        195                 200                 205

Leu Thr Ile Ser Gly Leu Gln Ala Glu Asp Glu Ala Asp Tyr Tyr Cys
    210                 215                 220

Ser Ser Tyr Thr Ser Ser Asn Thr Trp Val Phe Gly Gly Gly Thr Lys
225                 230                 235                 240

Val Thr Val Leu Gly
                245

<210> SEQ ID NO 53
<211> LENGTH: 249
<212> TYPE: PRT
<213> ORGANISM: Artificial sequence
```

<220> FEATURE:
<223> OTHER INFORMATION: T1006F07 scFv

<400> SEQUENCE: 53

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |

Ser Leu Arg Leu Ser Cys Ala Ala Ser Gly Phe Thr Phe Ser Ser Tyr
           20                      25                     30

Ala Met Ser Trp Val Arg Gln Ala Pro Gly Lys Gly Leu Glu Trp Val
           35                      40                     45

Ser Ala Ile Ser Gly Ser Gly Gly Ser Thr Tyr Tyr Ala Asp Ser Val
     50                      55                     60

Lys Gly Arg Phe Thr Ile Ser Arg Asp Asn Ser Lys Asn Thr Leu Tyr
65                      70                     75                     80

Leu Gln Met Asn Ser Leu Arg Ala Glu Asp Thr Ala Val Tyr Tyr Cys
           85                      90                     95

Ala Arg Glu Pro Ser Phe Gln Gln Trp Gly His Tyr Ser Tyr Gly Met
           100                     105                110

Asp Val Trp Gly Gln Gly Thr Met Val Thr Val Ser Ser Gly Gly Gly
         115                     120                125

Gly Ser Gly Gly Gly Gly Ser Gly Gly Gly Gly Ser Ala Gln Ser Val
     130                    135                140

Leu Thr Gln Pro Pro Ser Val Ser Val Ser Pro Gly Gln Ala Ala Arg
145                   150                     155                160

Ile Thr Cys Ser Gly Asp Lys Leu Gly Asp Lys Tyr Ala Ser Trp Tyr
           165                     170                175

Gln Gln Arg Pro Gly Gln Ser Pro Val Leu Val Ile Tyr Gln Asp Asn
         180                     185                190

Lys Arg Pro Ser Gly Ile Pro Glu Arg Phe Ser Gly Ser Asn Ser Gly
     195                    200                205

Asn Thr Ala Thr Leu Lys Ile Ser Gly Thr Gln Ala Met Asp Glu Ala
 210                   215                     220

Asp Tyr Tyr Cys Leu Ala Trp Asp Ser Ser Ala Asp Trp Val Phe Gly
225                   230                     235                240

Gly Gly Thr Lys Val Thr Val Leu Gly
           245

<210> SEQ ID NO 54
<211> LENGTH: 735
<212> TYPE: DNA
<213> ORGANISM: Artificial sequence
<220> FEATURE:
<223> OTHER INFORMATION: DNA encoding T1014A04 scFv

<400> SEQUENCE: 54

```
gaggtgcagc tggtgcagtc tggggctgac gtgaagaggc ctggggcctc agtgaaggtc      60
tcctgcaaga tttctggaga cagcttcaac gcctacttta ttcactgggt gcgtcaggcc     120
cctggacagg gcttgagtg gatgggatgg ttcaaccctg acagtggtac cgcagactct     180
gcacagaagt tcacggcag ggtcaccatg accagggaca cgtccagcag tactgccttc     240
ttggagctga gcagactgag atctgacgac acagccgtgt attactgtgt gagacaacat     300
cggggtaaca cgttcgcccc ctggggccgg gggacaatgg tcaccgtctc gagtggaggc     360
ggcggttcag gcggaggtgg ctctggcggt ggcggaagtg cacagtctgt gctgactcag     420
ccaccctccg cgtccgggtc tcctggacag tcagtcacca tctcctgcac tggaaccacc     480
```

| | |
|---|---:|
| agtgacgttg gtggttataa ctatgtctcc tggtaccaac agcacccagg caaagccccc | 540 |
| aaactcatga tttatggggt caatcagcgg ccctcagggg tccctgatcg cttctctggc | 600 |
| tccaagtctg gcaacacggc ctccctgacc gtctctgggc tccaggctga ggatgaggct | 660 |
| gattattact gcagttcata tgcaggcagc aacaattggg tgttcggcgg agggaccaag | 720 |
| ctgaccgtcc taggt | 735 |

<210> SEQ ID NO 55
<211> LENGTH: 735
<212> TYPE: DNA
<213> ORGANISM: Artificial sequence
<220> FEATURE:
<223> OTHER INFORMATION: DNA encoding T1014G03 scFv

<400> SEQUENCE: 55

| | |
|---|---:|
| gaggtccagc tggtacagtc tggagctgaa gtgaagatgc ctggggcctc agtcaagctc | 60 |
| tcctgcaggg tttctggaga caccttcacc gcctacttca ttcactgggt gcgacaggcc | 120 |
| cctggacaag gccttgagtg gatgggatgg ttcaaccctg tcagtggcac cgcaggctct | 180 |
| gctgagaagt tcgcggcag gtcgccatg accaggaca cgtccatcag cactgcctac | 240 |
| atggaattga acaggctgac atttgacgac acggccgtct attattgtgc gagacaacat | 300 |
| cgggggaata cgtttgaccc ctggggccag gcaccctgg tcaccgtctc gagtggaggc | 360 |
| ggcggttcag gcggaggtgg ctctggcggt ggcggaagtg cacagtctgc cctgactcag | 420 |
| cctgcctccg tgtctgggtc tcctggacag tcgatcacca tctcctgcac tggaaccagc | 480 |
| agtgacattg gtgcttataa gtatgtctcc tggtatcaac aacacccagg caaagccccc | 540 |
| aaacttgtga tttatgaggt cagtaatcgg ccctcagggg tttccagtcg cttctctggc | 600 |
| tccaagtctg gccagacggc ctccctgacc atctctgggc tccaggctga cgacgaggct | 660 |
| gattattact gcaactcata tcaaggttac aacacgtggg tgttcggcgg agggaccaag | 720 |
| gtcaccgtcc taggt | 735 |

<210> SEQ ID NO 56
<211> LENGTH: 732
<212> TYPE: DNA
<213> ORGANISM: Artificial sequence
<220> FEATURE:
<223> OTHER INFORMATION: DNA encoding T1014A02 scFv

<400> SEQUENCE: 56

| | |
|---|---:|
| caggtgcagc tgcaggagtc cggcccagga ctggtgaagc cctcggagac cctgtccctc | 60 |
| acctgcactg tctctggtgg ctccatcagt gattactact ggagttgggt ccggcagtcc | 120 |
| cccgggaagg gactggagtg gattgggtct atcgattatg ccggcagcac caattacaac | 180 |
| ccgtccctca gagccgagt caccatgaca atagacaagt ccaagaagca attccccctg | 240 |
| aagatagatt ctgtgaccgc cgcagatacg gccatgtatt actgtgcgag acaacttggg | 300 |
| cggatttctg actactgggg ccagggcacc ctggtcaccg tctcgagtgg aggcggcggt | 360 |
| tcaggcggag gtggctctgg cggtggcgga agtgcacttt cctatgtgct gactcagcca | 420 |
| ccctcagcgt ctgggacccc cgggcagagg gtcaccatct cttgtgctgg aagcagctcc | 480 |
| aacatcggag gaaatactgt aaactggtac cagcaactcc cagcaacggc ccccaaactc | 540 |
| ctcatcctata gtaataatca gcggccctca ggggtccctg accgattctc tggctccaag | 600 |
| tctggcacgt cagcctccct ggccatcagt gggctccagt ctgaggatga ggctgattat | 660 |
| tactgtgcaa catgggatga cagtcggggt ggttgggtgt tcggcggagg gaccaagctg | 720 |

```
accgtcctag gt                                                         732

<210> SEQ ID NO 57
<211> LENGTH: 735
<212> TYPE: DNA
<213> ORGANISM: Artificial sequence
<220> FEATURE:
<223> OTHER INFORMATION: DNA encoding T1014A12 scFv

<400> SEQUENCE: 57
gaggtccagc tggtgcagtc tggggctgac gtgaagaggc tggggcctc agtgaaggtc      60 tcctgcaaga tttctggaga cagcttcacc gcctactta ttcactgggt gcgtcaggcc    120
cctggacagg gcttgagtg gatgggatgg ttcaaccctg acagtggtac cgcagactct    180
gcacagaagt tcacggcag ggtcaccatg accagggaca cgtccagcag tactgccttc    240
ttggagctga gcagactgag atctgacgac accgccgtat attactgtgt gagacaacat    300
cggggtaaca cgttcgcccc ctggggccgg gggacaatgg tcaccgtctc gagtggaggc    360
ggcggttcag gcggaggtgg ctctggcggt ggcggaagtg cacagtctgc cctgactcag    420
cctgcctccg tgtctggtcc tcctggacag tcgatcacca tctcctgcac tggatccagc    480
agtgacgttg gtggttataa gtatgtctcc tggtaccaac aacacccagg caaagccccc    540
aaactcatta ttcatgatgt cagtaggcgg ccctcagagg tttctagtcg cttctctggc    600
tccaagtctg gcaacacggc ctccctgacc atctctgggc tccaggctga ggacgaggct    660
gagtactact gcagctcata ttcaagcacc aactcttggg tgttcggcgg agggaccaag    720
gtcaccgtcc taggt                                                     735

<210> SEQ ID NO 58
<211> LENGTH: 735
<212> TYPE: DNA
<213> ORGANISM: Artificial sequence
<220> FEATURE:
<223> OTHER INFORMATION: DNA encoding T1014B01 scFv

<400> SEQUENCE: 58
caggtccagc tggtgcagtc tggggctgag gtgaagaagc tggggcctc agtgaaggtc      60 tcctgcaaga tttctggaga caccttcgcc gcctactta ttcactgggt gcgacaggcc    120
cctggacaag gctggagtg gatgggatgg ttcaaccta acagtggtac cgcagactct    180
tcacagaagt tcacggcag ggtcaccatg accagggaca cgtccatcag cactgcctac    240
atggagttga gcaggctgag atctgacgac acggccgtgt attattgtgc gagacaacat    300
cggtctaata cgttcgaccc ctggggccaa gggacaatgg tcaccgtctc gagtggaggc    360
ggcggttcag gcggaggtgg ctctggcggt ggcggaagtg cacagtctgt cgtgacgcag    420
ccgccctcag tgtctgggtc tcctggacag tcagtcacca tctcctgcac tggaaccagc    480
agtgacattg gtgcttataa ttatgtctcc tggttccagc agcacccagg taaagccccc    540
aaactcataa tttctgaggt cagtaagcgg ccctcagggg tccctgatcg cctctctggc    600
tccaagtctg gcaacacggc ctccctgacc gtctccgggc tccaggctga ggatgaggct    660
gattattact gcggctcata tgcaggcagc aatatttggg tgttcggcgg agggaccaag    720
gtcaccgtcc taggt                                                     735

<210> SEQ ID NO 59
<211> LENGTH: 735
<212> TYPE: DNA
```

<213> ORGANISM: Artificial sequence
<220> FEATURE:
<223> OTHER INFORMATION: DNA encoding T1014B11 scFv

<400> SEQUENCE: 59

```
gaggtccagc tggtgcagtc tggggctgag gtgaagaagc tggggcctc agtaaaggtc      60
tcctgcaaga tttctggaga cagcttcacc gcctattta ttcactggct gcgacaggcc     120
cctggagaag gcttgagtg gatgggatgg ttcaatccta tcagcggtac cgccggctct     180
ccacagaagt ttcacggcag ggtcgccatg acccgtgaca cgtccatcag tactgcctac     240
atggagttga ccaggctggc atctgacgac acggccattt attattgtgc gagacaacat     300
cactctaata cgttcgaccc ctggggccaa ggaaccctgg tcaccgtctc gagtggaggc     360
ggcggttcag gcggaggtgg ctctggcggt ggcggaagtg cacaatctgc cctgactcag     420
cctgcctccg tgtctgggtc tcctggacag tcgatcacca tctcctgcac tggaaccaac     480
agtgacgttg gtggttacaa ctatgtctcc tggtaccaac acacccagg caaagccccc     540
aaactcatga tttatgaggt caataatcgg ccctcagggg tttctaatcg cttctctggc     600
tccaagtctg gcaacacggc ctccctgacc atctctgggc tccaggctga cgacgaggct     660
gattattact gcagctcata caaccagc aacacttggg tgttcggcgg agggaccaag     720
ctgaccgtcc taggt                                                      735
```

<210> SEQ ID NO 60
<211> LENGTH: 735
<212> TYPE: DNA
<213> ORGANISM: Artificial sequence
<220> FEATURE:
<223> OTHER INFORMATION: DNA encoding T1014F08 scFv

<400> SEQUENCE: 60

```
gaggtccagc tggtgcagtc tggggctgaa gtgaagaagc tggggcctc agtcaagctc      60
tcctgcaggg tttctggaga caccttcacc gcctacttca ttcactgggt gcgacaggcc     120
cctggacaag gcctgagtg gatgggatgg ttcaaccta tcagtggcac cgcaggctct     180
gctgcgaggt ttcgcggcag ggtcgccatg accagggaca cgtccatcag cactgcctac     240
atggaattga acaggctgac atttgacgac acggccgtct attattgtgc gagacaacat     300
cgggggaata cctttgaccc ctggggcaaa ggcaccctgg tcaccgtctc gagtggaggc     360
ggcggttcag gcggaggtgg ctctggcggt ggcggaagtg cactgcctgt gctgactcag     420
ccaccctccg cgtccgggtc tcctggacag tcagtcacca tctcctgcac tggaaccagc     480
agtgacgttg gtggttataa gtatgtctcc tggtaccaac agcacccagg caaagccccc     540
aaactcatga tttatgaggt cagtatgcgg ccgtcagggg tcccggatcg cttctctggc     600
tccaagtctg gcaacacggc ctccctgacc gtctctgggc tccaggctga ggatgaggct     660
gattattact gcgcctcata tgcaggcagc aacaattggg tgttcggcgg agggaccaag     720
ctgaccgtcc taggt                                                      735
```

<210> SEQ ID NO 61
<211> LENGTH: 735
<212> TYPE: DNA
<213> ORGANISM: Artificial sequence
<220> FEATURE:
<223> OTHER INFORMATION: DNA encoding T1014G04 scFv

<400> SEQUENCE: 61

```
gaagtgcagc tggtgcagtc tggggctgac gtgaagaggc tggggcctc agtgaaggtc      60
```

```
tcctgcaaga tttctggaga cagcttcacc gcctacttta ttcactgggt gcgtcaggcc    120
cctggacagg ggcttgagtg gatgggatgg ttcaaccctg acagtggtac cgcagactct    180
gcacagaagt tcacggcag ggtcaccatg accagggaca cgtccagcag tactgccttc    240
ttggagctga gcagactgag atctgacgac accgccgtat attactgtgt gagacaacat    300
cggggtaaca cgttcgcccc ctggggcagg gaaccctgg tcaccgtctc gagtggaggc    360
ggcggttcag gcggaggtgg ctctggcggt ggcggaagtg cacagcctgt gctgactcag    420 ccccctccg cgtccgggtc gcctggacag tcagtcacca ctcctgcac tggaaccagc    480 agtgacgttg gtagttatga gtatgtctcc tggtaccaac aacacccagg caaagcccc    540 agactcatga tttctgaggt caataagcgg ccctcagggg tccctaatcg cttctctggc    600
tccaagtctg gcaacacggc ctccctgacc gtctctgggc tccaggctga cgatgaggct    660
gattactact gcagctcata tgcaggcagc aacaattggg tgttcggcgg agggaccaag    720
gtcaccgtcc taggt                                                     735

<210> SEQ ID NO 62
<211> LENGTH: 750
<212> TYPE: DNA
<213> ORGANISM: Artificial sequence
<220> FEATURE:
<223> OTHER INFORMATION: DNA encoding T1015A02 scFv

<400> SEQUENCE: 62
caggtgcagc tgcaggagtc gggcccagga ctggtgaagc cttcacagac cctgtccctc     60
aaatgcaatg tctctggtgg ctccattggt actggtgatt actattggag ttggatccgc    120
cagcccccag ggaagggcct ggagtggatt ggctacatcc atagcagtgg gagcacttat    180 acaagccgt ccctcaggag tcgacttacc gtatcgatgg atacgtccag gaatcagttc    240
tccctgaagc tgacctctgt gactgccgca gacacggcac tgtattactg tgtcagagag    300
tgggccaatg gtgaccactg gagtgcattt gacctctggg gccaaggaac cctggtcacc    360
gtctcgagtg gaggcggcgg ttcaggcgga ggtggctctg gcggtggcgg aagtgcacag    420
gctgtgctga ctcagccgtc ctcagcgtct ggaccccccg ggcagagggt cactatcccc    480
tgttctggaa gcagctccaa catcggagg aatactgtta attggtacca acaactccca    540
ggaacggccc ccaaactcct catctatggt aatgatcagc ggccgtcagg ggtccctgac    600
cgattctctg gctccaagtc tggcacctca gcctcctgg ccatcactgg gctccagtct    660
gaggatgagg ctgattatta ctgtgcagca tgggatgaca gcctgattgg ttatgtcttc    720
ggaactggga cccagctcac cgttttargt                                     750

<210> SEQ ID NO 63
<211> LENGTH: 735
<212> TYPE: DNA
<213> ORGANISM: Artificial sequence
<220> FEATURE:
<223> OTHER INFORMATION: DNA encoding T1015A07 scFv

<400> SEQUENCE: 63
gaagtgcagc tggcgcagtc tggcgctgag gtgaataagc ctggggcctc agtaaaggtc     60
tcctgcaaga tttctggaga cagcttcacc gcctatttta ttcactggct gcgacaggcc    120
cctggagaag ggcttgagtg gatgggatgg ttcaatccta tcagcggtac cgccgactct    180
ccacagaagt tcacggcag ggtcgccatg acccgtgaca cgtccatcag tactgcctac    240
```

```
atggagttga ccaggctggc atctgacgac acggccattt attattgtgc gagacaacat    300
cactctaata cgttcgaccc ctggggccaa ggaaccctgg tcaccgtctc gagtggaggc    360
ggcggttcag gcggaggtgg ctctggcggt ggcggaagtg cacagtctgc cctgactcag    420
cctgcctcca tgtctgggtc tcctggacag tcgatcacca tctcctgcac tggaaccagc    480
agtgacgttg gtggttataa ctatgtctcc tggtaccaac agcacccagg caaagccccc    540
aaactcatga tttatgcggt cactaatcgg ccctcagggg tttctaatcg cttctctgcc    600
tccaagtctg gcaacacggc ctccctgacc atctctgggc tccaggctga ggacgaggct    660
gattattact gcagctcata taagcagc aacacttggg tgttcggcgg agggaccaag    720
gtcaccgtcc taggt                                                     735
```

<210> SEQ ID NO 64
<211> LENGTH: 735
<212> TYPE: DNA
<213> ORGANISM: Artificial sequence
<220> FEATURE:
<223> OTHER INFORMATION: DNA encoding T1015E01 scFv

<400> SEQUENCE: 64

```
gaagtgcags tggygcagkc tggsgctgas gtgaakaagc ctggsgcctc agtaaaggtc    60
tcctgcawga tttctggaga cagcttcacc gcctatttta ttcactgget gcgacaggcc    120 cctggagaag gcttgagtg gatgggatgg ttcaatccta tcagcggtac cgccgactct    180
ccacagaagt ttcacggcag ggtcgccatg acccgtgaca cgtccatcag tactgcctac    240
atggagttga ccaggctggc atctgacgac acggccattt attattgtgc gagacaacat    300
cactctaata cgttcgaccc ctggggccaa ggaaccctgg tcaccgtctc gagtggaggc    360
ggcggttcag gcggaggtgg ctctggcggt ggcggaagtg cacagtctgc cctgactcag    420
cctgcctcca tgtctgggtc tcctggacag tcgatcacca tctcctgcac tggaaccagc    480
agtgacgttg gtggttataa ctatgtctcc tggtaccaac agcacccagg caaagccccc    540
aaactcatga tttatgcggt cactaatcgg ccctcagggg tttctaatcg cttctctgcc    600
tccaagtctg gcaacacggc ctccctgacc atctctgggc tccaggctga ggacgaggct    660
gattattact gcagctcata taagcagc aacacttggg tgttcggcgg agggaccaag    720
gtcaccgtcc taggt                                                     735
```

<210> SEQ ID NO 65
<211> LENGTH: 747
<212> TYPE: DNA
<213> ORGANISM: Artificial sequence
<220> FEATURE:
<223> OTHER INFORMATION: DNA encoding T1006F07 scFv

<400> SEQUENCE: 65

```
gaggtgcagc tgttggagtc tgggggaggc ttggtacagc ctggggggtc cctgagactc    60
tcctgtgcag cctctggatt cacctttagc agctatgcca tgagctgggt ccgccaggct    120
ccagggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagaacca    300
tcctttcagc agtggggcca ctactcctac ggtatggacg tctggggcca ggggacaatg    360
gtcaccgtct cgagtggagg cggcggttca ggcggaggtg gctctggcgg tggcggaagt    420
gcacagtctg tgctgactca gccaccgtca gtgtccgtgt ccccaggaca ggcagccaga    480
```

-continued

```
atcacctgct ctggagataa gttgggggat aaatatgctt cgtggtatca acagaggcca    540
ggccagtccc ctgttttggt catctatcaa gataacaaaa ggccctcagg gatccctgag    600
cgattctctg gctccaattc tgggaacaca gccactctga aaatcagcgg gacccaggct    660
atggatgagg ctgactatta ctgtctggcg tgggacagca gcgctgattg ggtcttcggc    720
ggagggacca aggtcaccgt cctaggt                                       747
```

<210> SEQ ID NO 66
<211> LENGTH: 281
<212> TYPE: PRT
<213> ORGANISM: Homo sapiens
<400> SEQUENCE: 66

```
Met Ala Met Met Glu Val Gln Gly Gly Pro Ser Leu Gly Gln Thr Cys
  1               5                  10                  15

Val Leu Ile Val Ile Phe Thr Val Leu Leu Gln Ser Leu Cys Val Ala
             20                  25                  30

Val Thr Tyr Val Tyr Phe Thr Asn Glu Leu Lys Gln Met Gln Asp Lys
         35                  40                  45

Tyr Ser Lys Ser Gly Ile Ala Cys Phe Leu Lys Glu Asp Asp Ser Tyr
     50                  55                  60

Trp Asp Pro Asn Asp Glu Glu Ser Met Asn Ser Pro Cys Trp Gln Val
 65                  70                  75                  80

Lys Trp Gln Leu Arg Gln Leu Val Arg Lys Met Ile Leu Arg Thr Ser
                 85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

<210> SEQ ID NO 67
<211> LENGTH: 137
<212> TYPE: PRT
<213> ORGANISM: Homo sapiens
<220> FEATURE:

<223> OTHER INFORMATION: human mature J chain

<400> SEQUENCE: 67

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135
```

<210> SEQ ID NO 68
<211> LENGTH: 137
<212> TYPE: PRT
<213> ORGANISM: Artificial sequence
<220> FEATURE:
<223> OTHER INFORMATION: Mutant form of human mature J chain with C134S
      mutation compared to wild type Mature form of human J chain
      (SEQ ID NO:67)

<400> SEQUENCE: 68

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Ser Tyr Pro Asp
    130                 135
```

<210> SEQ ID NO 69
<211> LENGTH: 112
<212> TYPE: PRT
<213> ORGANISM: Artificial sequence
<220> FEATURE:
<223> OTHER INFORMATION: Mutant form of human mature J chain with amino
      acids 113-137 deleted compared to wild type Mature form of human J
      chain (SEQ ID NO:67)

```
<400> SEQUENCE: 69

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
                100                 105                 110

<210> SEQ ID NO 70
<211> LENGTH: 137
<212> TYPE: PRT
<213> ORGANISM: Artificial sequence
<220> FEATURE:
<223> OTHER INFORMATION: Mutant form of human mature J chain with C109S
      and C134S mutation compared to wild type mature form of human J
      chain (SEQ ID NO:67)

<400> SEQUENCE: 70

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Ser Tyr Thr Ala
                100                 105                 110

Val Val Pro Leu Val Tyr Gly Gly Glu Thr Lys Met Val Glu Thr Ala
                115                 120                 125

Leu Thr Pro Asp Ala Ser Tyr Pro Asp
    130                 135
```